United States Patent
Linge et al.

(10) Patent No.: US 11,365,167 B2
(45) Date of Patent: Jun. 21, 2022

(54) MATERIALS FOR ORGANIC ELECTROLUMINESCENT DEVICES

(71) Applicant: Merck Patent GmbH, Darmstadt (DE)

(72) Inventors: Rouven Linge, Darmstadt (DE); Lara-Isabel Rodriguez, Darmstadt (DE); Sebastian Meyer, Aschaffenburg (DE); Holger Heil, Frankfurt am Main (DE); Miriam Engel, Darmstadt (DE); Aaron Lackner, Mannheim (DE)

(73) Assignee: MERCK PATENT GMBH, Darmstadt (DE)

( * ) Notice: Subject to any disclaimer, the term of this patent is extended or adjusted under 35 U.S.C. 154(b) by 743 days.

(21) Appl. No.: 16/316,177

(22) PCT Filed: Jul. 5, 2017

(86) PCT No.: PCT/EP2017/066712
§ 371 (c)(1),
(2) Date: Jan. 8, 2019

(87) PCT Pub. No.: WO2018/007421
PCT Pub. Date: Jan. 11, 2018

(65) Prior Publication Data
US 2021/0053894 A1    Feb. 25, 2021

(30) Foreign Application Priority Data
Jul. 8, 2016  (EP) ..................... 16178596

(51) Int. Cl.
| | |
|---|---|
| C07C 13/62 | (2006.01) |
| C07C 13/70 | (2006.01) |
| C07D 307/91 | (2006.01) |
| C07D 333/76 | (2006.01) |
| C09K 11/06 | (2006.01) |
| C07D 209/82 | (2006.01) |
| H01L 51/00 | (2006.01) |
| H01L 51/50 | (2006.01) |

(52) U.S. Cl.
CPC ............. *C07C 13/62* (2013.01); *C07C 13/70* (2013.01); *C07D 209/82* (2013.01); *C07D 307/91* (2013.01); *C07D 333/76* (2013.01); *C09K 11/06* (2013.01); *H01L 51/008* (2013.01); *H01L 51/0067* (2013.01); *H01L 51/0072* (2013.01); *H01L 51/0073* (2013.01); *H01L 51/0074* (2013.01); *H01L 51/0094* (2013.01); *C07C 2603/54* (2017.05); *C07C 2603/92* (2017.05); *H01L 51/5012* (2013.01)

(58) Field of Classification Search
CPC ..................................... C07C 13/62
See application file for complete search history.

(56) References Cited

U.S. PATENT DOCUMENTS

| | | |
|---|---|---|
| 4,539,507 A | 9/1985 | VanSlyke et al. |
| 8,241,763 B2 | 8/2012 | Buesing et al. |
| 8,334,058 B2 | 12/2012 | Heil et al. |
| 8,471,064 B2 | 6/2013 | Pan et al. |
| 8,852,756 B2 | 10/2014 | Vestweber et al. |
| 8,932,732 B2 | 1/2015 | Buesing et al. |
| 10,559,756 B2 * | 2/2020 | Heil ............... C07C 209/10 |
| 2007/0141389 A1 | 6/2007 | Coggan et al. |
| 2014/0231754 A1 | 8/2014 | Yen |
| 2015/0255724 A1 | 9/2015 | Pan |
| 2016/0254456 A1 | 9/2016 | Heil et al. |
| 2018/0248129 A1 | 8/2018 | Heil et al. |

FOREIGN PATENT DOCUMENTS

| | | |
|---|---|---|
| CN | 101228250 A | 7/2008 |
| CN | 101495535 A | 7/2009 |
| CN | 105636944 A | 6/2016 |
| CN | 107848911 A | 3/2018 |
| EP | 2172534 A1 | 4/2010 |
| TW | 201434876 A | 9/2014 |
| TW | 201514130 A | 4/2015 |
| WO | 2006108497 A1 | 10/2006 |
| WO | 2007140847 A1 | 12/2007 |
| WO | 2008006449 A1 | 1/2008 |
| WO | 2009/016964 A1 | 2/2009 |
| WO | 2014/094954 A1 | 6/2014 |
| WO | 2014111269 A2 | 7/2014 |

OTHER PUBLICATIONS

International Search Report for PCT/EP2017/066712, dated Sep. 25, 2017.
Written Opinion of the International Searching Authority for PCT/EP2017/066712, dated Sep. 25, 2017.
Sonntag et al., "Synthesis of a novel liquid crystalline bisindenocarbazole derivative", Liquid Crystals, vol. 34, No. 1, Jan. 2007, pp. 49-57.

\* cited by examiner

*Primary Examiner* — Vu A Nguyen
(74) *Attorney, Agent, or Firm* — Faegre Drinker Biddle & Reath LLP

(57) ABSTRACT

The present invention relates to compounds of the formula (1) which are suitable for use in electronic devices, in particular organic electroluminescent devices, and to electronic devices which comprise these compounds.

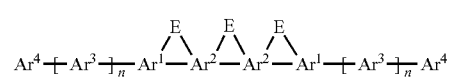

(1)

20 Claims, No Drawings

MATERIALS FOR ORGANIC ELECTROLUMINESCENT DEVICES

RELATED APPLICATIONS

This application is a national stage entry, filed pursuant to 35 U.S.C. § 371, of PCT/EP2017/066712, filed Jul. 5, 2017, which claims the benefit of European Patent Application No. 16178596.9, filed Jul. 8, 2016, which is incorporated herein by reference in its entirety.

The present invention relates to a compound of the formula (1), to the use of the compound in an electronic device, and to an electronic device comprising a compound of the formula (1). The present invention furthermore relates to a process for the preparation of a compound of the formula (1) and to a formulation comprising one or more compounds of the formula (1).

The development of functional compounds for use in electronic devices is currently the subject of intensive research. The aim is, in particular, the development of compounds with which improved properties of electronic devices in one or more relevant points can be achieved, such as, for example, power efficiency, lifetime or colour coordinates of the emitted light.

In accordance with the present invention, the term electronic device is taken to mean, inter alia, organic integrated circuits (ICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices called OLEDs. The general structure and the functional principle of OLEDs are known to the person skilled in the art and are described, for example, in U.S. Pat. No. 4,539,507.

Further improvements are still necessary with respect to the performance data of OLEDs, in particular with a view to broad commercial use, for example in display devices or as light sources. Of particular importance in this connection are the lifetime, the efficiency and the operating voltage of the OLEDs and as well as the colour values achieved. In particular in the case of blue-emitting OLEDs, there is potential for improvement with respect to the lifetime of the devices.

An important starting point for achieving the said improvements is the choice of the emitter compound employed in the electronic device.

Blue-fluorescent emitters known from the prior art are a multiplicity of compounds, in particular arylamines containing one or more condensed aryl groups and/or indenofluorene groups. Examples thereof are benzoindenofluorenamines, for example in accordance with WO 2008/006449, and dibenzoindenofluorenamines, for example in accordance with WO 2007/140847.

Benzoindenofluorene derivatives and dibenzoindenofluorene derivatives may also be employed as matrix materials in OLEDs and in other electronic devices, for examples in accordance with WO 2008/006449 and WO 2007/140847.

Furthermore, indenofluorene derivatives may be employed as hole-transport materials in OLEDs and in other electronic devices, for examples in accordance with WO 2006/108497.

Thus, compounds based on indenofluorene derivatives, benzoindenofluorene derivatives and dibenzoindenofluorene derivatives have been successfully used as materials in OLEDs over the past years.

However, further improvements with regard to this type of compounds are still necessary with respect to the lifetime, the efficiency and the colour values achieved in the case of blue-emitting OLEDs. More particularly, there is a need for deep-blue fluorescent emitters for OLEDs, which exhibit very good colour properties in terms of colour-depth and narrow emission band and at the same time still exhibit good properties in terms of lifetime, efficiency and operating voltage of the OLEDs. Furthermore, there is a need for compounds that are suitable for solution processing, especially in the case of blue-emitting OLEDs.

The present invention is thus based on the technical object of providing compounds which are suitable for use in electronic devices, such as OLEDs, which can be employed as blue emitters, as matrix materials and/or as hole-transport materials and which are suitable for solution processing.

In investigations on novel compounds for use in electronic devices, it has now been found, unexpectedly, that compounds of formula (1) as defined below are eminently suitable for use in electronic devices. In particular, they achieve one or more, preferably all, of the above-mentioned technical objects of provision of OLEDs having deep-blue colour coordinates of the emitted light, provision of OLEDs having a long lifetime and provision of compounds having good solubility in organic solvents.

The invention thus relates to a compound of a formula (1),

formula (1)

where the following applies to the symbols and indices used:
$Ar^1$ stands on each occurrence, identically or differently, for an aryl or heteroaryl group having 6 to 18 aromatic ring atoms, which may in each case be substituted by one or more radicals $R^1$, wherein at least one of the group $Ar^1$ in formula (1) has 10 or more aromatic ring atoms;
$Ar^2$ stands on each occurrence, identically or differently, for an aryl or heteroaryl group having 6 aromatic ring atoms, which may in each case be substituted by one or more radicals $R^1$;
$Ar^3$, $Ar^4$ stand on each occurrence, identically or differently, for an aromatic or heteroaromatic ring systems having 5 to 25 aromatic ring atoms, which may in each case be substituted by one or more radicals $R^1$;
E is identically or differently on each occurrence, selected from —$BR^0$—, —$C(R^0)_2$—, —$C(R^0)_2$—$C(R^0)_2$—, —$C(R^0)_2$—O—, —$C(R^0)_2$—S—, —$R^0C$=$CR^0$—, —$R^0C$=N—, $Si(R^0)_2$, —$Si(R^0)_2$—$Si(R^0)_2$—, —C(=O)—, —C(=$NR^0$)—, —C(=$C(R^0)_2$)—, —O—, —S—, —S(=O)—, —$SO_2$—, —$N(R^0)$—, —$P(R^0)$— and —P((=O)$R^0$)—, and two groups E may be in a cis- or trans-position relative to each other;
$R^0$, $R^1$ stand on each occurrence, identically or differently, for H, D, F, C, Br, I, CHO, CN, $N(Ar^5)_2$, C(=O)$Ar^5$, P(=O)($Ar^5$)$_2$, S(=O)$Ar^5$, S(=O)$_2Ar^5$, $NO_2$, $Si(R^2)_3$, $B(OR^2)_2$, $OSO_2R^2$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^2$, where in each case one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $P(=O)(R^2)$, $SO$, $SO_2$, $O$, $S$ or $CONR^2$ and where one or more H atoms may be replaced by D, F, C, Br, I, CN or $NO_2$, an aromatic or heteroaromatic ring systems having 5 to 60 aromatic ring atoms, which may in each case be substituted by one or more radicals $R^2$, or an aryloxy groups having 5 to 40 aromatic ring atoms, which may be substituted by one or more radicals $R^2$, where two adjacent substituents $R^0$ and/or two adjacent substituents $R^1$ may form a mono- or polycyclic, aliphatic ring system or aromatic ring system, which may be substituted by one or more radicals $R^2$;

$R^2$ stands on each occurrence, identically or differently, for H, D, F, C, Br, I, CHO, CN, $N(Ar^5)_2$, $C(=O)Ar^5$, $P(=O)(Ar^5)_2$, $S(=O)Ar^5$, $S(=O)_2Ar^5$, $NO_2$, $Si(R^3)_3$, $B(OR^3)_2$, $OSO_2R^3$, a straight-chain alkyl, alkoxy or thioalkyl groups having 1 to 40 C atoms or branched or cyclic alkyl, alkoxy or thioalkyl groups having 3 to 40 C atoms, each of which may be substituted by one or more radicals $R^3$, where in each case one or more non-adjacent $CH_2$ groups may be replaced by $R^3C=CR^3$, $C\equiv C$, $Si(R^3)_2$, $Ge(R^3)_2$, $Sn(R^3)_2$, $C=O$, $C=S$, $C=Se$, $P(=O)(R^3)$, $SO$, $SO_2$, $O$, $S$ or $CONR^3$ and where one or more H atoms may be replaced by D, F, C, Br, I, CN or $NO_2$, an aromatic or heteroaromatic ring systems having 5 to 60 aromatic ring atoms, which may in each case be substituted by one or more radicals $R^3$, or an aryloxy group having 5 to 60 aromatic ring atoms, which may be substituted by one or more radicals $R^3$, where two adjacent substituents $R^2$ may form a mono- or polycyclic, aliphatic ring system or aromatic ring system, which may be substituted by one or more radicals $R^3$;

$R^3$ stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent $CH_2$ groups may be replaced by $SO$, $SO_2$, O, S and where one or more H atoms may be replaced by D, F, C, Br or I, or an aromatic or heteroaromatic ring system having 5 to 24 C atoms;

$Ar^5$ is an aromatic or heteroaromatic ring system having 5 to 24 aromatic ring atoms, preferably 5 to 18 aromatic ring atoms, which may in each case also be substituted by one or more radicals $R^3$;

n is an integer from 1 to 20;

wherein if n is equal to 1 and at least one of the group $Ar^3$ or $Ar^4$ stands for a phenyl group, then the compound of formula (1) bears at least one group $R^0$ or $R^1$, which stands for a straight-chain alkyl group having 2 to 40 C atoms or a branched or cyclic alkyl group having 3 to 40 C atoms, each of which may be substituted by one or more radicals $R^2$.

Concerning formula (1), the bonding between a group E and the groups $Ar^1$ and $Ar^2$ that are adjacent to this group E can occur at each free position of the adjacent groups $Ar^1$ and $Ar^2$. In the same way, the bonding between a group E and two groups $Ar^2$ that are adjacent to this group E can occur at each free position of these two adjacent groups $Ar^2$. Thus, it is to be understood that the groups E can be in cis- or in trans-position relative to each other, as mentioned in the definition of the group E above.

Adjacent substituents in the sense of the present invention are substituents which are bonded to atoms which are linked directly to one another or which are bonded to the same atom.

Furthermore, the following definitions of chemical groups apply for the purposes of the present application:

An aryl group in the sense of this invention contains 6 to 60 aromatic ring atoms, preferably 6 to 40 aromatic ring atoms, more preferably 6 to 20 aromatic ring atoms; a heteroaryl group in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system, preferably 6 to 40 C atoms, more preferably 6 to 20 C atoms. A heteroaromatic ring system in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp³-hybridised C, Si, N or O atom, an sp²-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroine, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-ctylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following schemes:

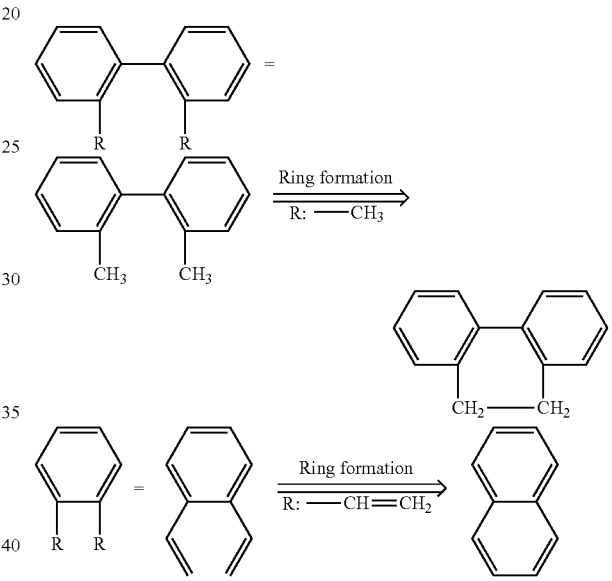

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

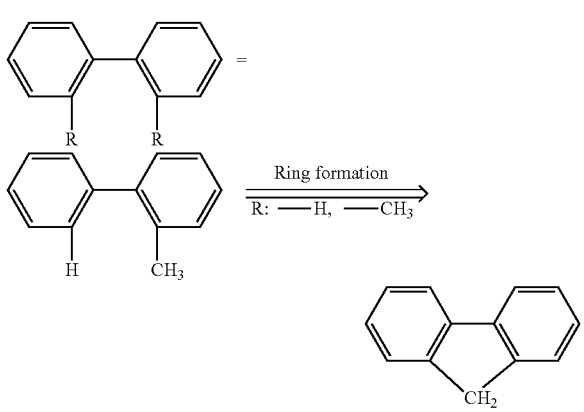

In accordance with a preferred embodiment, the bond between two adjacent groups $Ar^2$ and $Ar^1$ and the bond between two adjacent groups $Ar^2$ are in para positions.

In accordance with a preferred embodiment, n is an integer from 1 to 10, more preferably from 2 to 8, particularly preferably from 2 to 4.

In accordance with a preferred embodiment of the invention, the compounds of formula (1) bear at least one group $R^0$ or $R^1$, which stands for a straight-chain alkyl group having 2 to 40 C atoms, preferably 3 to 20 C atoms, very preferably 6 to 10 C atoms, or a branched or cyclic alkyl group having 3 to 40 C atoms, preferably 4 to 20 C atoms, very preferably 6 to 10 C atoms, each of which may be substituted by one or more radicals $R^2$.

It is very preferred that the compounds of formula (1) contain two adjacent groups $R^0$, which are selected, identically or differently, from a straight-chain alkyl group having 2 to 40 C atoms, preferably 3 to 20 C atoms, very preferably 6 to 10 C atoms, and a branched or cyclic alkyl group having 3 to 40 C atoms, preferably 4 to 20 C atoms, very preferably 6 to 10 C atoms, each of which may be substituted by one or more radicals $R^2$.

It is furthermore preferred that $Ar^1$ stands on each occurrence, identically or differently, for an aryl or heteroaryl group having 6 to 14 aromatic ring atoms, which may in each case be substituted by one or more radicals $R^1$, wherein at least one of the group $Ar^1$ in formula (1) has 10 or more aromatic ring atoms.

It is furthermore preferred that $Ar^2$ stands for a phenyl group, which may in each case be substituted by one or more radicals $R^1$;

In accordance to a preferred embodiment, both groups $Ar^1$ in formula (1) stand on each occurrence, identically or differently, for an aryl or heteroaryl group having 10 to 14 aromatic ring atoms, which may in each case be substituted by one or more radicals $R^1$.

More preferably, both groups $Ar^1$ in formula (1) stand for an aryl group having 10 aromatic ring atoms, which may in each case be substituted by one or more radicals $R^1$.

Particularly preferably, both groups $Ar^1$ stand for a naphthyl group, which may be substituted by one or more radicals $R^1$ and $Ar^2$ stand for a phenyl group, which may be substituted by one or more radicals $R^1$.

In accordance to a further preferred embodiment, one group $Ar^1$ in formula (1) stands for an aryl or heteroaryl group having 10 aromatic ring atoms and one group $Ar^1$ stands for an aryl or heteroaryl group having 6 aromatic ring, which may in each case be substituted by one or more radicals $R^1$.

Particularly preferably, one group $Ar^1$ stands for a naphthyl group and one group $Ar^1$ stands for a phenyl, which may in each case be substituted by one or more radicals $R^1$, and $Ar^2$ stand for a phenyl group, which may be substituted by one or more radicals $R^1$.

It is preferred that the group E is, identically or differently, on each occurrence, selected from $-C(R^0)_2-$, $-C(R^0)_2-C(R^0)_2-$, $-R^0C=CR^0-$, $-S(R^0)_2$, $-C(=O)-$, $-O-$, $-S-$, $-S(O_2)-$ and $N(R^0)$, more preferably from $-C(R^0)_2-$, $-C(R^0)_2-C(R^0)_2-$, $-O-$, $-S-$ and $N(R^0)$. It is particularly preferred that E stands for $-C(R^0)_2-$.

Preferably, $R^0$ is selected on each occurrence, identically or differently, from the group consisting of H, D, F, CN, $Si(R^2)_3$, a straight-chain alkyl having 1 to 10 C atoms or a branched or cyclic alkyl group having 3 to 10 C atoms, each of which may be substituted by one or more radicals $R^2$, where in each case one or more H atoms may be replaced by F, or an aryl or heteroaryl group having 5 to 40 aromatic ring atoms, which may in each case be substituted by one or more radicals $R^2$, where two adjacent substituents $R^0$, may form a mono- or polycyclic, aliphatic ring system or aromatic ring system, which may be substituted by one or more radicals $R^2$.

According to a preferred embodiment of the invention, E stands for $-C(R^0)_2$ and the two adjacent substituents $R^0$ of the group $-C(R^0)_2-$ form a ring system, so that a spiro group is formed. More preferably, the two adjacent substituent $R^0$ form a spiro-cyclohexane ring or a spiro-cyclopentane ring.

It is furthermore preferred that $R^1$ is selected, identically or differently on each occurrence, from the group consisting of H, D, F, CN, a straight-chain alkyl or alkoxy group having 1 to 10 C atoms or a branched or cyclic alkyl or alkoxy group having 3 to 10 C atoms, each of which may be substituted by one or more radicals $R^2$, where one or more non-adjacent $CH_2$ groups may be replaced by 0 and where one or more H atoms may be replaced by F, an aromatic or heteroaromatic ring system having 5 to 24 aromatic ring atoms, which may in each case be substituted by one or more radicals $R^2$.

It is furthermore preferred that $R^2$ is selected, identically or differently on each occurrence, from the group consisting of H, D, F, CN, a straight-chain alkyl or alkoxy group having 1 to 10 C atoms or a branched or cyclic alkyl or alkoxy group having 3 to 10 C atoms, each of which may be substituted by one or more radicals $R^3$, where one or more non-adjacent $CH_2$ groups may be replaced by O and where one or more H atoms may be replaced by F, an aromatic or heteroaromatic ring system having 5 to 24 aromatic ring atoms, which may in each case be substituted by one or more radicals $R^3$.

The compounds of formula (1) are preferably selected from the compounds of formula (1-1) and formula (1-2), formula (1-1)

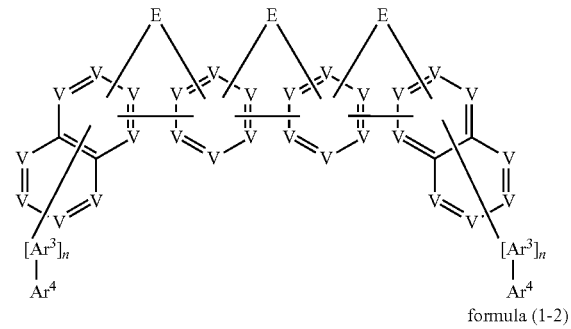

formula (1-2)

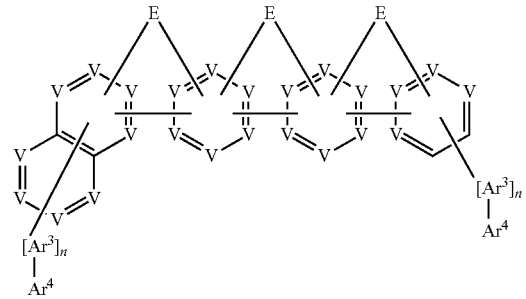

where the symbols E, $Ar^3$, $Ar^4$ and the index n have the same meaning as above, and where:

V is on each occurrence, identically or differently, $CR^1$ or N, wherein V is C when V is bonded to a group $Ar^3$ or to a group E.

Concerning formulae (1-1) and (1-2), the bonding between a group E and an adjacent 6-membered ring containing X or an adjacent 10-membered ring containing E can occur at each free position. Thus, it is to be understood that the groups E can be in cis- or in trans-position relative to each other, as mentioned in the definition of the group E above.

It is preferred that maximal two groups V per 6-membered ring are equal to N. More preferably, V stands on each occurrence for $CR^1$.

In accordance with a preferred embodiment of the invention, the compounds of formula (1), (1-1) and (1-2) are selected from the compounds of the following formulae (1-1-1) to (1-1-11) and (1-2-1) to (1-2-7), formula (1-1-1)

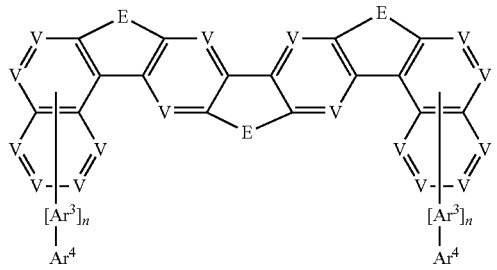

formula (1-1-2)

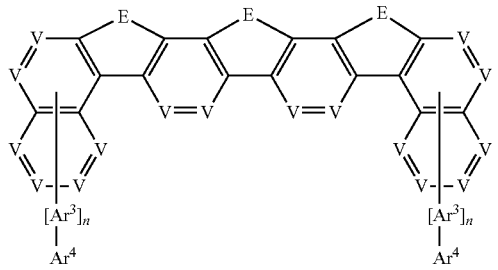

formula (1-1-3)

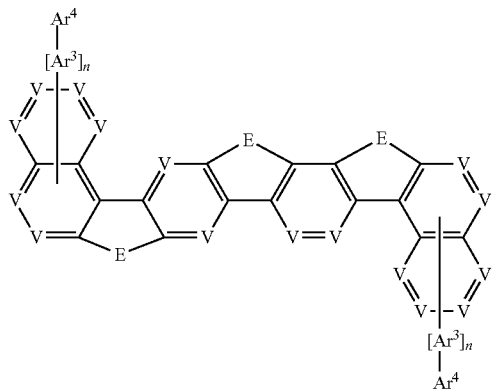

formula (1-1-4)

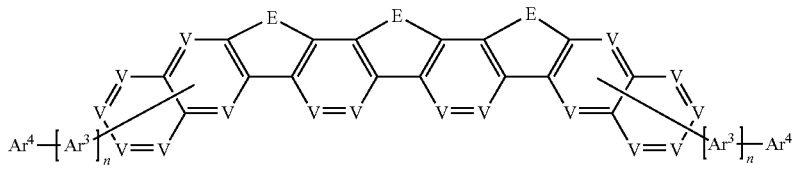

formula (1-1-5)

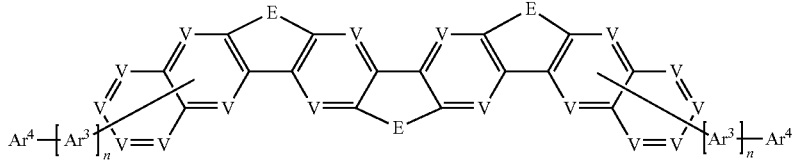

formula (1-1-6)

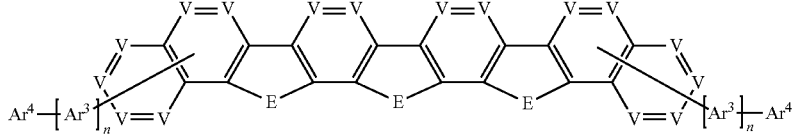

formula (1-1-7)

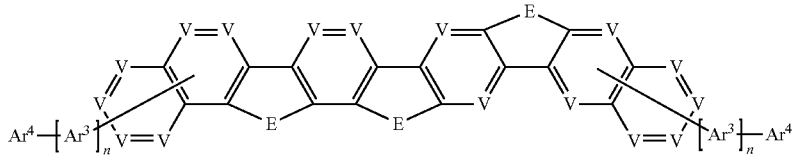

formula (1-1-8)
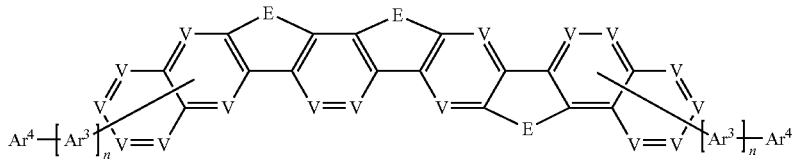
formula (1-1-9)
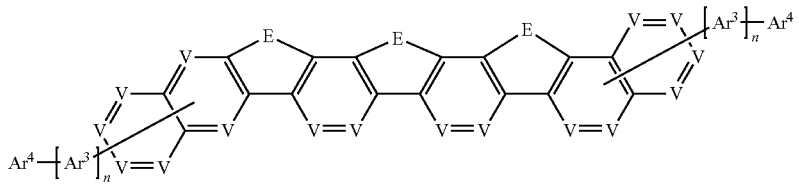
formula (1-1-10)
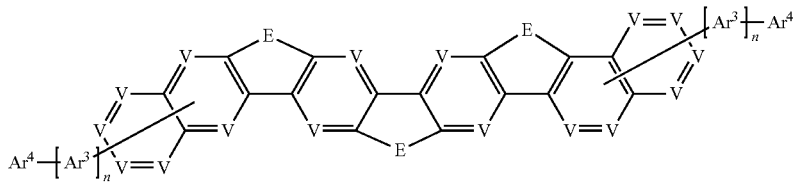
formula (1-1-11)
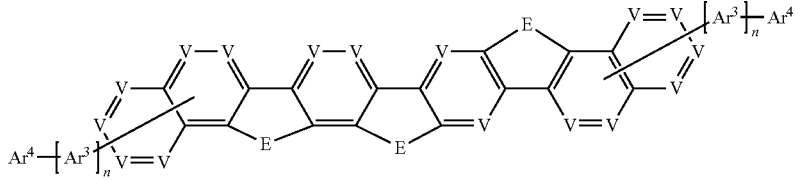
formula (1-2-1)
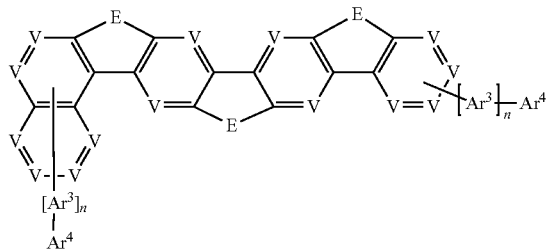
formula (1-2-2)
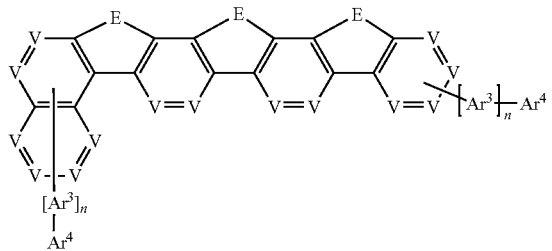
formula (1-2-3)
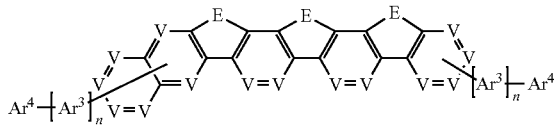
formula (1-2-4)
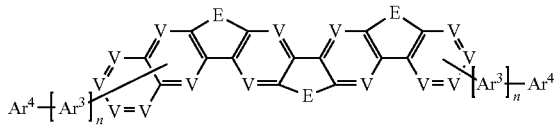
formula (1-2-5)
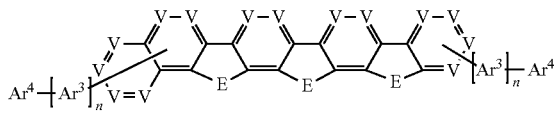
formula (1-2-6)
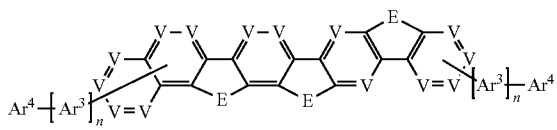

-continued

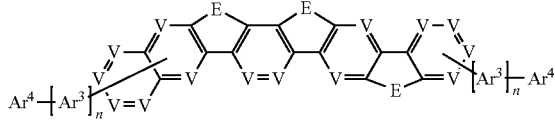

formula (1-2-7)

where the symbols V, E, $Ar^3$, $Ar^4$ and the index n have the same meaning as above.

Among formulae (1-1-1) to (1-1-11) and (1-2-1) to (1-2-7), the formulae (1-1-1) to (1-1-11) are preferred. Formulae (1-1-1) and (1-1-2) are particularly preferred. Formula (1-1-1) is very particularly preferred.

In accordance with a very preferred embodiment of the invention, the compounds of formula (1), (1-1) and (1-2), (1-1-1) to (1-1-11) and (1-2-1) to (1-2-7) are selected from the compounds of the formulae (1-1-1-a) to (1-1-11-a) and (1-2-1-a) to (1-2-7-a),

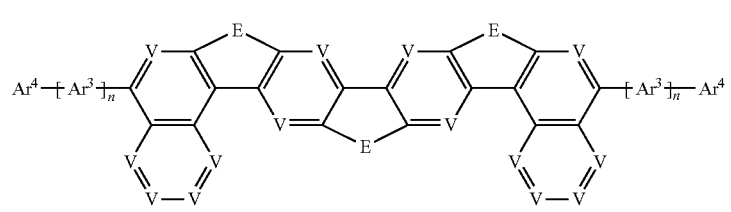

formula (1-1-1-a)

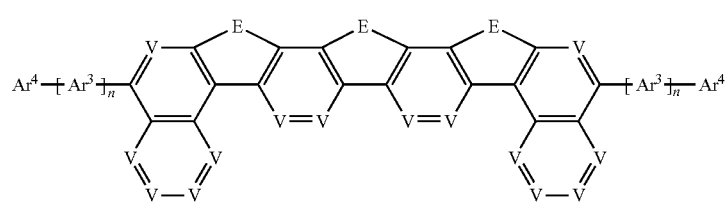

formula (1-1-2-a)

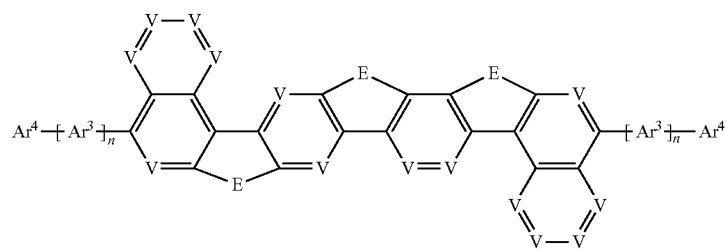

formula (1-1-3-a)

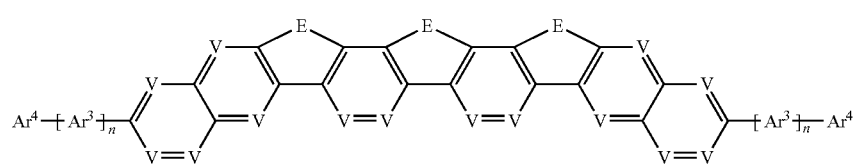

formula (1-1-4-a)

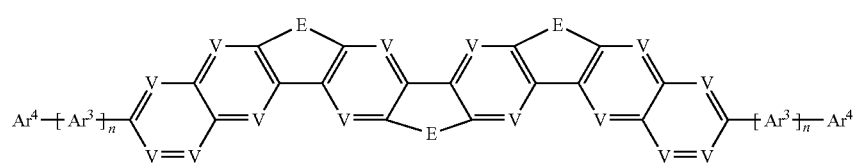

formula (1-1-5-a)

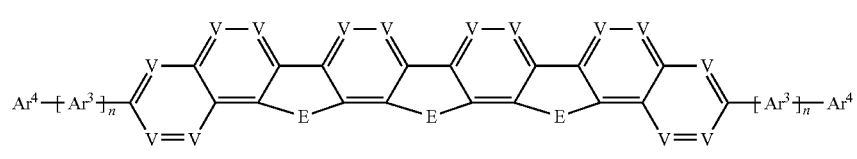

formula (1-1-6-a)

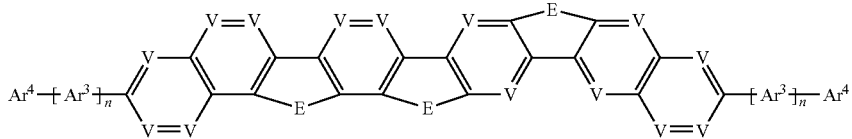
formula (1-1-7-a)
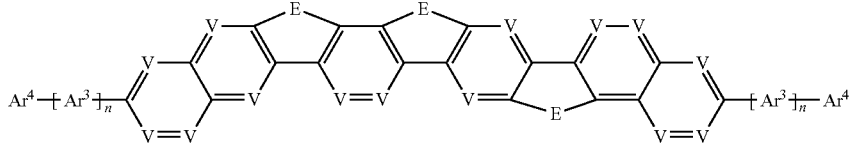
formula (1-1-8-a)
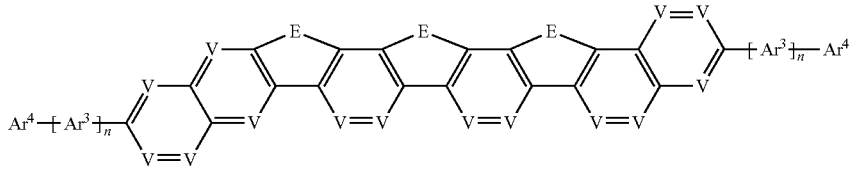
formula (1-1-9-a)
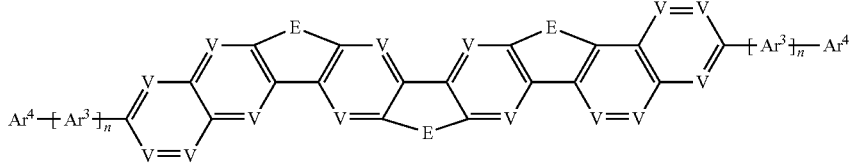
formula (1-1-10-a)
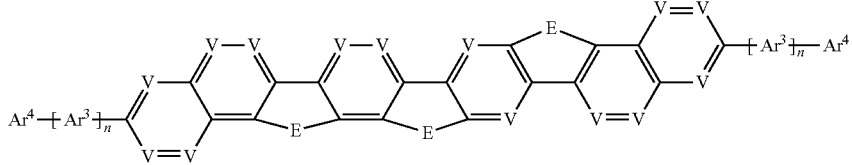
formula (1-1-11-a)
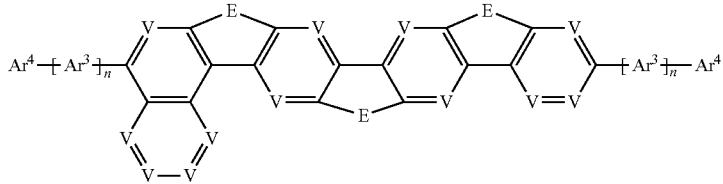
formula (1-2-1-a)
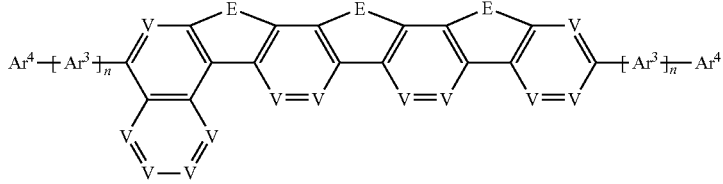
formula (1-2-2-a)
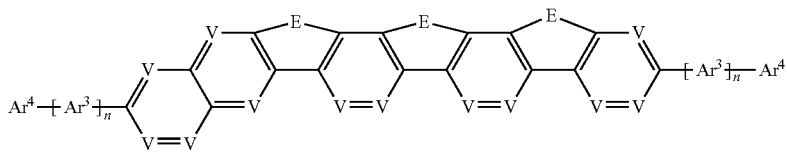
formula (1-2-3-a)

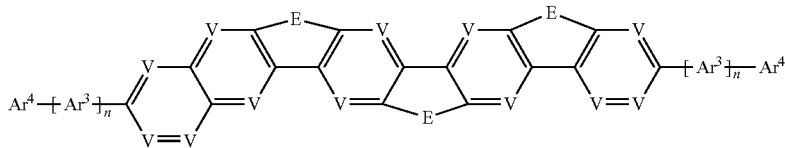

formula (1-2-4-a)

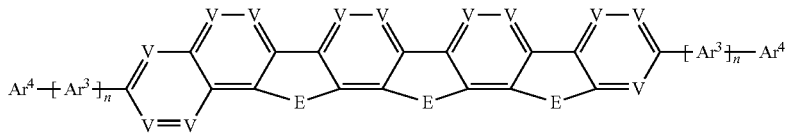

formula (1-2-5-a)


formula (1-2-6-a)

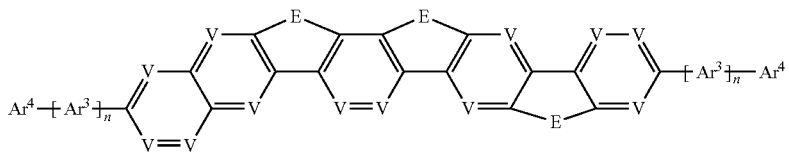

formula (1-2-7-a)

where the symbols V, E, Ar³, Ar⁴ and the index n have the same meaning as above.

Among formulae (1-1-1-a) to (1-1-11-a) and (1-2-1-a) to (1-2-7-a), the formulae (1-1-1-a) to (1-1-11-a) are preferred. Formulae (1-1-1-a) and (1-1-2-a) are particularly preferred. Formula (1-1-1-a) is very particularly preferred.

In accordance with a preferred embodiment, Ar³ is selected from one of the formulae (Ar3-1) to (Ar3-25),

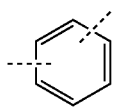

(Ar3-1)

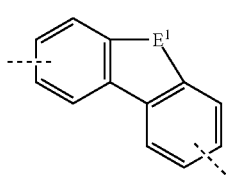

(Ar3-2)

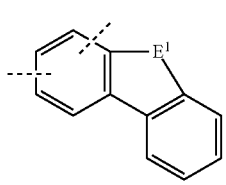

(Ar3-3)

-continued

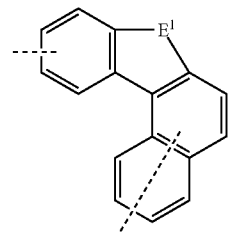

(Ar3-4)

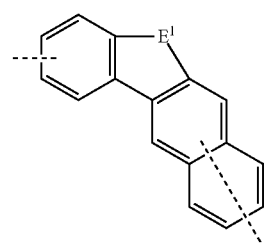

(Ar3-5)

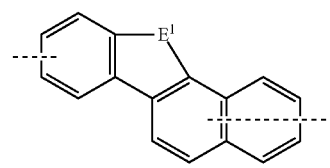

(Ar3-6)

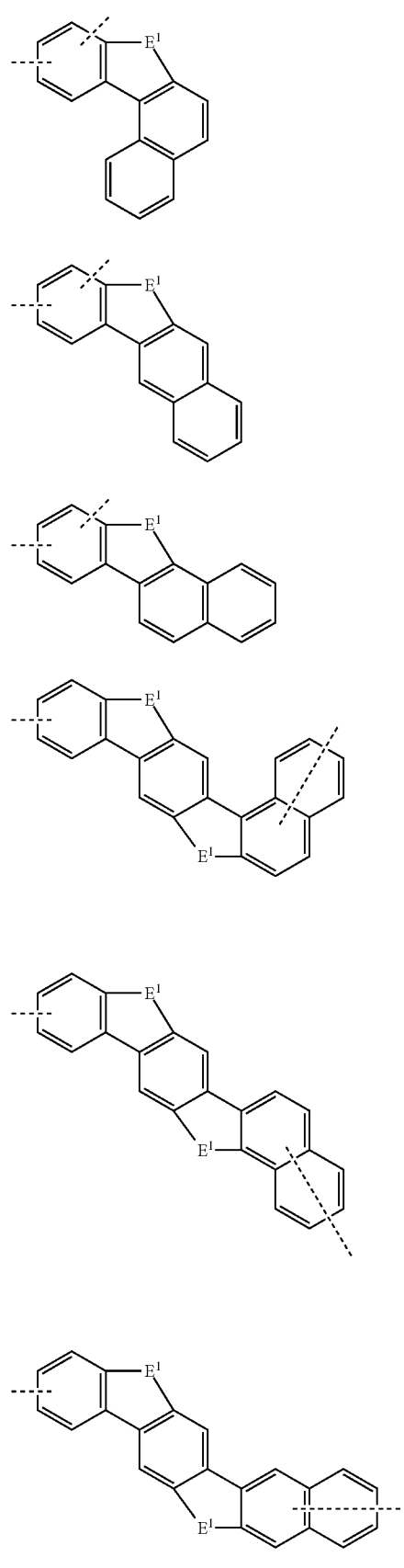
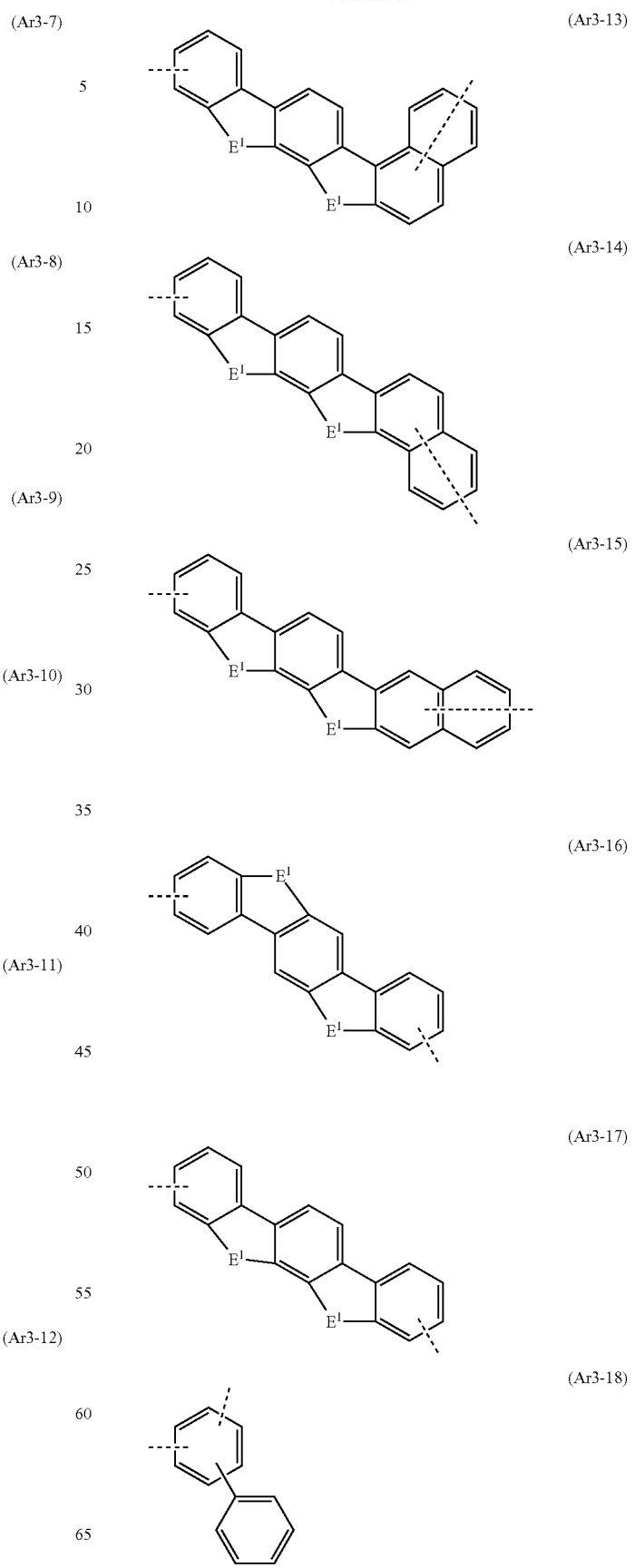

-continued

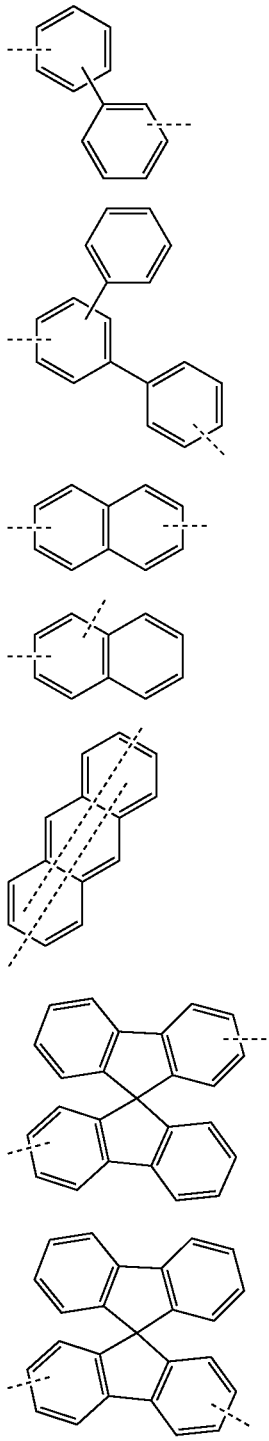

(Ar3-19)
(Ar3-20)
(Ar3-21)
(Ar3-22)
(Ar3-23)
(Ar3-24)
(Ar3-25)

where the dashed bonds indicate the bonding to Ar¹ and to a group Ar³ or Ar⁴ and the groups of formulae (Ar3-1) to (Ar3-25) may be substituted at each free position by a group $R^1$, which has the same meaning as above, and where $E^1$ is selected from —B(R⁰)—, —C(R⁰)$_2$—, —C(R⁰)$_2$—C(R⁰)$_2$—, —Si(R⁰)$_2$, —C(O)—, —C(=NR⁰)—, —C=(C(R⁰))$_2$—, —O—, —S—, —S(=O)—, —SO$_2$—, —N(R⁰)—, —P(R⁰)— and —P((=O)R⁰)—, where the substituent $R^0$ has the same meaning as above.

Preferably, $E^1$ is selected from —C(R⁰)$_2$—, —C(R⁰)$_2$—C(R⁰)$_2$—, —O—, —S— and —N(R⁰)—, where the substituent $R^0$ has the same meaning as above. Very preferably, $E^1$ stands for —C(R⁰)$_2$—.

Among formulae (Ar3-1) to (Ar3-25), formulae (Ar3-1), (Ar3-2), (Ar3-4), (Ar3-10), (Ar3-13), (Ar3-16), (Ar3-19) and (Ar3-22) are preferred. Formulae (Ar3-1), (Ar3-2), (Ar3-4) and (Ar3-19) are particularly preferred.

In accordance with a very preferred embodiment, Ar³ is selected from one of the formulae (Ar3-1-1) to (Ar3-25-3),

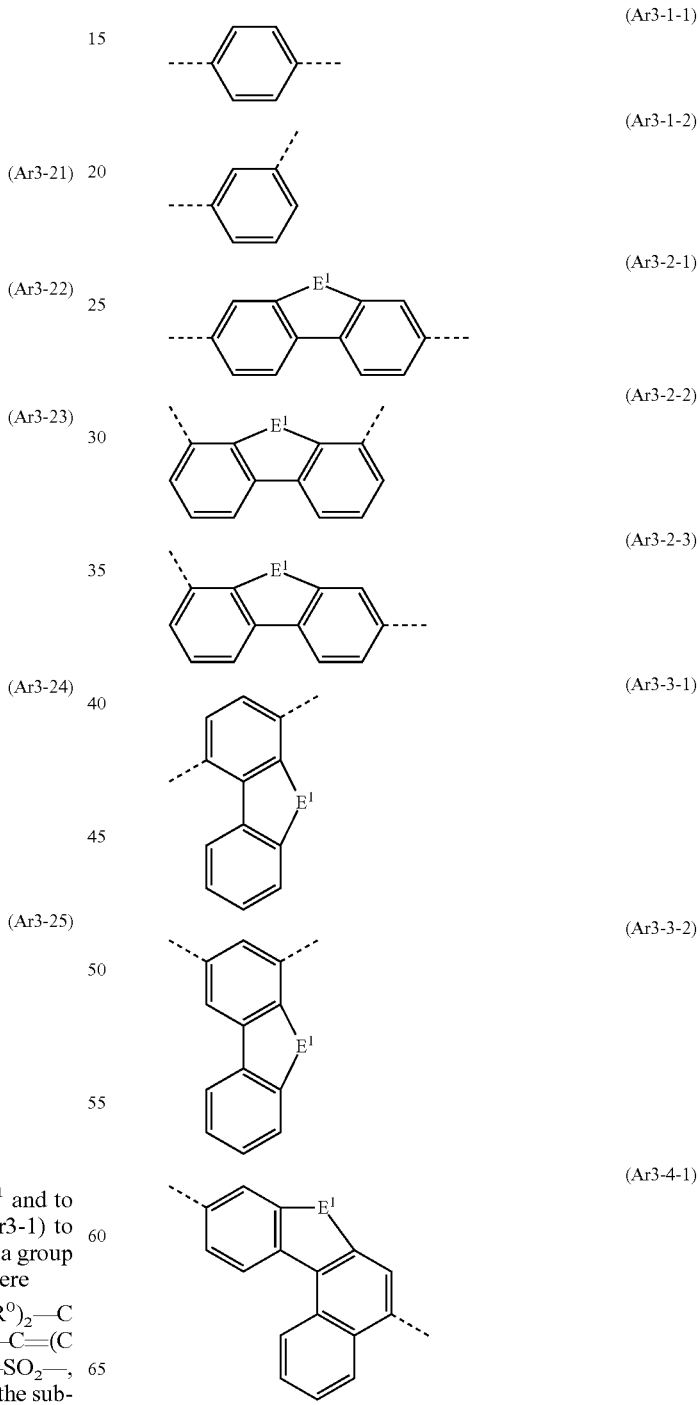

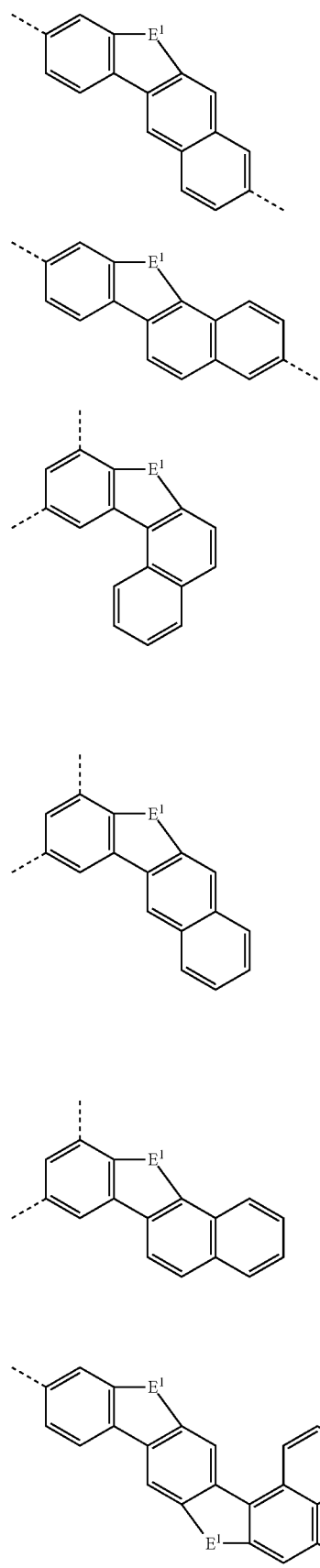
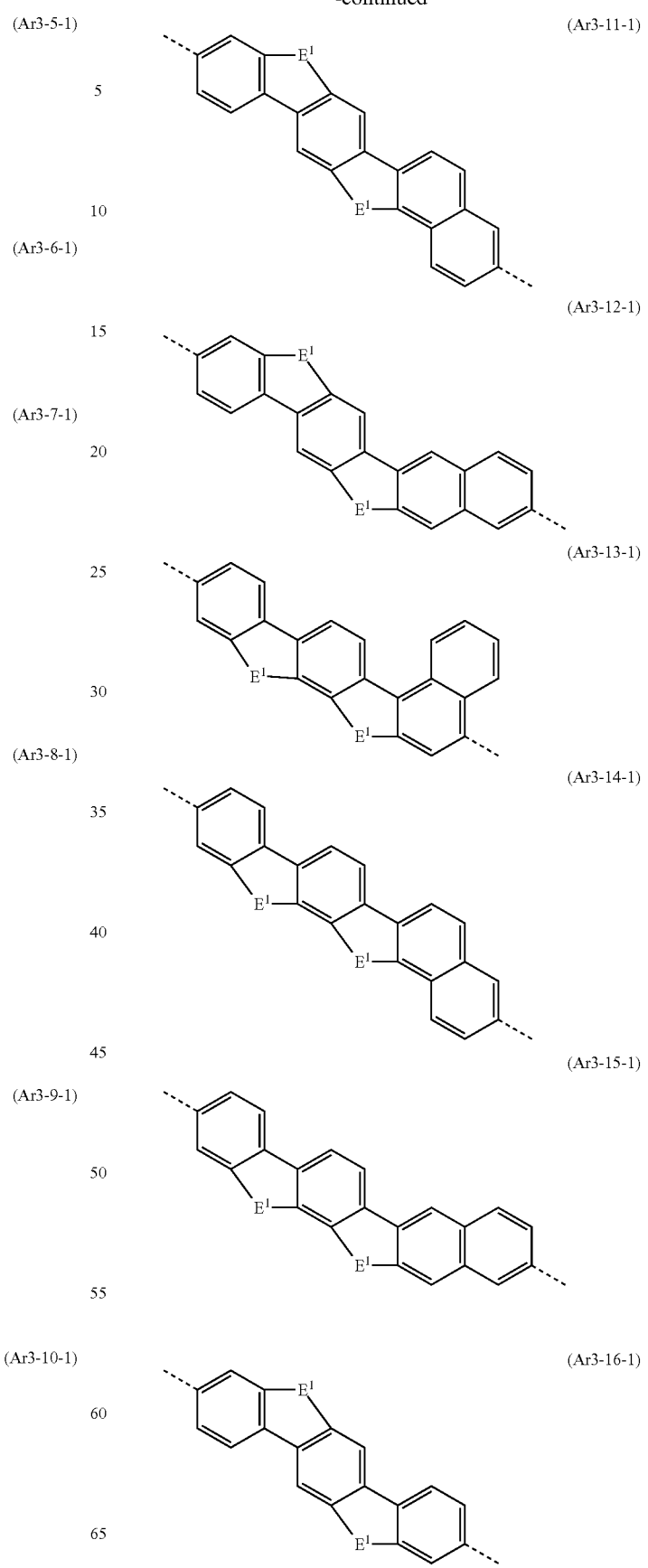

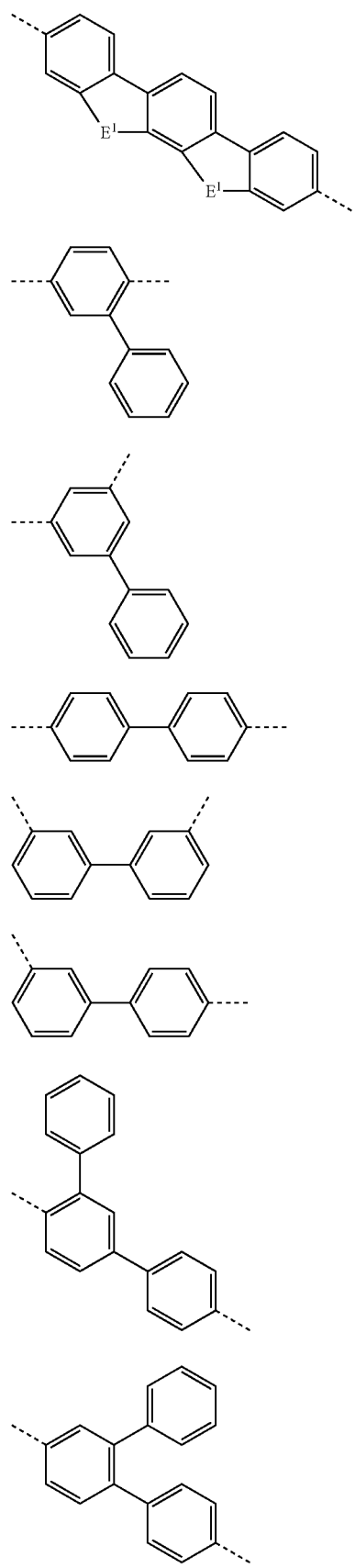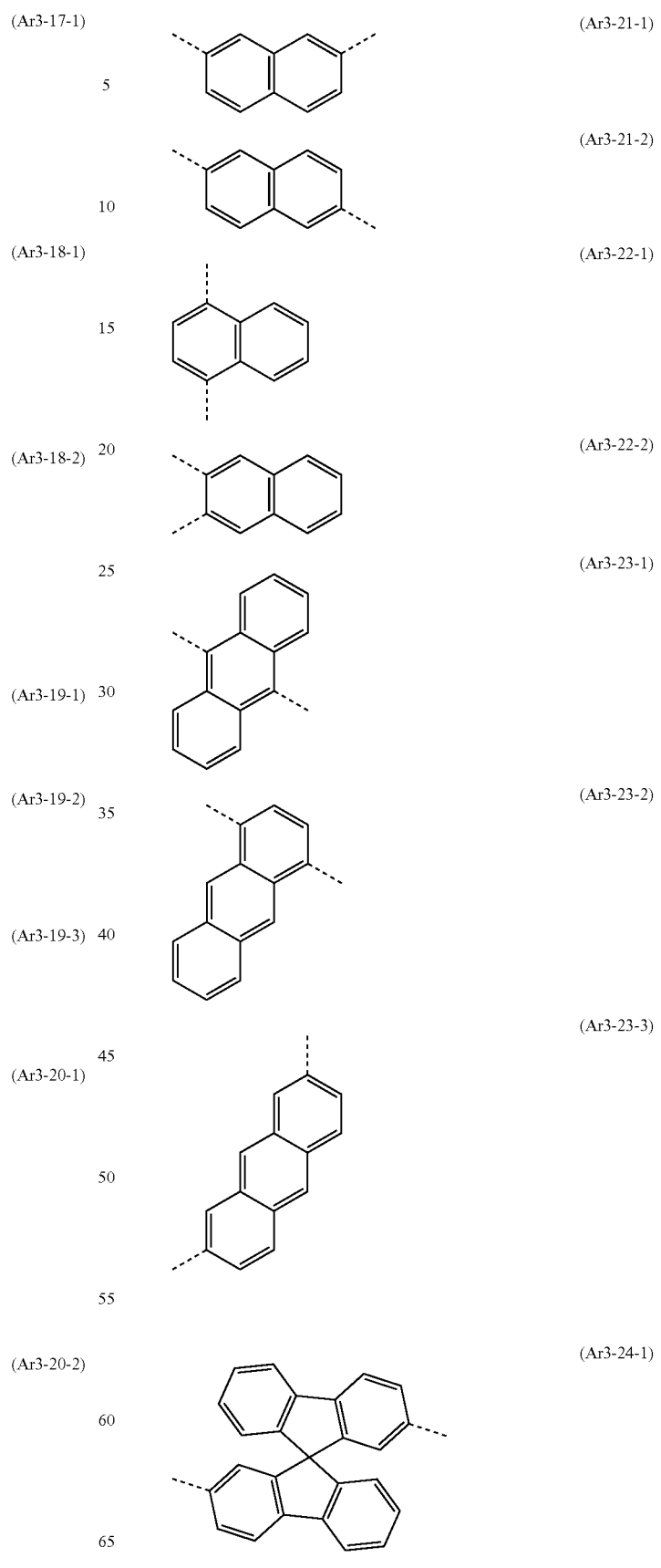

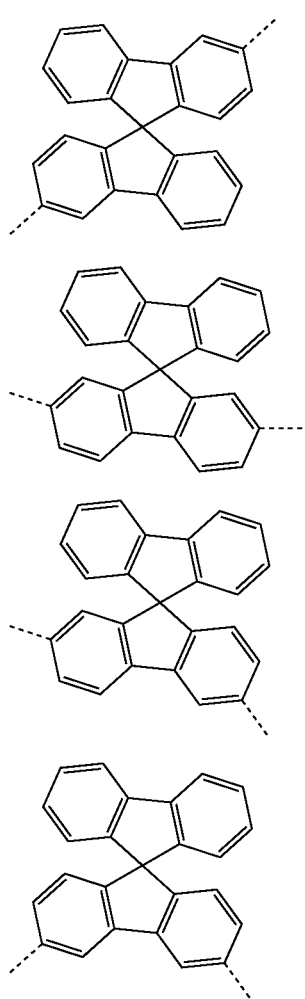

(Ar3-24-2)

(Ar3-25-1)

(Ar3-25-2)

(Ar3-25-3)

where the dashed bonds indicate the bonding to Ar$^1$ and to a group Ar$^3$ or Ar$^4$ and the groups of formulae (Ar3-1-1) to (Ar3-25-3) may be substituted at each free position by a group R$^1$, which has the same meaning as above, and where E$^1$ has the same meaning as above.

Among formulae (Ar3-1-1) to (Ar3-25-3), formulae (Ar3-1-1), (Ar3-2-1), (Ar3-4-1), (Ar3-10-1), (Ar3-13-1), (Ar3-16-1), (Ar3-19-1) and (Ar3-22-1) are preferred. Formulae (Ar3-1-1), (Ar3-2-1) and (Ar3-4-1) and (Ar3-19-1) are particularly preferred.

In accordance with a preferred embodiment, Ar$^4$ is selected from one of the formulae (Ar4-1) to (Ar4-27),

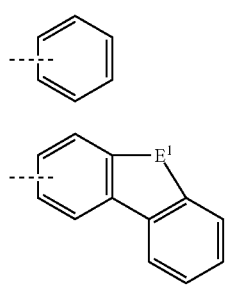

(Ar4-1)

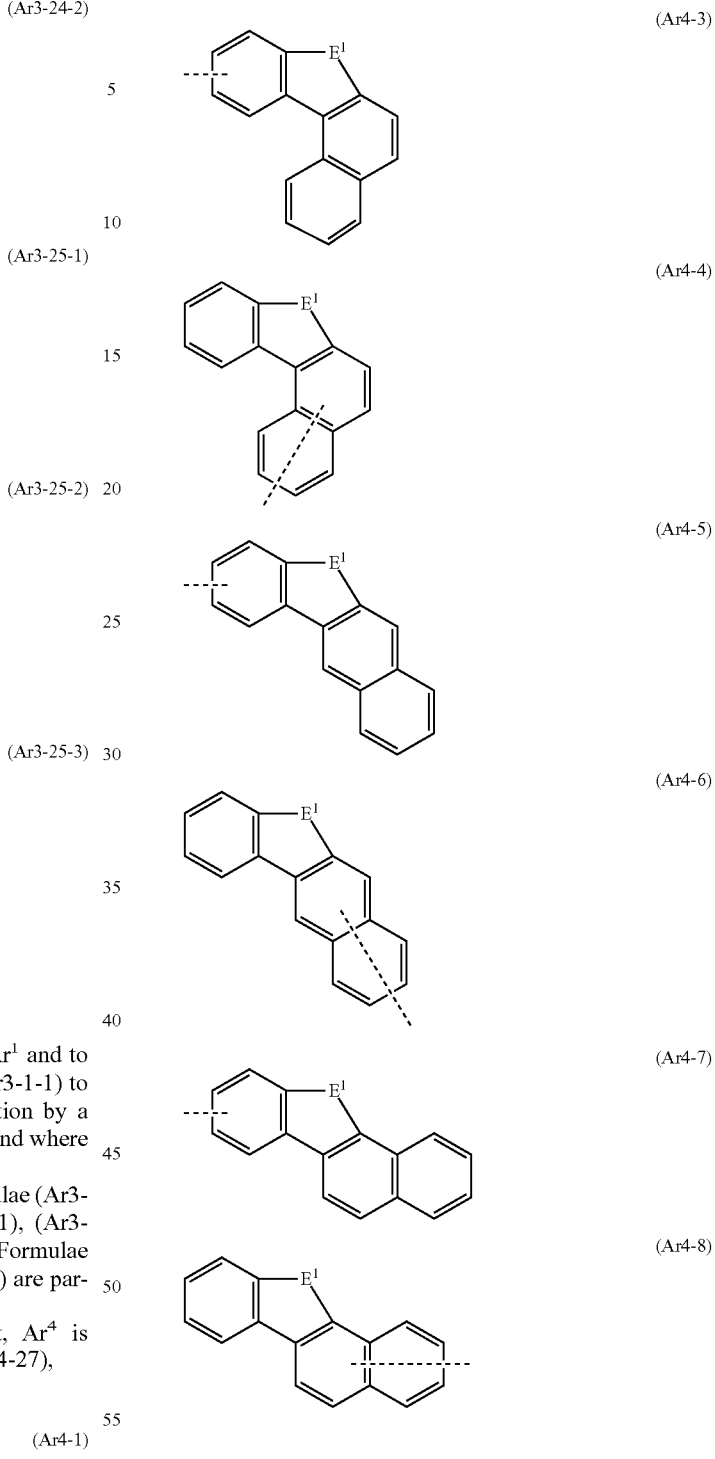

(Ar4-2)

(Ar4-3)

(Ar4-4)

(Ar4-5)

(Ar4-6)

(Ar4-7)

(Ar4-8)

(Ar4-9)

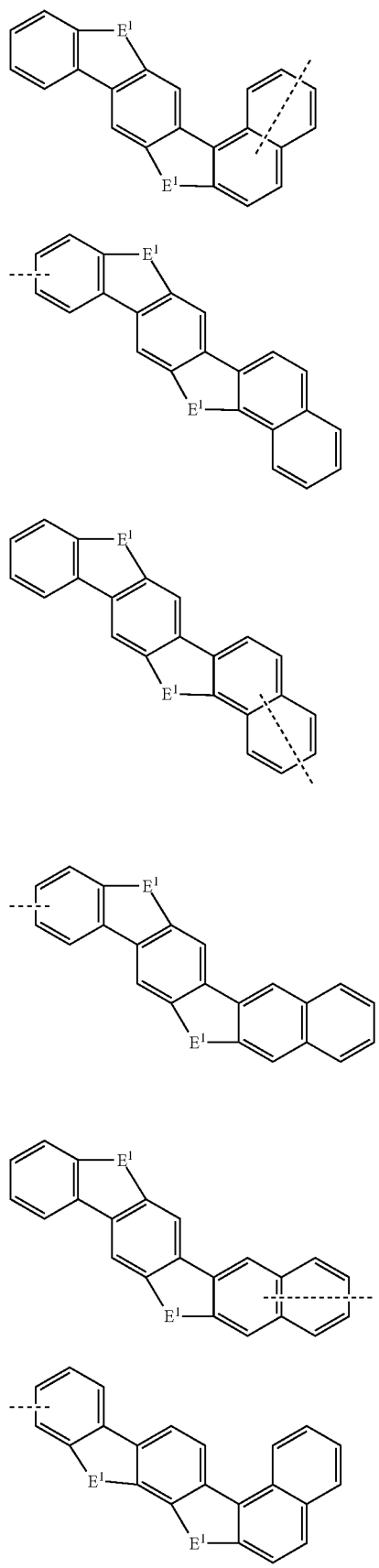
(Ar4-10)
(Ar4-11)
(Ar4-12)
(Ar4-13)
(Ar4-14)
(Ar4-15)
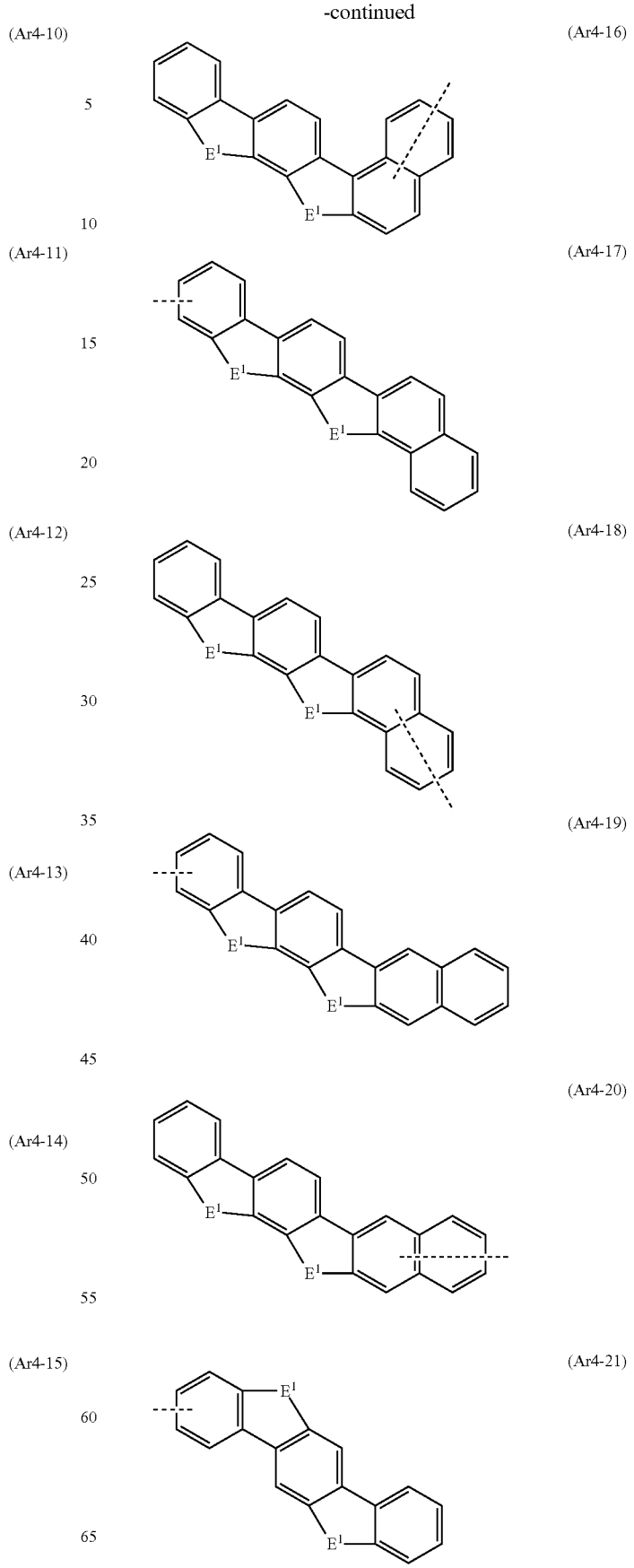
(Ar4-16)
(Ar4-17)
(Ar4-18)
(Ar4-19)
(Ar4-20)
(Ar4-21)

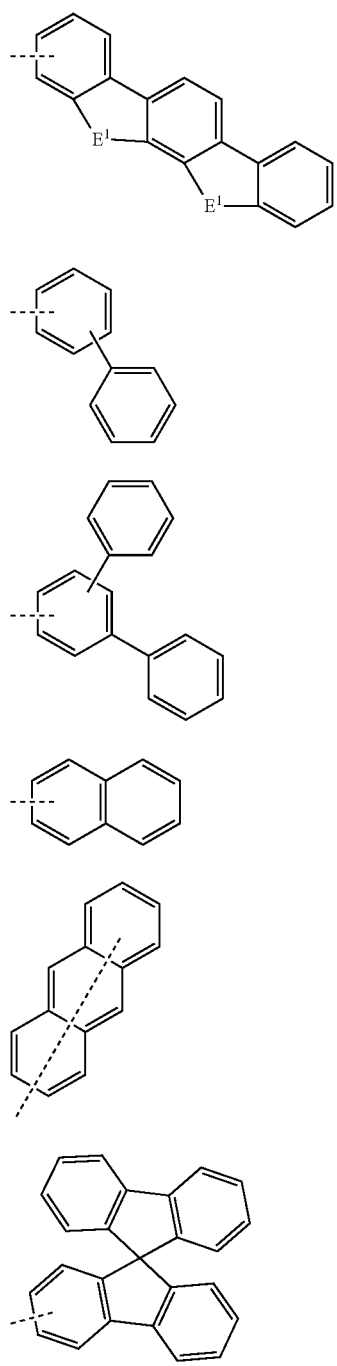
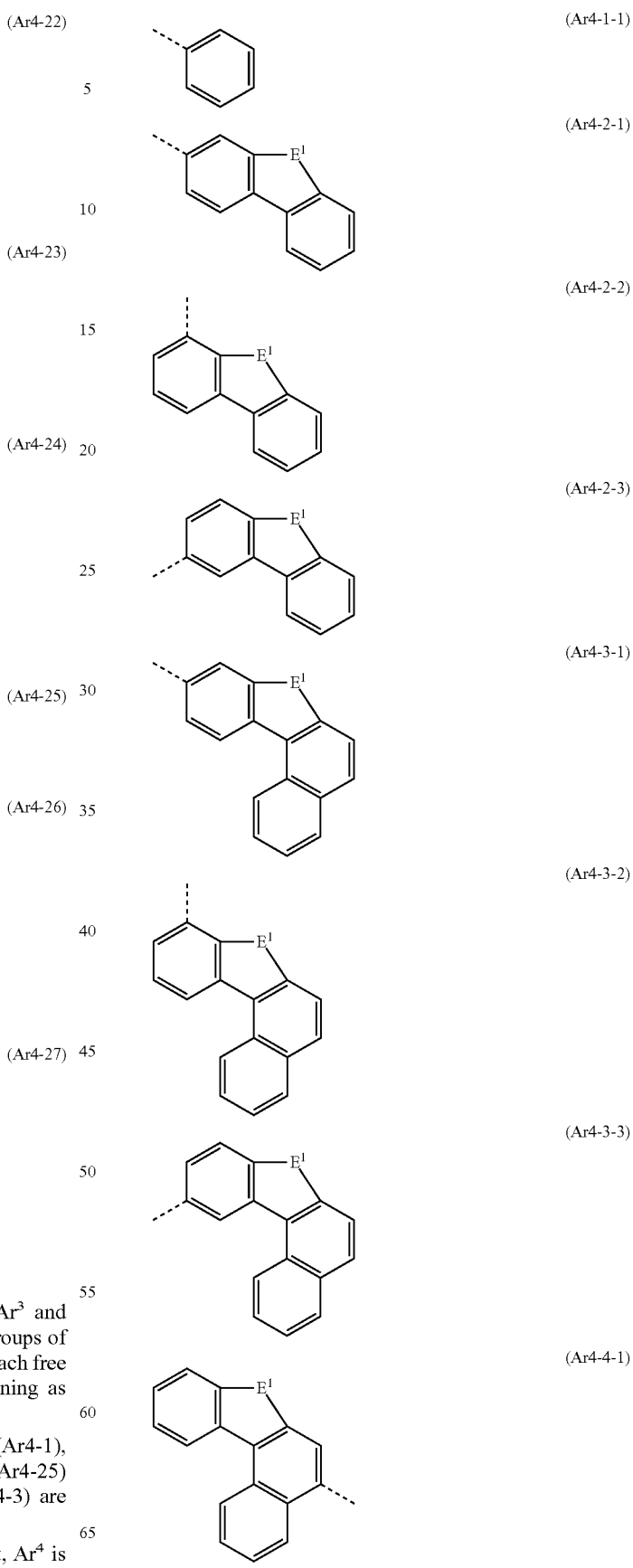

where the dashed bond indicates the bonding to Ar³ and where E¹ has the same meaning as above and the groups of formulae (Ar4-1) to (Ar4-27) may be substituted at each free position by a group R¹, which has the same meaning as above.

Among formulae (Ar4-1) to (Ar4-27), formulae (Ar4-1), (Ar4-2), (Ar4-3), (Ar4-9), (Ar4-15), (Ar4-23), and (Ar4-25) are preferred. Formulae (Ar4-1), (Ar4-2) and (Ar4-3) are particularly preferred.

In accordance with a very preferred embodiment, Ar⁴ is selected from one of the formulae (Ar4-1-1) to (Ar4-27-3),

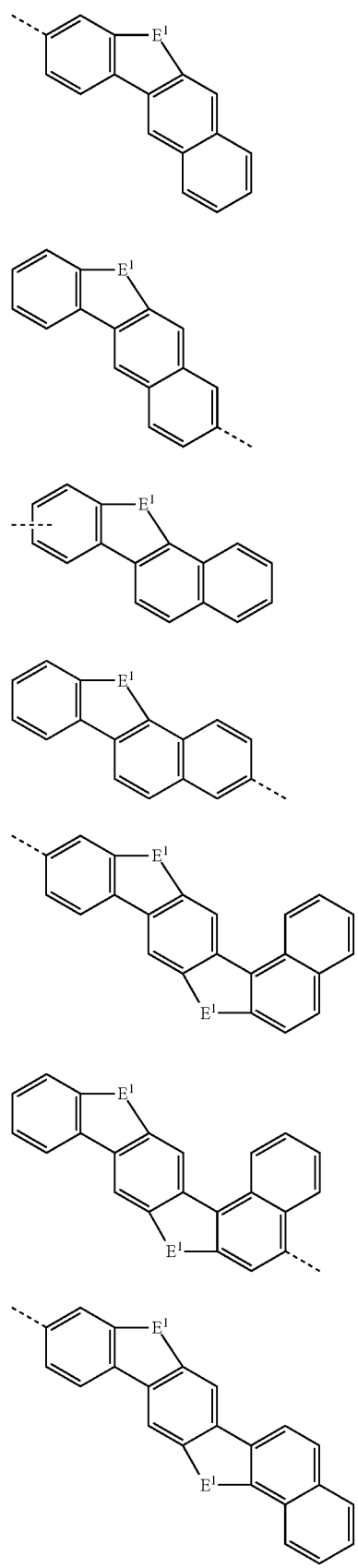
(Ar4-5-1)
(Ar4-6-1)
(Ar4-7-1)
(Ar4-8-1)
(Ar4-9-1)
(Ar4-10-1)
(Ar4-11-1)
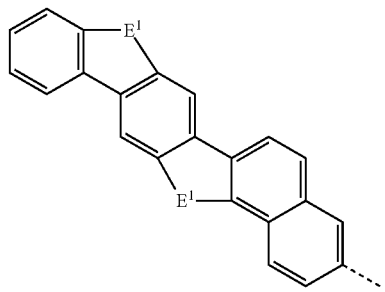
(Ar4-12-1)
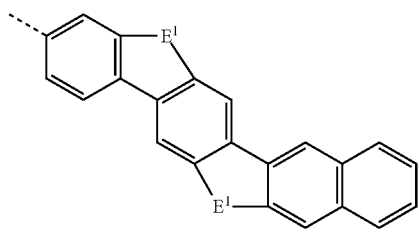
(Ar4-13-1)
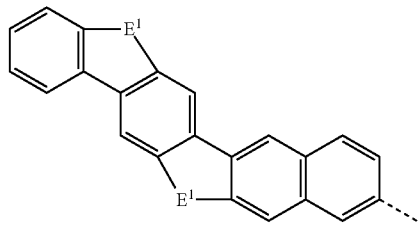
(Ar4-14-1)
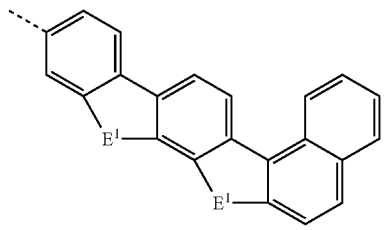
(Ar4-15-1)
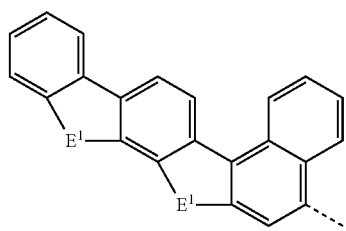
(Ar4-16-1)
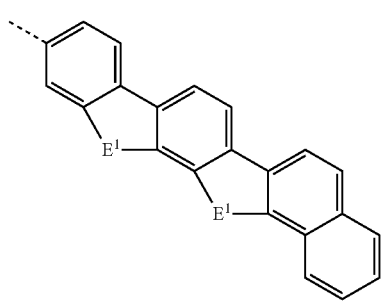
(Ar4-17-1)

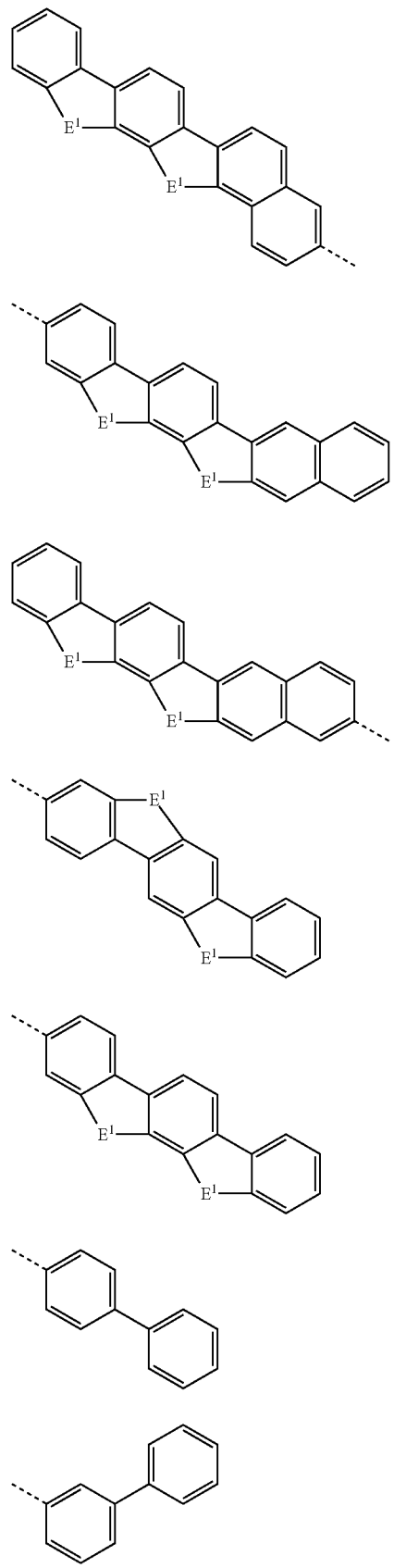
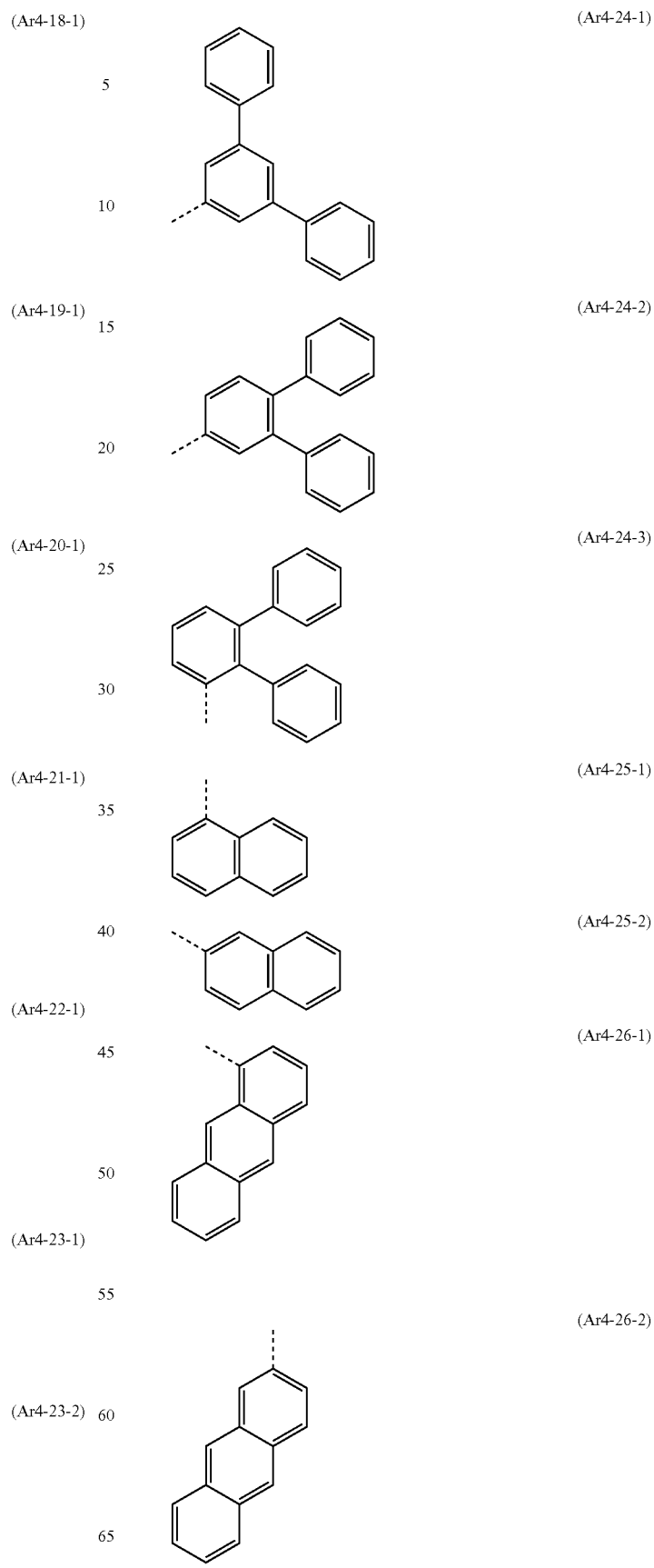

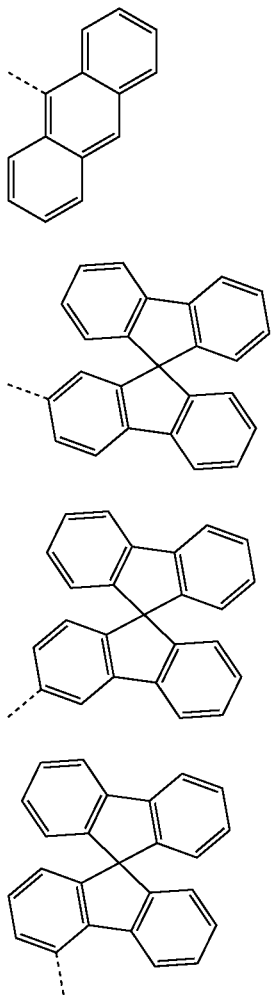

(Ar4-26-3)

(Ar4-27-1)

(Ar4-27-2)

(Ar4-27-3)

where the dashed bond indicates the bonding to Ar³ and where E¹ has the same meaning as above and the groups of formulae (Ar4-1-1) to (Ar4-27-3) may be substituted at each free position by a group R¹, which has the same meaning as above.

Among formulae (Ar4-1-1) to (Ar4-27-3), formulae (Ar4-1-1), (Ar4-2-1), (Ar4-3-1), (Ar4-9-1), (Ar4-15-1), (Ar4-23-1) and (Ar4-25-1) are preferred. Formulae (Ar4-1-1), (Ar4-2-1) and (Ar4-3-1) are particularly preferred.

In accordance with a preferred embodiment, compounds of formula (1), (1-1) and (1-2), (1-1-1) to (1-1-11) and (1-2-1) to (1-2-7) as well as (1-1-1-a) to (1-1-11-a) and (1-2-1-a) to (1-2-7-a) contain at least one group Ar³, which stands for a group of formula (Ar3-2) and/or at least one group Ar⁴, which stands for a group of formula (Ar4-2),

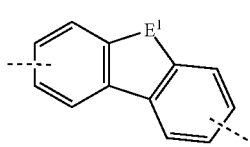

(Ar3-2)

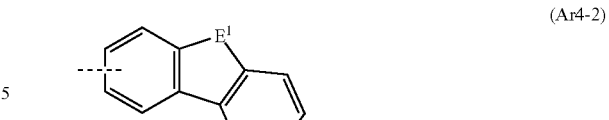

(Ar4-2)

where
the dashed bonds in formula (Ar3-2) indicate the bonding to Ar¹ and to a group Ar³ or Ar⁴;
the dashed bond in formula (Ar4-2) indicates the bonding to Ar³;
E¹ has the same meaning as above; and
the groups of formulae (Ar3-2) and (Ar4-2) may be substituted at each free position by a group R¹, which has the same meaning as above.

It is very particularly preferred that the compounds of formula (1) and the compounds corresponding to the preferred embodiments of formula (1) contain at least contain at least one group Ar³, which stands for a group of formula (Ar3-2) and/or at least one group Ar⁴, which stands for a group of formula (Ar4-2), in both chains "Ar⁴—(Ar³)ₙ—" that are represented in formulae (1), (1-1) and (1-2), (1-1-1) to (1-1-11) and (1-2-1) to (1-2-7) as well as (1-1-1-a) to (1-1-11-a) and (1-2-1-a) to (1-2-7-a).

In accordance with a very preferred embodiment, compounds of formula (1), (1-1) and (1-2), (1-1-1) to (1-1-11) and (1-2-1) to (1-2-7) as well as (1-1-1-a) to (1-1-11-a) and (1-2-1-a) to (1-2-7-a) contain at least one group Ar³, which stands for a group of formula (Ar3-2-1) and/or at least one group Ar⁴, which stands for a group of formula (Ar4-2-1),

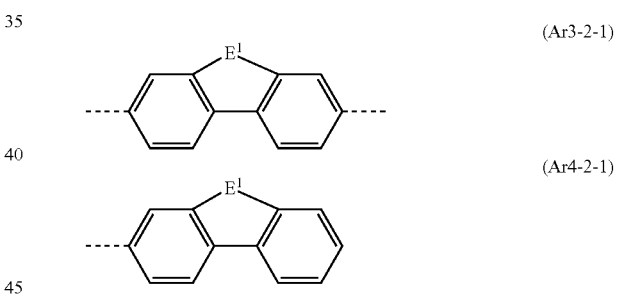

(Ar3-2-1)

(Ar4-2-1)

where
the dashed bonds in formula (Ar3-2-1) indicate the bonding to Ar¹ and to a group Ar³ or Ar⁴;
the dashed bond in formula (Ar4-2-1) indicates the bonding to Ar³;
E¹ has the same meaning as above; and
the groups of formulae (Ar3-2-1) and (Ar4-2-1) may be substituted at each free position by a group R¹, which has the same meaning as above.

It is particularly preferred that the compounds of formula (1) and the compounds corresponding to the preferred embodiments of formula (1) contain at least contain at least one group Ar³, which stands for a group of formula (Ar3-2-1) and/or at least one group Ar⁴, which stands for a group of formula (Ar4-2-1), in both chains "Ar⁴—(Ar³)ₙ—" that are represented in formulae (1), (1-1) and (1-2), (1-1-1) to (1-1-11) and (1-2-1) to (1-2-7) as well as (1-1-1-a) to (1-1-11-a) and (1-2-1-a) to (1-2-7-a).

In accordance with a preferred embodiment, compounds of formula (1), (1-1) and (1-2), (1-1-1) to (1-1-11) and (1-2-1) to (1-2-7) as well as (1-1-1-a) to (1-1-11-a) and (1-2-1-a) to (1-2-7-a) contain at least one group Ar³, which stands for a group of formula (Ar3-2-1b) and/or at least one group Ar⁴, which stands for a group of formula (Ar4-2-1b),

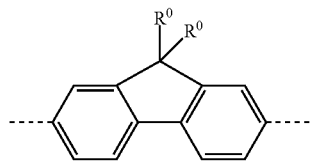

formula (Ar3-2-1b)

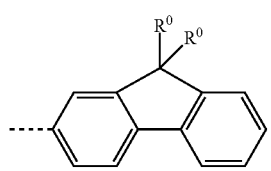

formula (Ar4-2-1b)

where
  the dashed bonds in formula (Ar3-2-1b) indicate the bonding to Ar¹ and to a group Ar³ or Ar⁴;
  the dashed bonds in formula (Ar4-2-1b) indicates the bonding to Ar³;
  R⁰ has the same meaning as in claim 1; and
  the groups of formulae (Ar3-2-1b) and (Ar4-2-1b) may be substituted at each free position by a group R¹, which has the same meaning as in claim 1.

It is very particularly preferred that the compounds of formula (1) and the compounds corresponding to the preferred embodiments of formula (1) contain at least contain at least one group Ar³, which stands for a group of formula (Ar3-2-1b) and/or at least one group Ar⁴, which stands for a group of formula (Ar4-2-1b), in both chains "Ar⁴—(Ar³)$_n$—" that are represented in formulae (1), (1-1) and (1-2), (1-1-1) to (1-1-11) and (1-2-1) to (1-2-7) as well as (1-1-1-a) to (1-1-11-a) and (1-2-1-a) to (1-2-7-a).

The following compounds are examples of compounds of the formula (1):

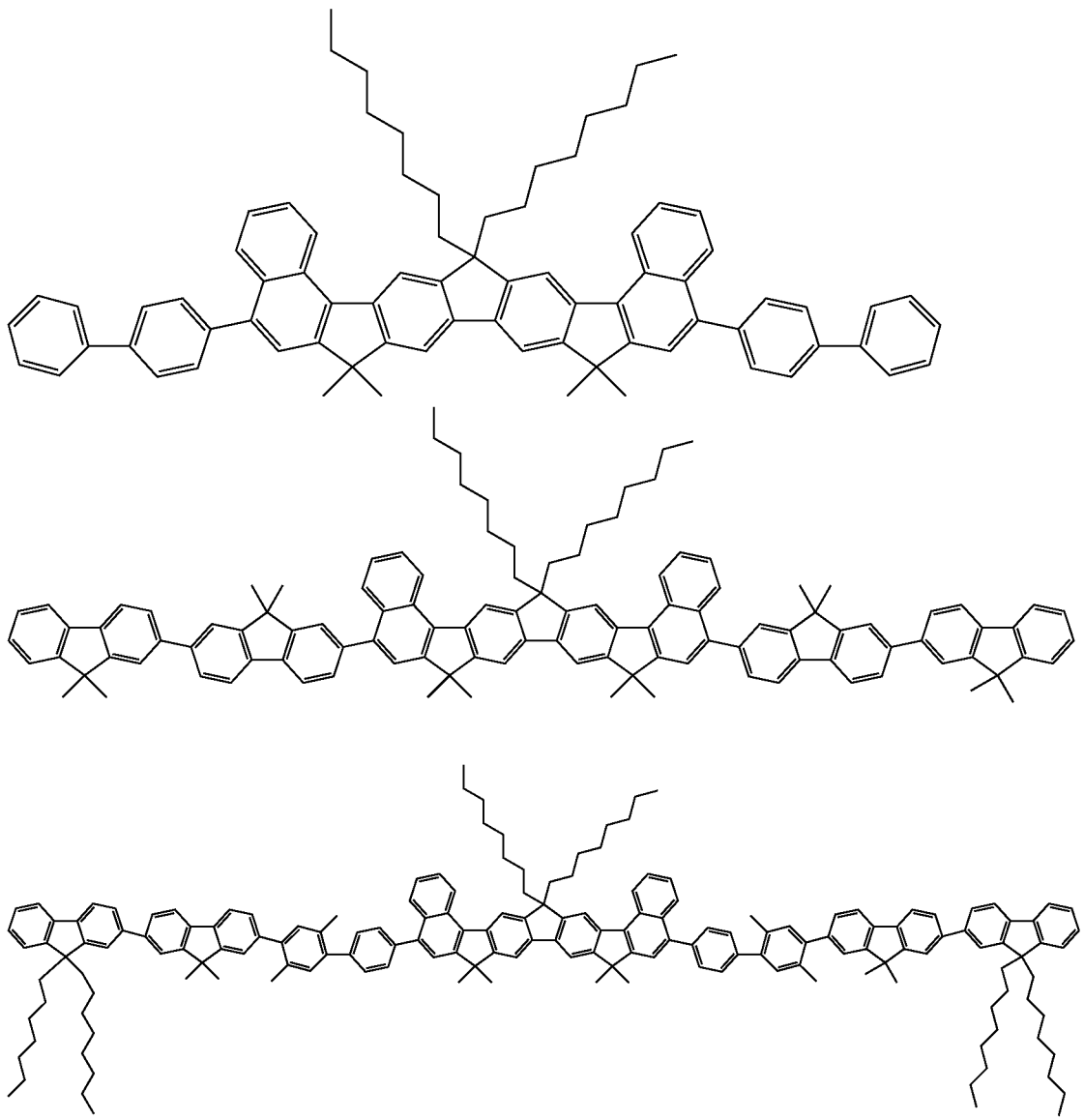

-continued
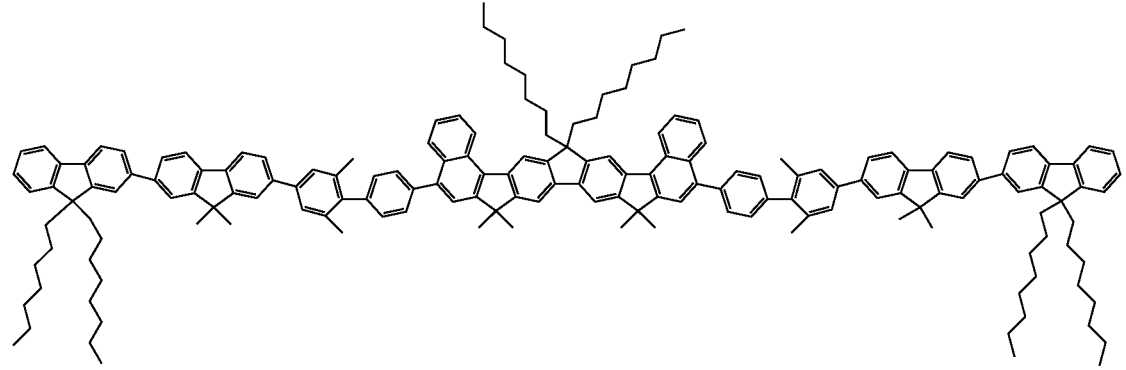
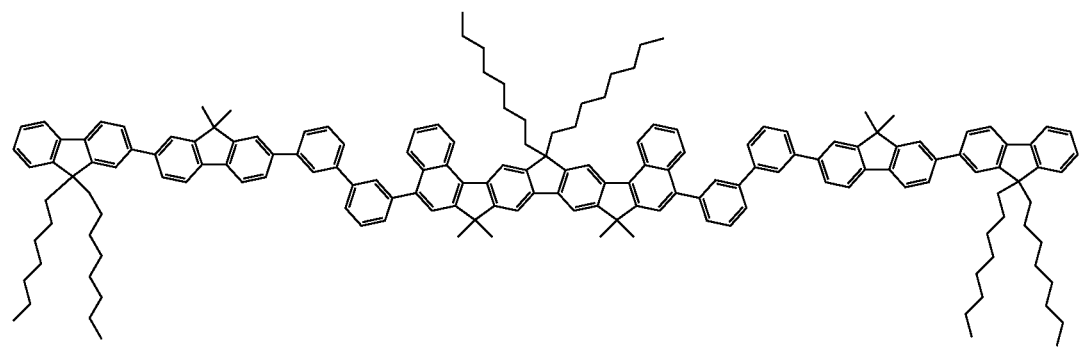
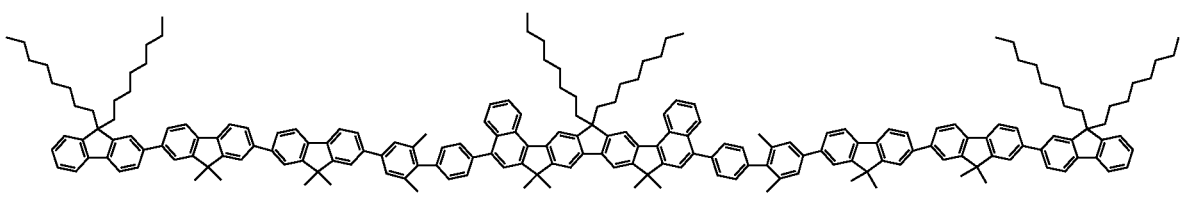
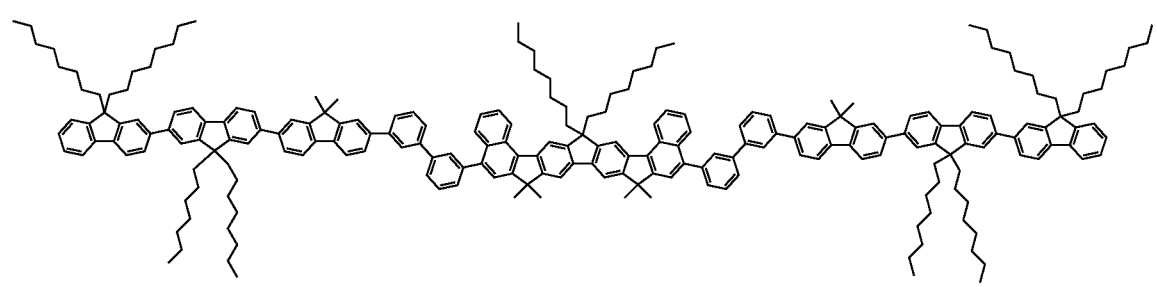
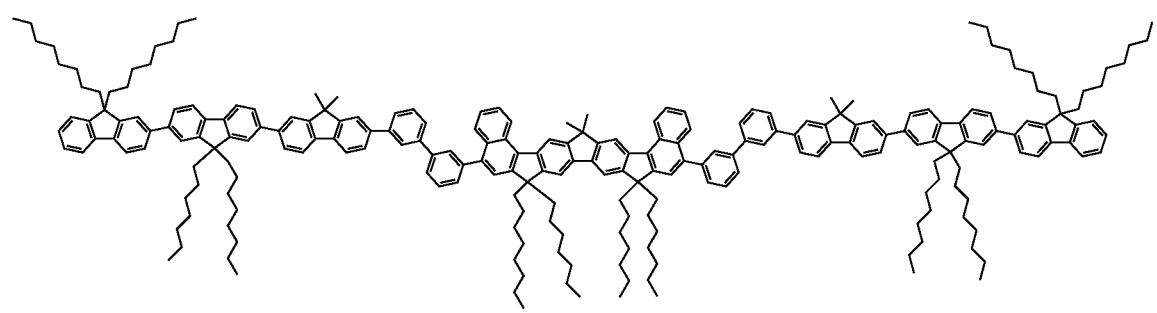

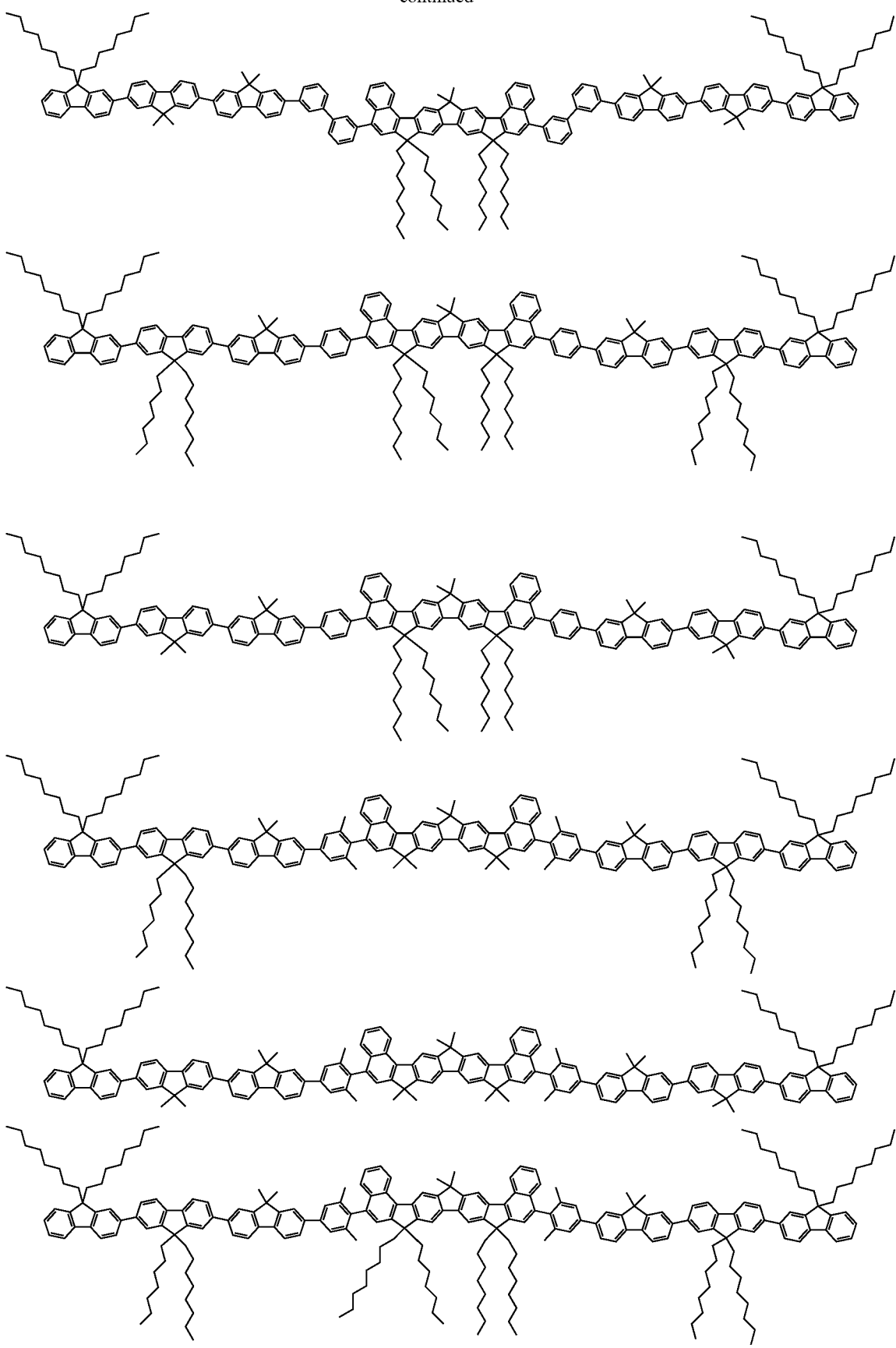

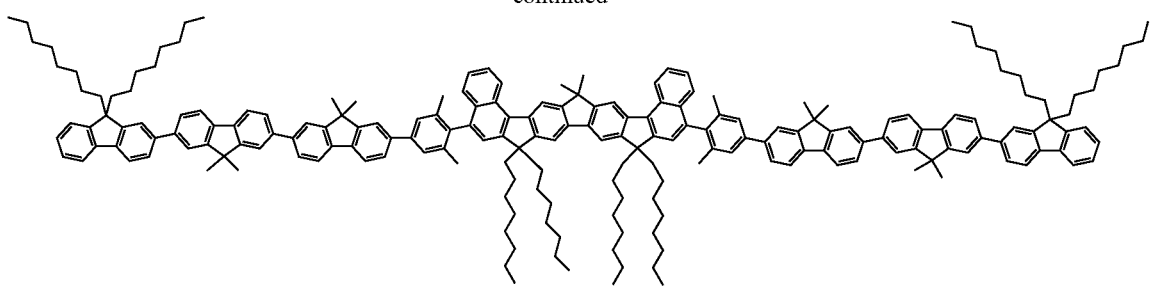
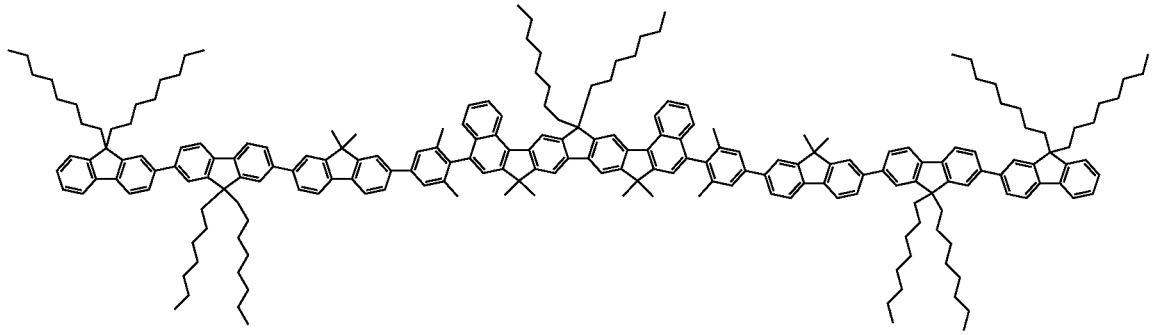 [SMILES: CCCCCCCCC1(CCCCCCC)c2cc(-c3ccc4c(c3)C(C)(C)c3cc(-c5cc(C)c(-c6cc7c(c8ccccc68)-c6cc8c(cc6C7(C)C)-c6cc7c(cc6C8(CCCCCCC)CCCCCCCC)-c6c(cc(-c8c(C)cc(-c9ccc%10c(c9)C(C)(C)c9cc(-c%11ccc%12c(c%11)C(CCCCCCCC)(CCCCCCCC)c%11cc(-c%13ccc%14c(c%13)C(CCCCCCCC)(CCCCCCCC)c%13ccccc%13-%14)ccc%11-%12)ccc9-%10)cc8C)c8ccccc68)C7(C)C)c(C)c5)ccc3-4)ccc2-c2ccc(-c3ccc4c(c3)C(CCCCCCCC)(CCCCCCCC)c3ccccc3-4)cc21]
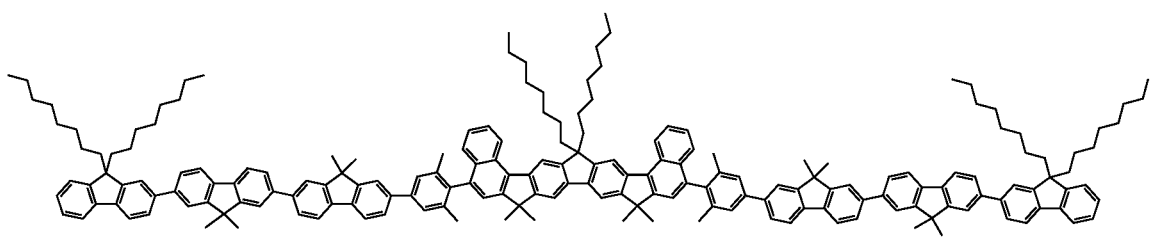
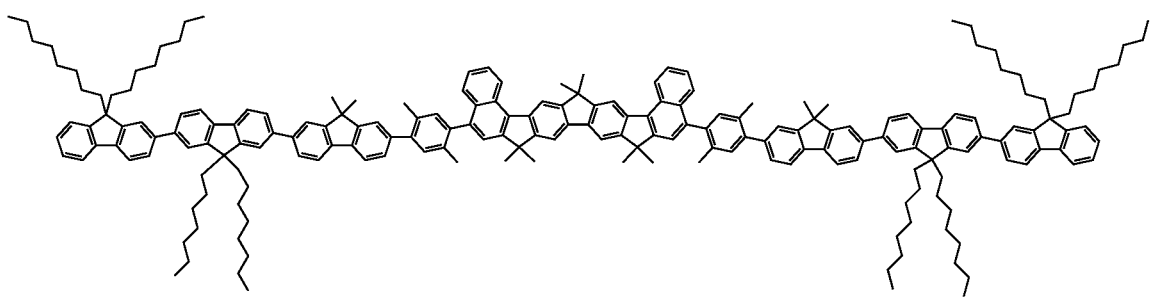
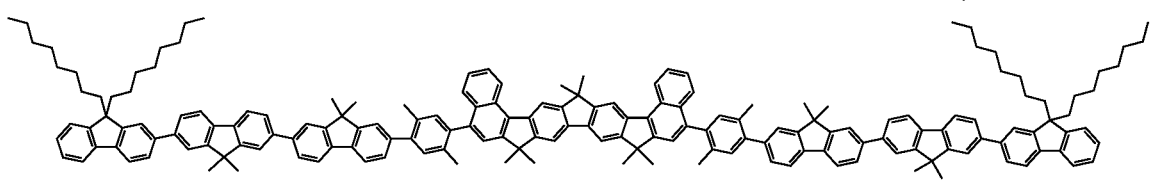
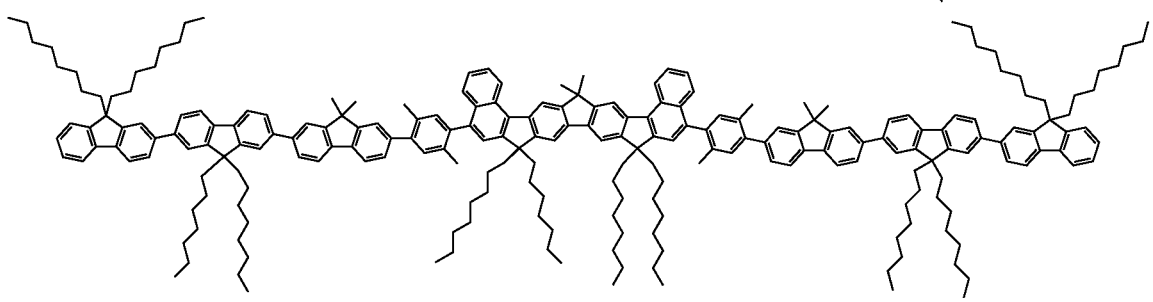

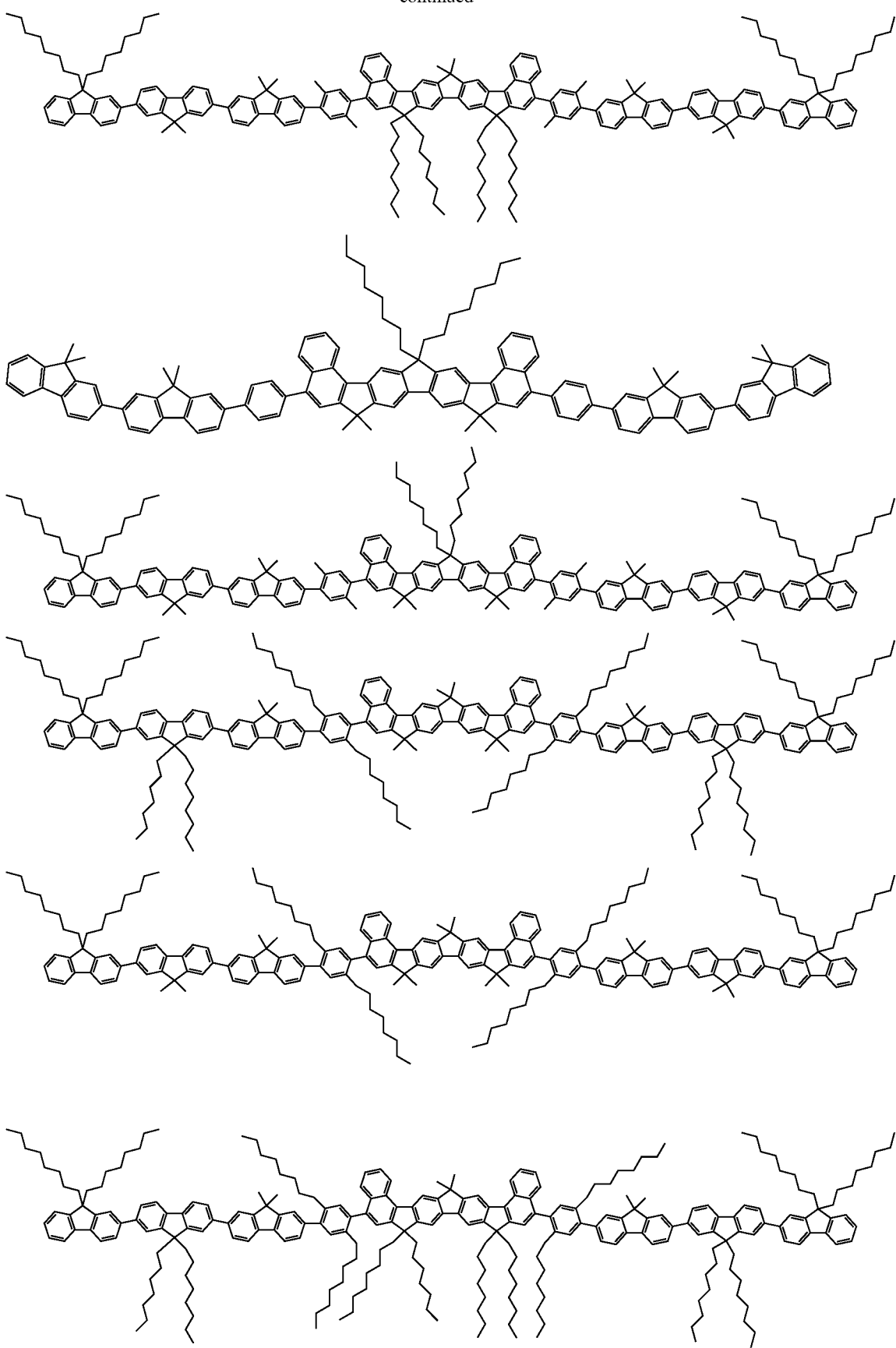

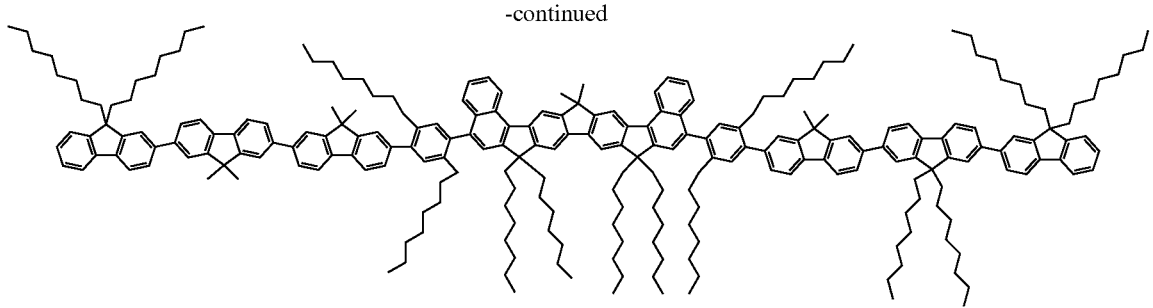
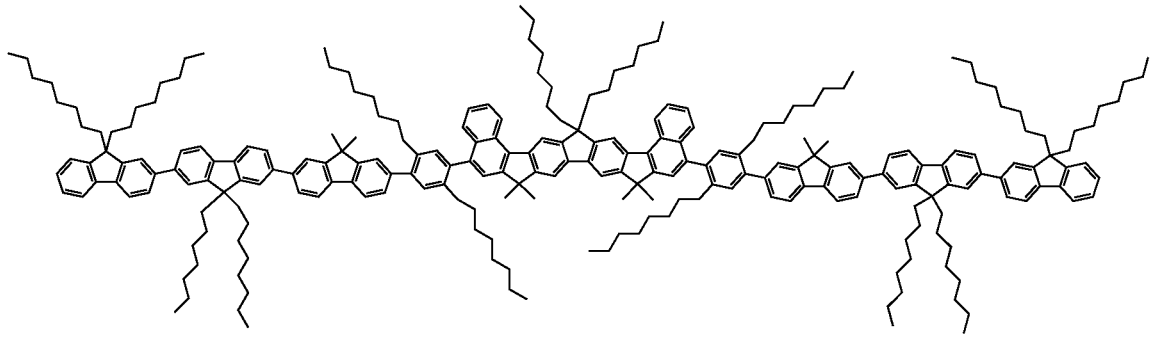
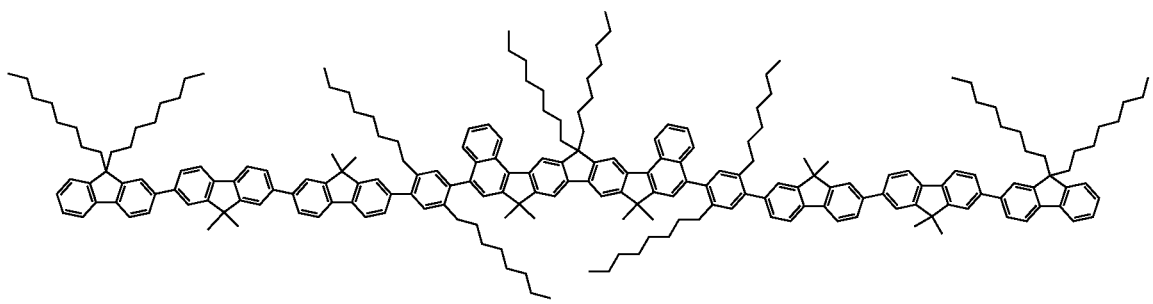
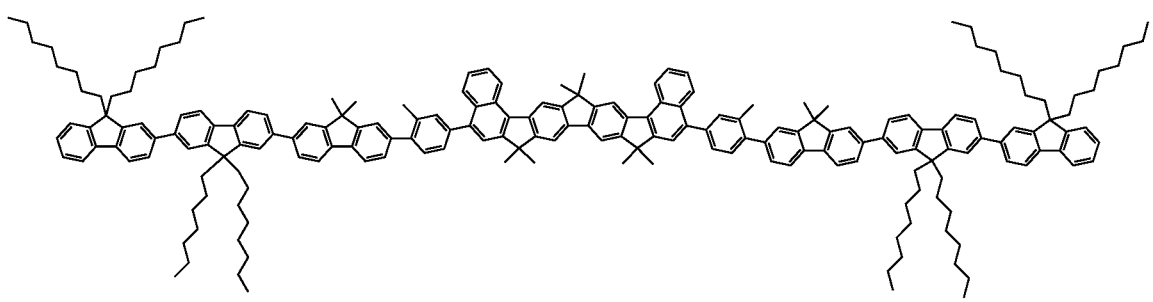
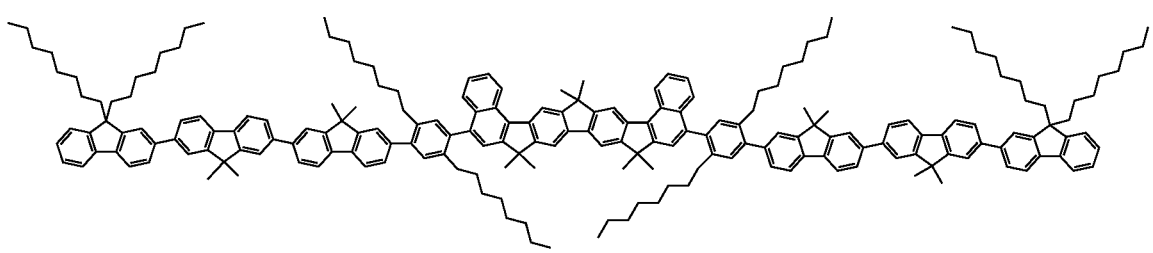

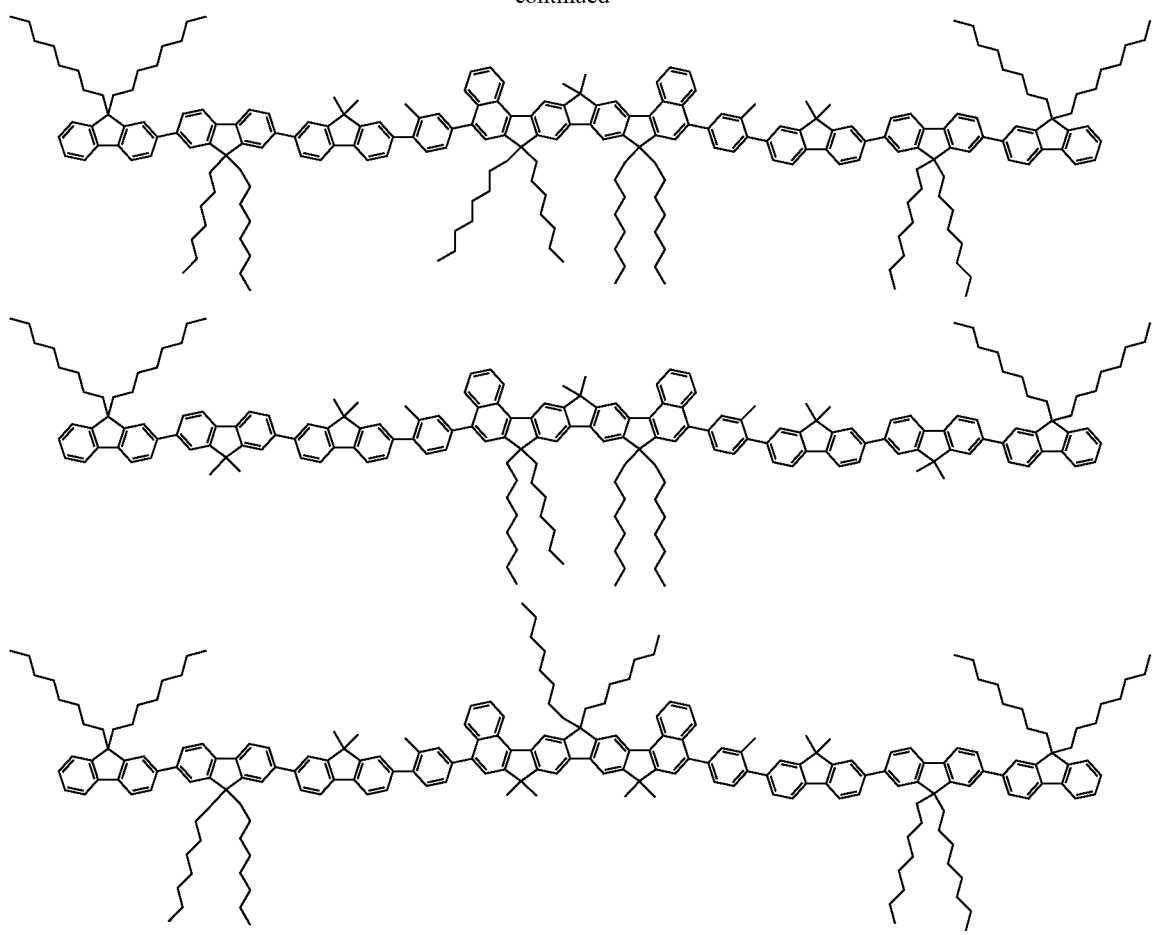
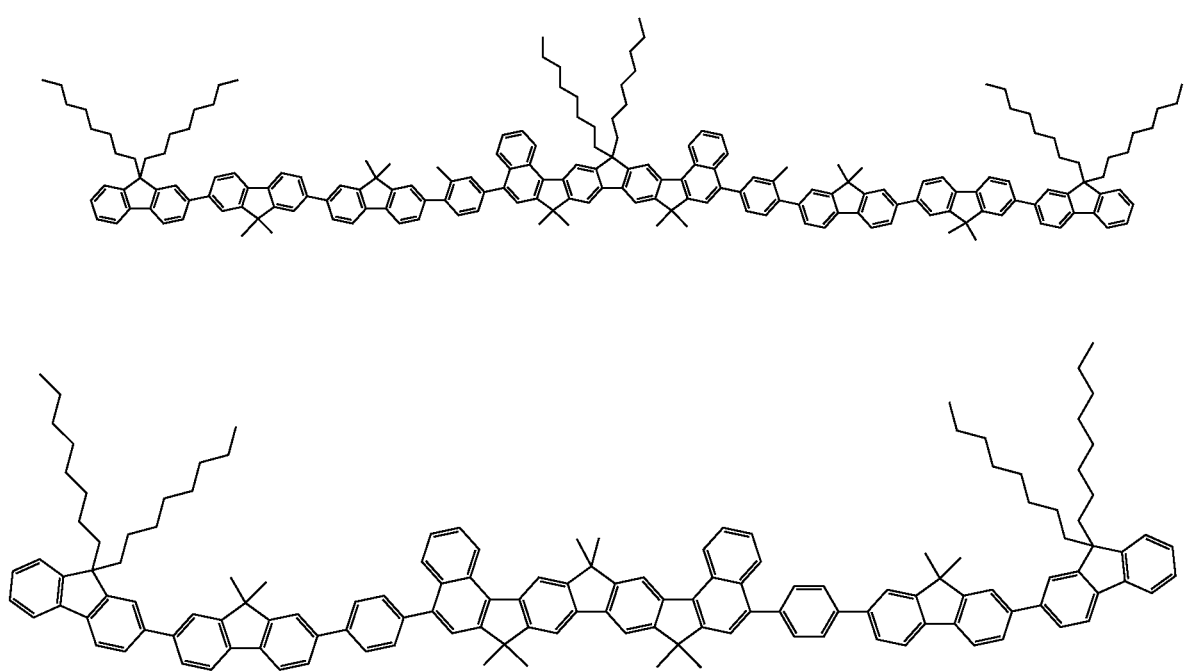

-continued
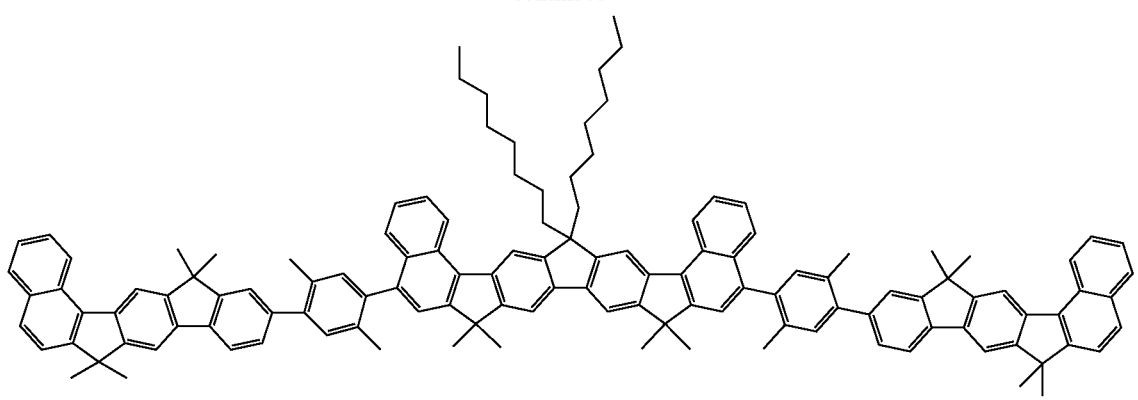
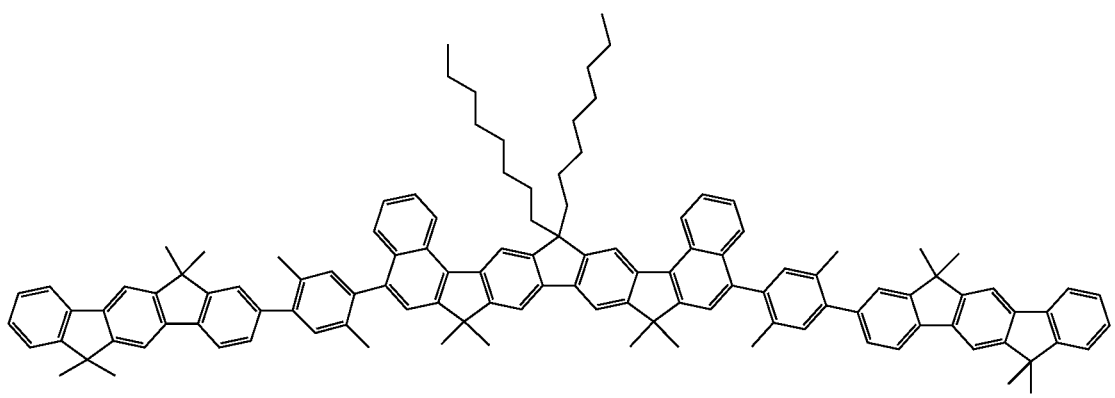
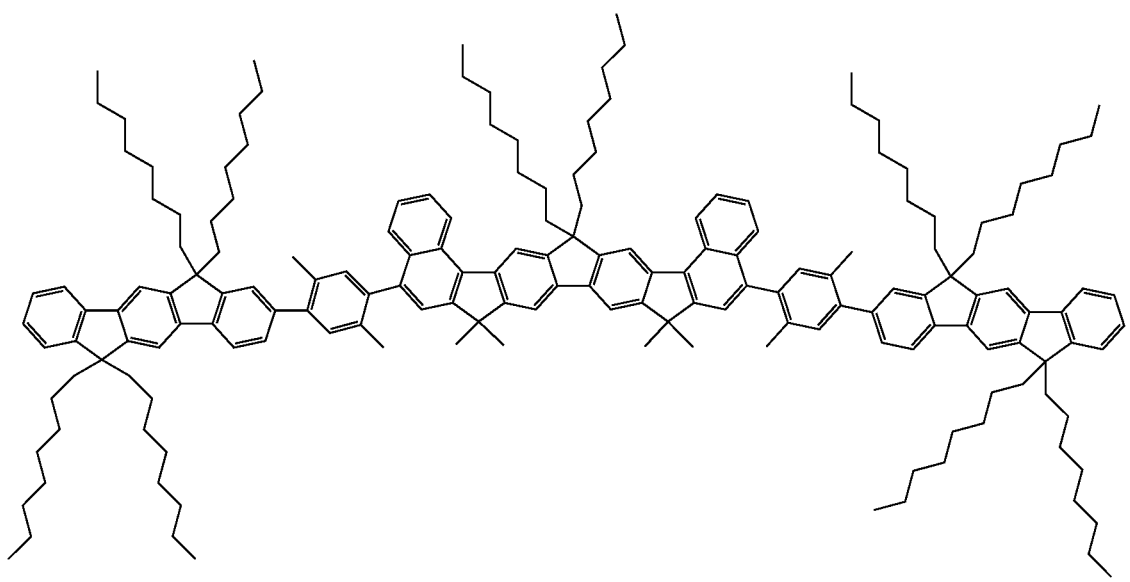

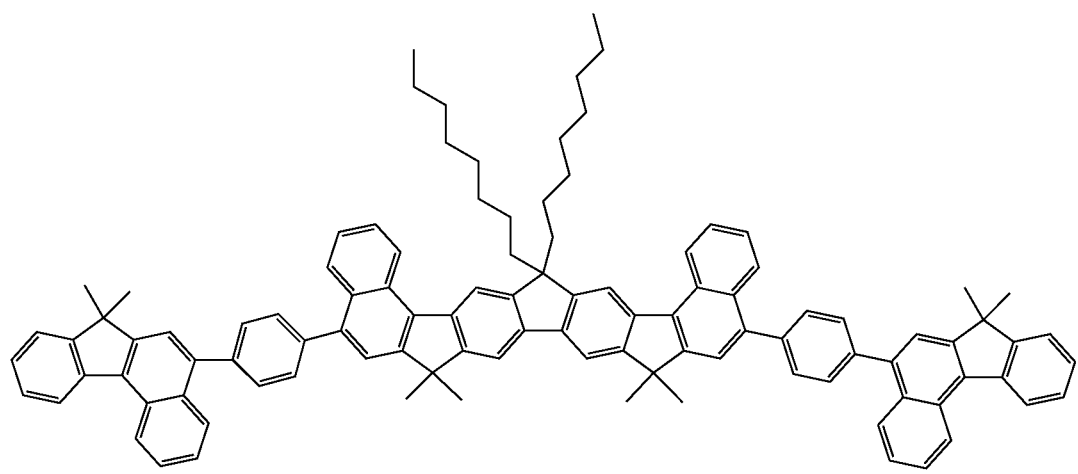
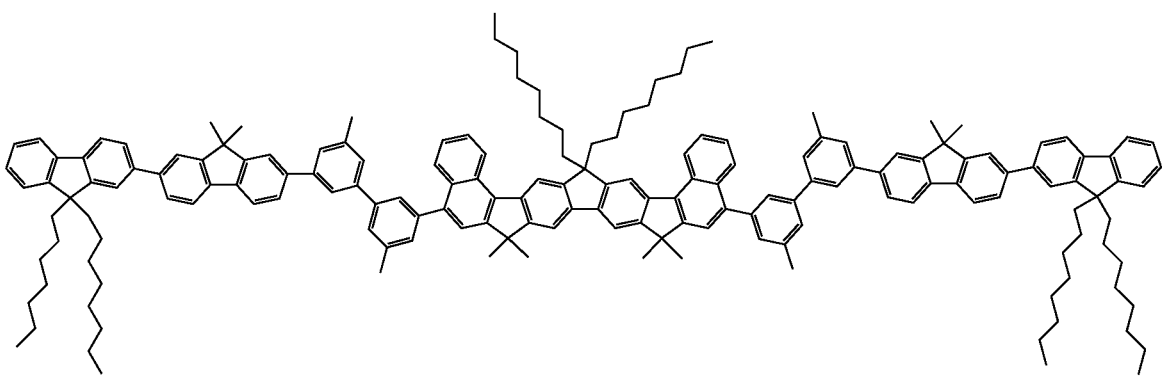
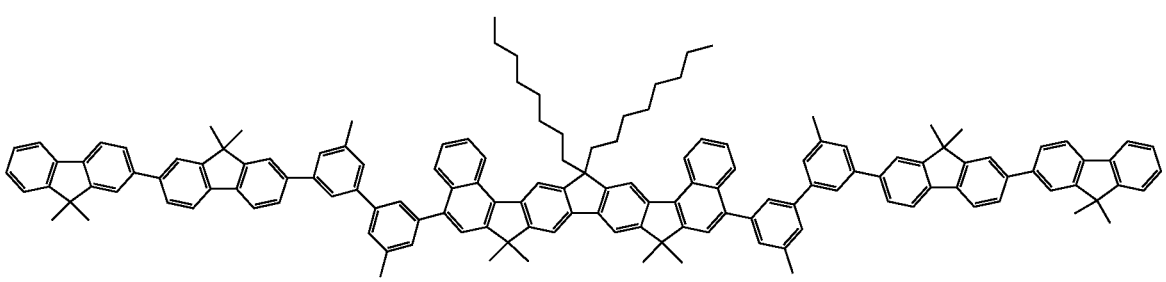
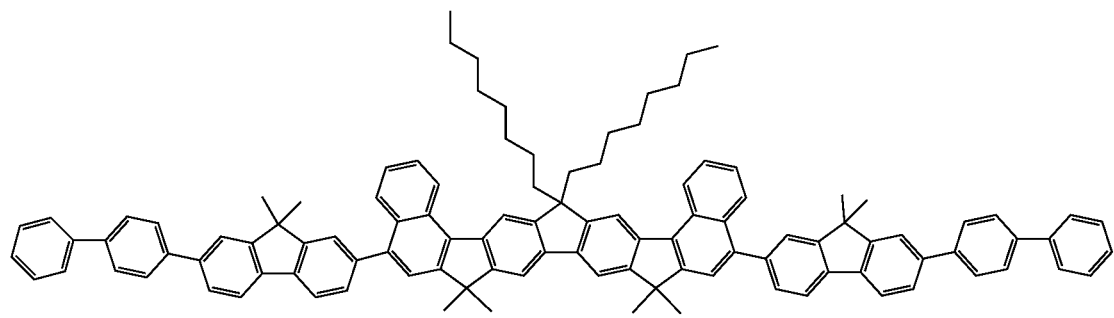

-continued
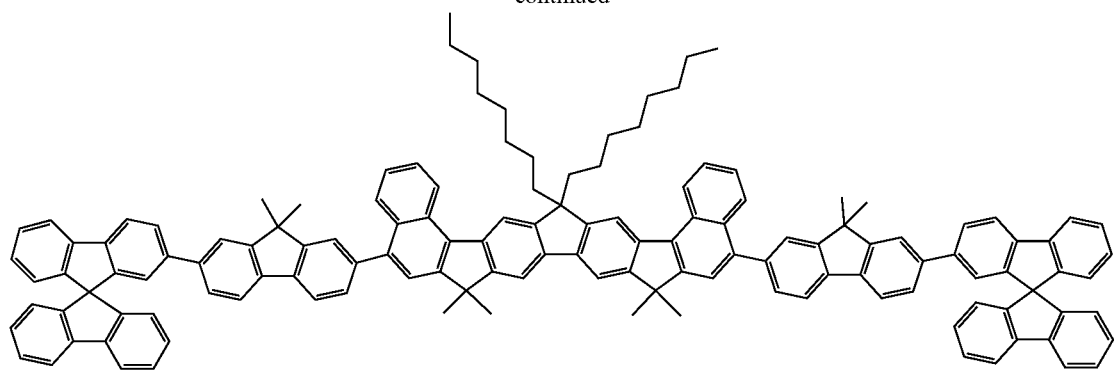
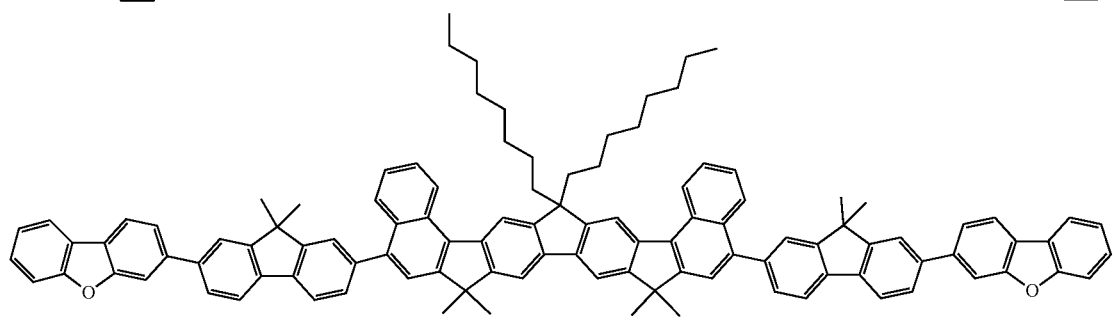
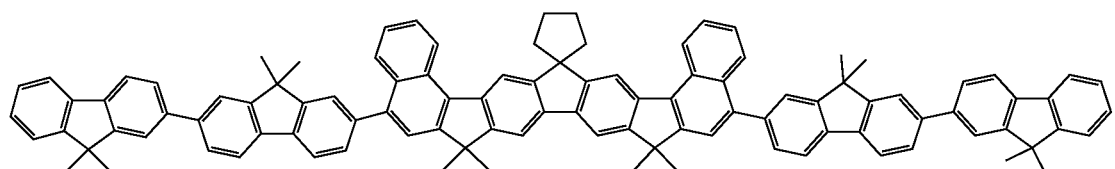
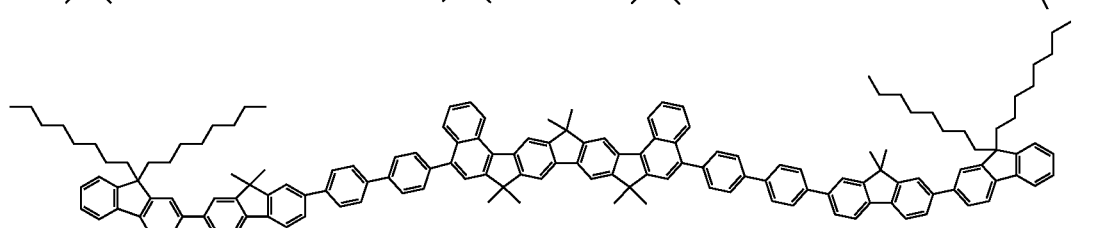
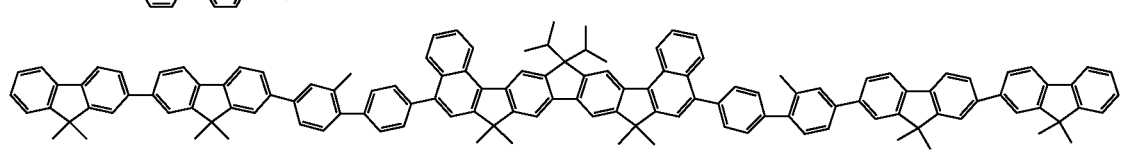
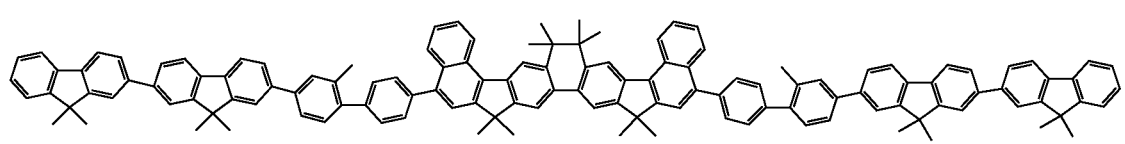
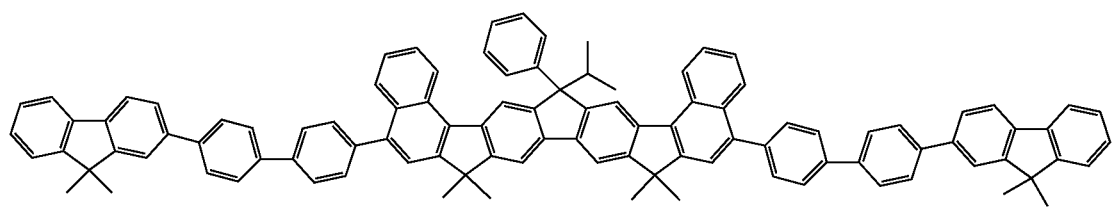

-continued
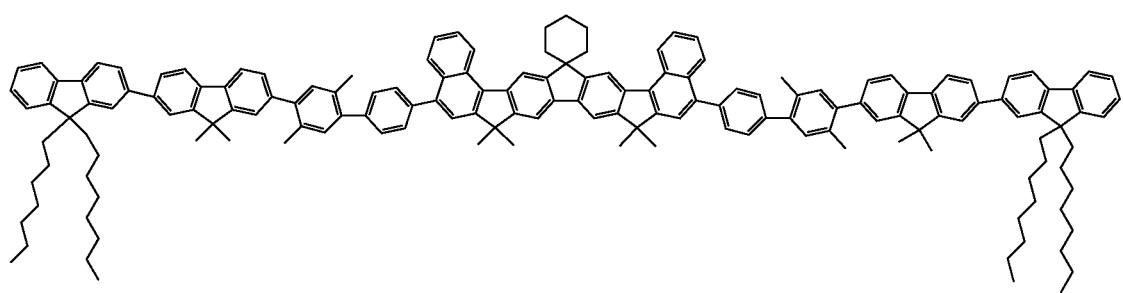
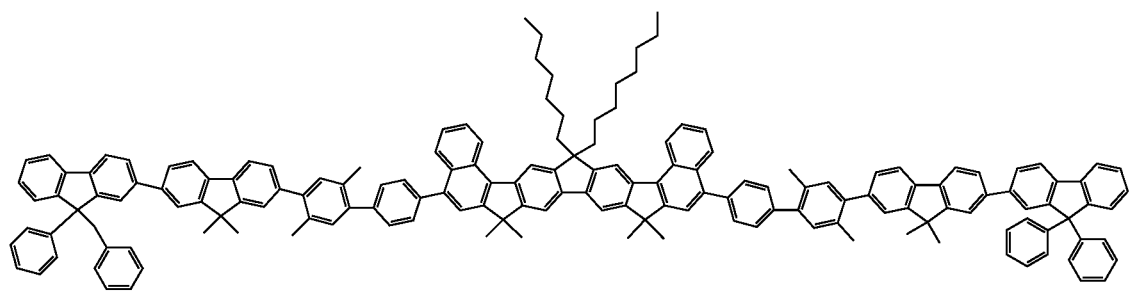
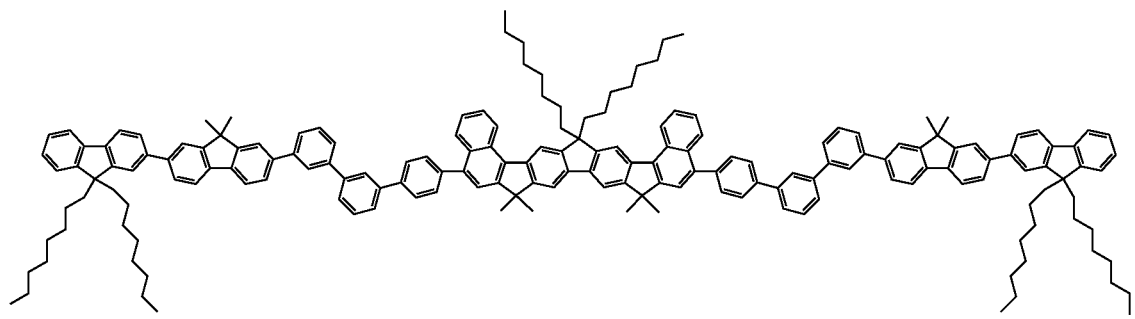
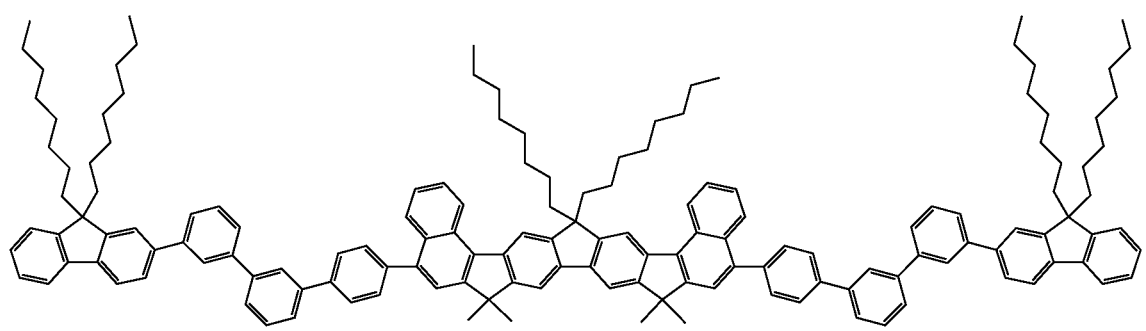 [SMILES: CCCCCCCCC1(CCCCCCCC)c2ccccc2-c2ccc(-c3cccc(-c4cccc(-c5ccc(-c6cc7c(c8ccccc68)-c6cc8c(cc6C7(C)C)-c6cc7c(cc6C8(CCCCCCCC)CCCCCCCC)-c6c(cc(-c8ccc(-c9cccc(-c%10cccc(-c%11ccc%12c(c%11)C(CCCCCCCC)(CCCCCCCC)c%11ccccc%11-%12)c%10)c9)cc8)c8ccccc68)C7(C)C)cc5)c4)c3)cc21]
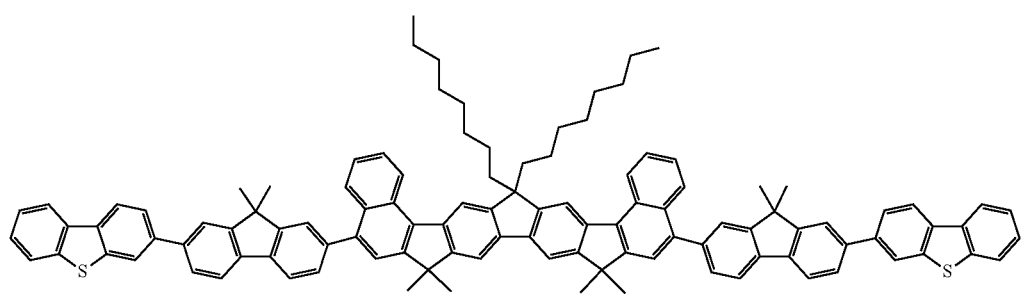

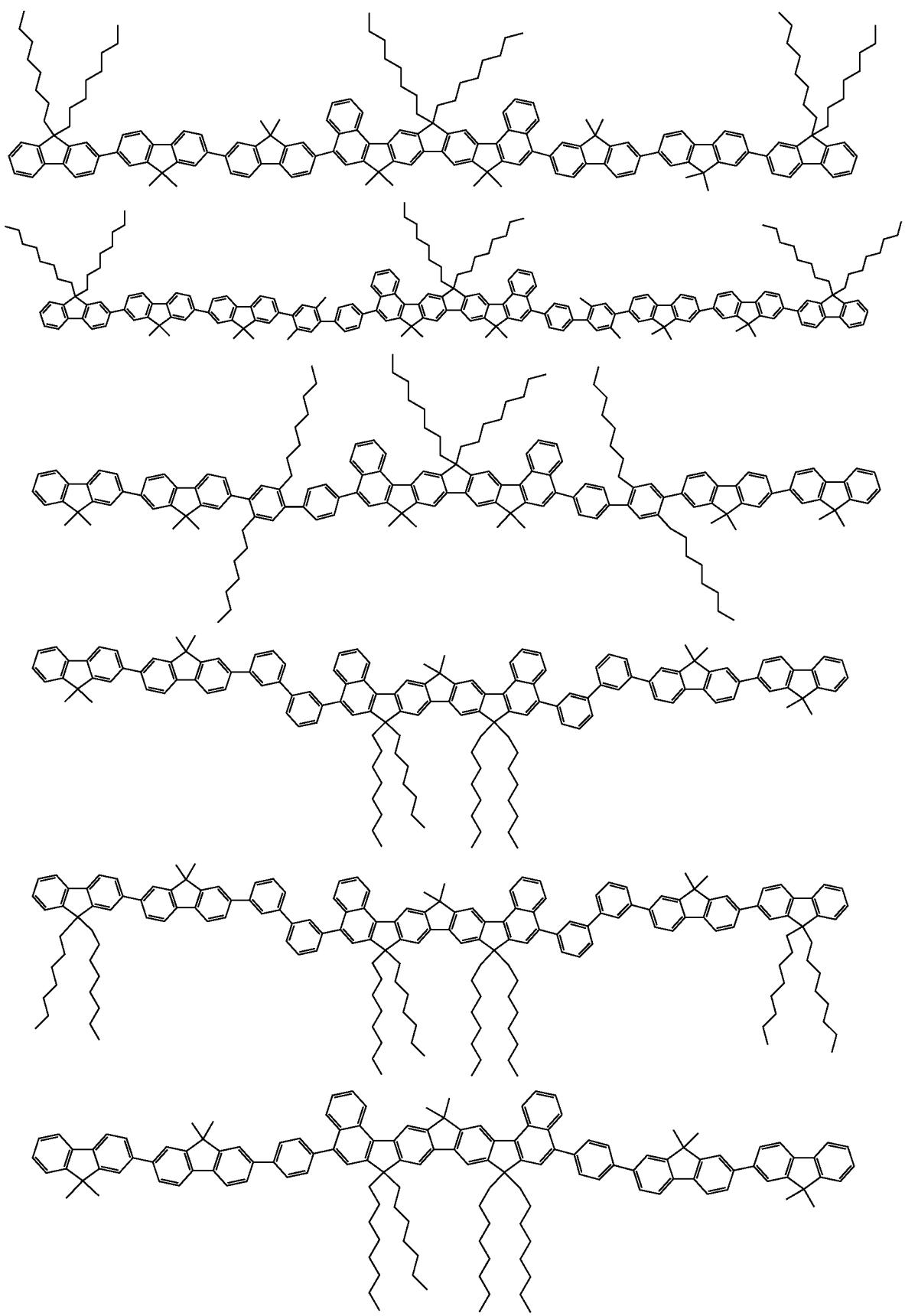

-continued
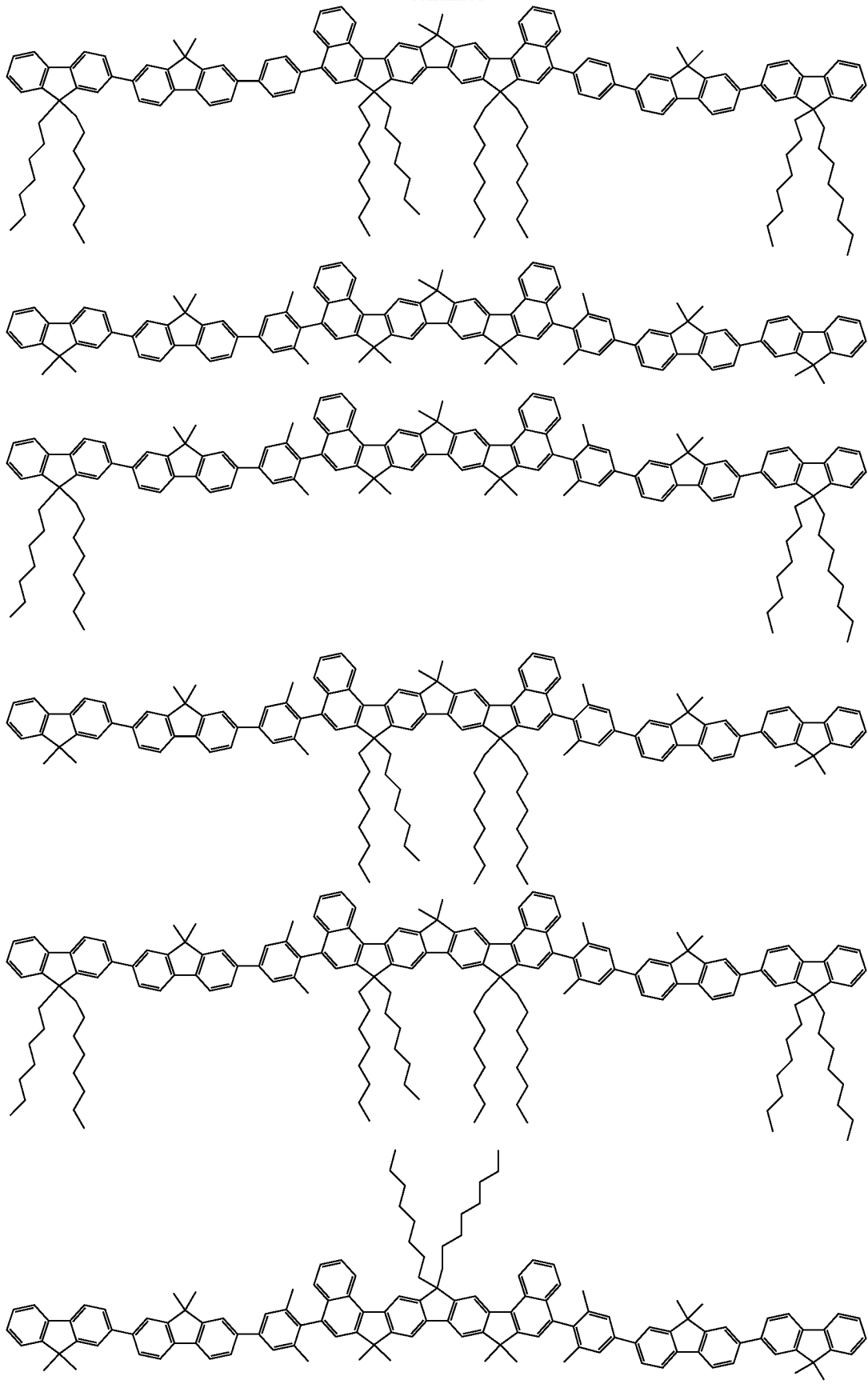

-continued
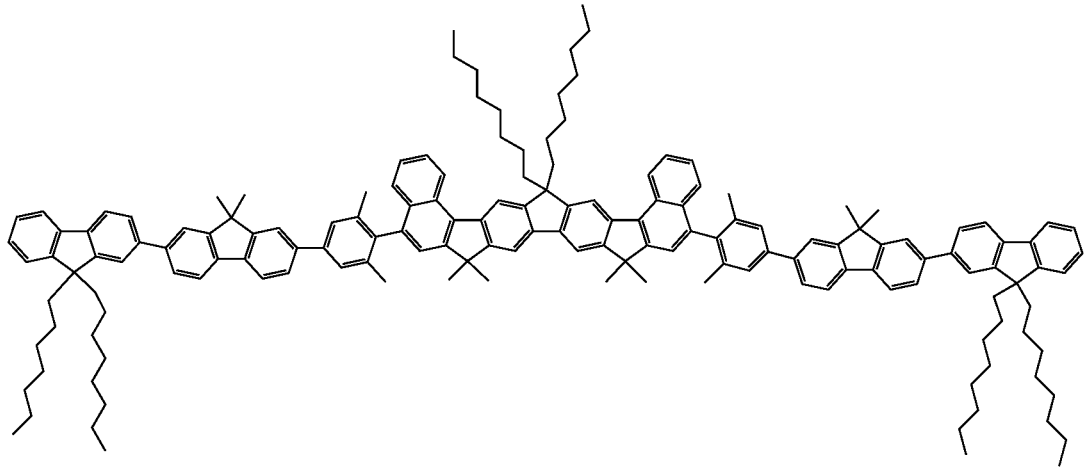
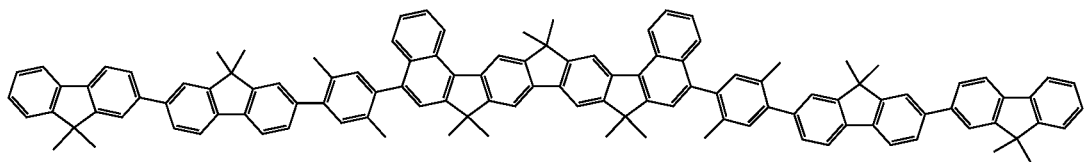
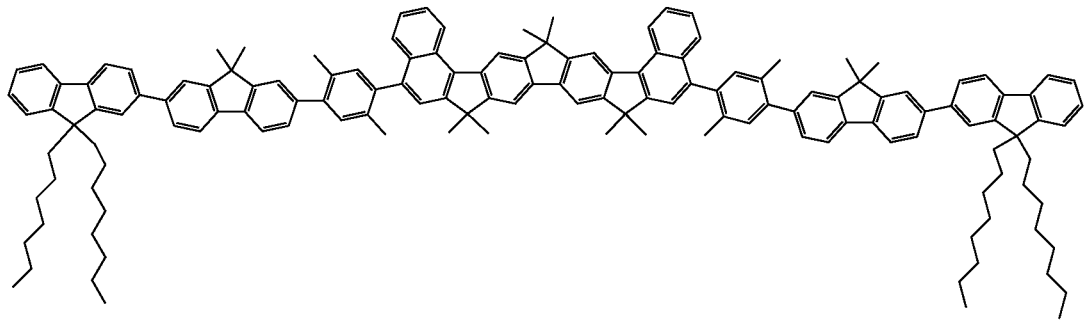
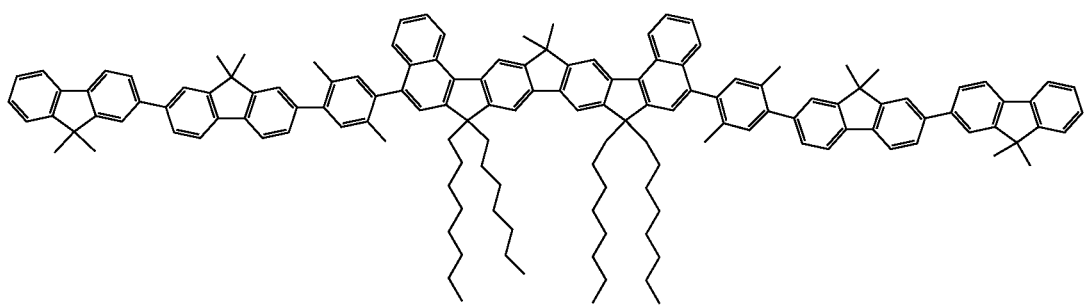
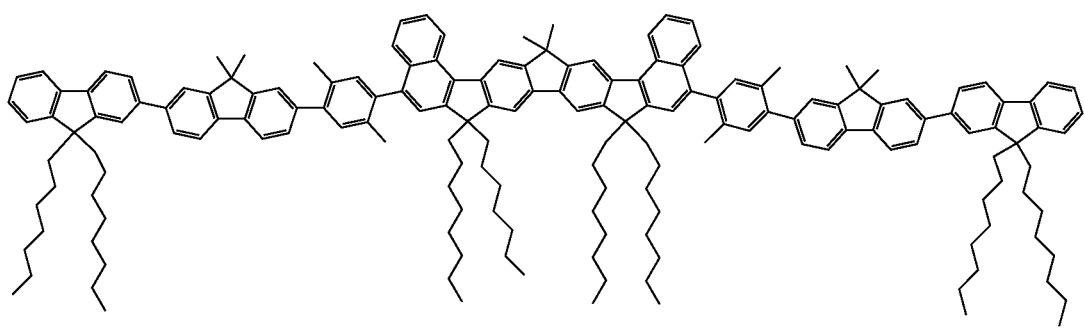

-continued
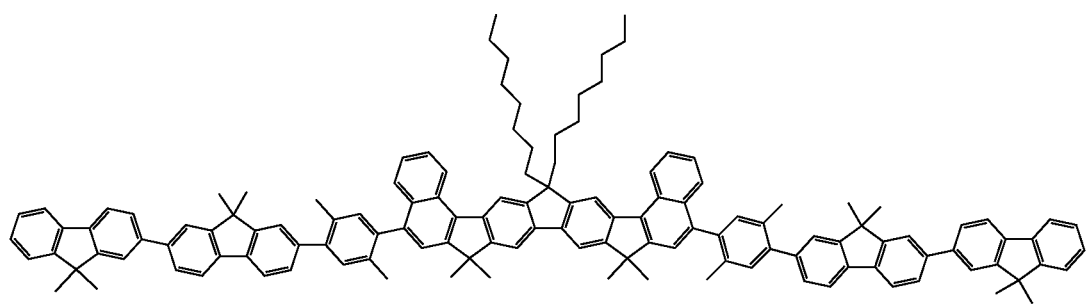
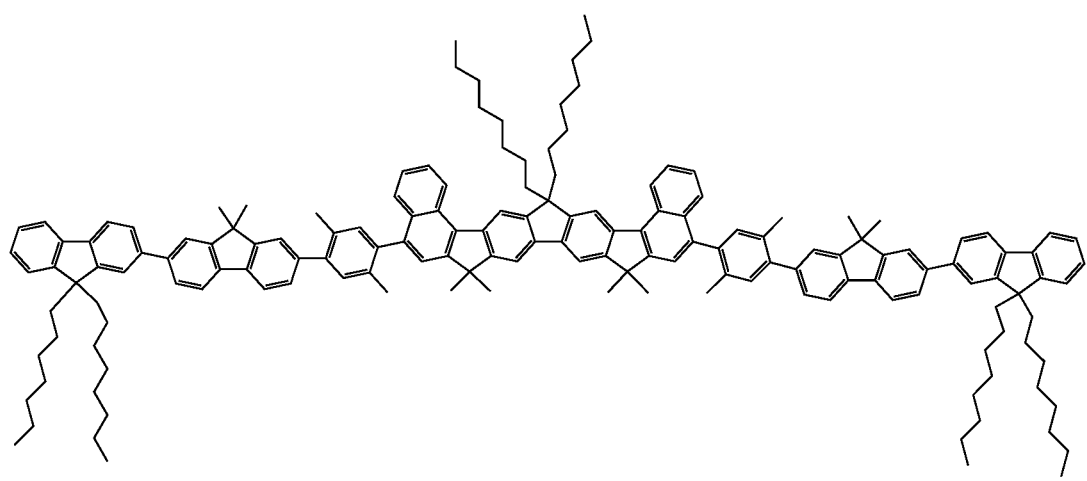
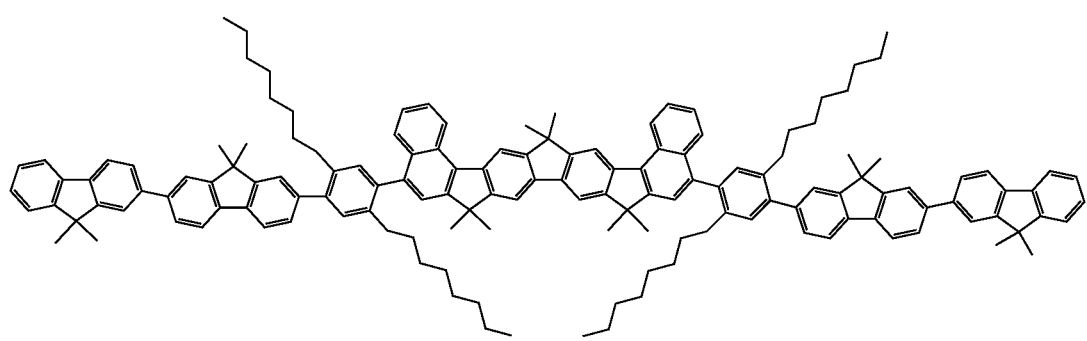
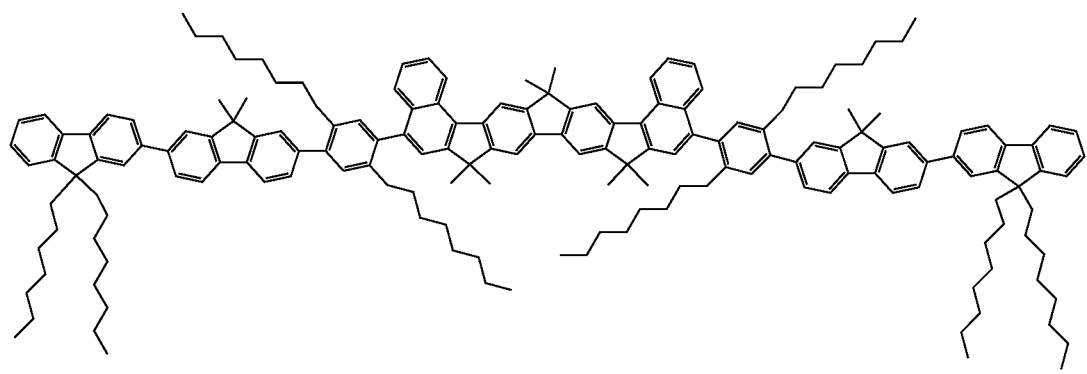

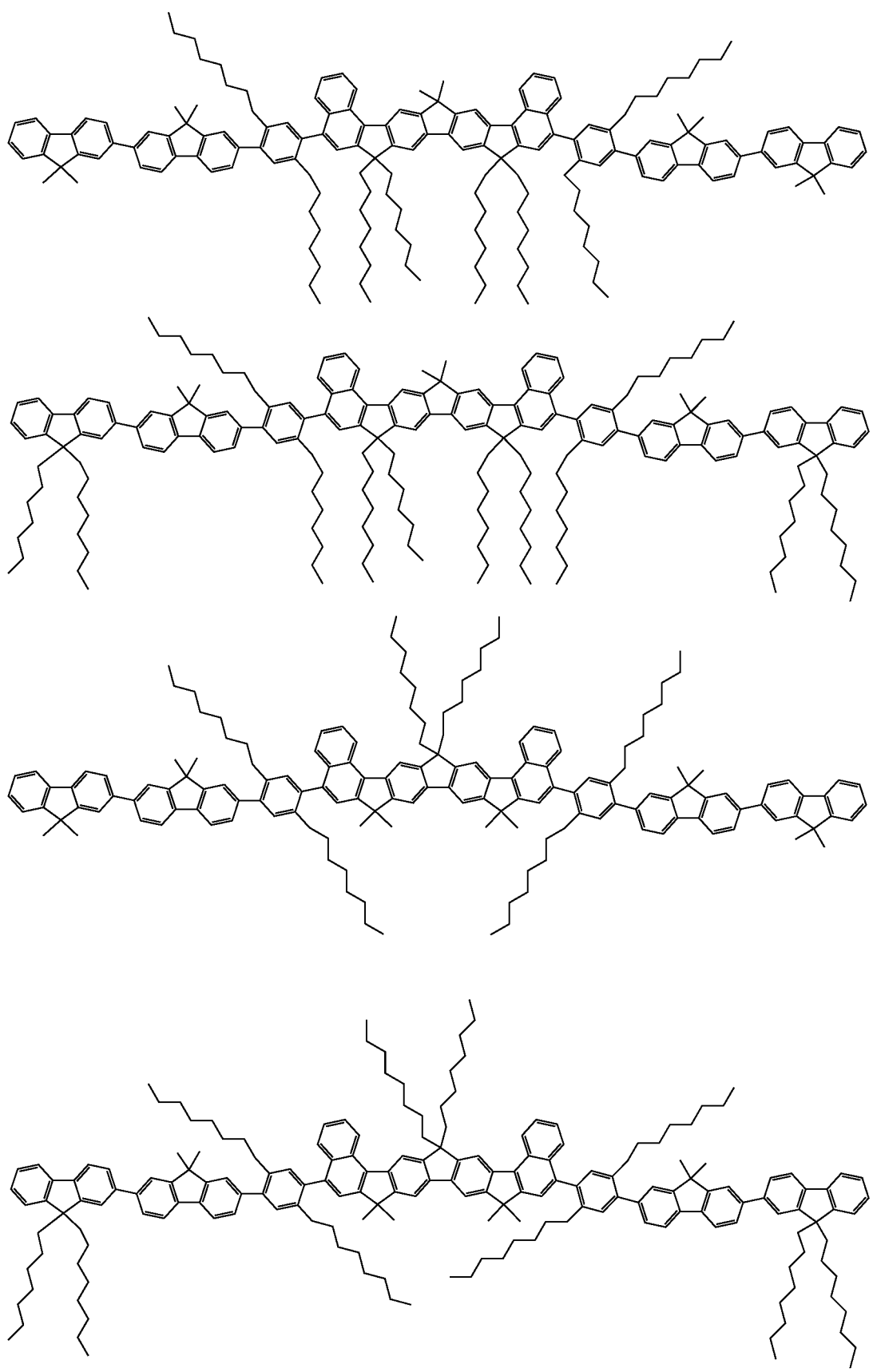

-continued
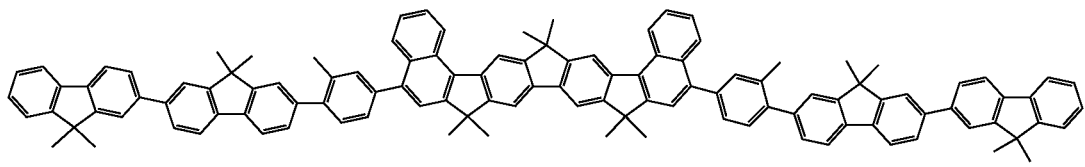
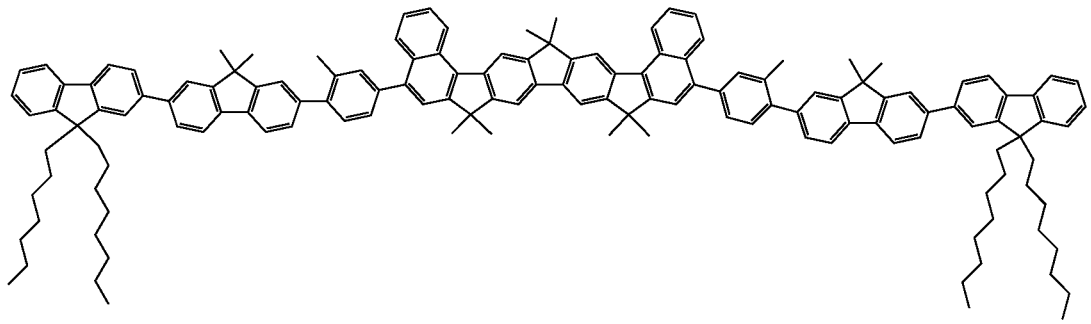
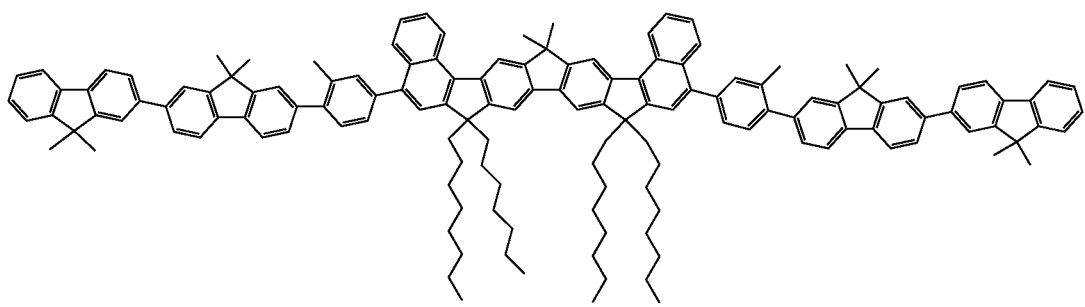
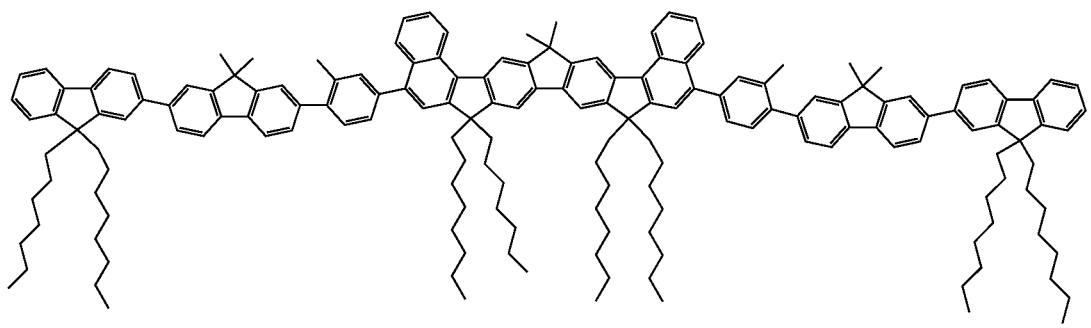
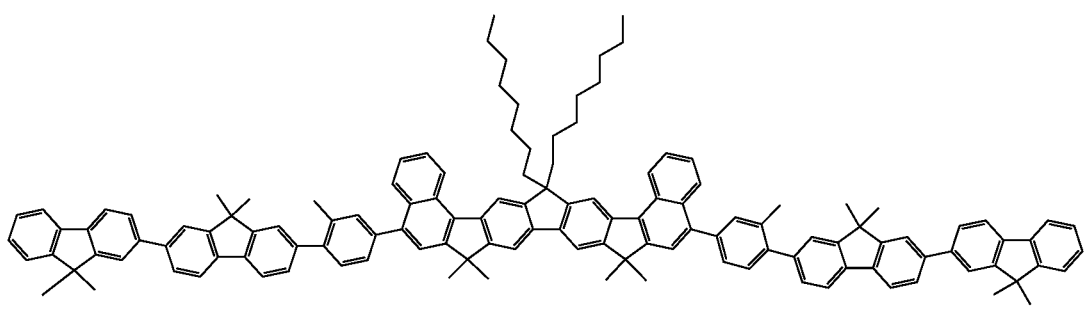

-continued
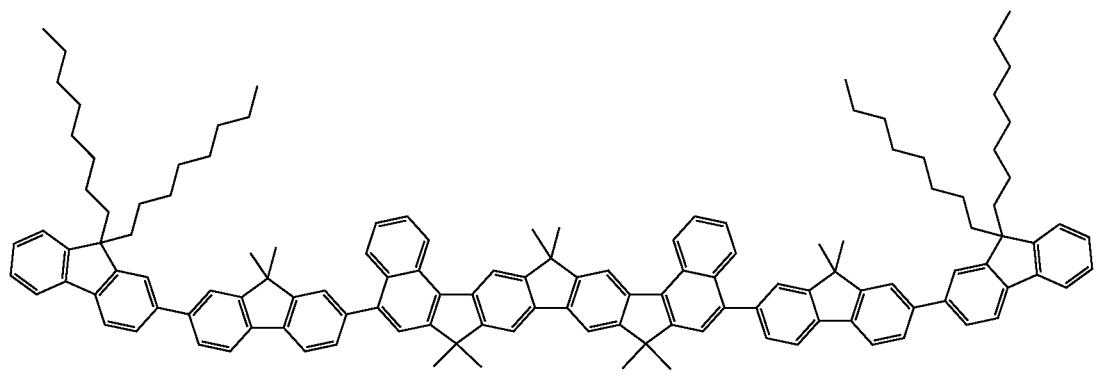
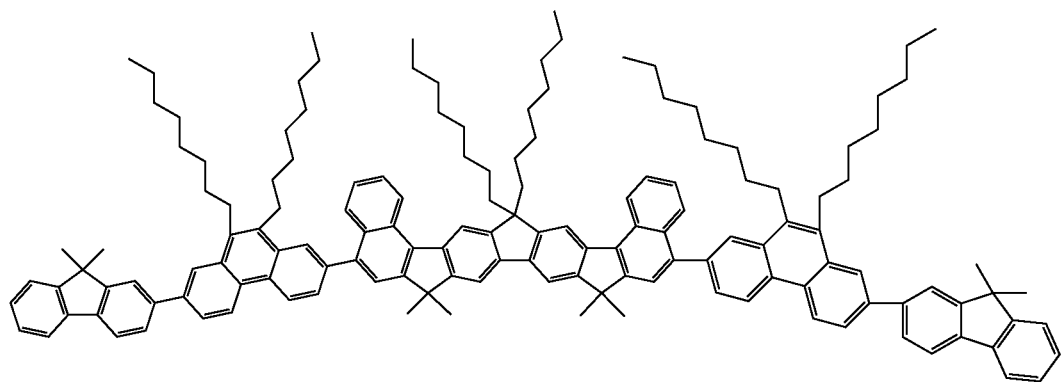
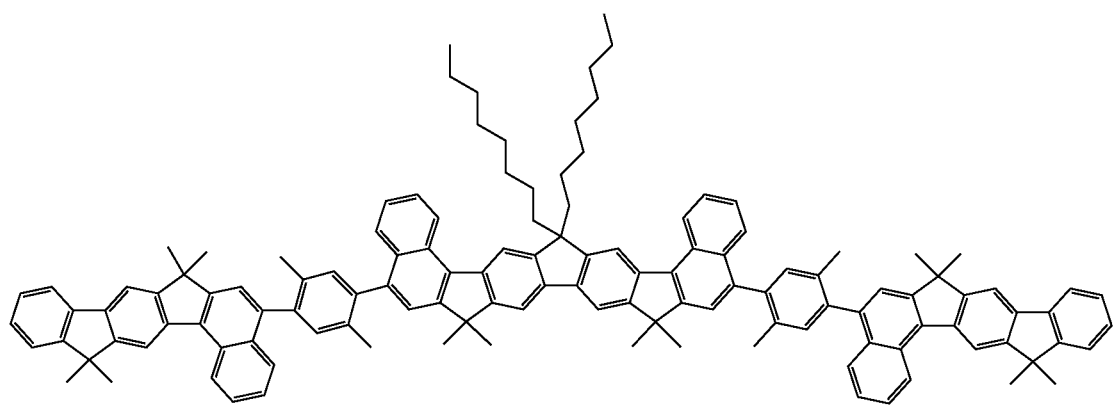
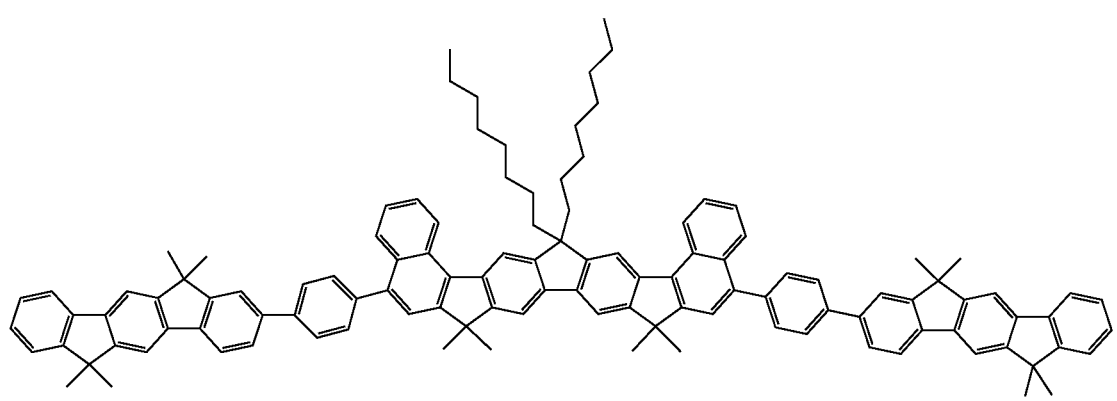 [SMILES: CCCCCCCCC1(CCCCCCCC)c2cc3c(cc2-c2cc4c(cc21)-c1c(cc(-c2ccc(-c5ccc6c(c5)C(C)(C)c5cc7c(cc5-6)C(C)(C)c5ccccc5-7)cc2)c2ccccc12)C4(C)C)C(C)(C)c1cc(-c2ccc(-c4ccc5c(c4)C(C)(C)c4cc6c(cc4-5)C(C)(C)c4ccccc4-6)cc2)c2ccccc2c1-3]

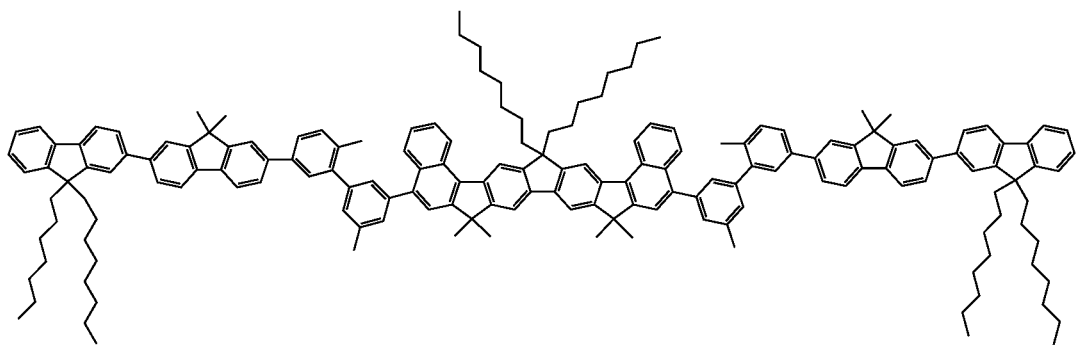
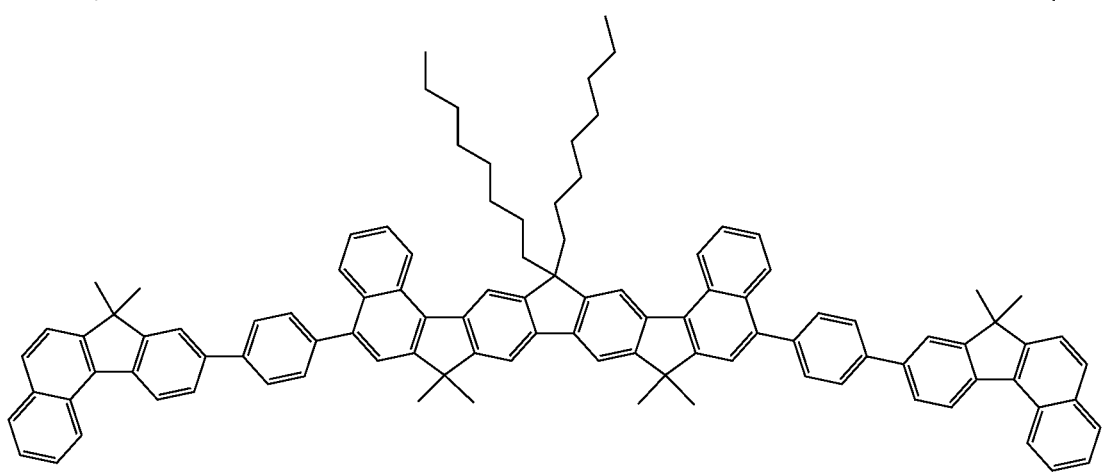
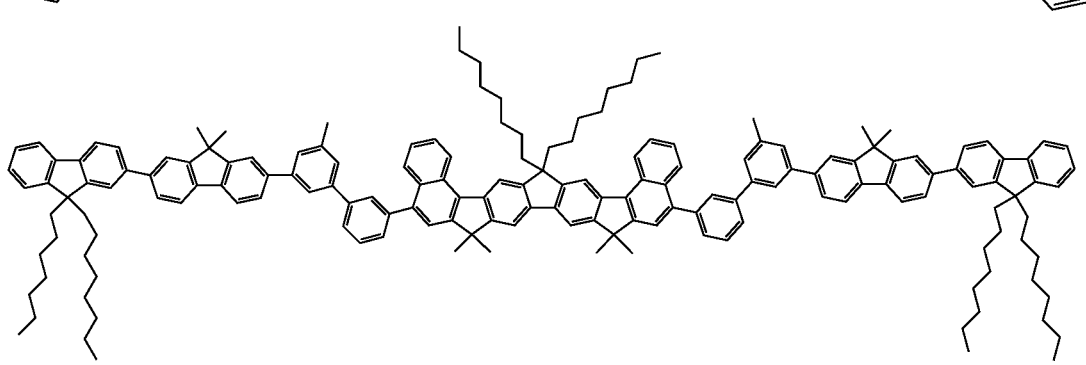
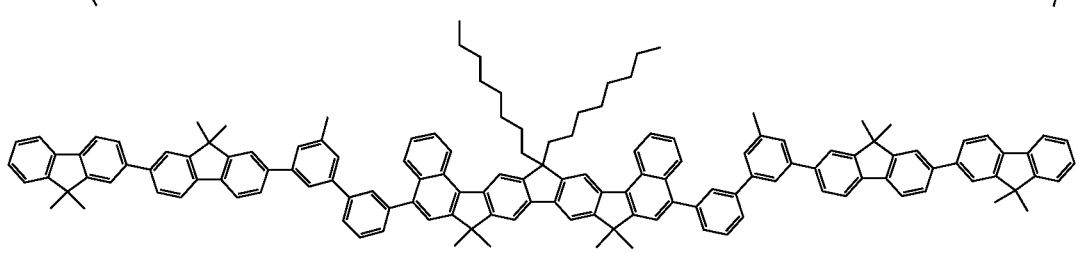
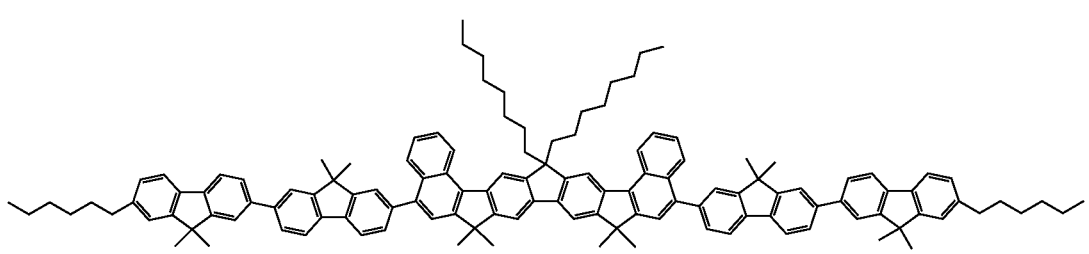

-continued
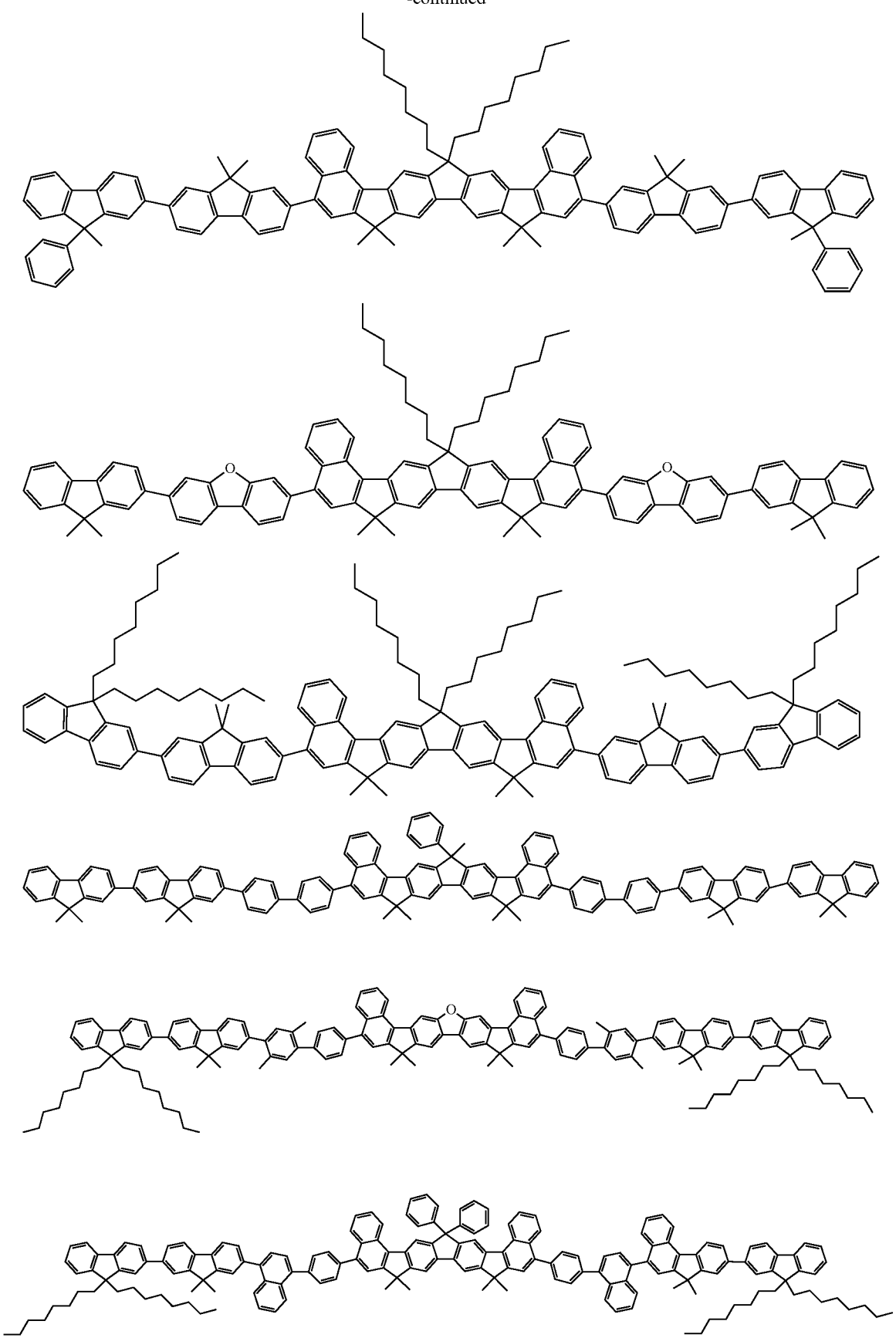

-continued
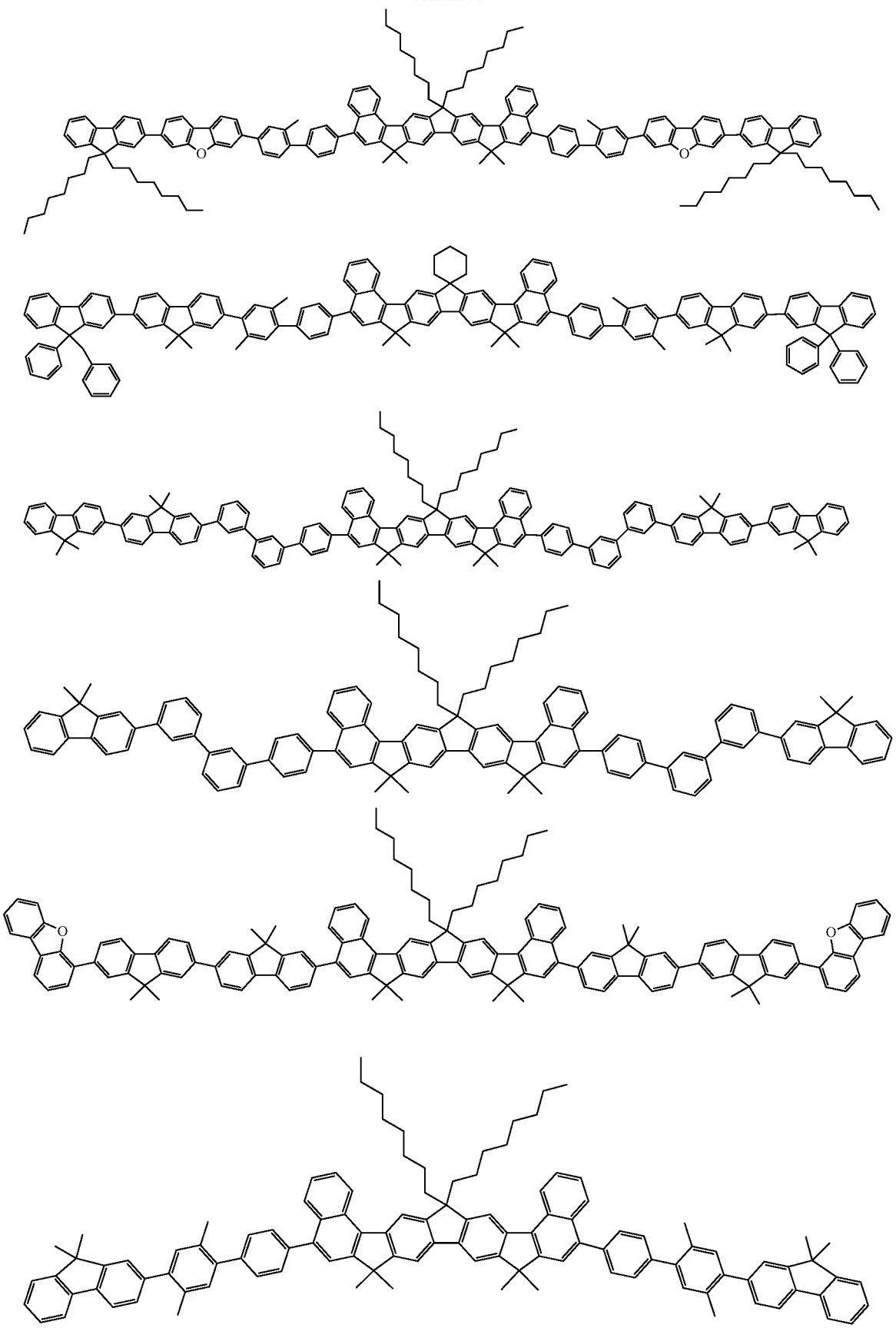

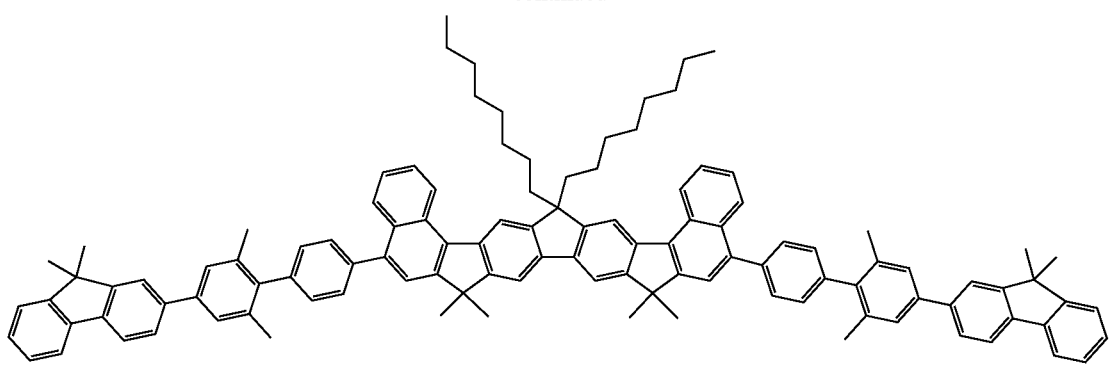
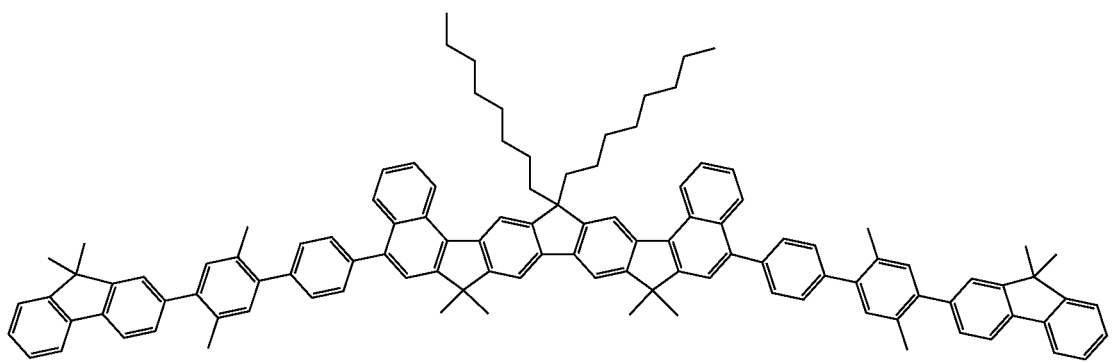
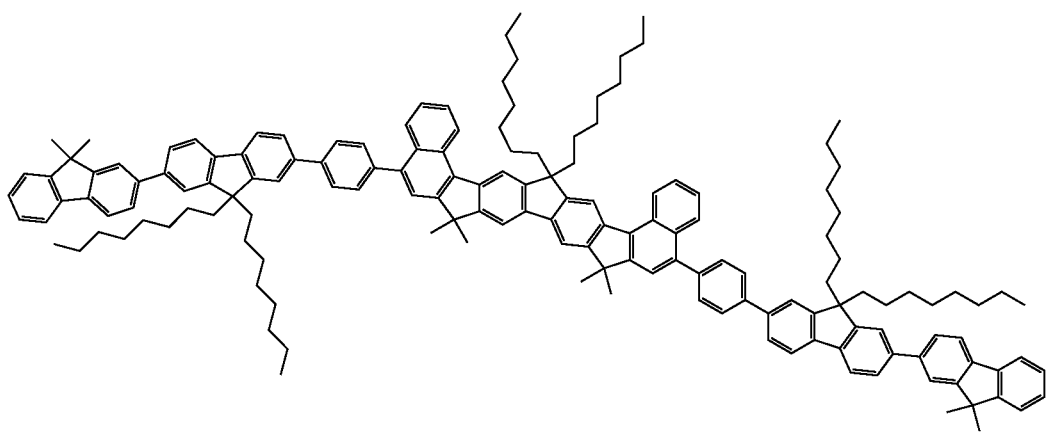

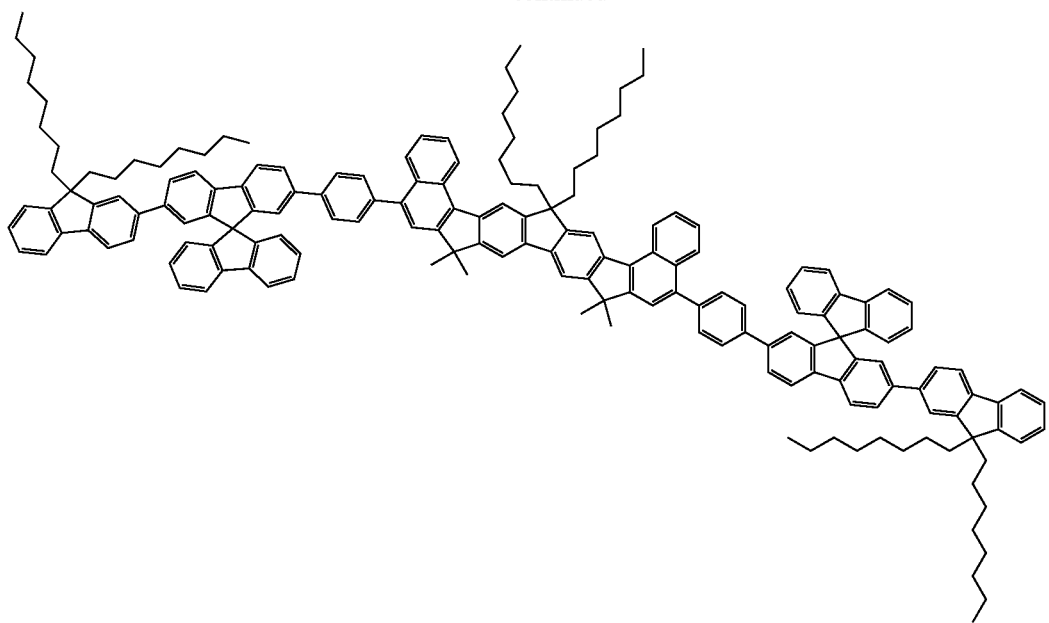
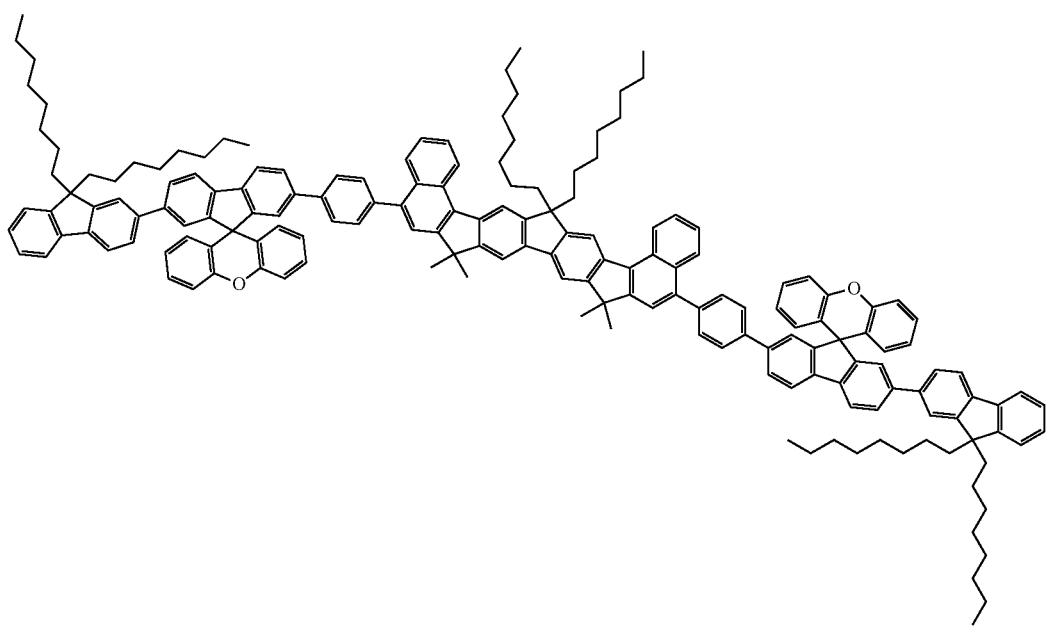
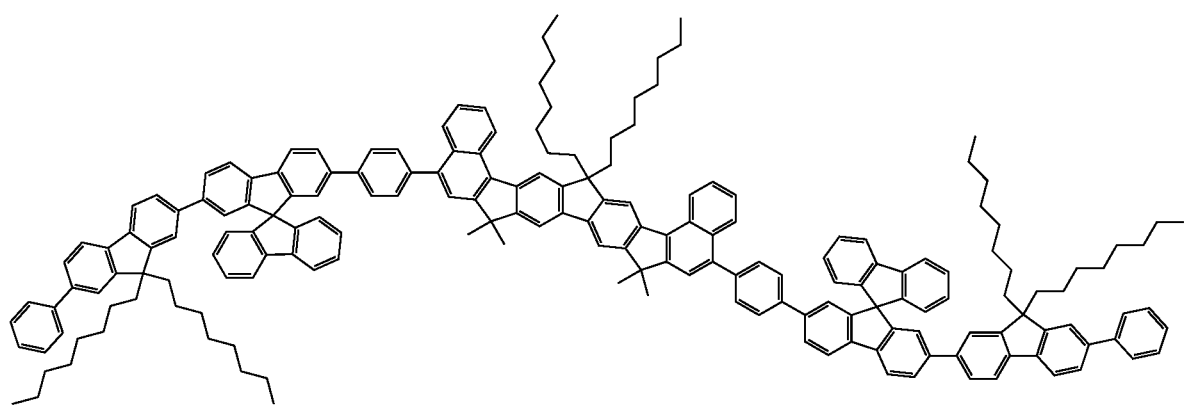

-continued
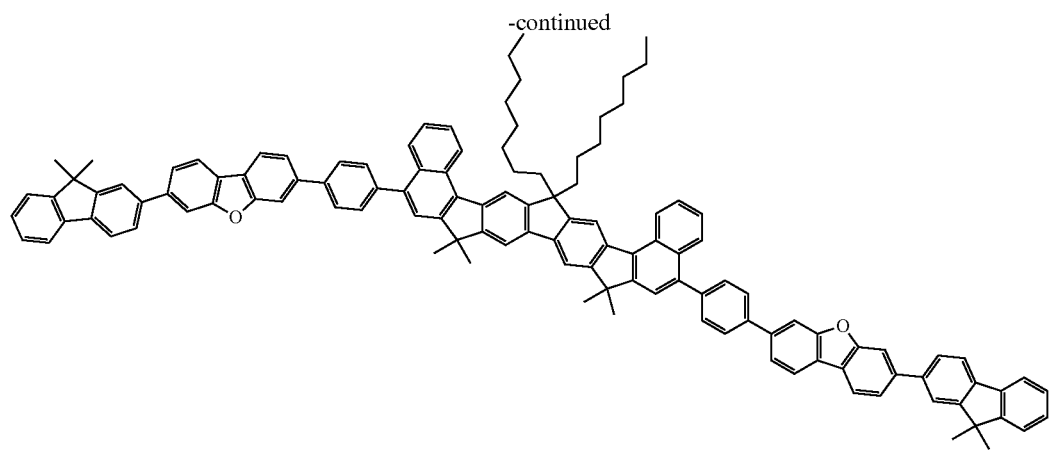
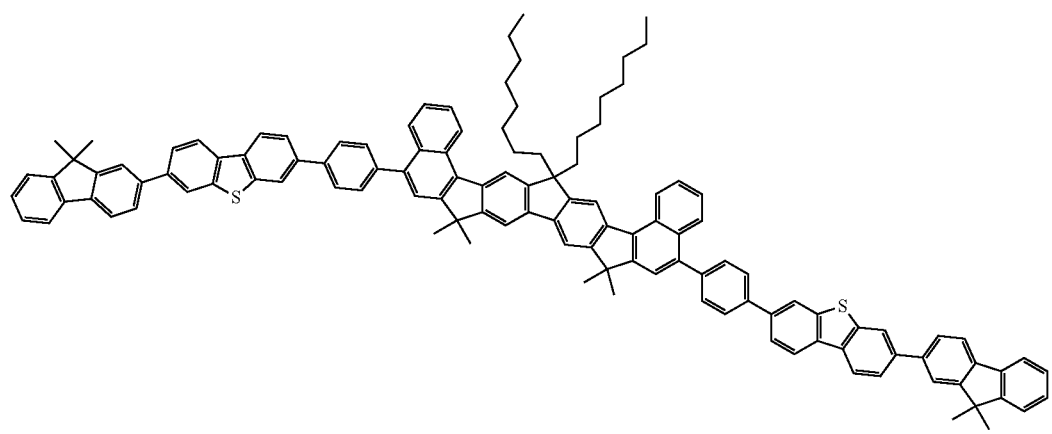
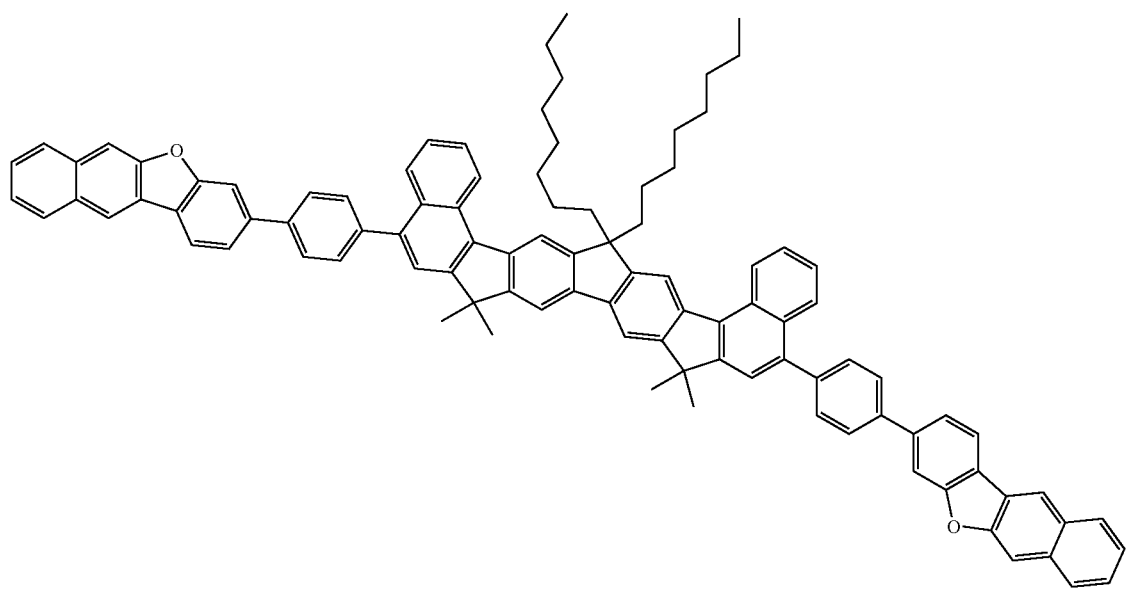

-continued
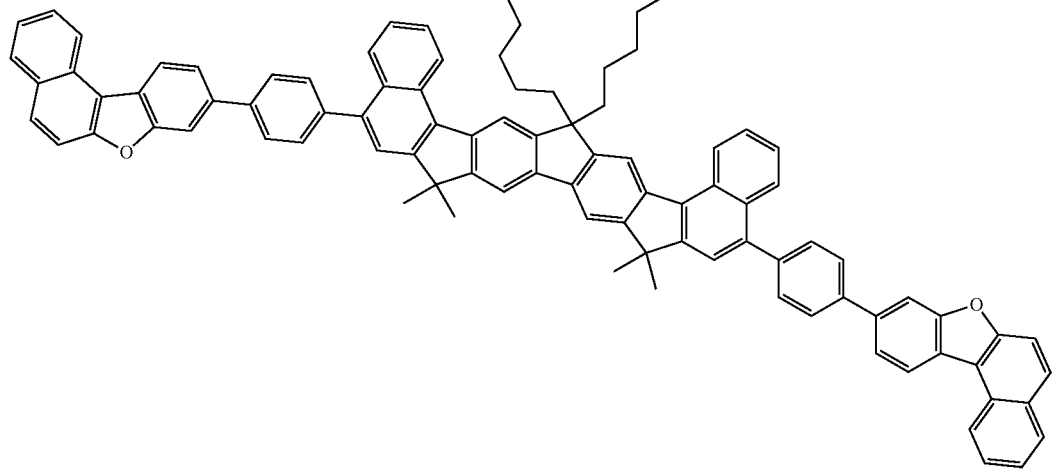
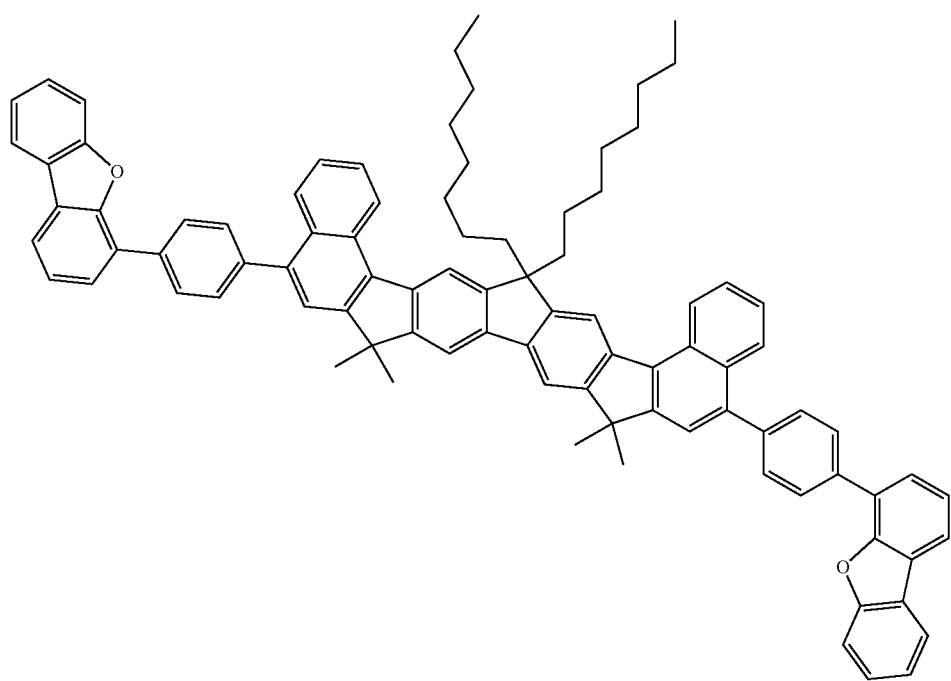

-continued
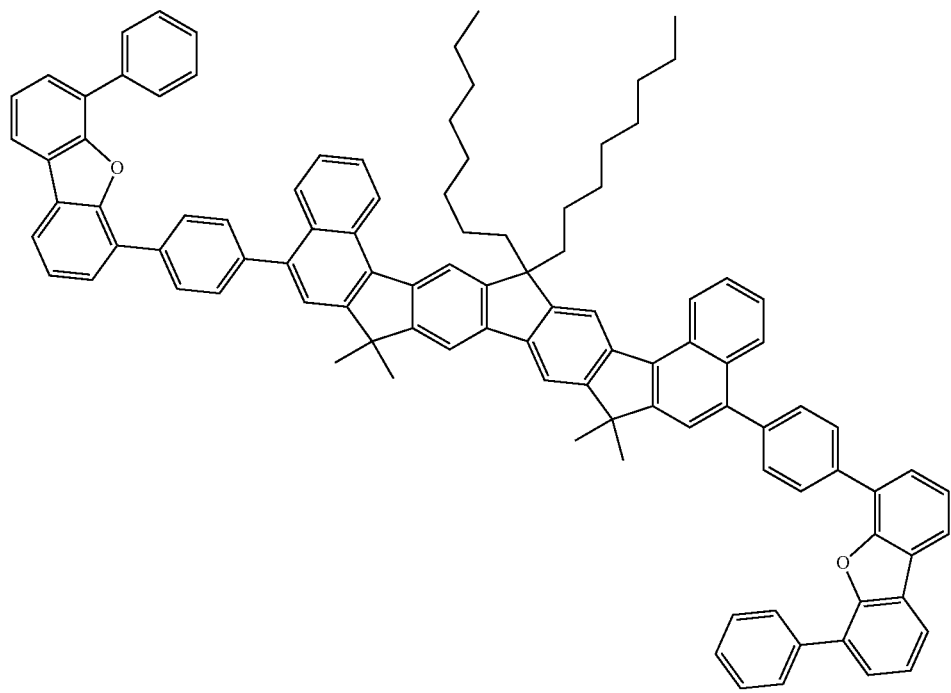
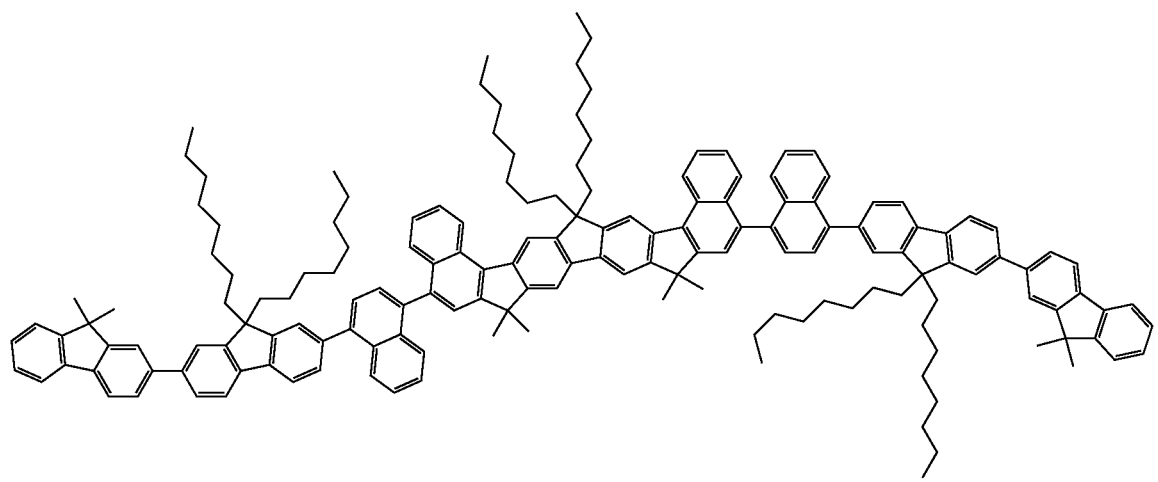

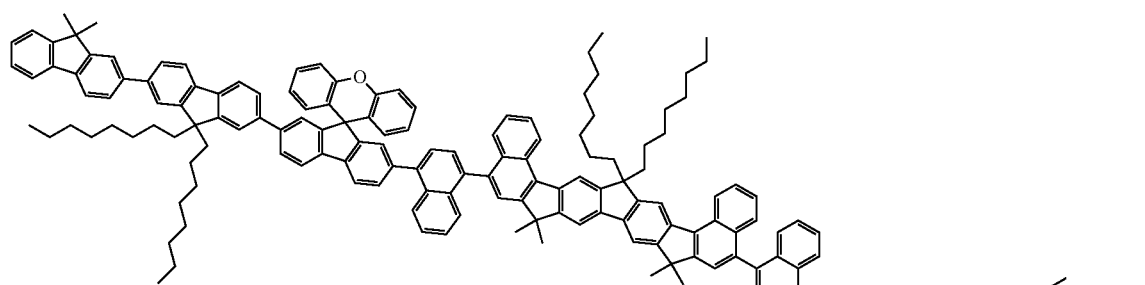
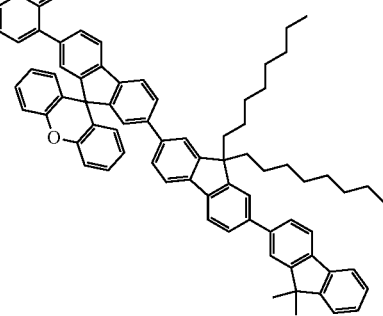
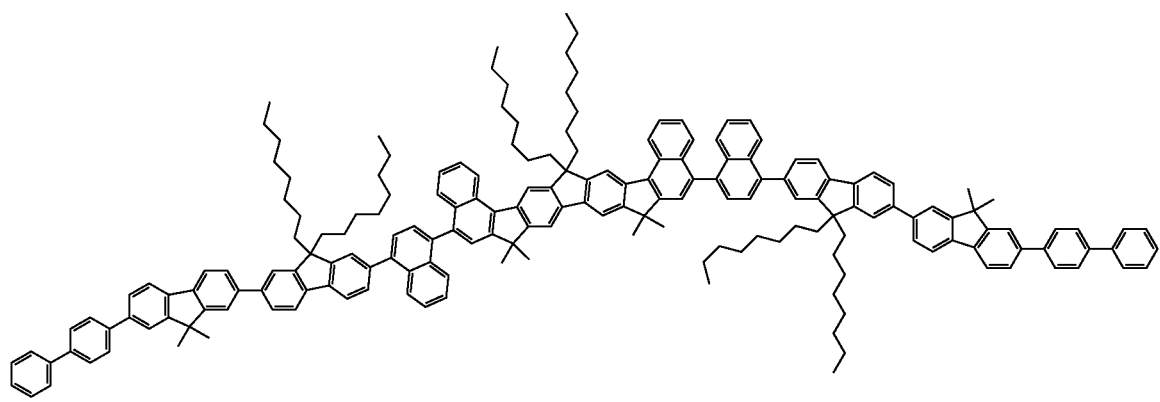
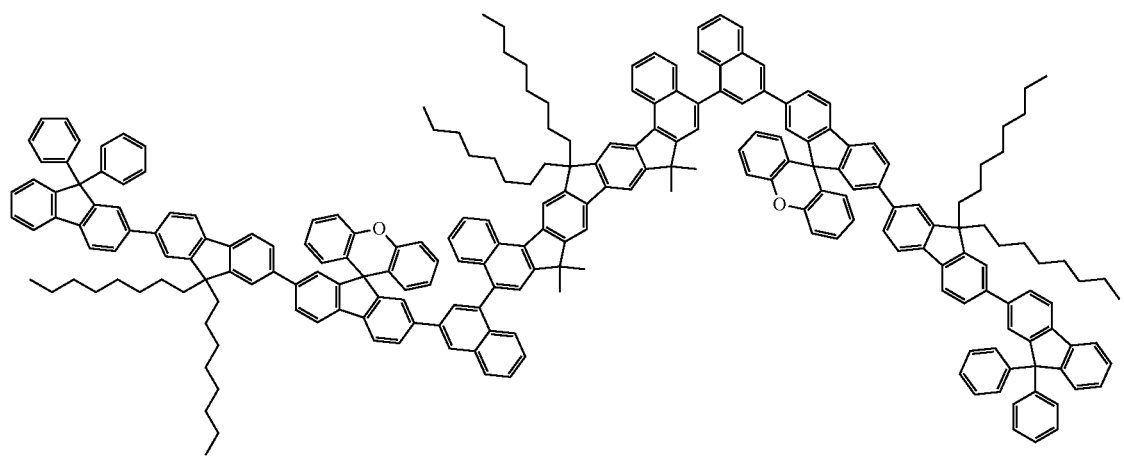

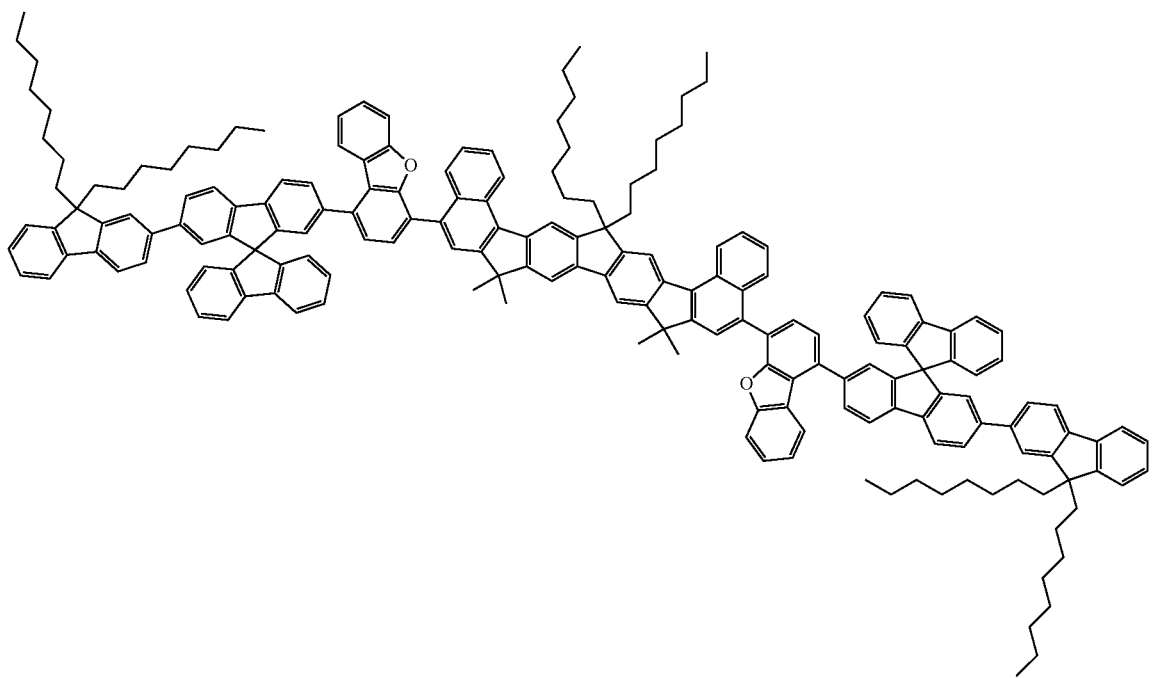
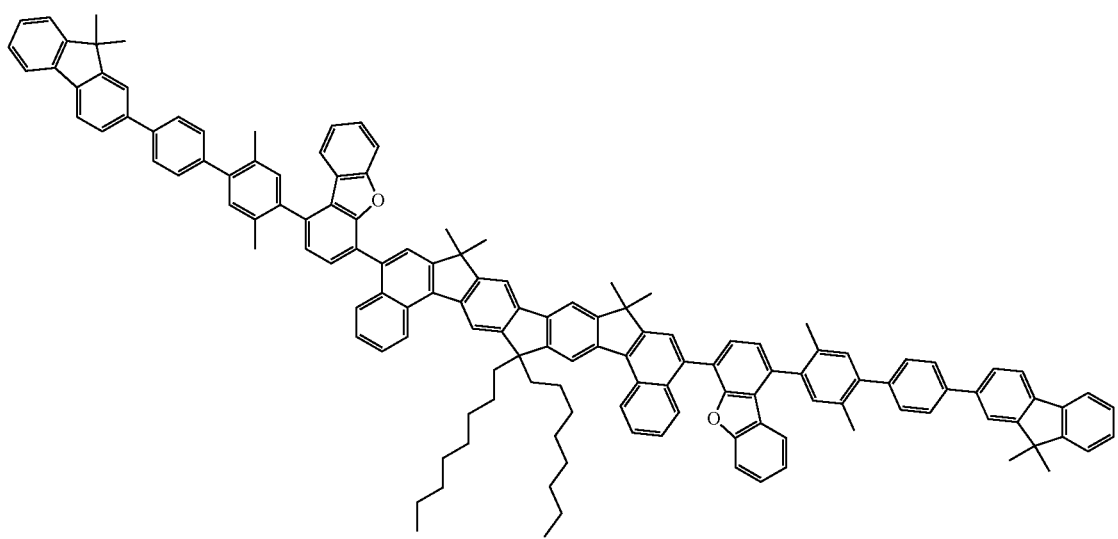

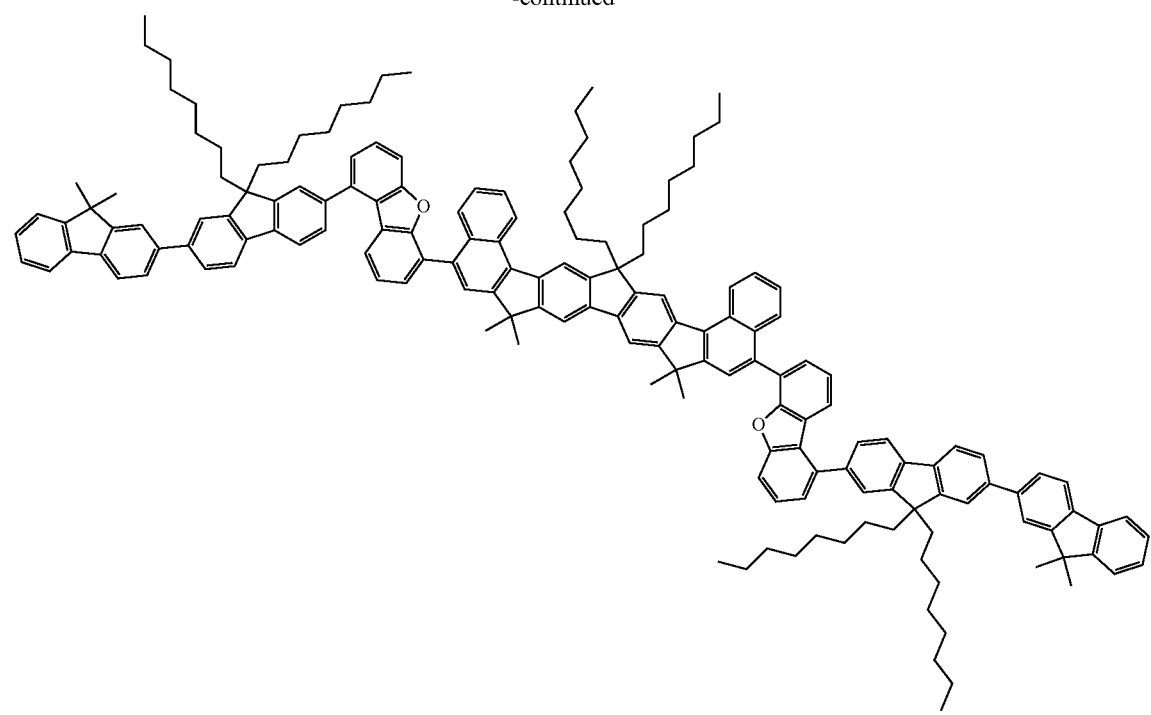
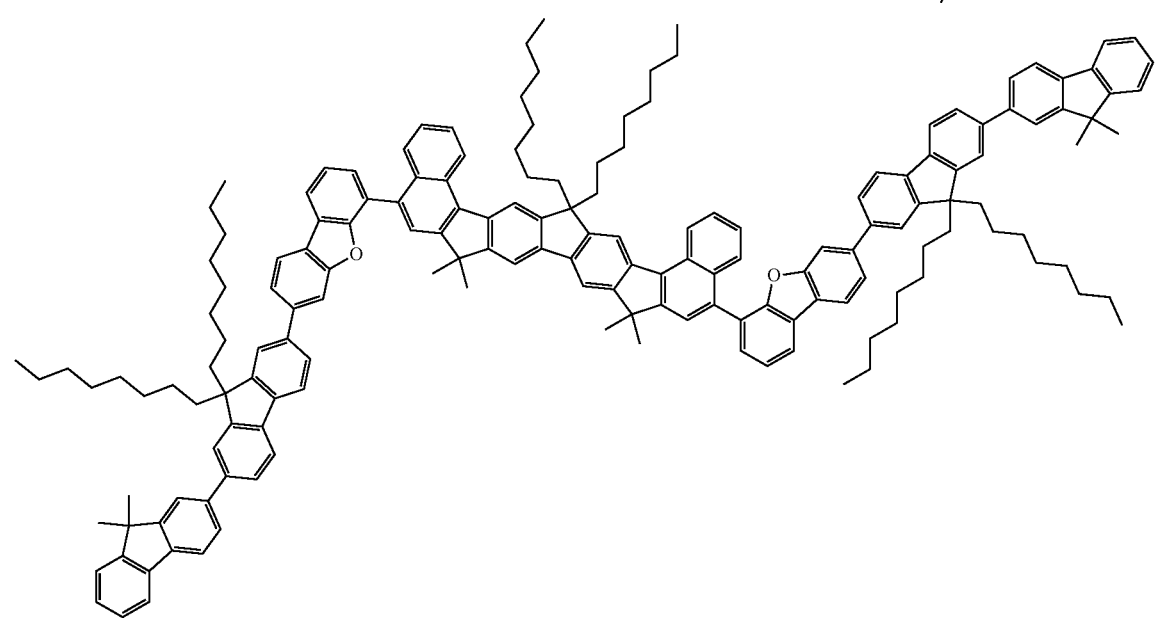
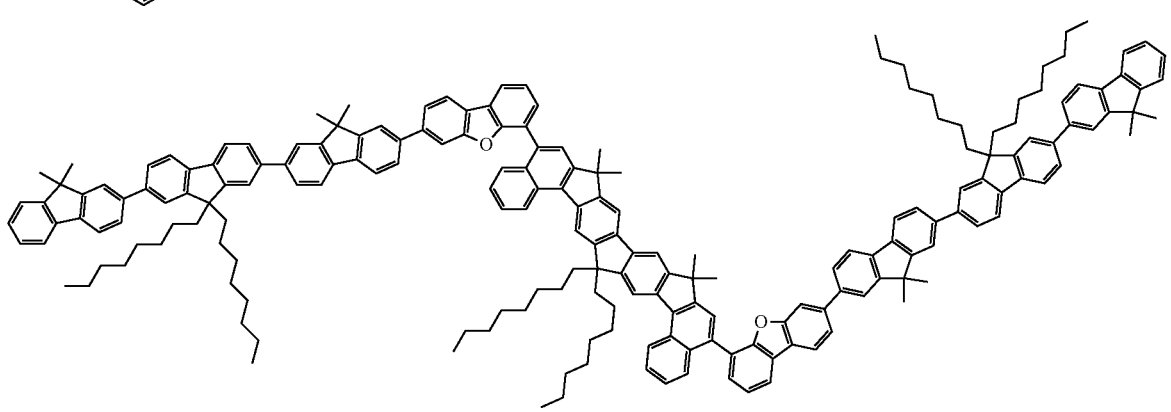

-continued
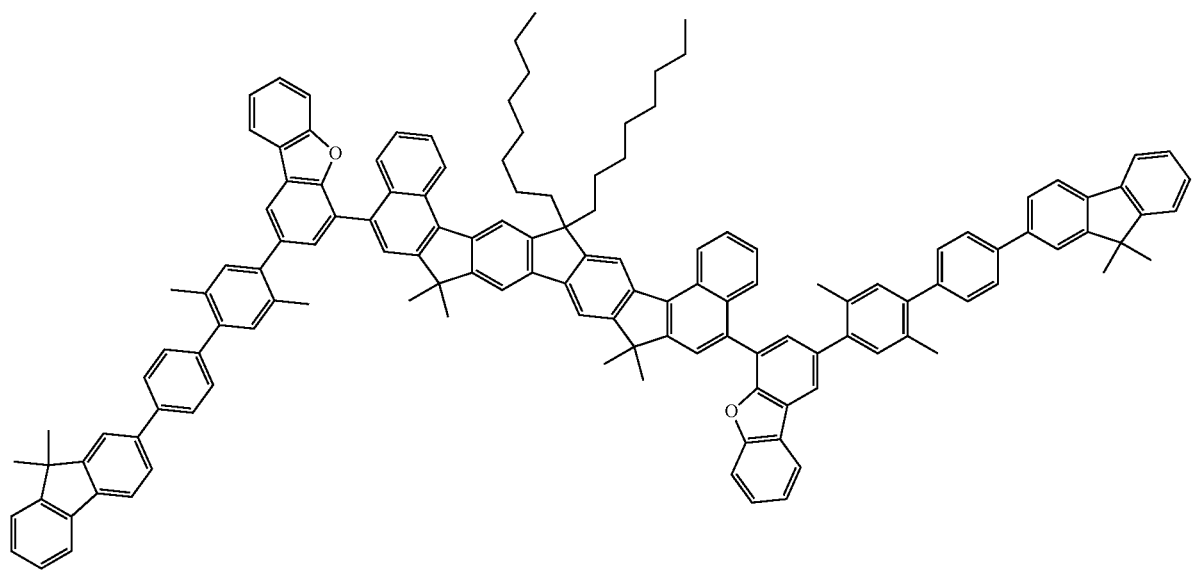
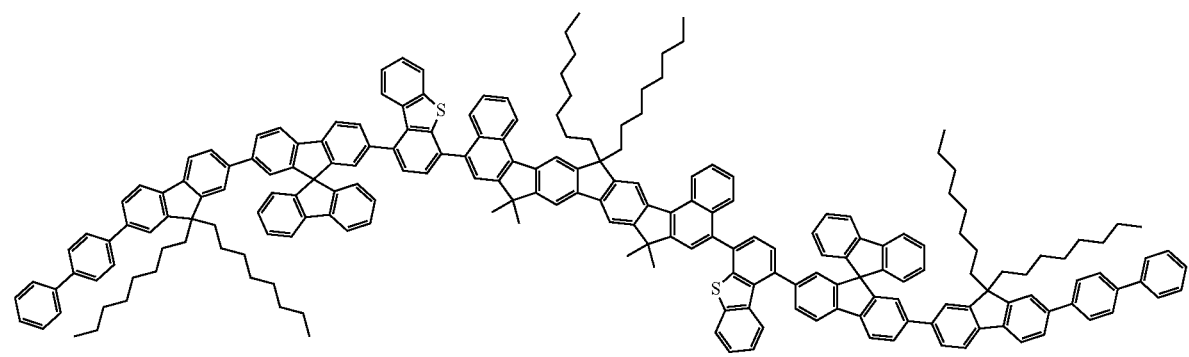
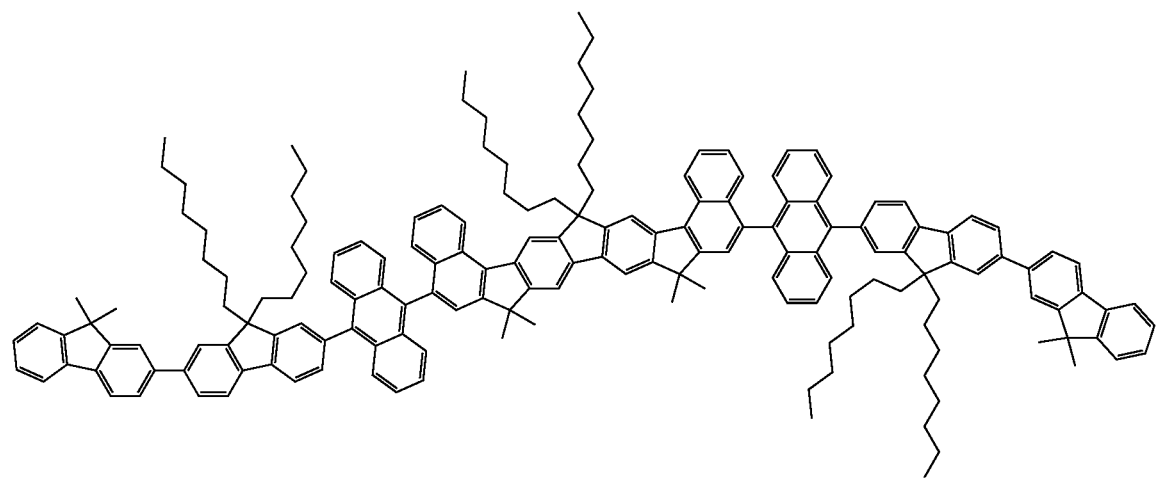

-continued
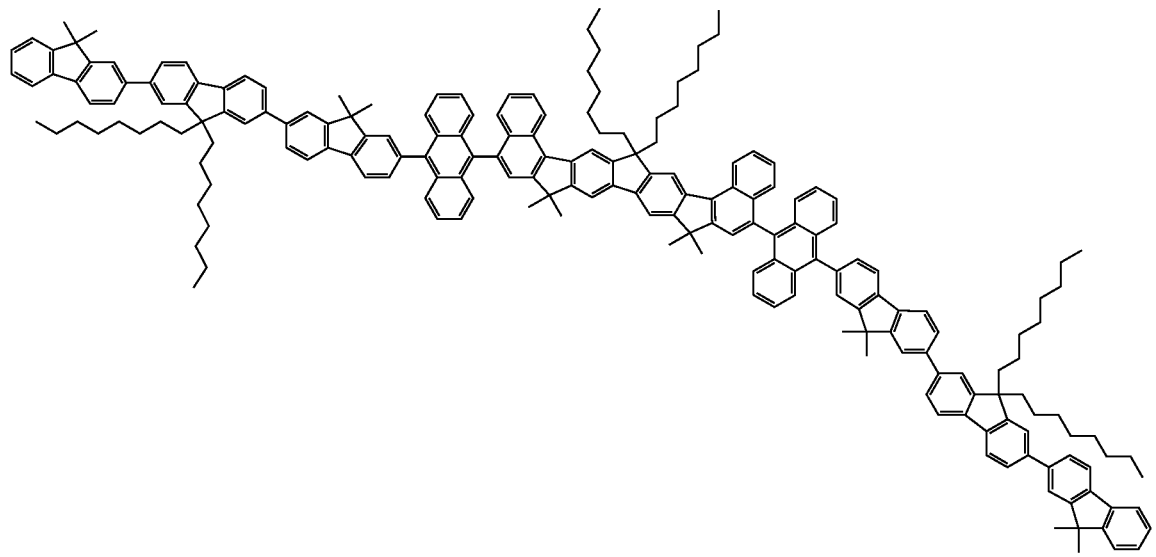
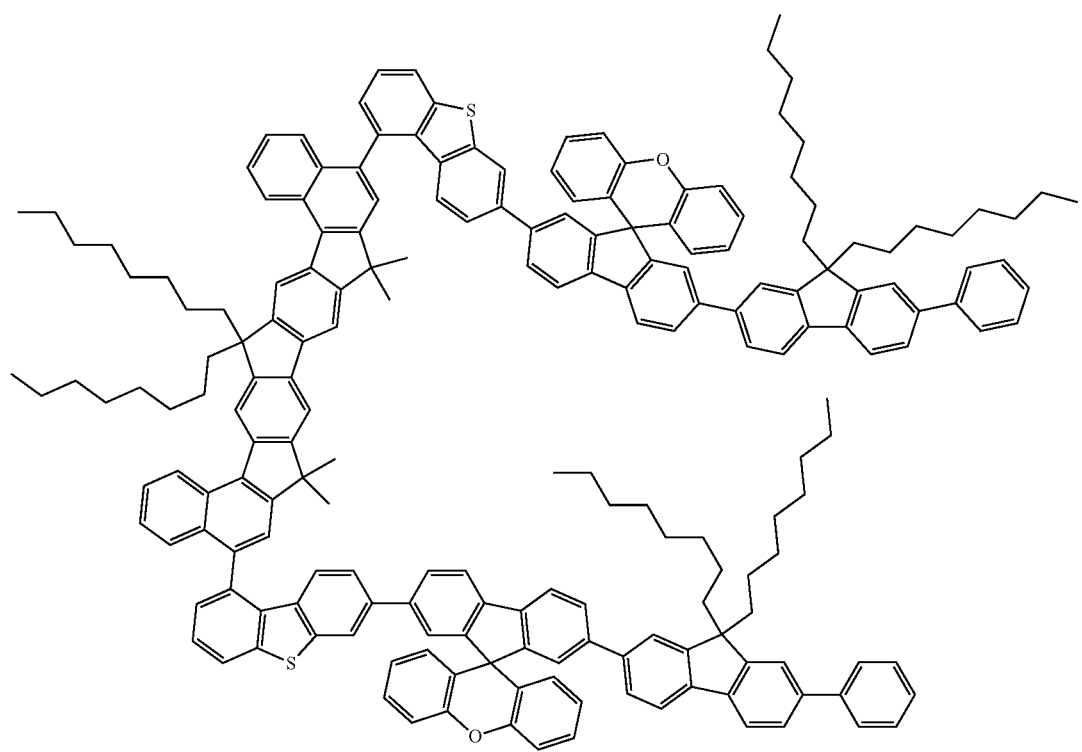

-continued
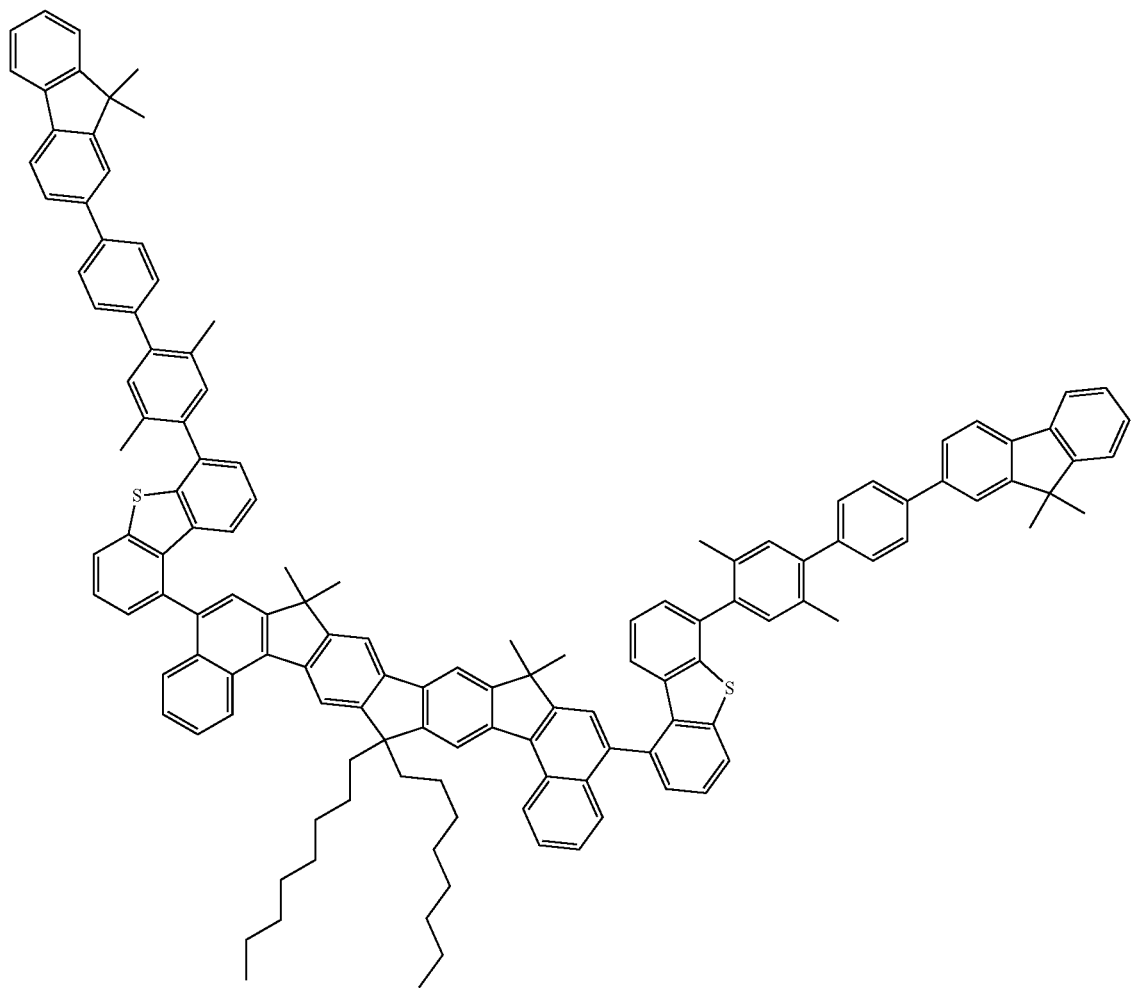
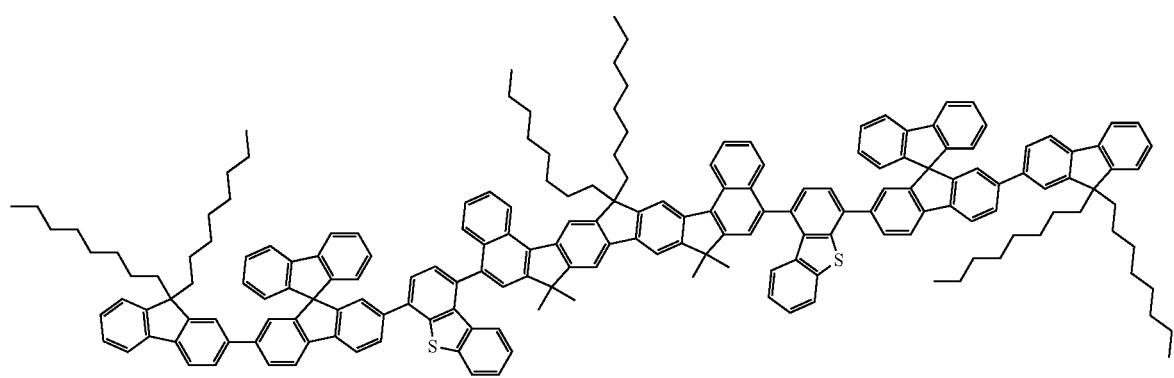

103 104
-continued
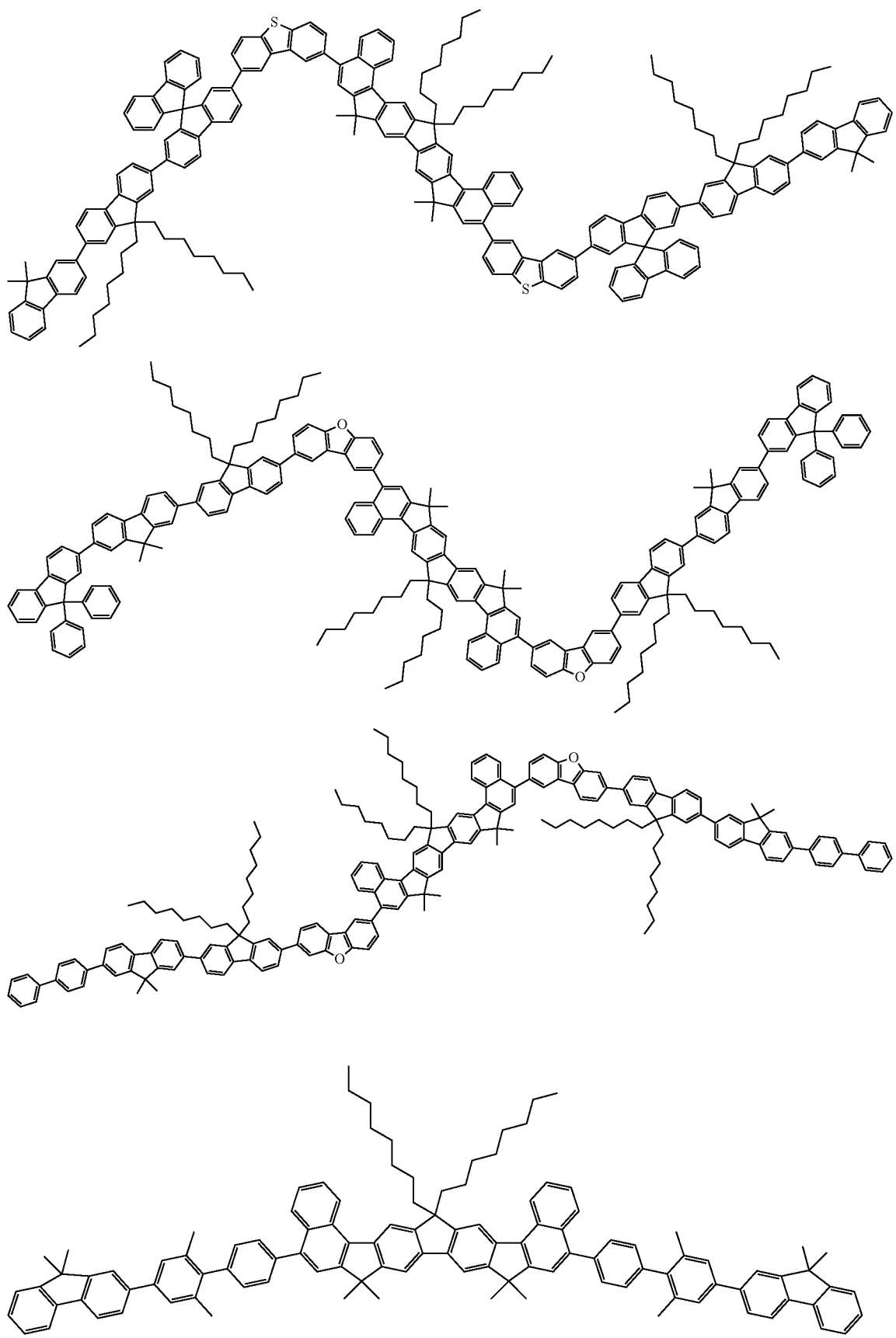

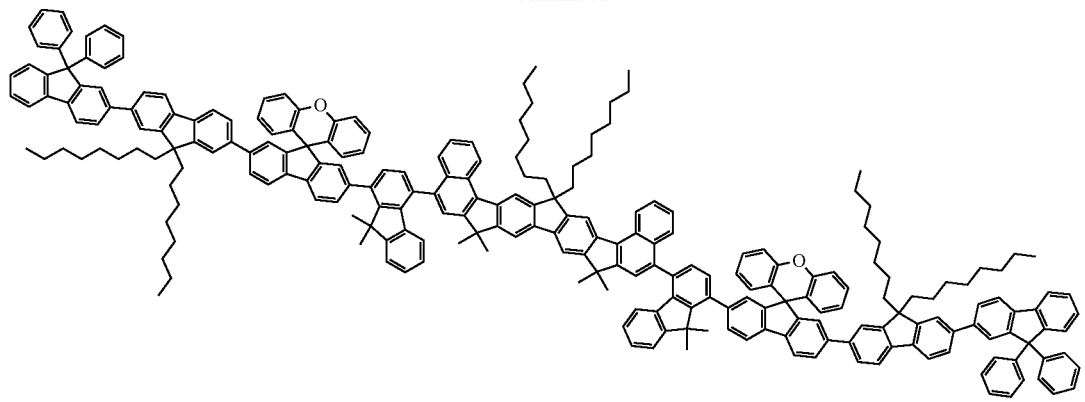
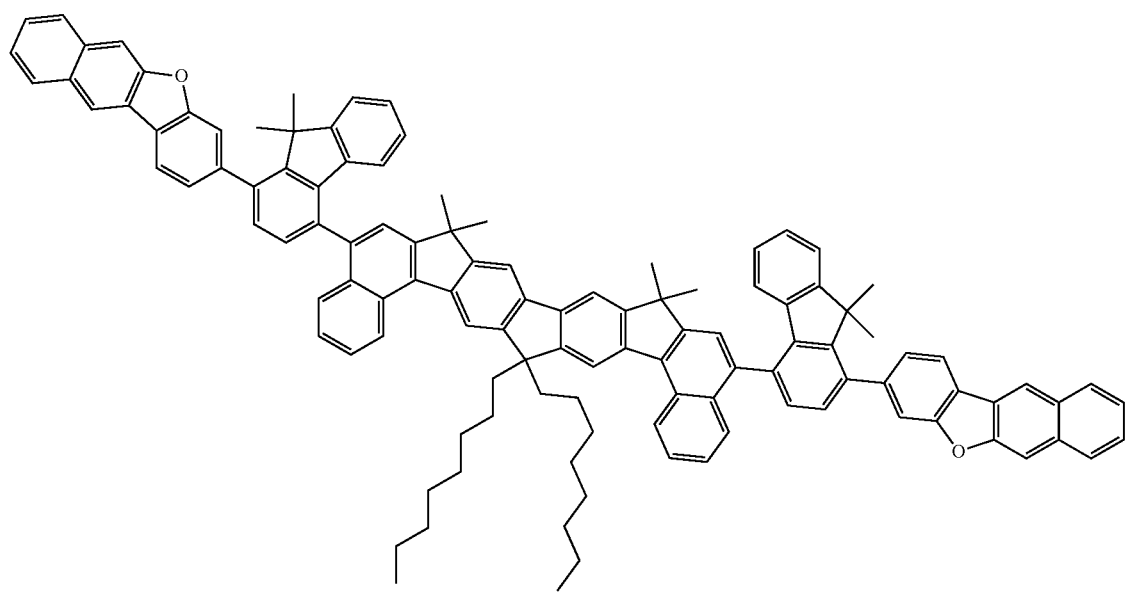
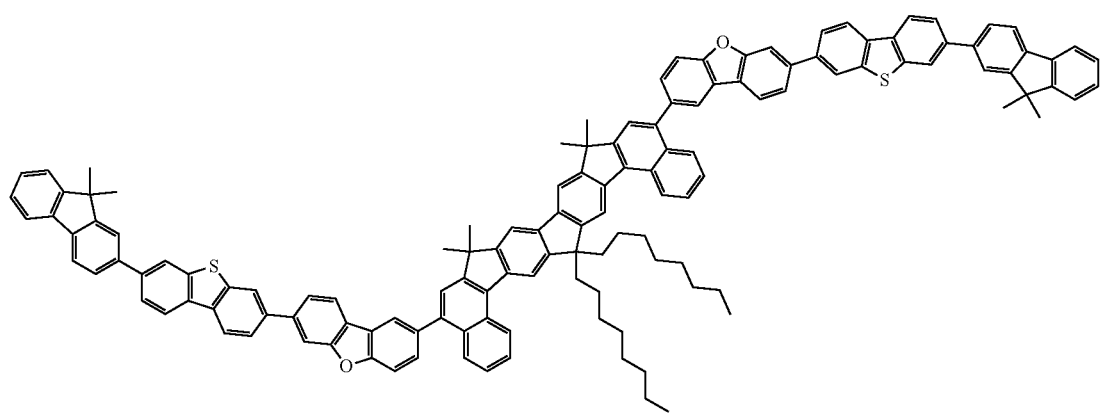

-continued
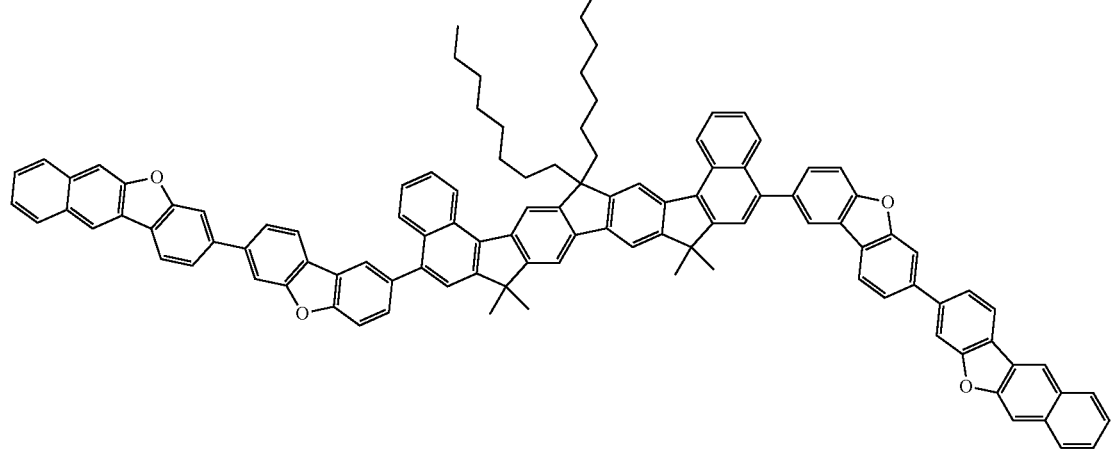
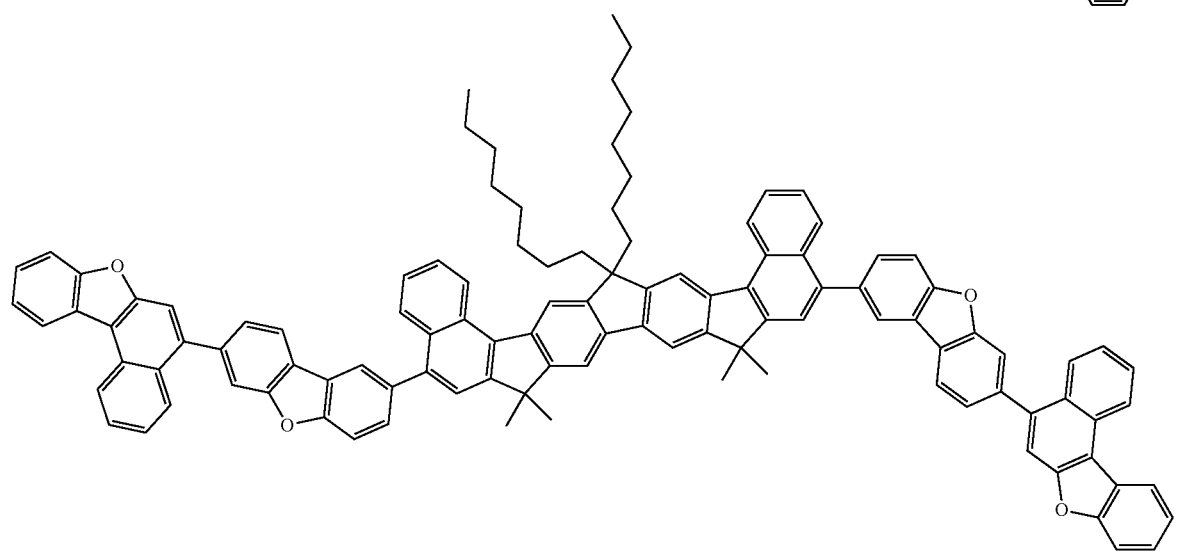
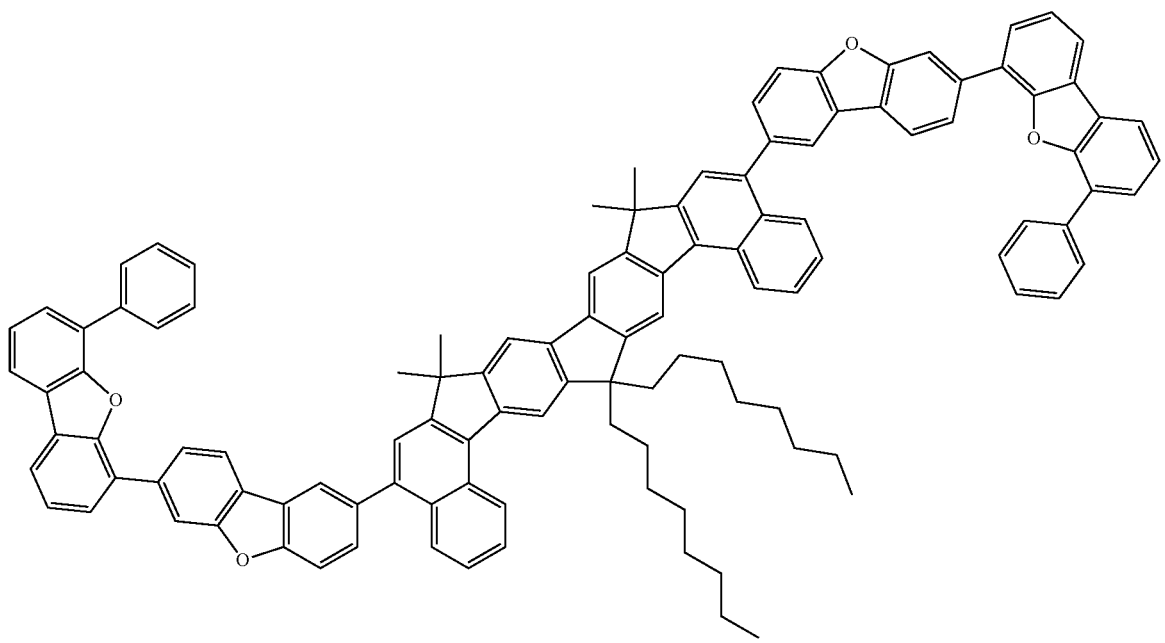

-continued
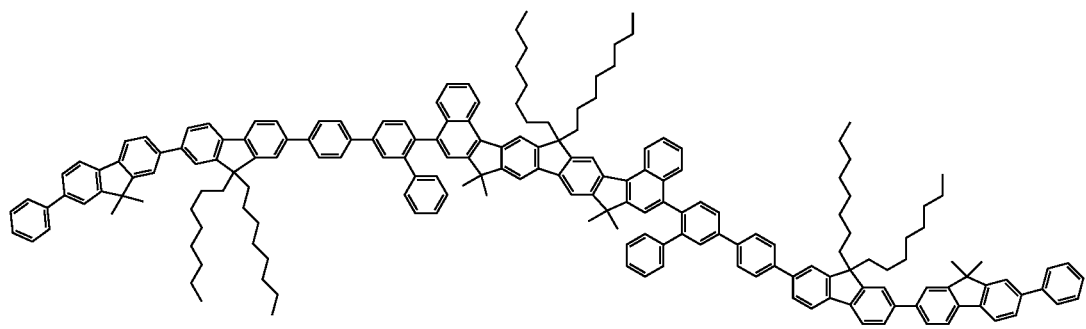
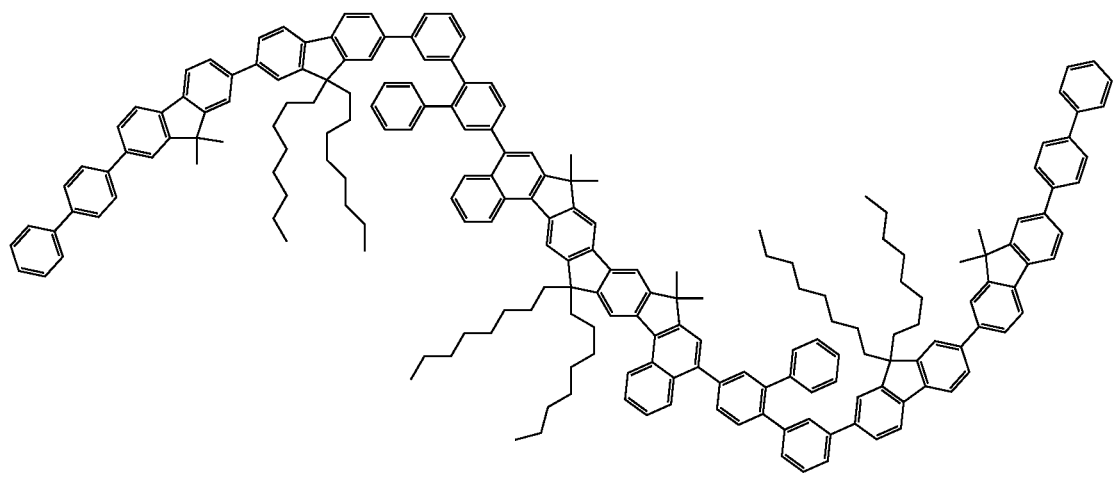
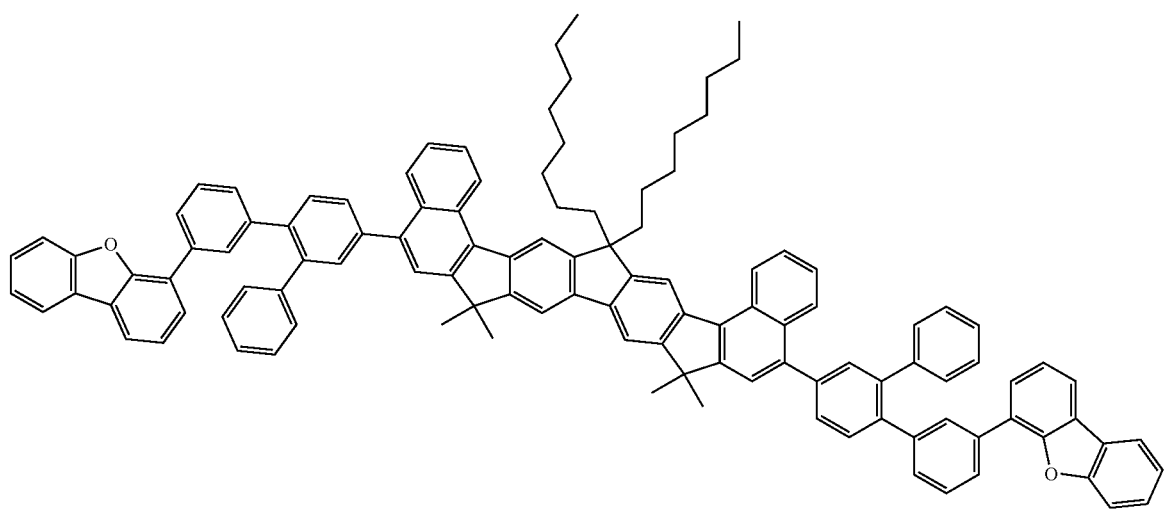

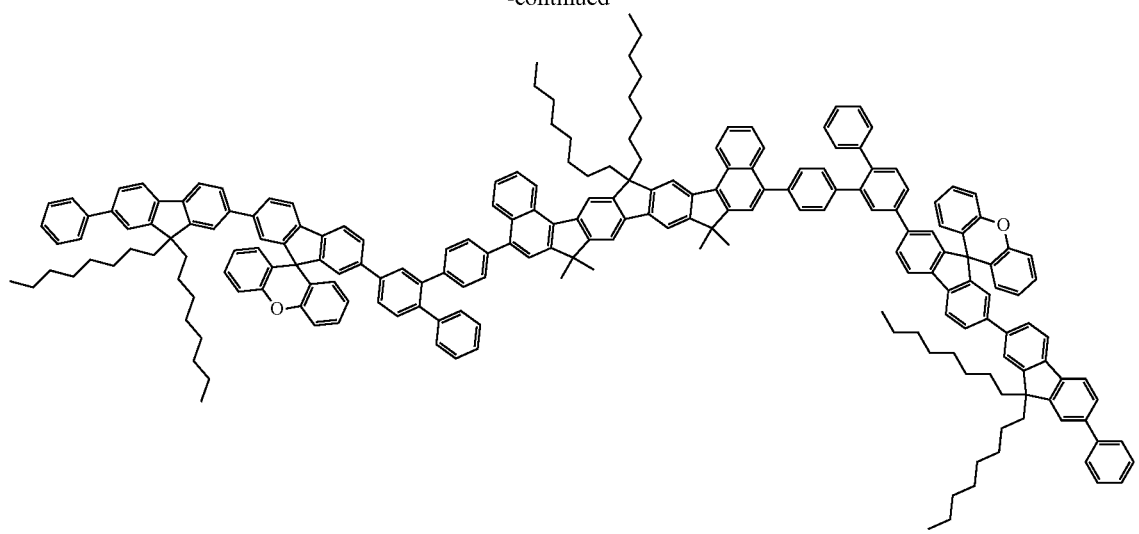
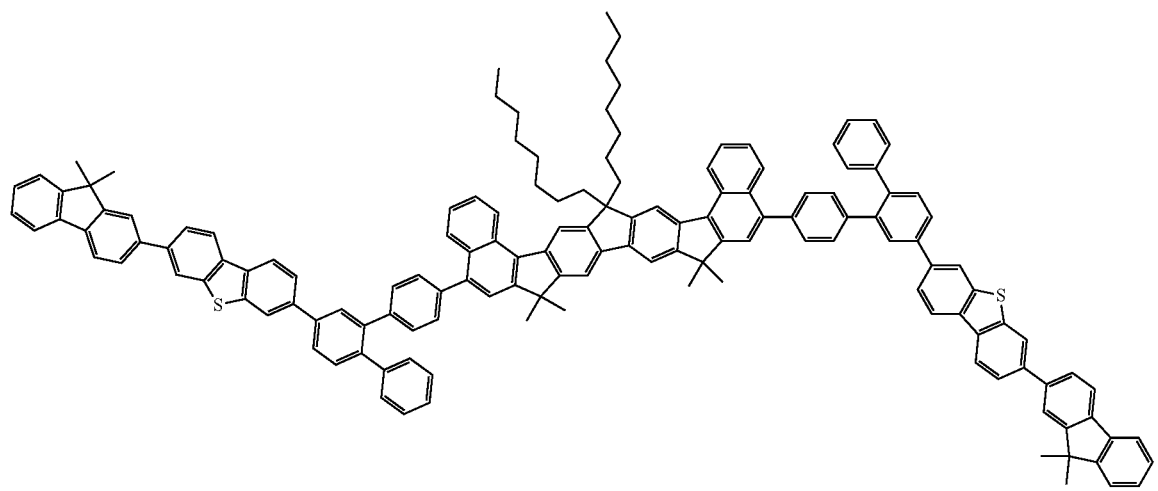
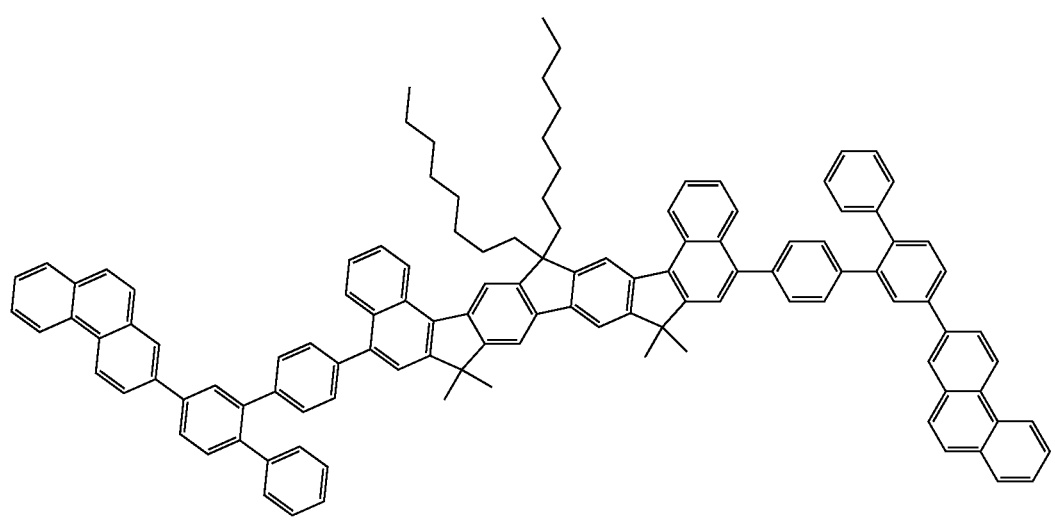

-continued
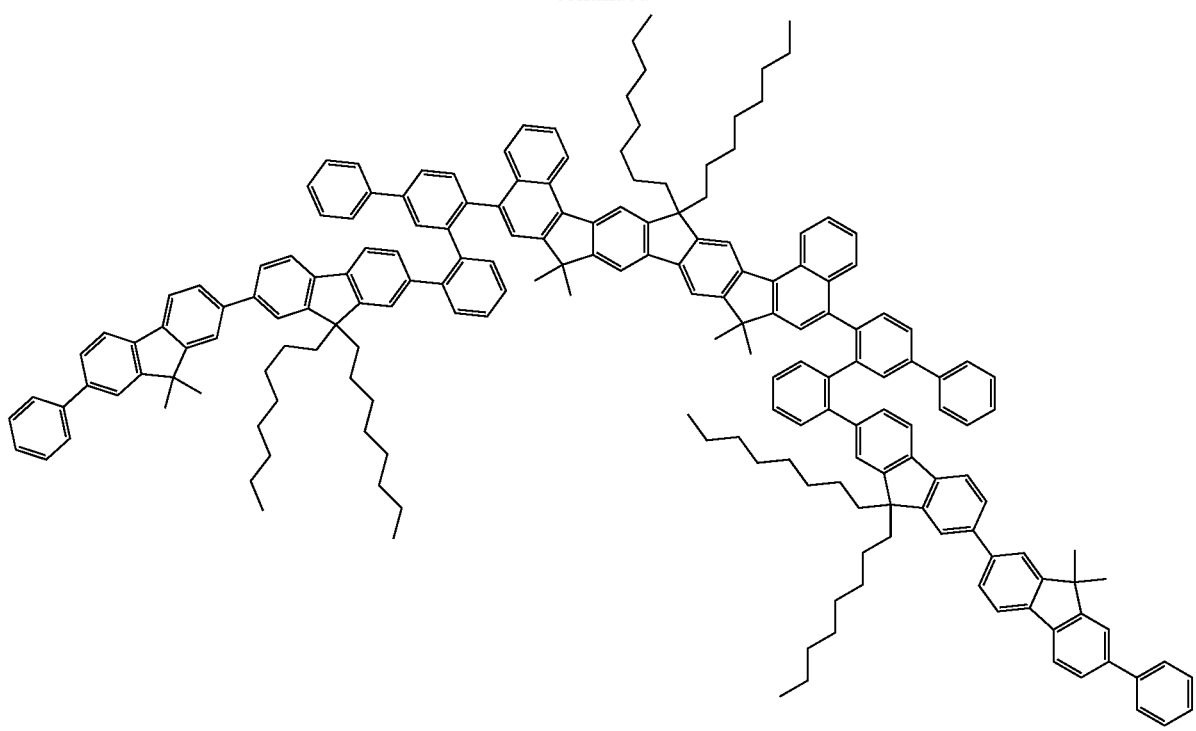
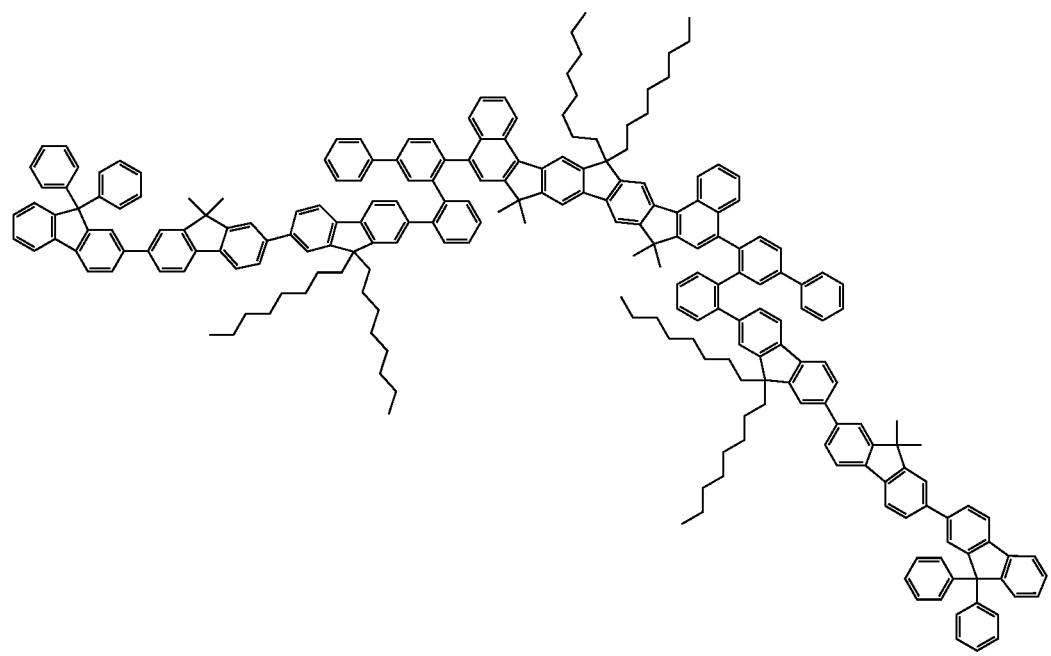

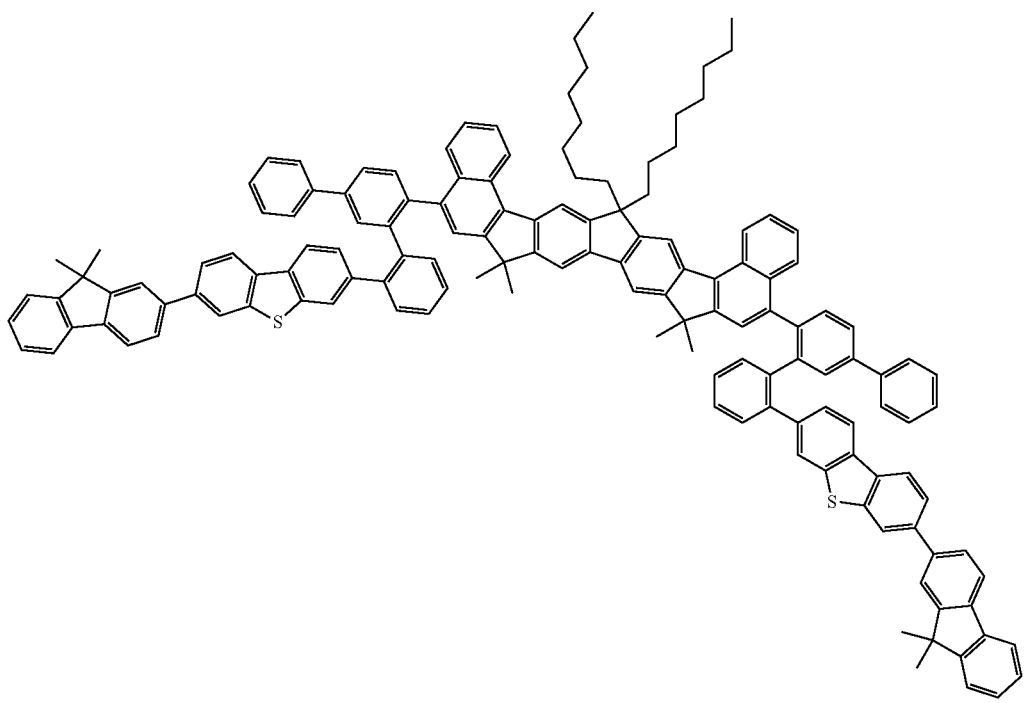
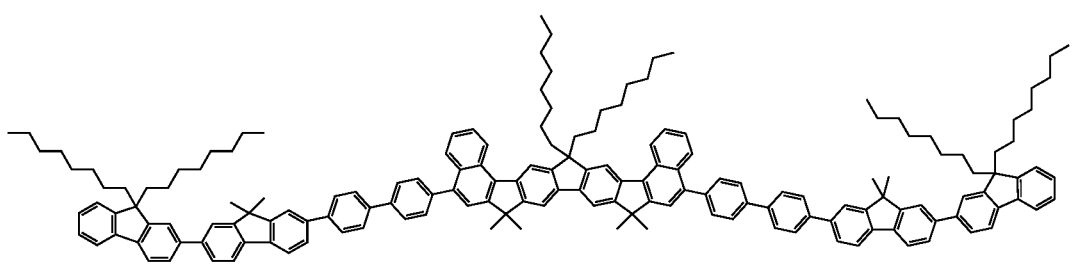
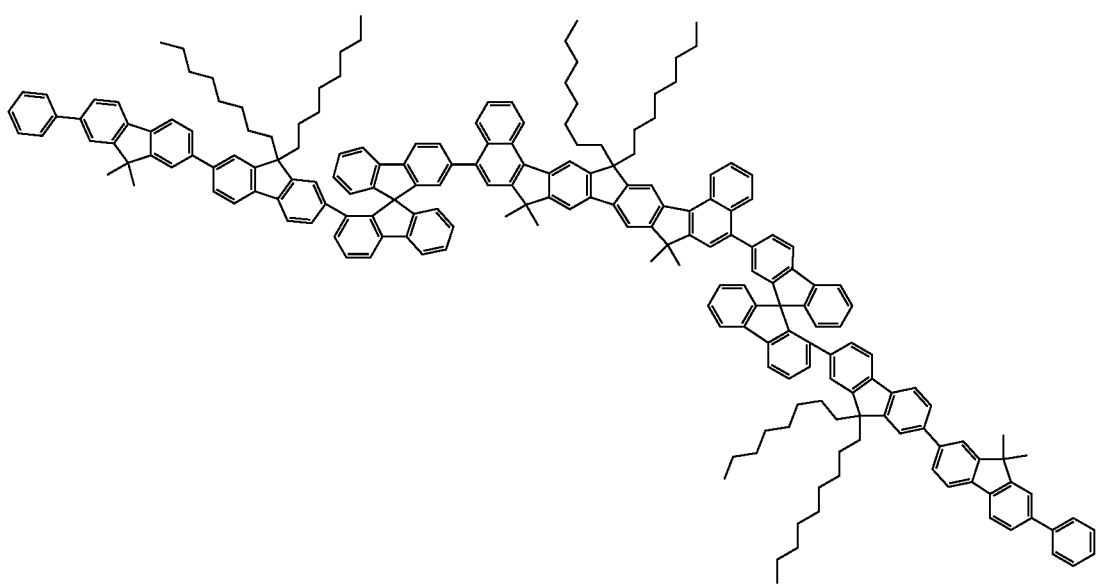

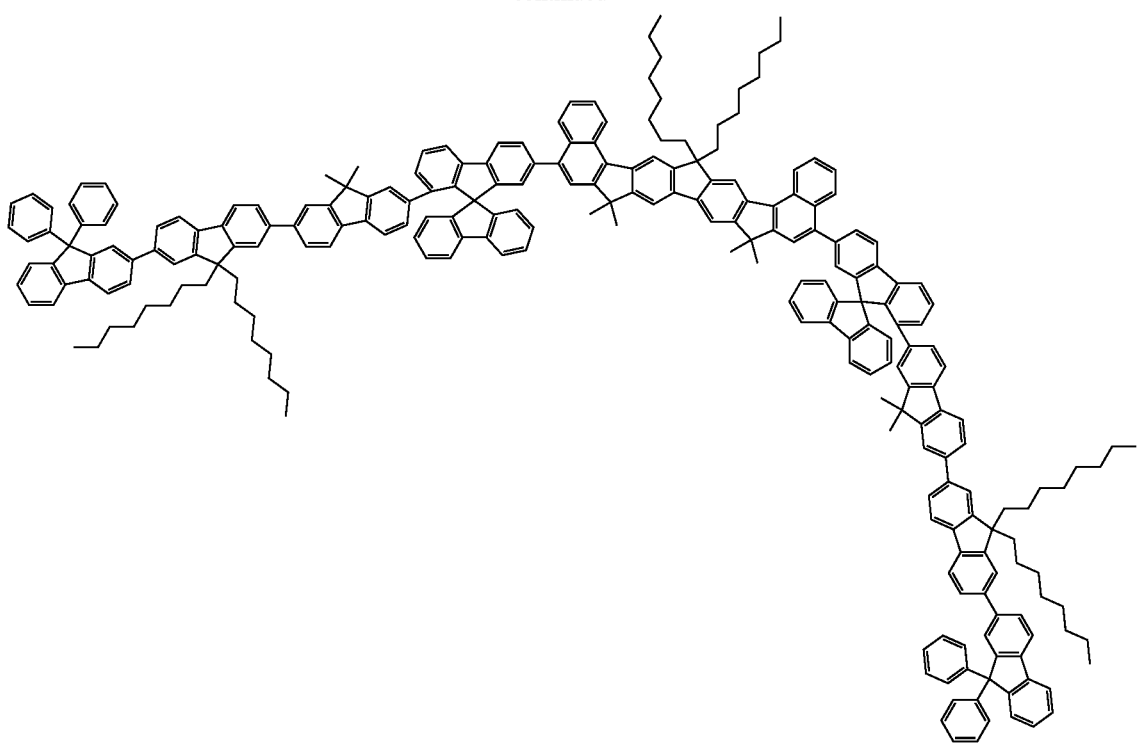
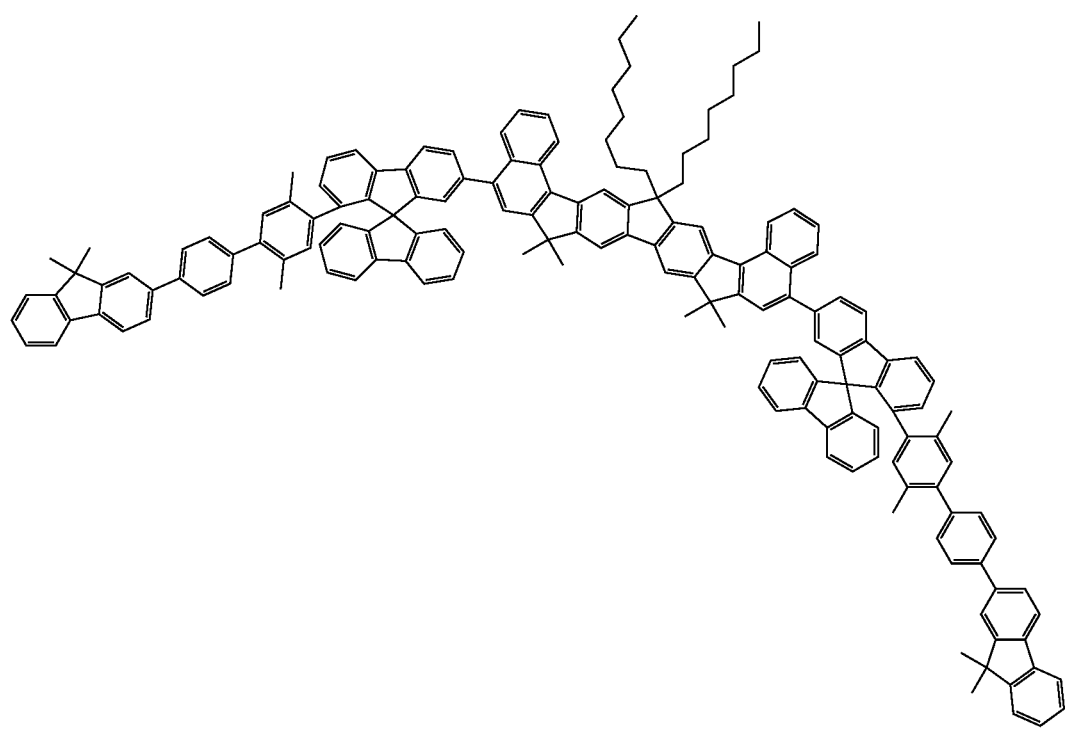

-continued
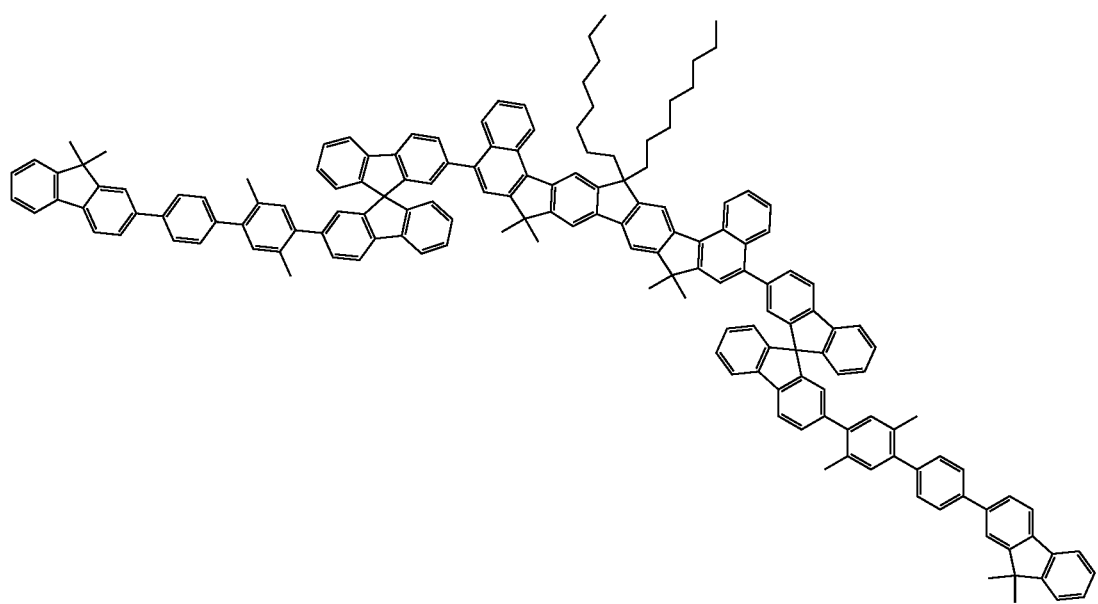
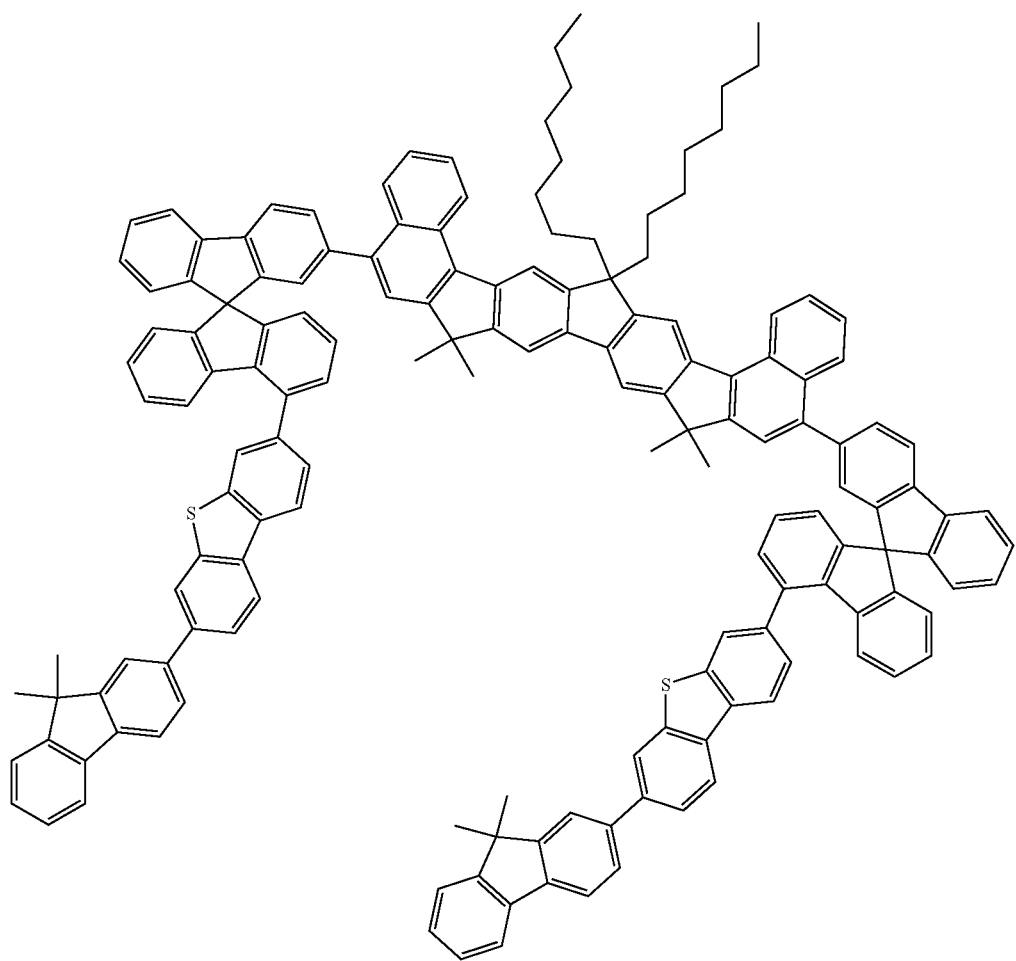

121
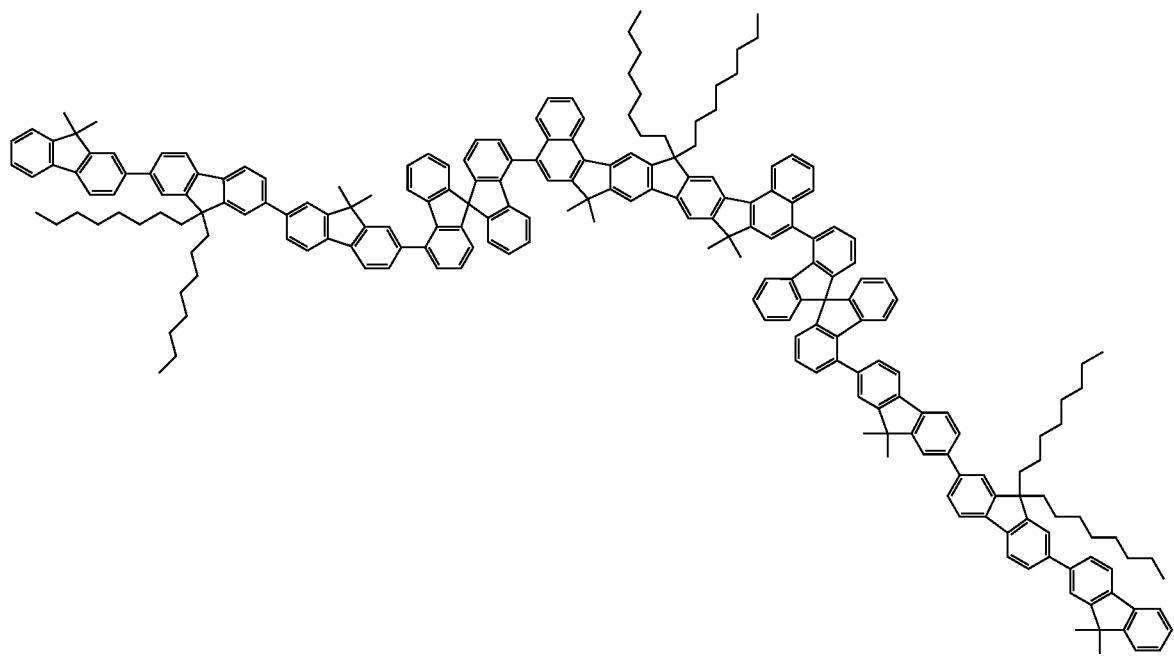
-continued
122
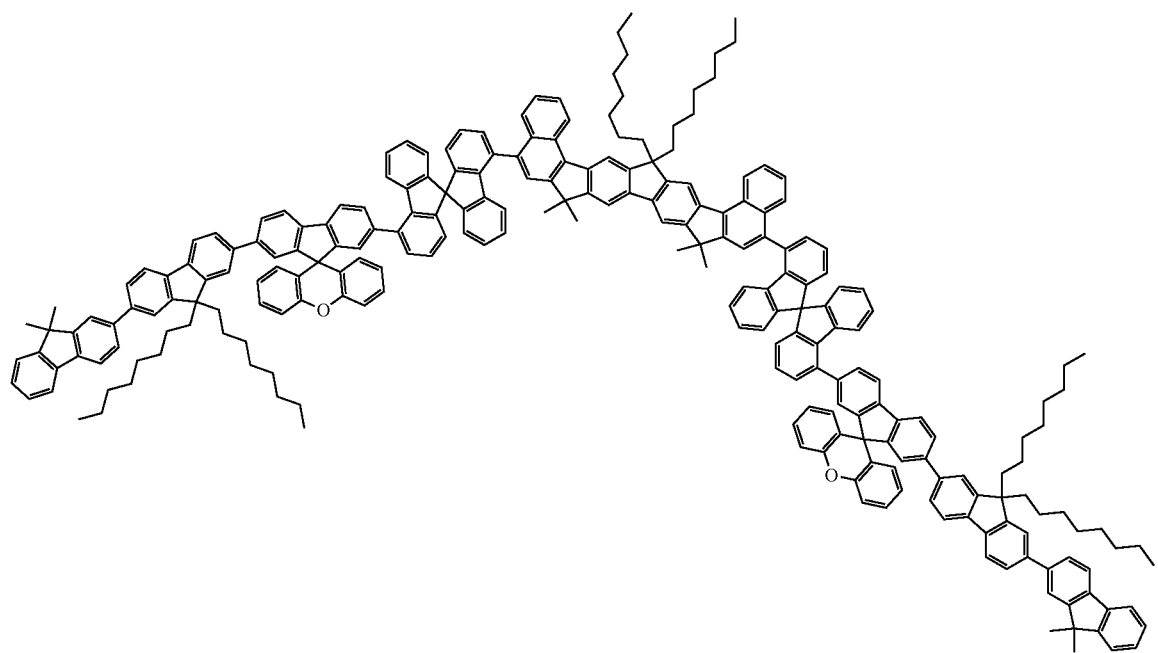

-continued
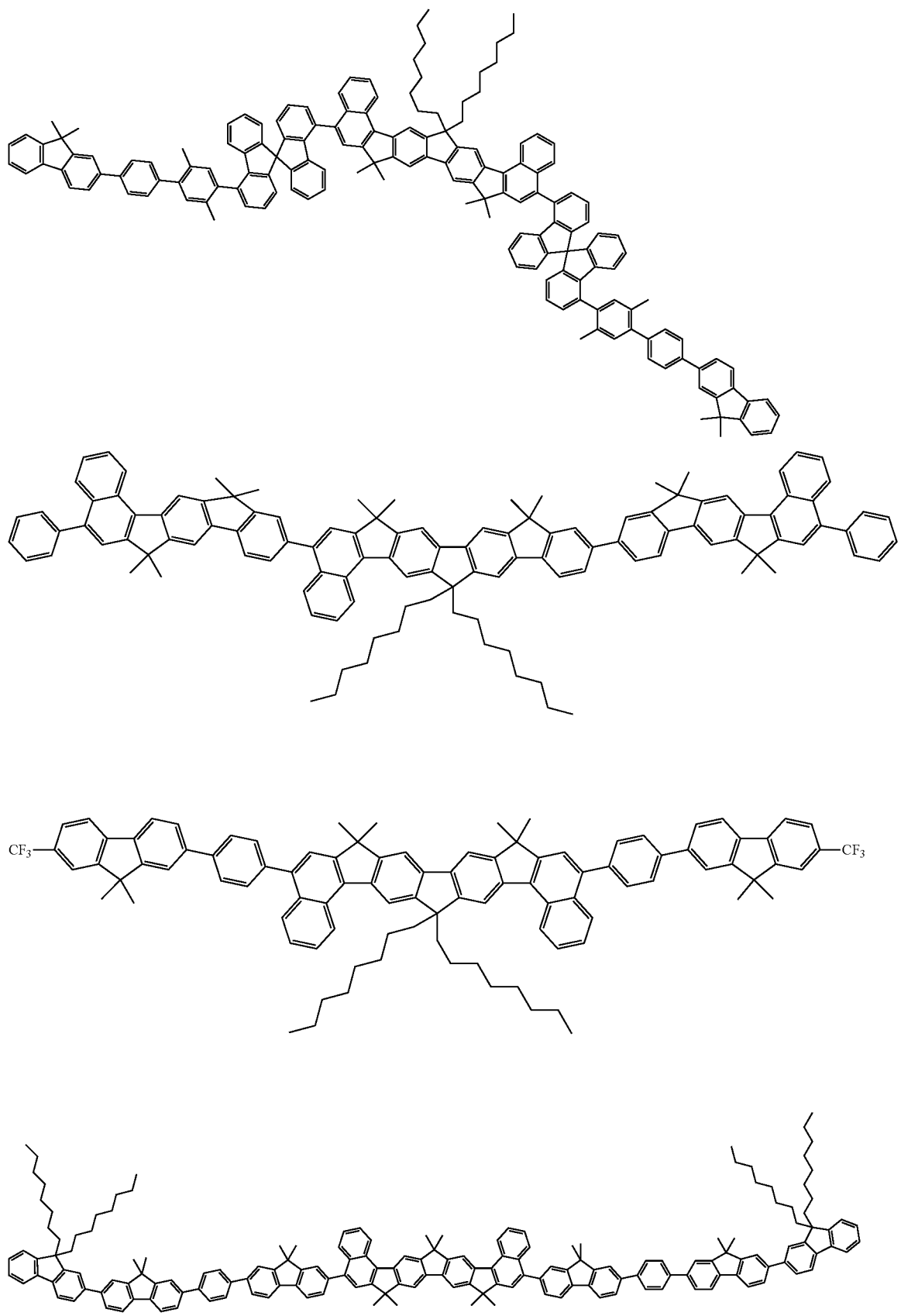

-continued
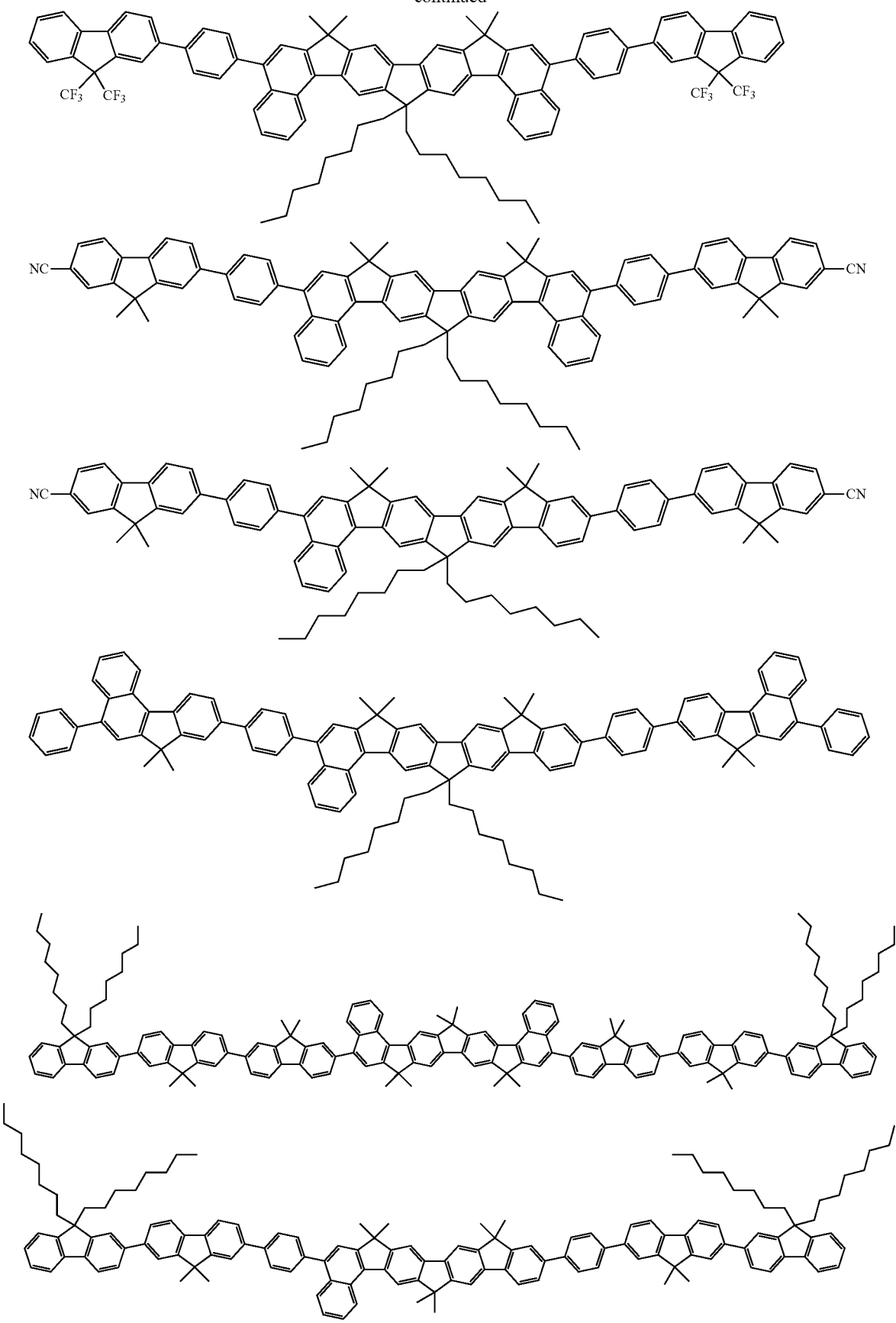

-continued
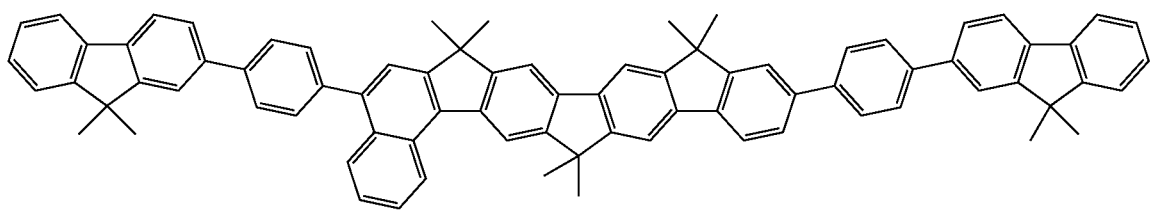
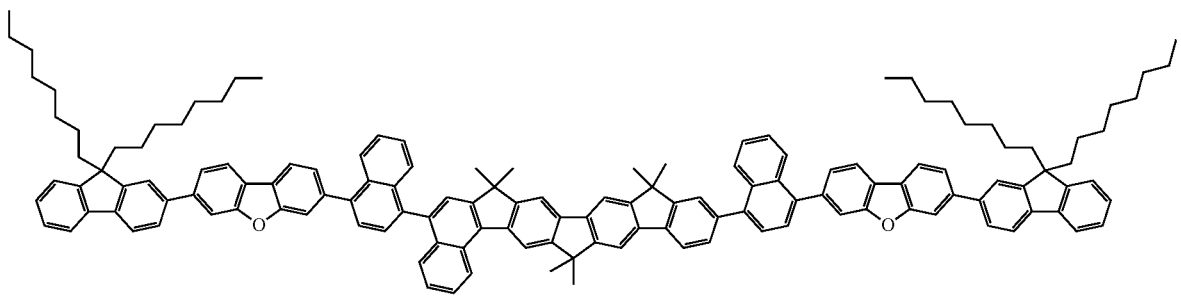
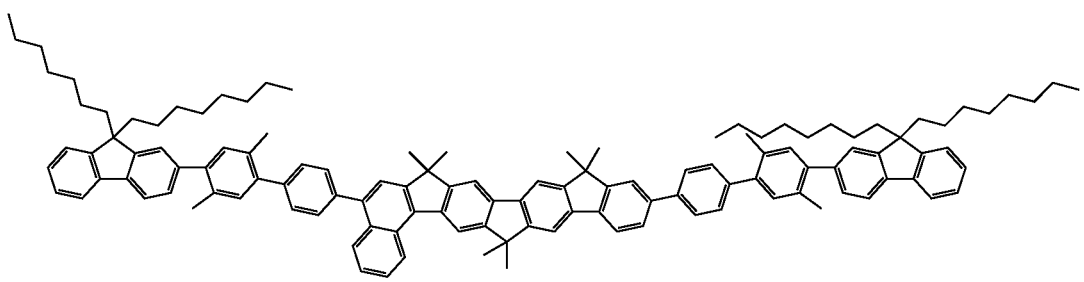
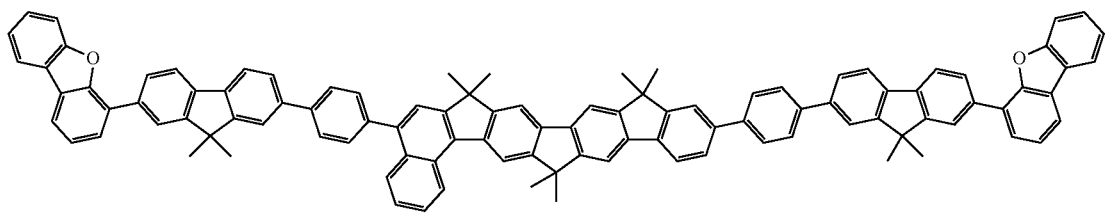
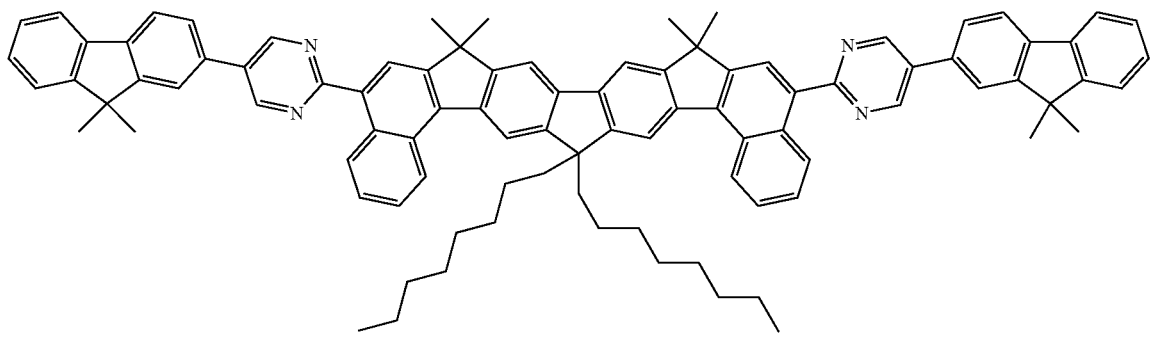

-continued
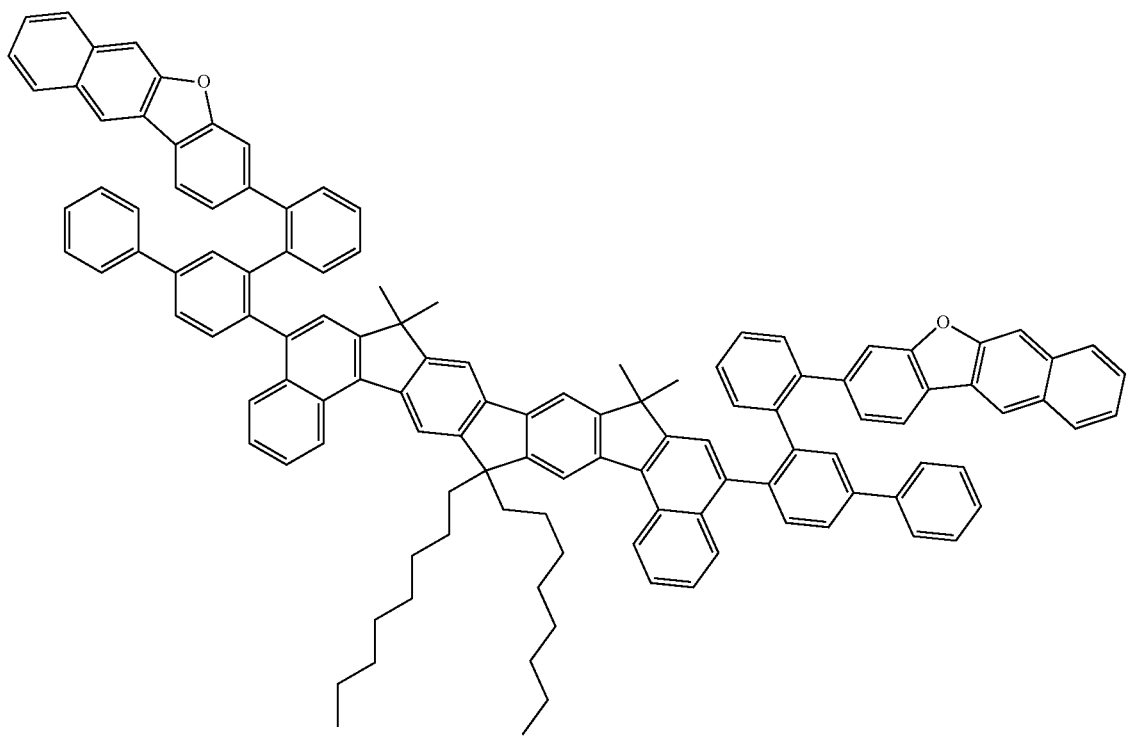
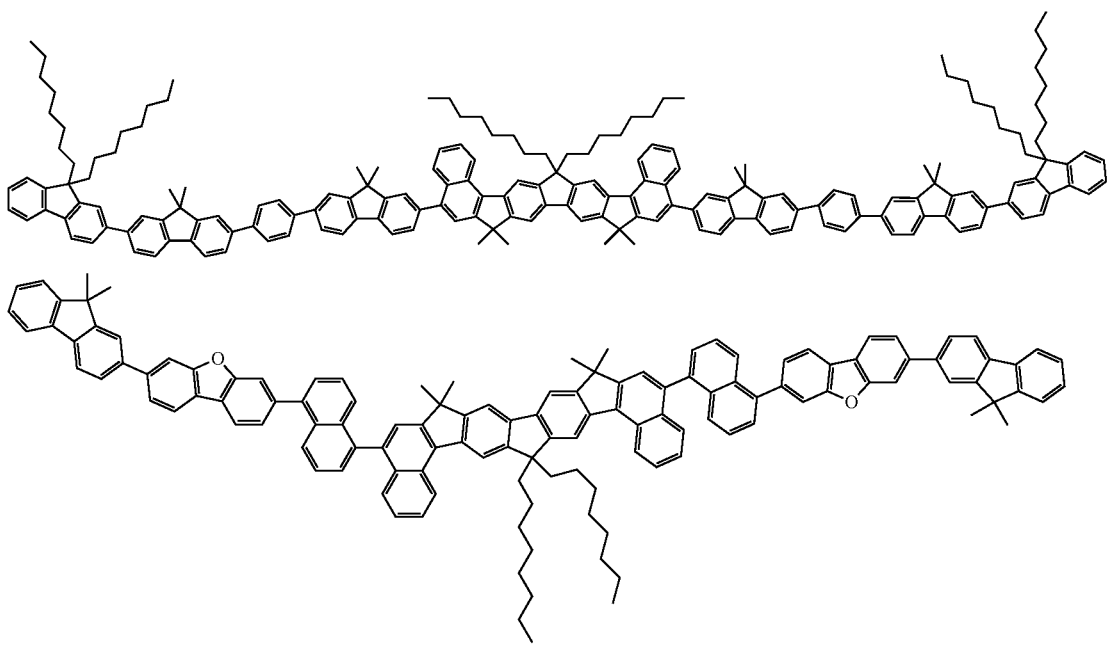
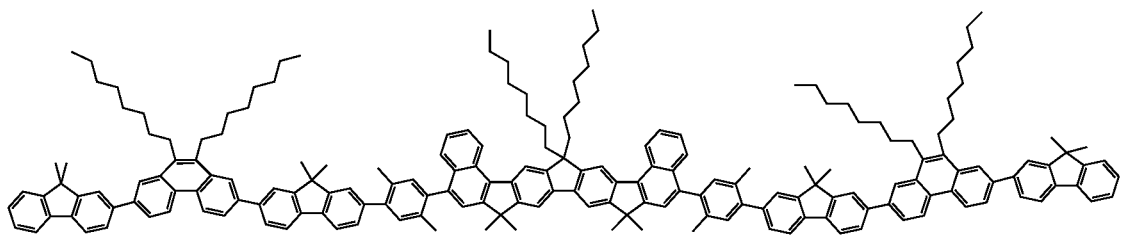

131
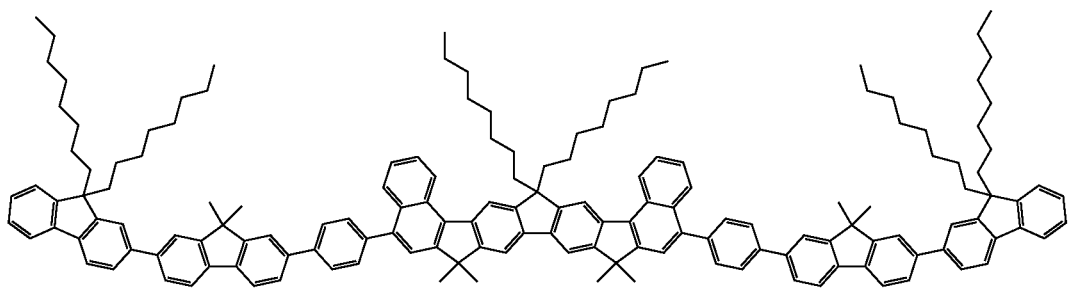
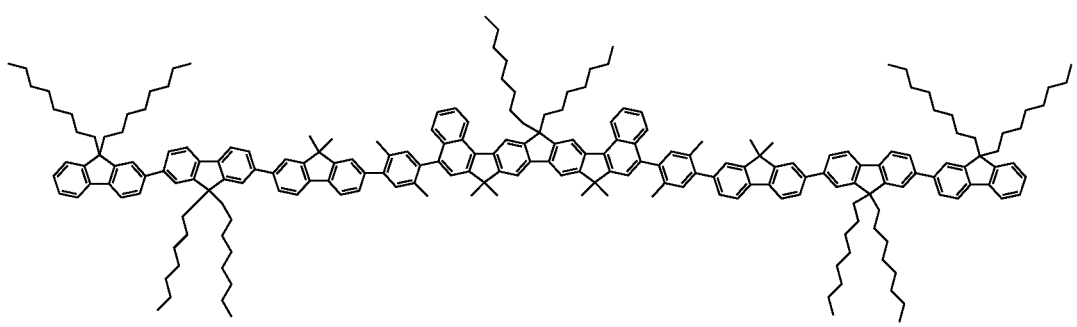
132
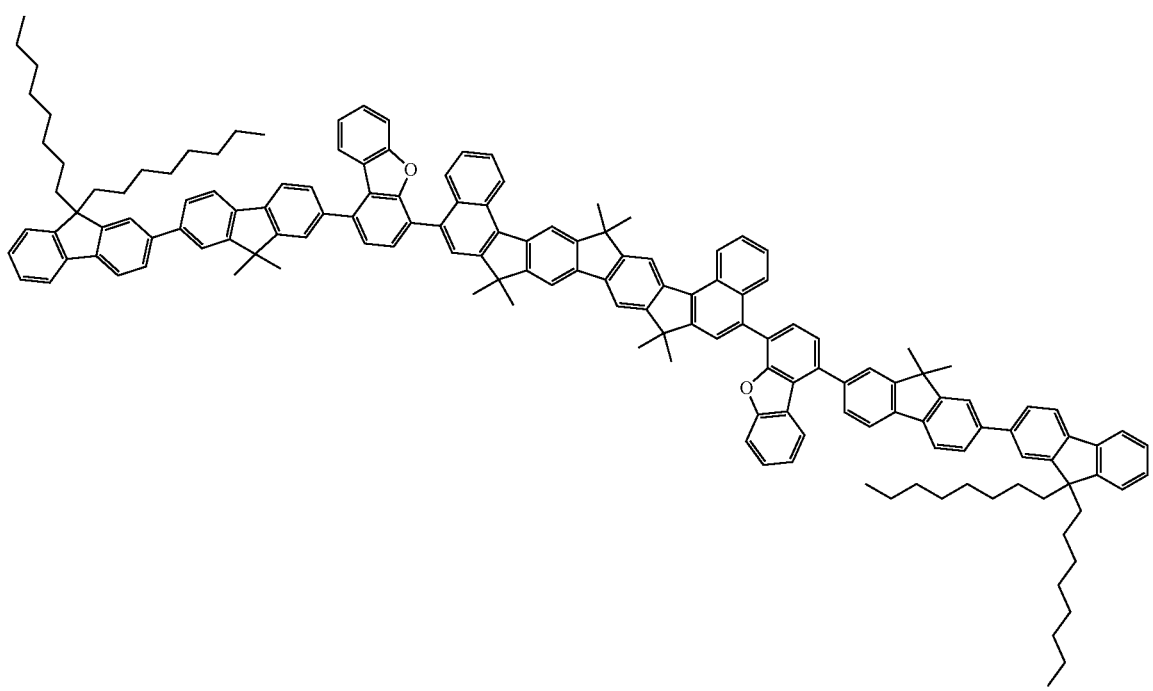

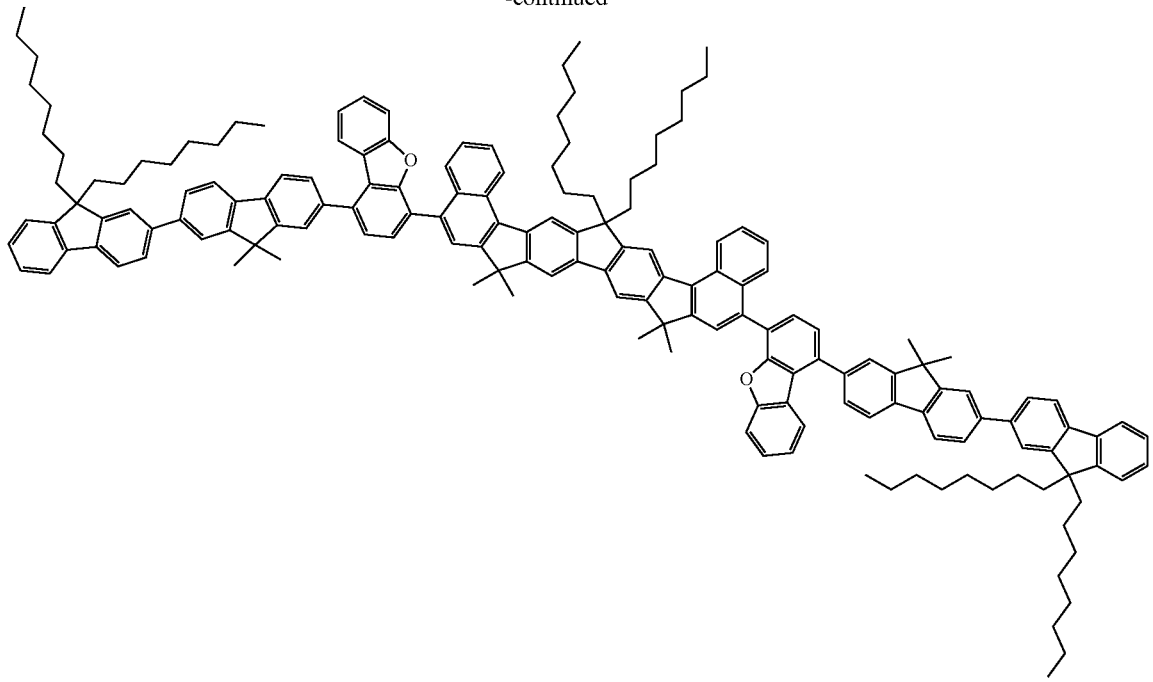

The compounds according to the invention can be prepared, for example, in accordance with the following reaction scheme:

1) First Step According to Scheme 1 or Scheme 2

Scheme 1

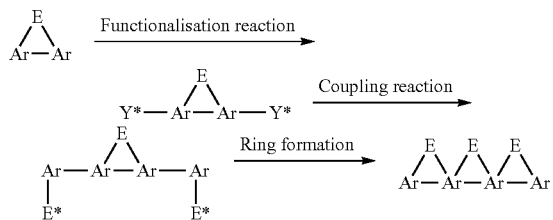

Ar: aromatic or heteroaromatic group
E: bridging group
E*: precursor of the bridging group
Y*: reactive group like Cl, Br, I Reactive groups are introduced in a starting compound, which is commercially available in many cases, for example by bromination, or by bromination and subsequent boronation. Subsequently, two other aromatic groups are introduced via a double coupling reaction, for example a Suzuki coupling reaction. These other aromatic groups contain a functional group E*, which can form a ring comprising the bridging group E.

Alternatively, as shown in scheme 2, one can start from a compound which already contains two bridging groups E. A process for the preparation of such compounds is known form the skilled person, for example from WO 2008/006449. The subsequent steps are the same as in scheme 1.

Scheme 2

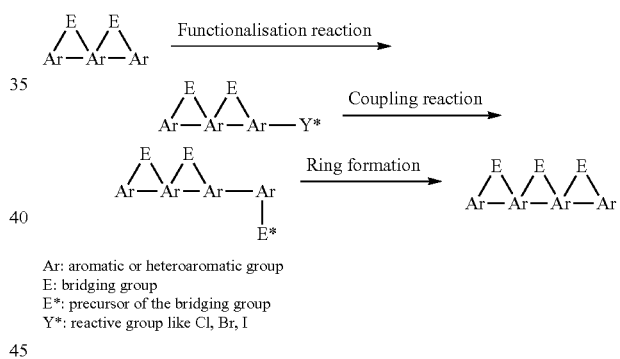

Ar: aromatic or heteroaromatic group
E: bridging group
E*: precursor of the bridging group
Y*: reactive group like Cl, Br, I 2) Second Step According to Scheme 3

Scheme 3

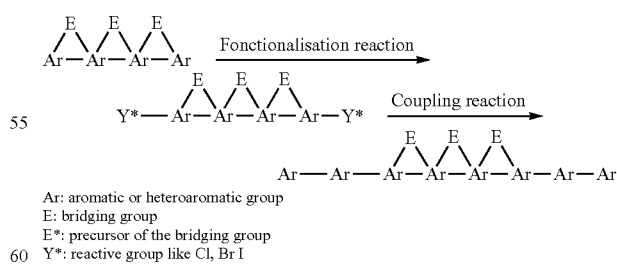

Ar: aromatic or heteroaromatic group
E: bridging group
E*: precursor of the bridging group
Y*: reactive group like Cl, Br I The compound obtained in step 1 is further functionalized (introduction of reactive groups via bromination or via bromination and subsequent boronation), so that two other aromatic groups are introduced via a double coupling reaction, for example a Suzuki coupling reaction.

The application therefore relates to a process for the preparation of a compound of the formula 1, characterized in that it
a) at least one coupling reaction occurs, preferably via a transition metal-catalyzed coupling reaction, more preferably via a Suzuki coupling reaction;
b) a ring formation reaction occurs;
c) at least two further coupling reaction occur, preferably via a transition metal-catalyzed coupling reaction, more preferably via a Suzuki coupling reaction.

The compounds according to the invention described above, in particular compounds which are substituted by reactive leaving groups, such as bromine, iodine, chlorine, boronic acid or boronic acid ester, can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (1), where the bond(s) to the polymer, oligomer or dendrimer may be localised at any desired positions in formula (1) that are substituted by $R^1$. Depending on the linking of the compound of the formula (1), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (1) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (1) may be linked via a trivalent or polyvalent group, for example via a trivalent or polyvalent aromatic or heteroaromatic group, to form a branched or dendritic oligomer or polymer.

The same preferences as described above for compounds of the formula (1) apply to the recurring units of the formula (1) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 1992/18552), carbazoles (for example in accordance with WO 04/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers and oligomers according to the invention are generally prepared by polymerisation of one or more types of monomer, at least one monomer of which results in recurring units of the formula (1) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, □-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (1) or at least one polymer, oligomer or dendrimer containing at least one unit of the formula (1), and at least one solvent, preferably an organic solvent. The way in which solutions of this type can be prepared is known to the person skilled in the art and is described, for example, in WO 2002/072714, WO 2003/019694 and the literature cited therein.

The compounds according to the invention are suitable for use in electronic devices, in particular in organic electroluminescent devices (OLEDs). Depending on the substitution, the compounds are employed in different functions and layers.

The compounds according to the invention can be employed in any function in the organic electroluminescent device, for example as emitting material, as matrix material, as hole-transporting material or as electron-transporting material. Preference is given to the use as emitting material, preferably as fluorescent emitting material, in an emitting layer of an organic electroluminescent device and the use as matrix material in an emitting layer, preferably a fluorescent emitting layer.

The invention therefore furthermore relates to the use of a compound of the formula (1) in an electronic device. The electronic device here is preferably selected from the group consisting of organic integrated circuits (ICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates to an electronic device comprising at least one compound of the formula (1). The electronic device here is preferably selected from the devices indicated above. Particular preference is given to an organic electroluminescent device comprising anode, cathode and at least one emitting layer, characterised in that at least one organic layer comprises at least one organic compound of the formula (1). Very particular preference is given to an organic electroluminescent device comprising anode, cathode and at least one emitting layer comprising at least one organic compound of the formula (1).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device is preferably the following:
anode-hole-injection layer-hole-transport layer-emitting layer-electron-transport layer-electron-injection layer-cathode. It is not necessary for all of the said layers to be resent here, and in addition further layers may be present, for example an electron-blocking layer adjacent to the emitting layer on the anode side, or a hole-blocking layer adjacent to the emitting layer on the cathode side.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (1) and where the three layers exhibit blue, green and orange or red emission (for the basic structure see, for example, WO 2005/011013). It should be noted that, for the generation of white light, an emitter compound used individually which emits in a broad wavelength range may also be suitable instead of a plurality of emitter compounds emitting in colour. The compounds according to the invention may alternatively and/or additionally also be present in the hole-transport layer or in another layer in an organic electroluminescent device of this type.

The compound according to the invention is particularly suitable for use as matrix compound for an emitter compound, preferably a blue-emitting emitter compound, or as emitter compound, preferably as blue-emitting emitter compound.

The compound according to the invention is preferably employed as emitting compound in an emitting layer. In this case, it is preferably employed in combination with one or more matrix materials. The preferred proportions of emitting compound and matrix material here are as indicated below.

The compound according to the invention can also be used as matrix compound for emitter compounds. Preference is given to the use as matrix compound for fluorescent emitter compounds. However, the compound according to the invention can also be used as matrix compound for emitter compounds which exhibit thermally activated delayed fluorescence (TADF). The basic principles of the emission mechanism in TADF are disclosed in H. Uoyama et al., Nature 2012, 492, 234.

If the compound according to the invention is employed as matrix material, it can be employed combined with any desired emitting compounds known to the person skilled in the art. It is preferably employed in combination with the preferred emitting compounds indicated below, particularly the preferred fluorescent compounds indicated below.

In the case where the emitting layer of the organic electroluminescent device comprises a mixture of an emitting compound and a matrix compound, the following applies:

The proportion of the emitting compound in the mixture of the emitting layer is preferably between 0.1 and 50.0%, particularly preferably between 0.5 and 20.0%, and very particularly preferably between 1.0 and 10.0%. Correspondingly, the proportion of the matrix material or matrix materials is preferably between 50.0 and 99.9%, particularly preferably between 80.0 and 99.5%, and very particularly preferably between 90.0 and 99.0%.

The indications of the proportions in % in the context of the present application are taken to mean % by vol. if the compounds are applied from the gas phase, and they are taken to mean % by weight if the compounds are applied from solution.

The compound according to the invention can furthermore also be employed as electron-transporting compound in an electron-transport layer, a hole-blocking layer or an electron-injection layer. For this purpose, it is preferred for the compound according to the invention to contain one or more substituents selected from electron-deficient heteroaryl groups, such as, for example, triazine, pyrimidine or benzimidazole.

Generally preferred classes of material for use as corresponding functional materials in the organic electroluminescent devices according to the invention are indicated below.

Suitable phosphorescent emitting compounds are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitting compounds used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent emitting compounds described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able, without inventive step, to employ further phosphorescent complexes in combination with the compounds according to the invention in OLEDs.

Preferred fluorescent emitters, besides the compounds according to the invention, are selected from the class of the arylamines. An arylamine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrenarylamines disclosed in WO 2012/048780 and WO 2013/185871. Preference is likewise given to the benzoindenofluorenamines disclosed in WO 2014/037077, the benzofluorene-amines disclosed in WO 2014/106522 and the extended indenofluorenes disclosed in WO 2014/111269.

Preferred fluorescent emitting compounds, besides the compounds according to the invention, are depicted in the following table:

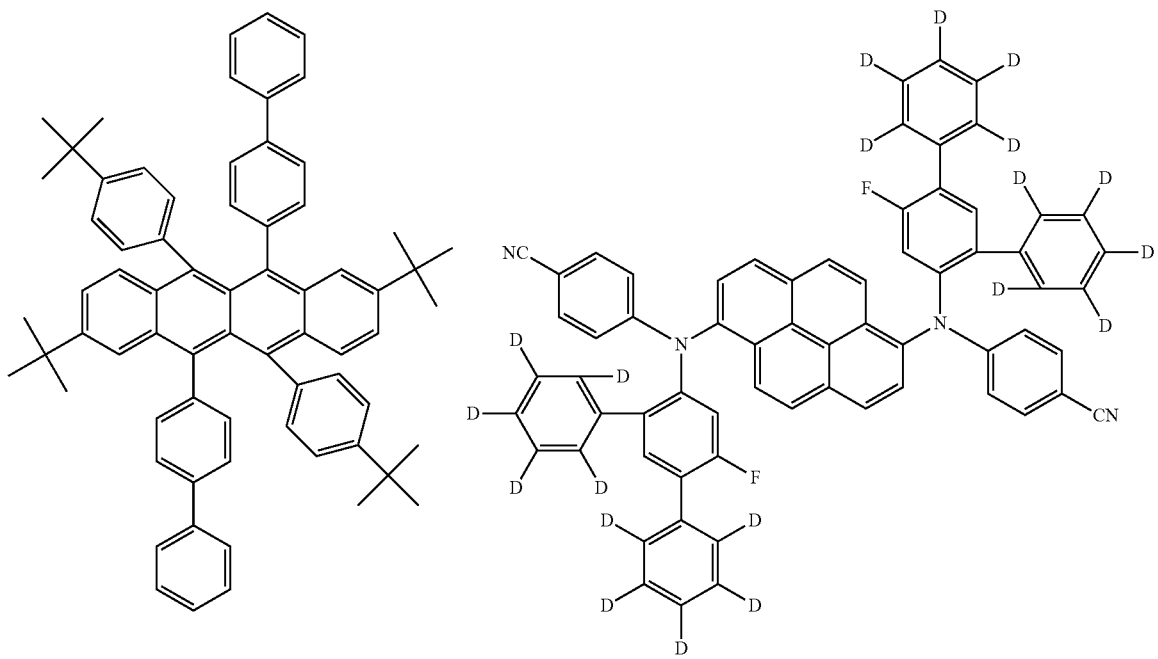

141
-continued
142
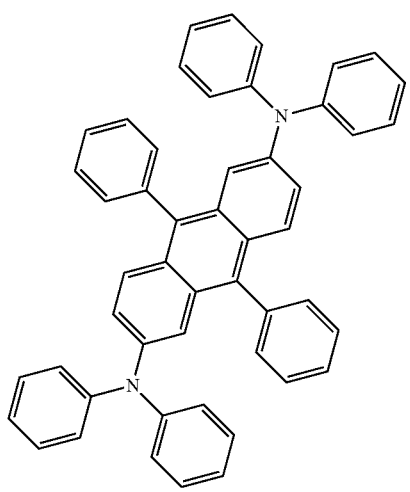
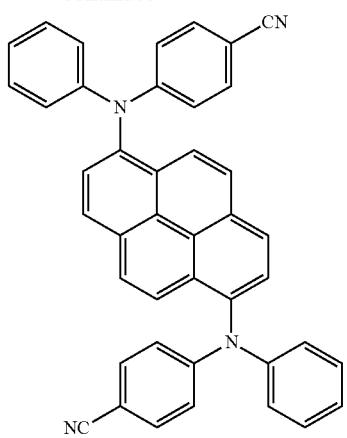
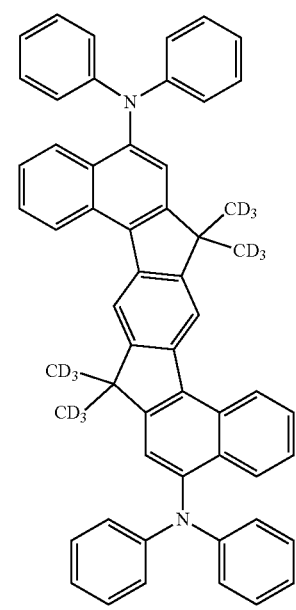
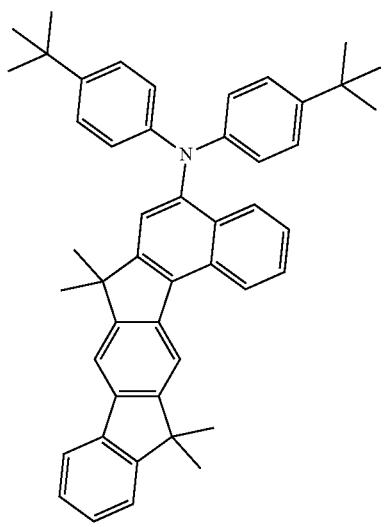
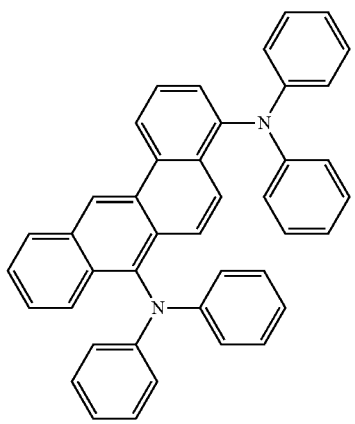
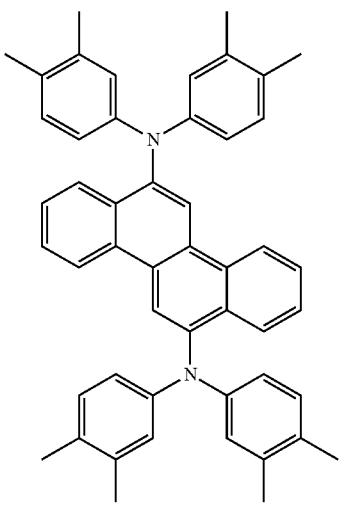
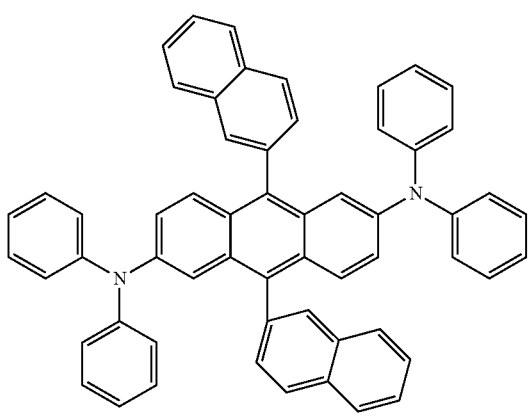

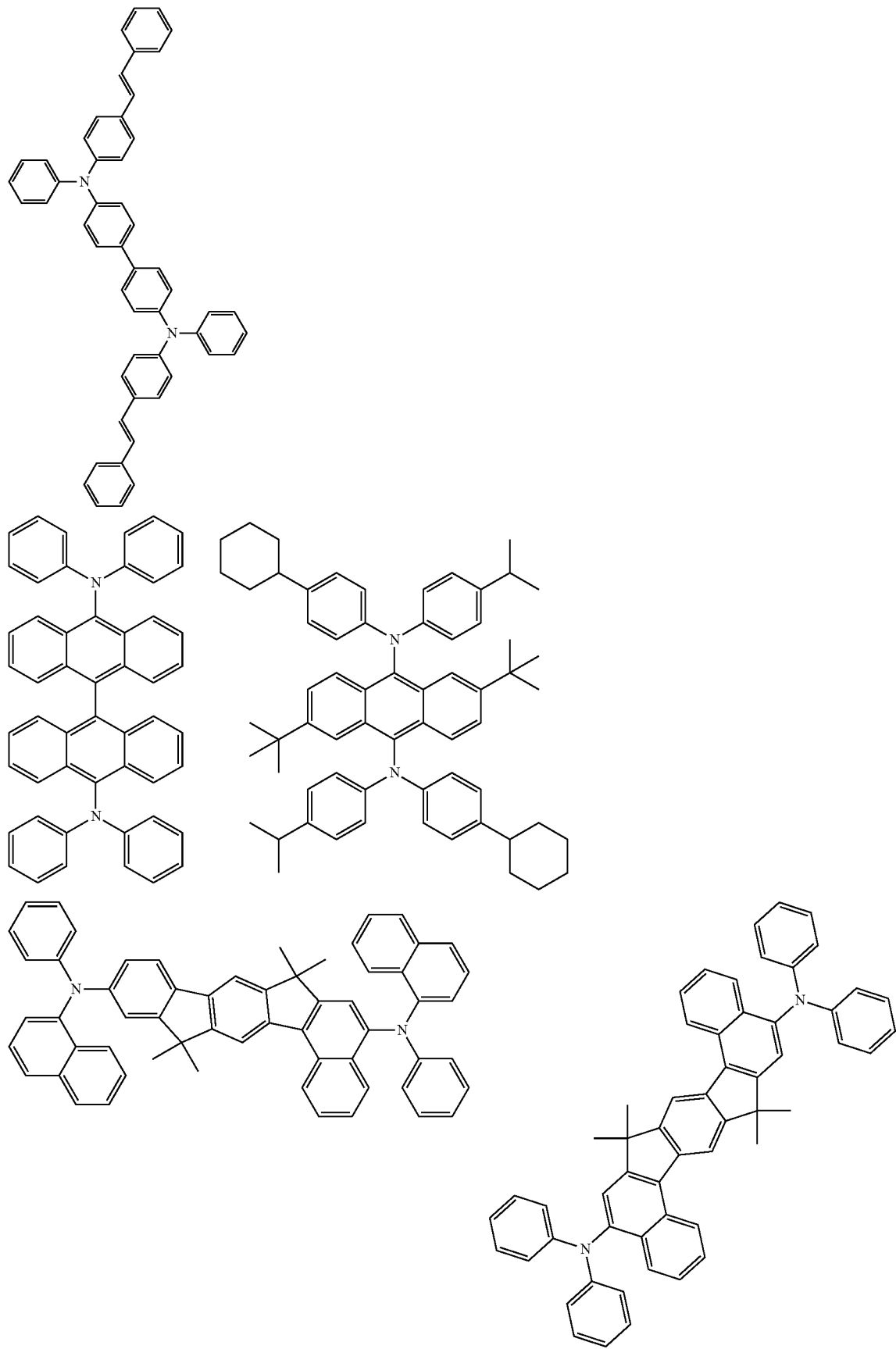

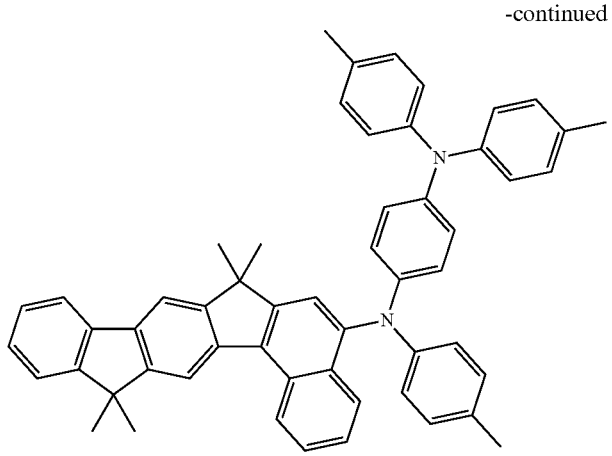
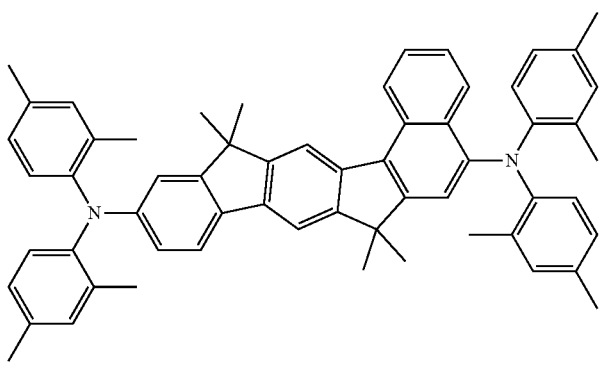
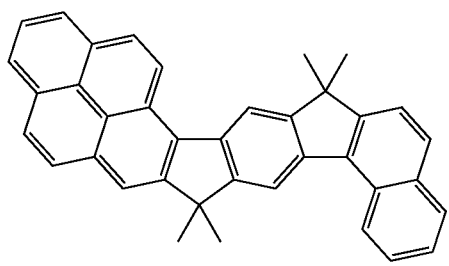
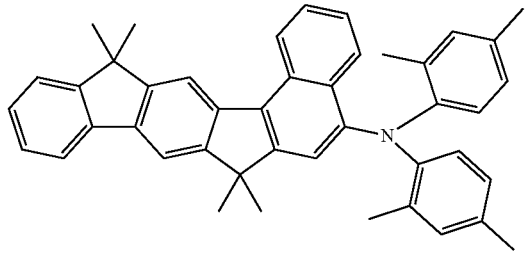
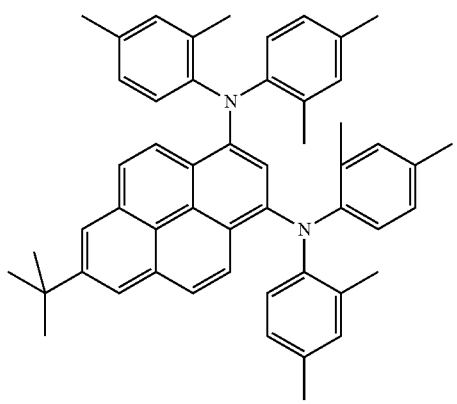

147 148
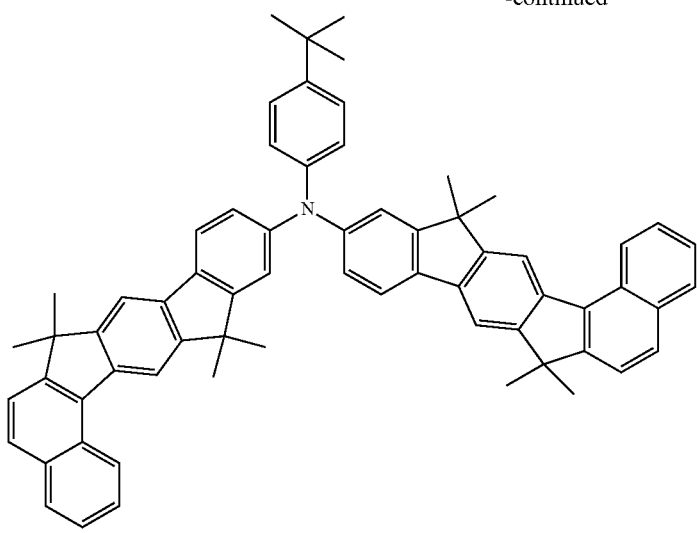
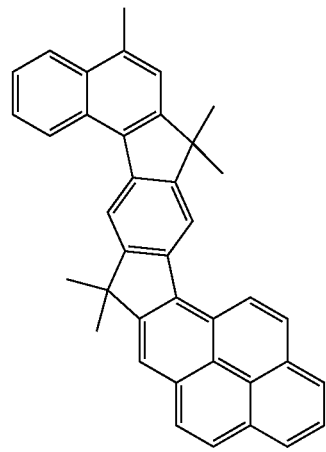
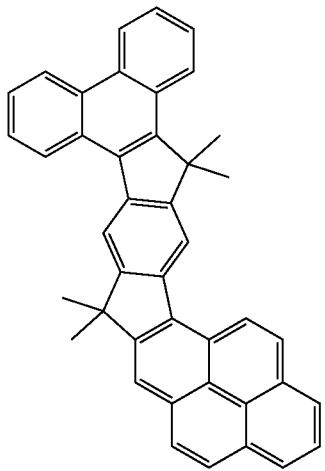
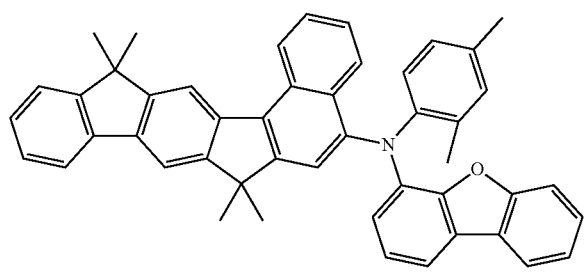
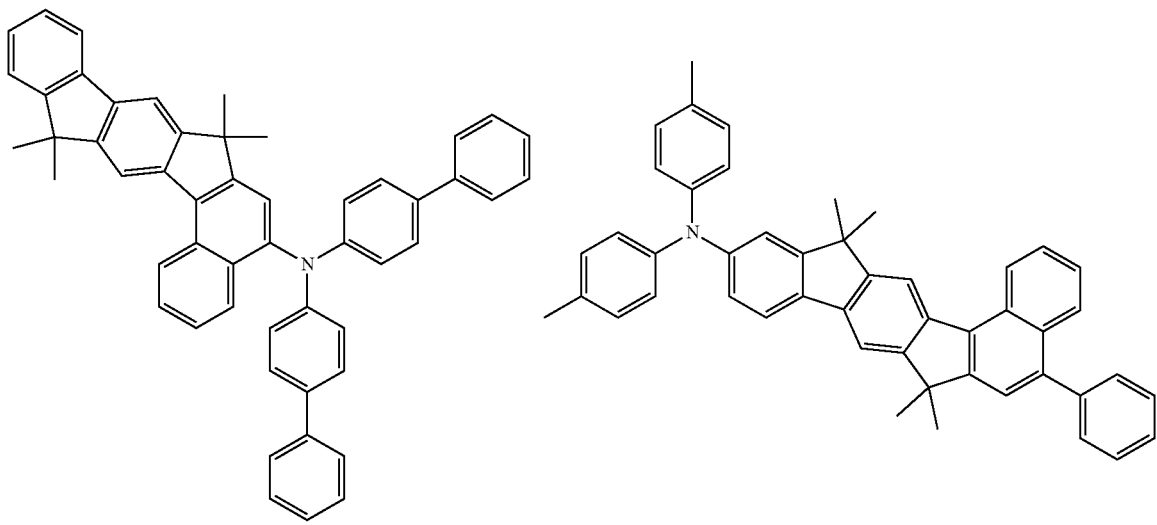

-continued
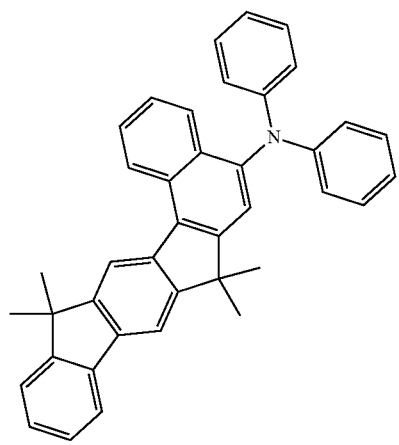
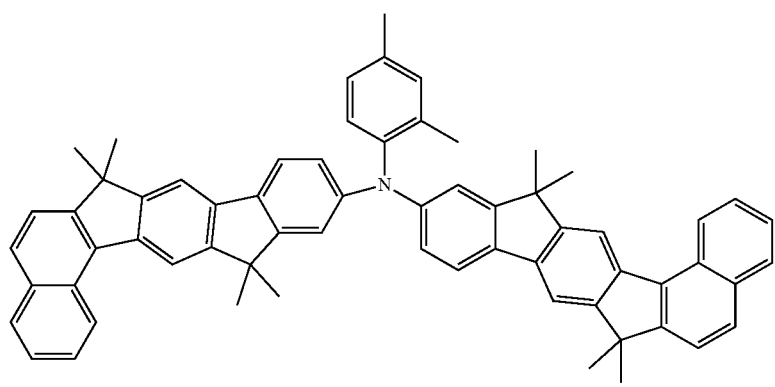
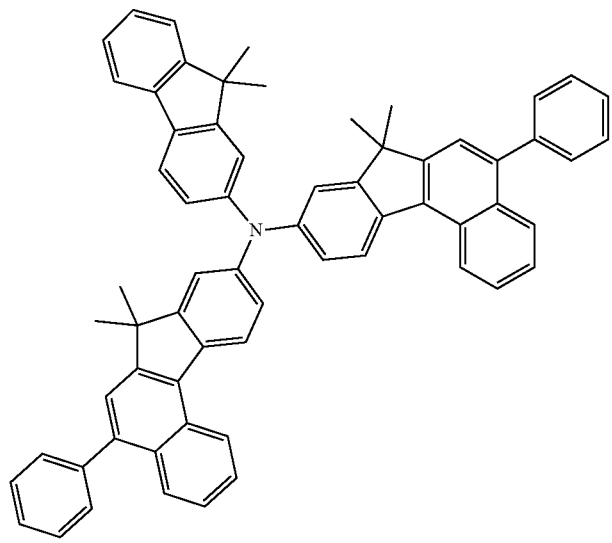

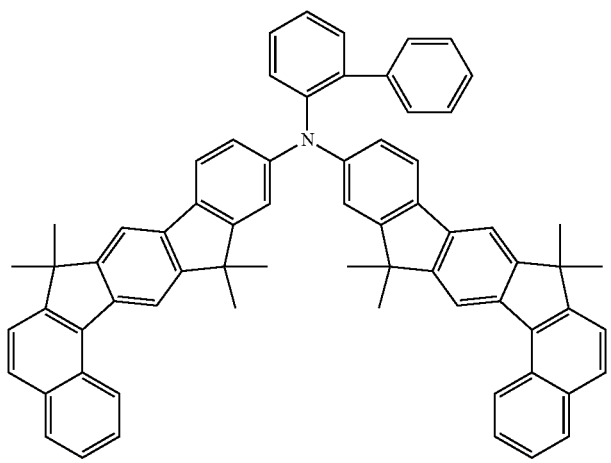
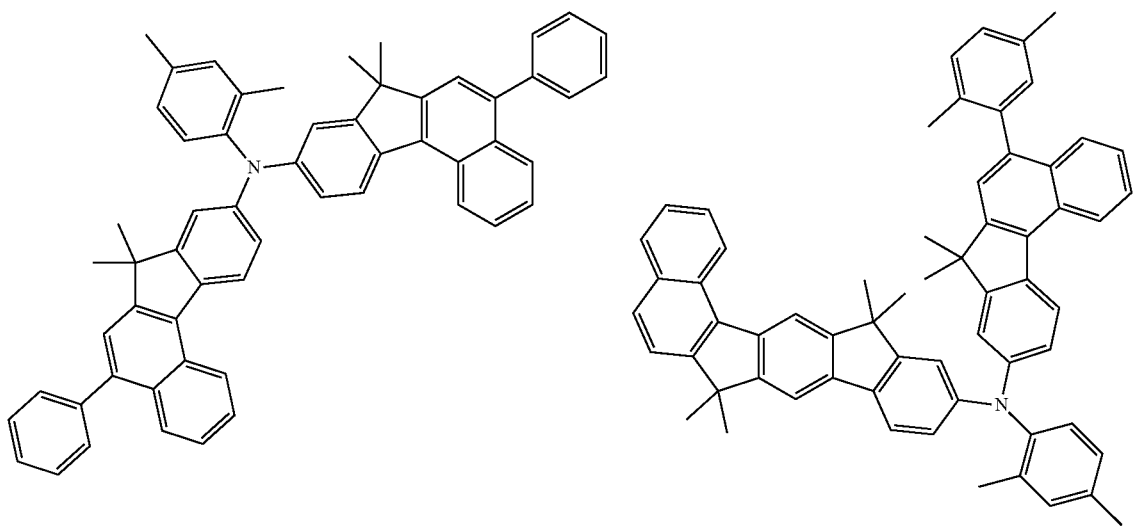
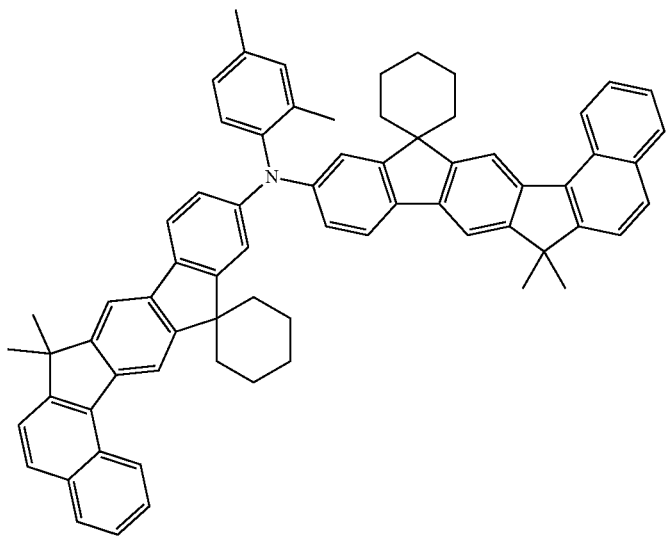

-continued
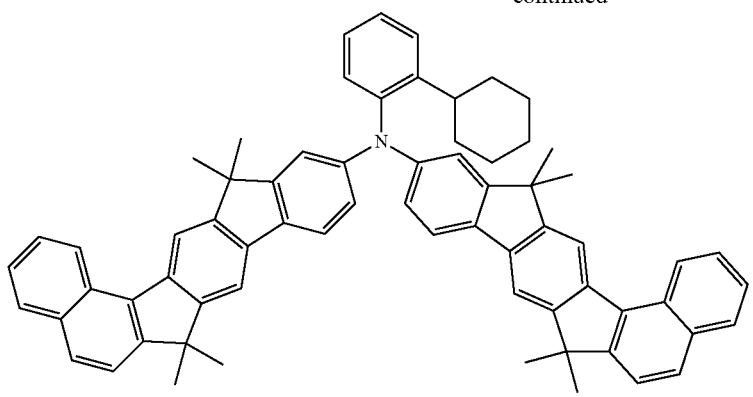
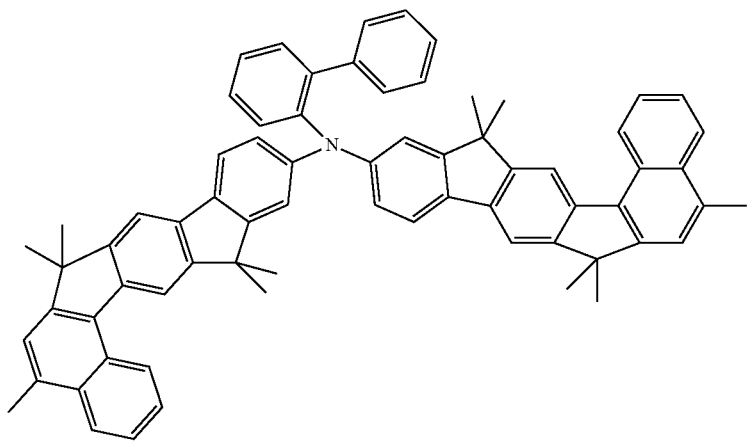
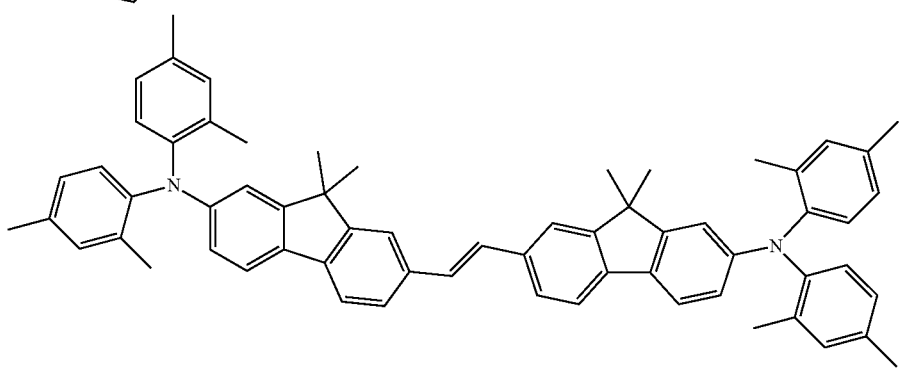
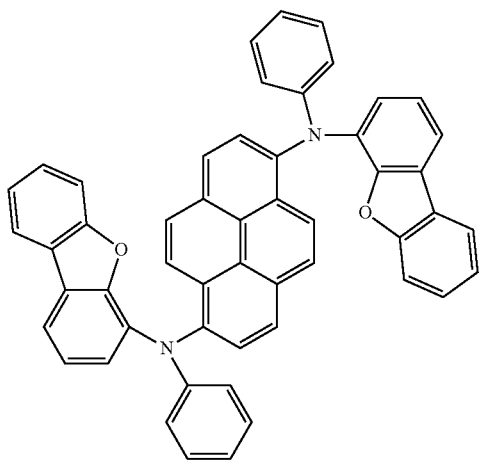
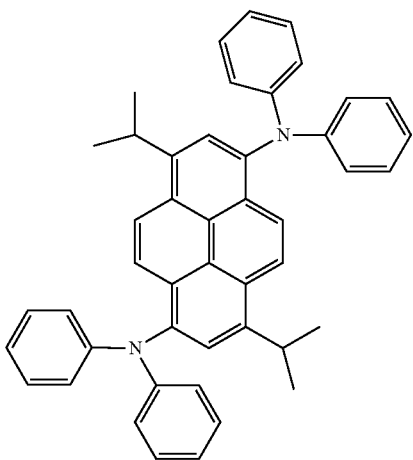

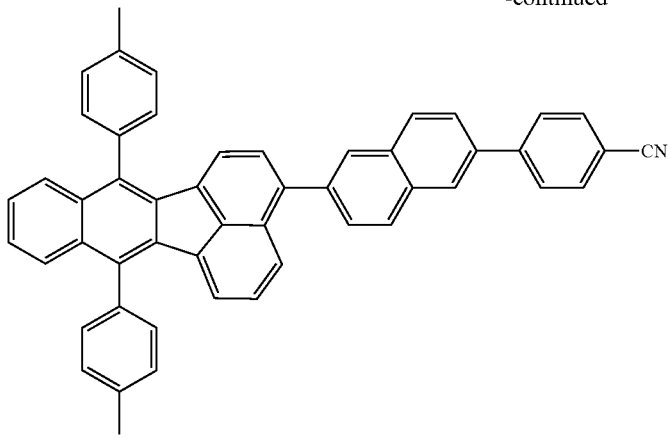

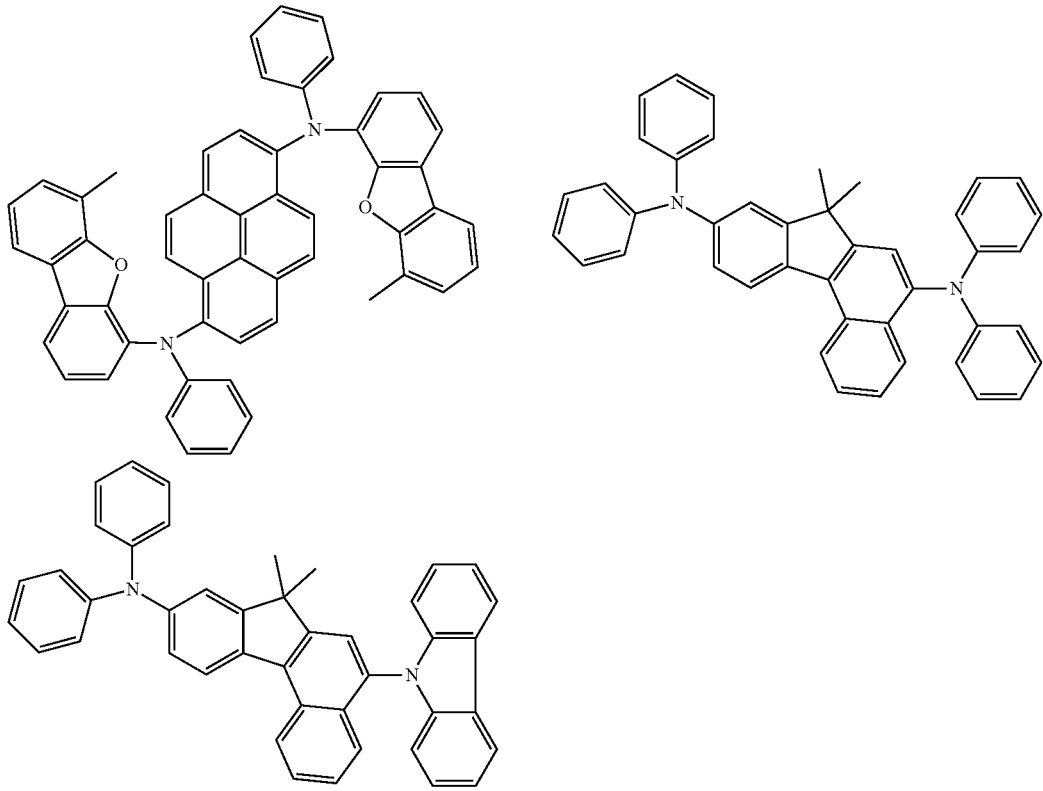

Preferred matrix materials for phosphorescent emitting compounds are aromatic amines, in particular triarylamines, for example in accordance with US 2005/0069729, carbazole derivatives (for example CBP, N,N-bis-carbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole 25 derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, and diazaphosphole derivatives, for example in accordance with WO 2010/054730.

Preferred matrix materials for use in combination with fluorescent emitting compounds, besides the compounds according to the invention, are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Examples of preferred matrix materials for use in combination with fluorescent emitting compounds, besides the compounds according to the invention, are represented in the table below:

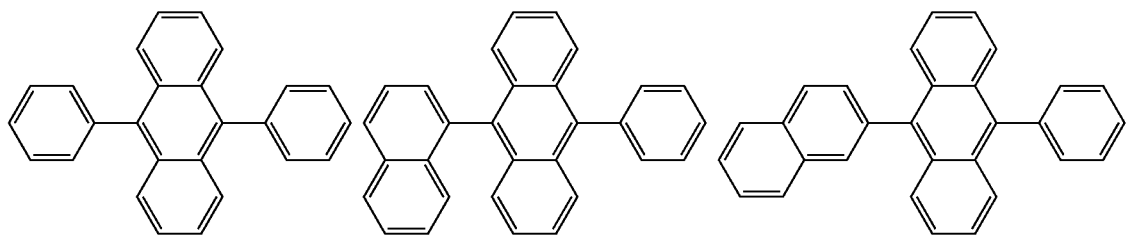

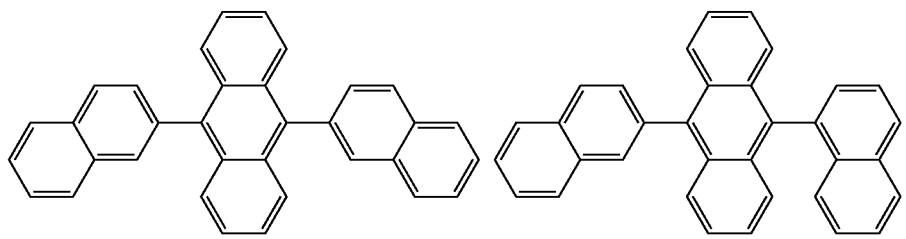

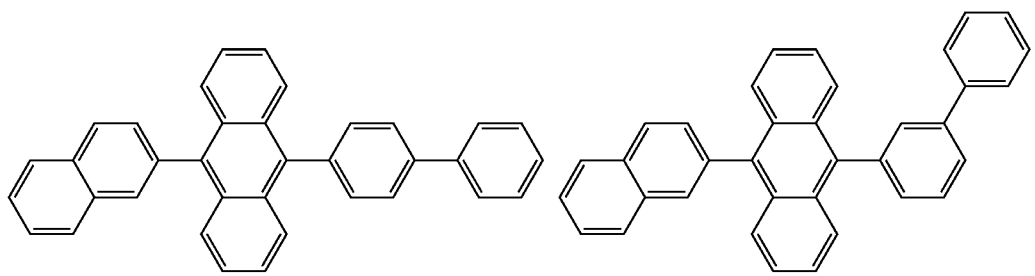

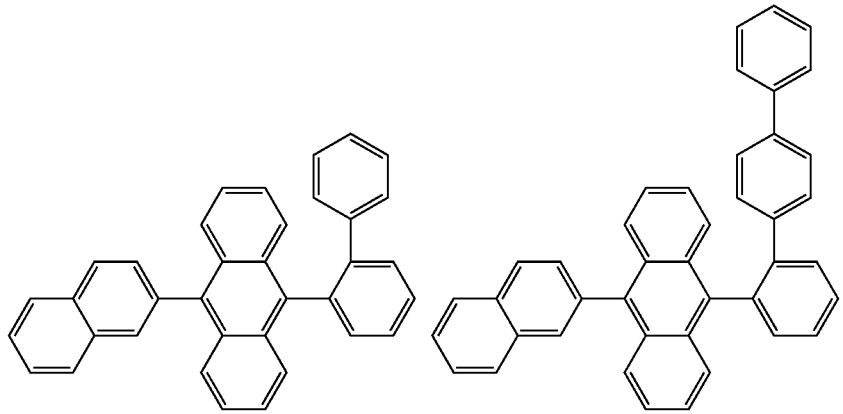

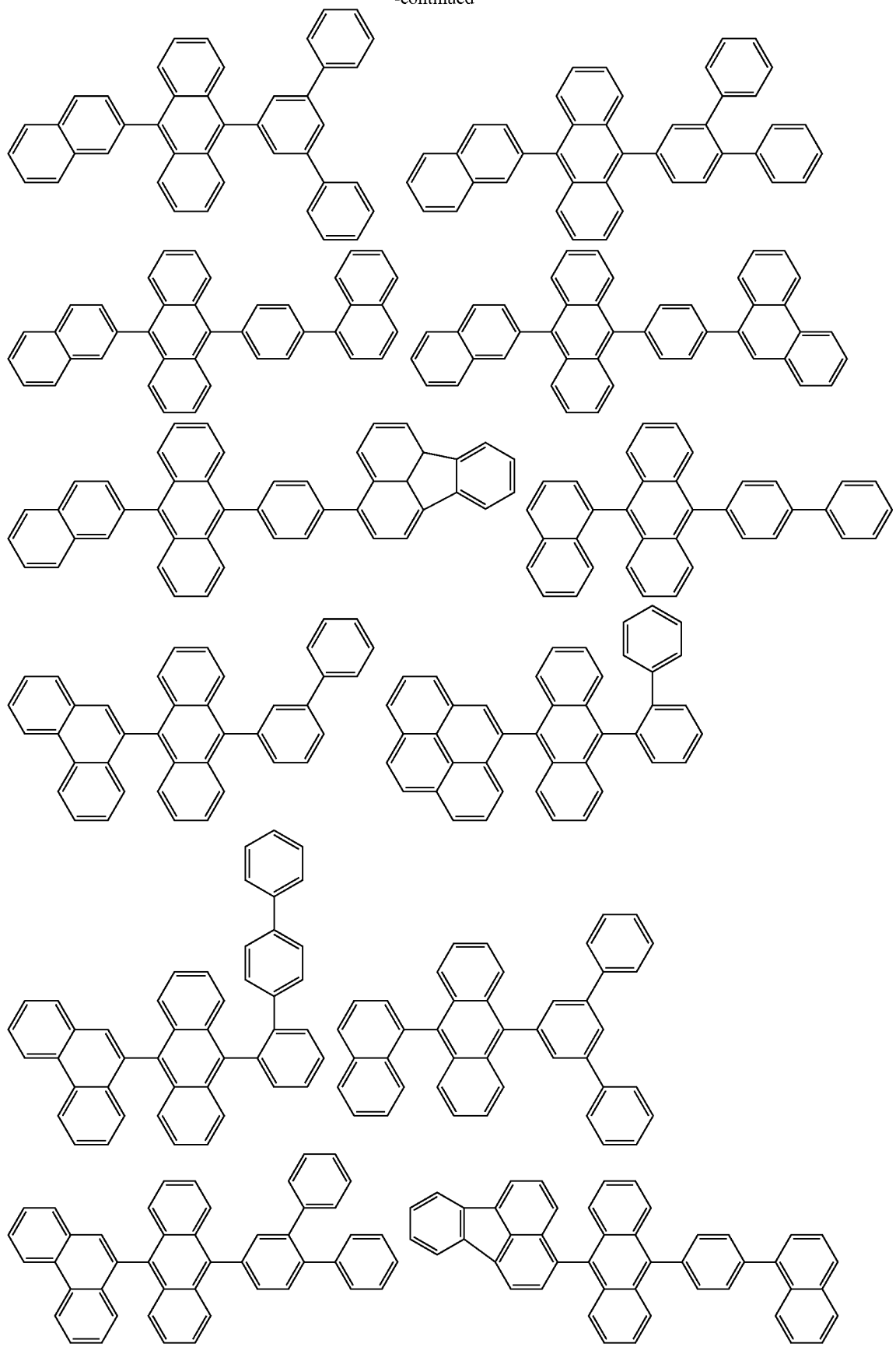

-continued
| 161 | 162 |
|---|---|
| 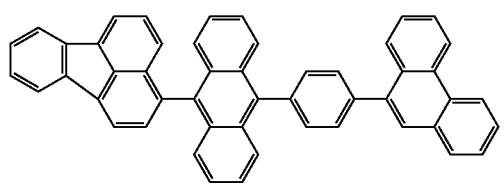 | 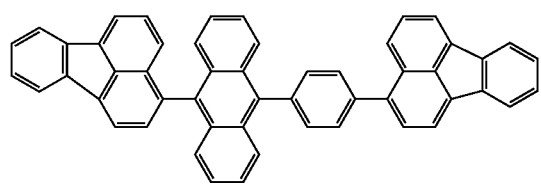 |
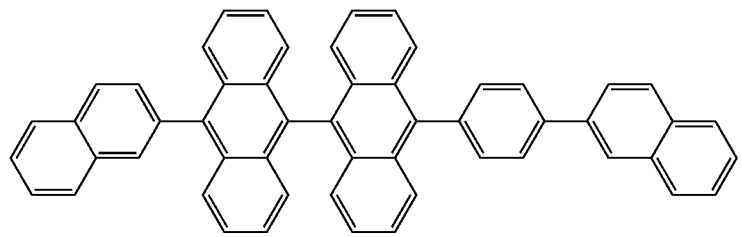
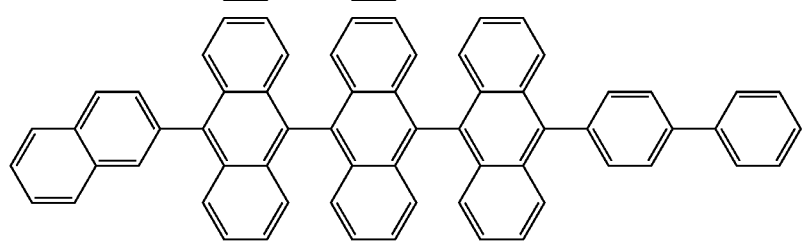
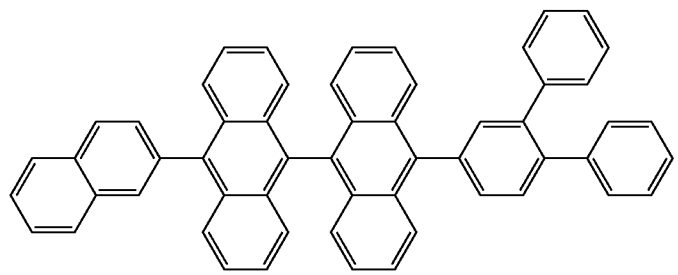
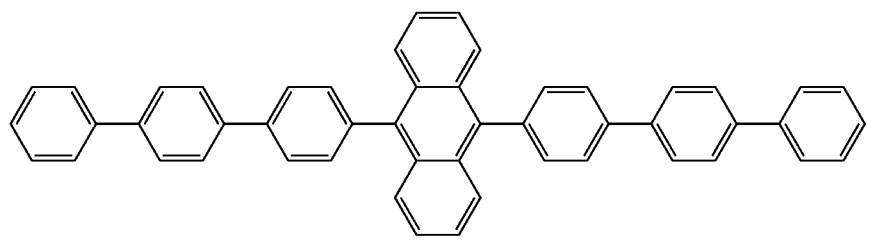
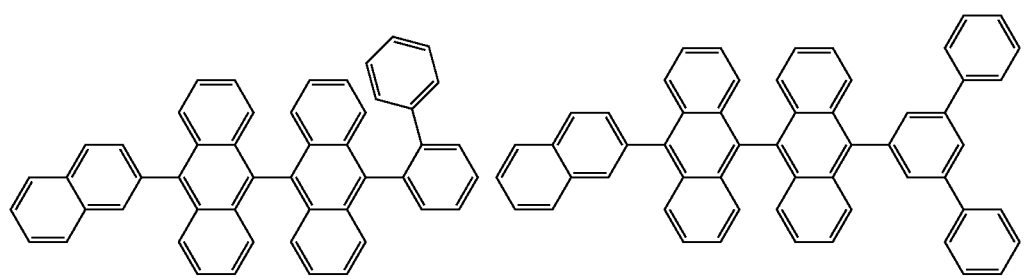

-continued
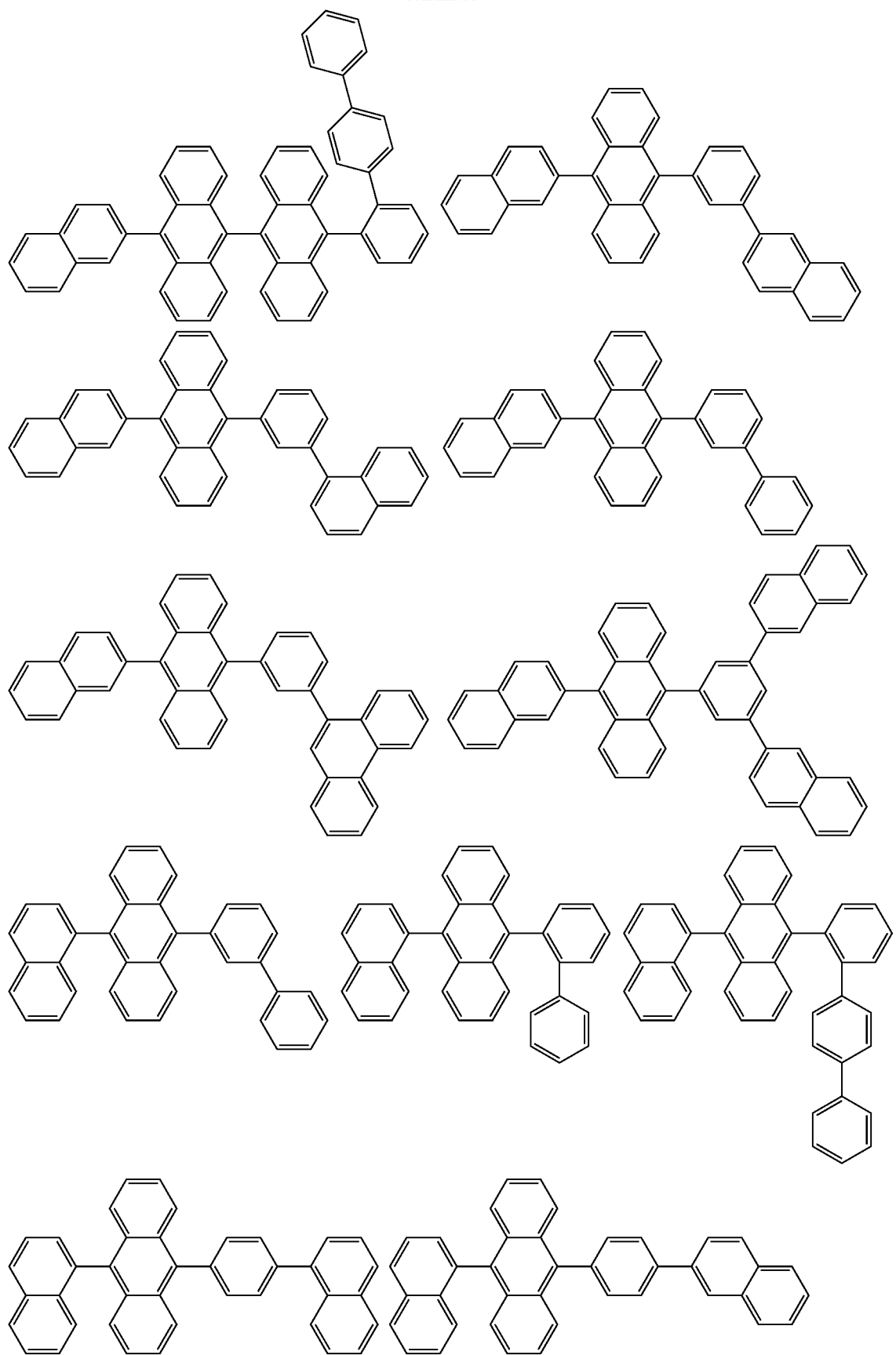

-continued
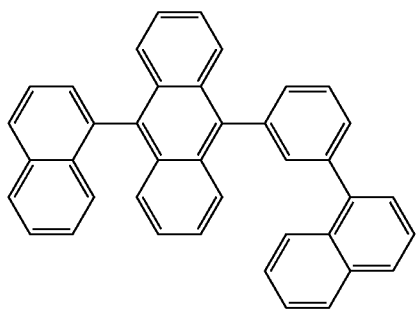
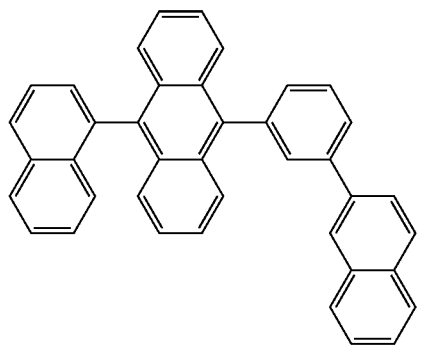
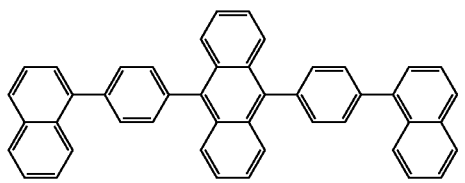
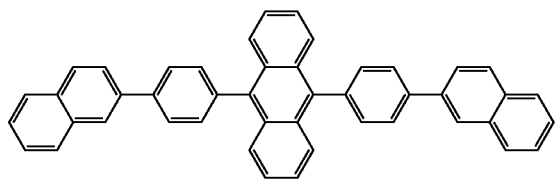
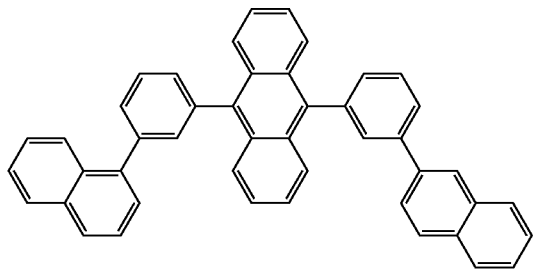
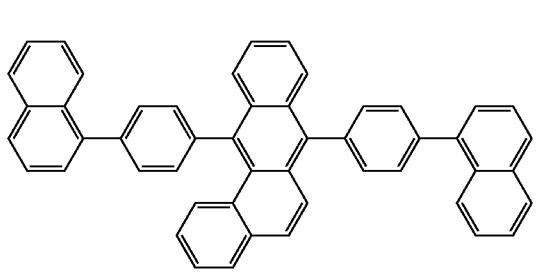
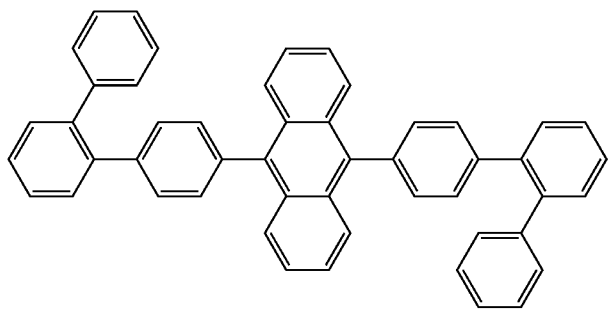
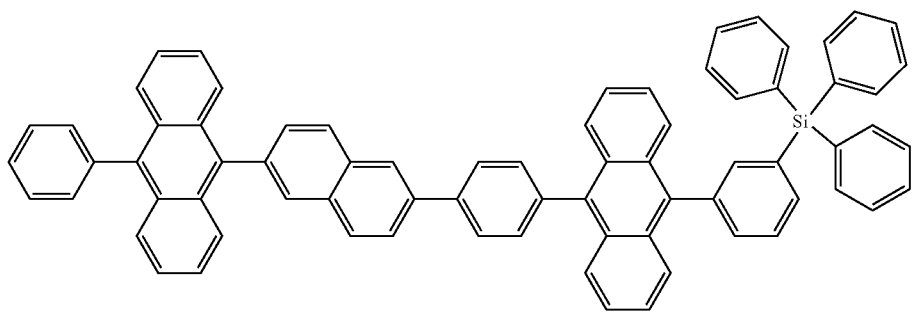
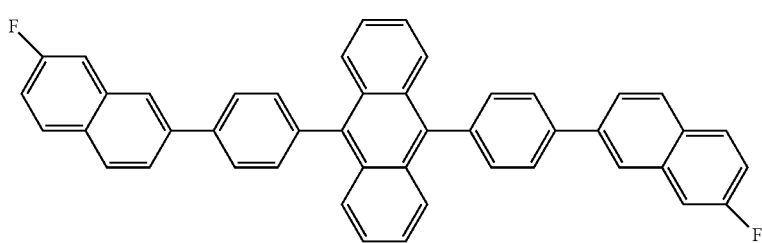

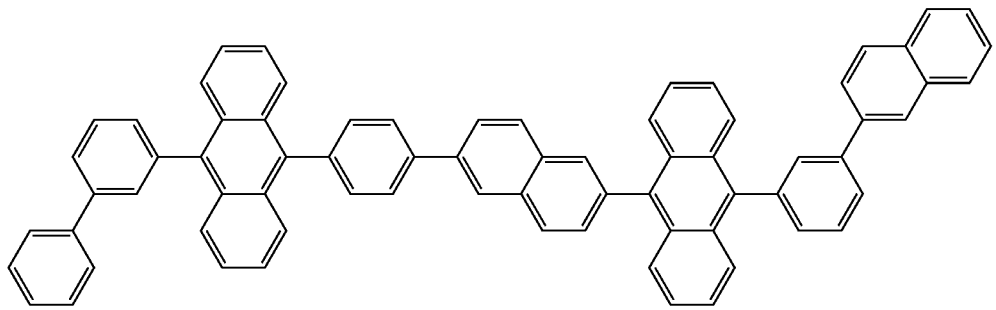
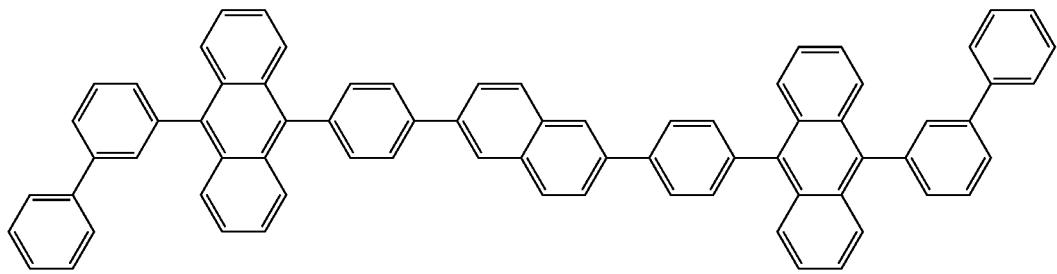
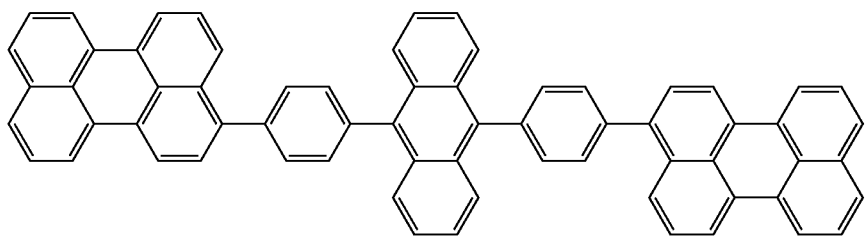
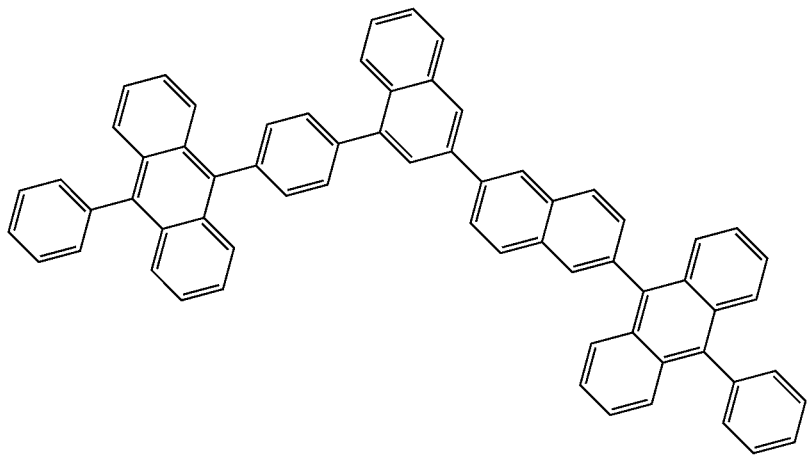
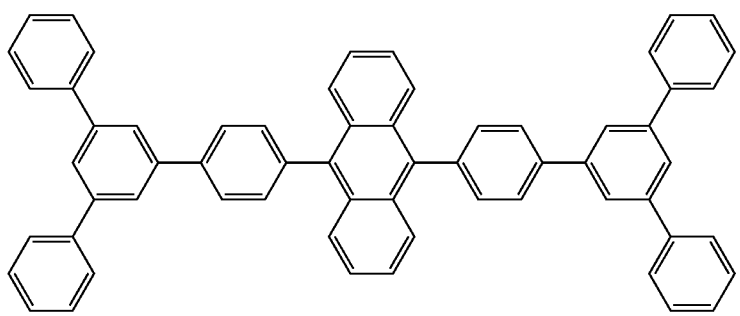

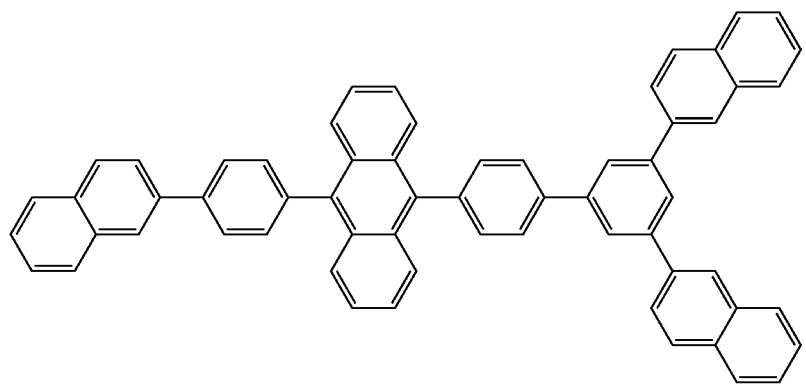
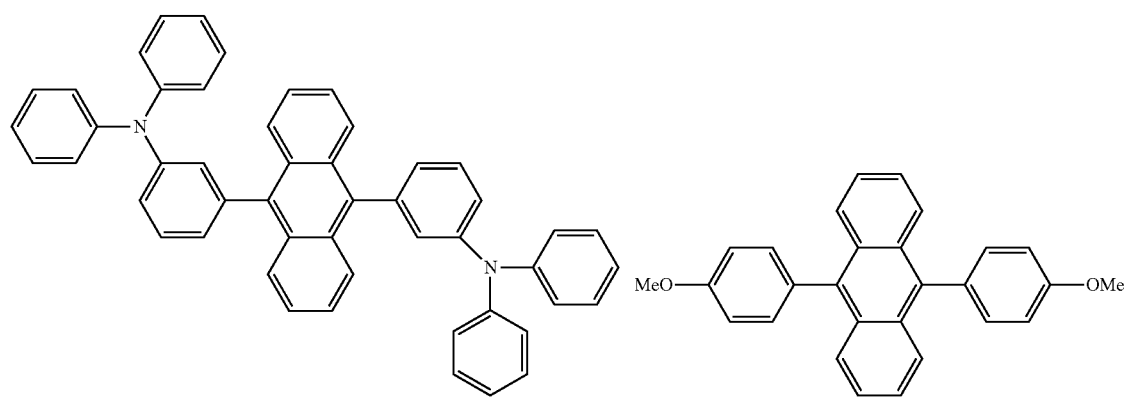
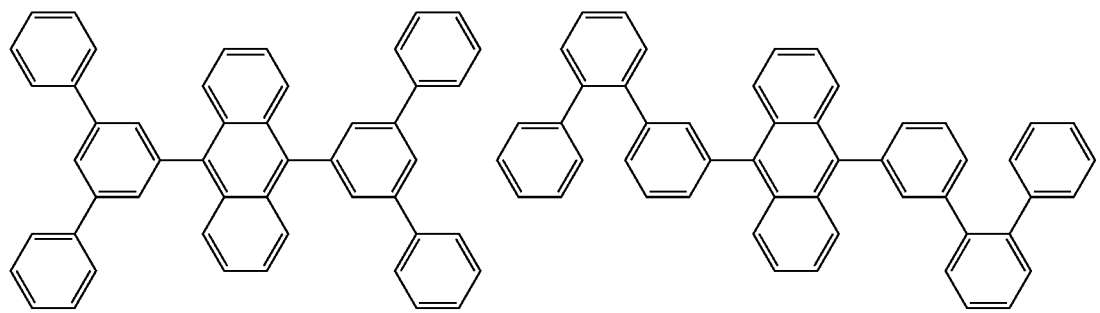
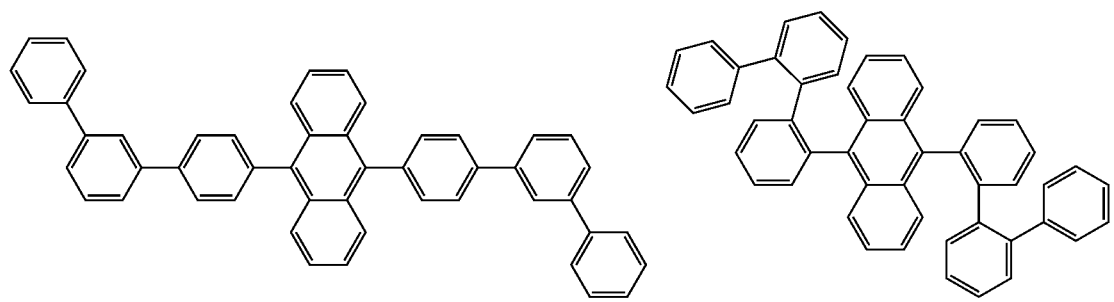

-continued
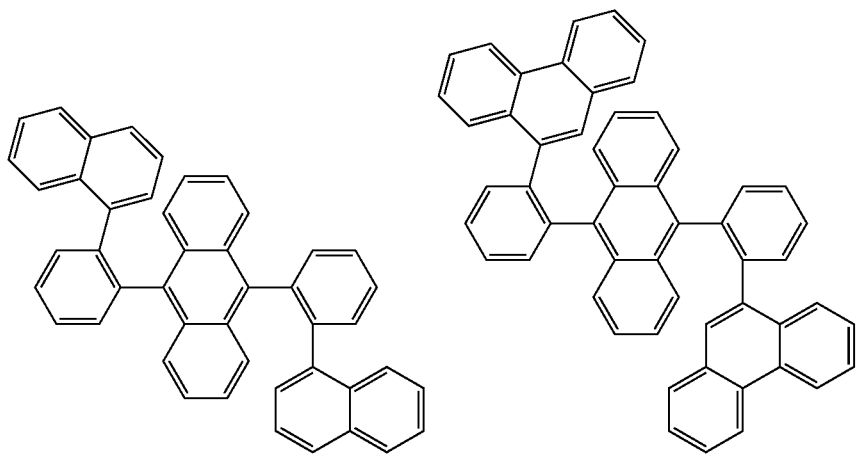
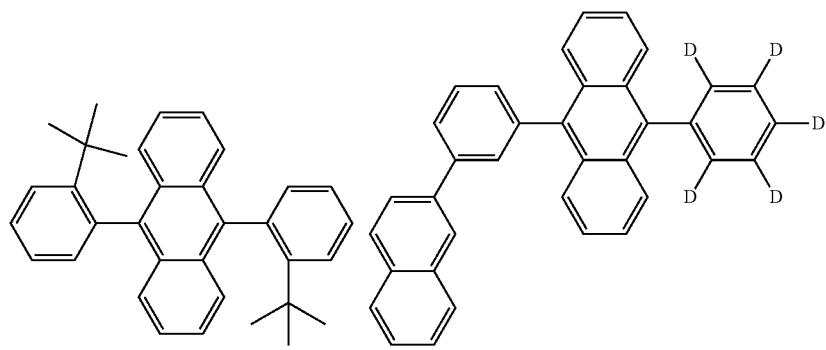
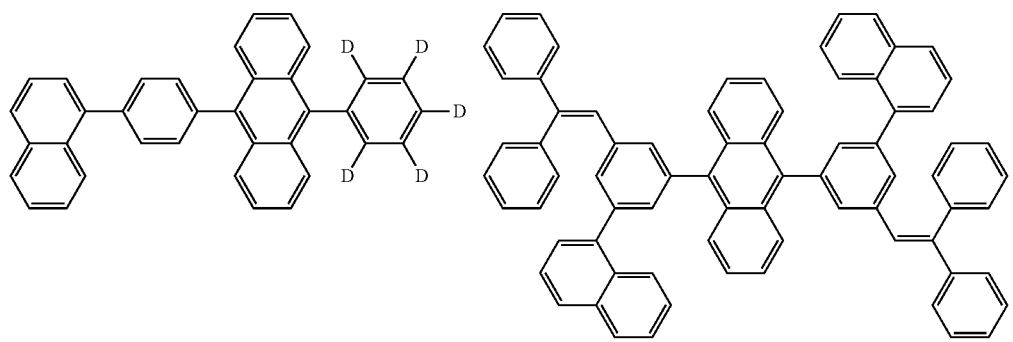
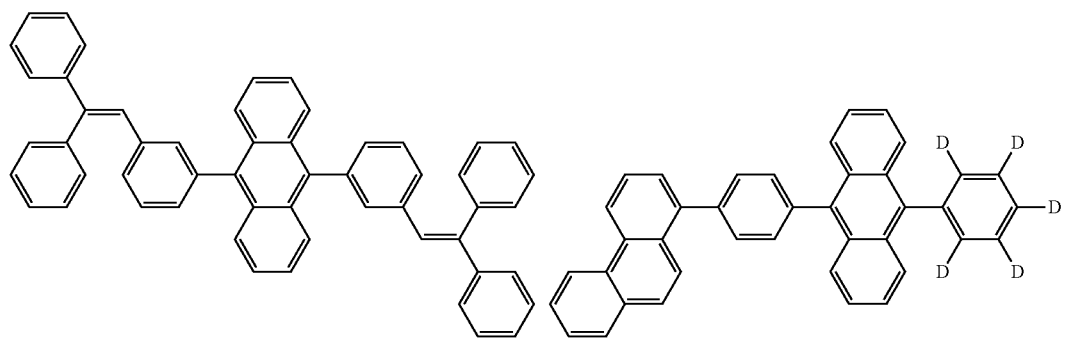

173 174
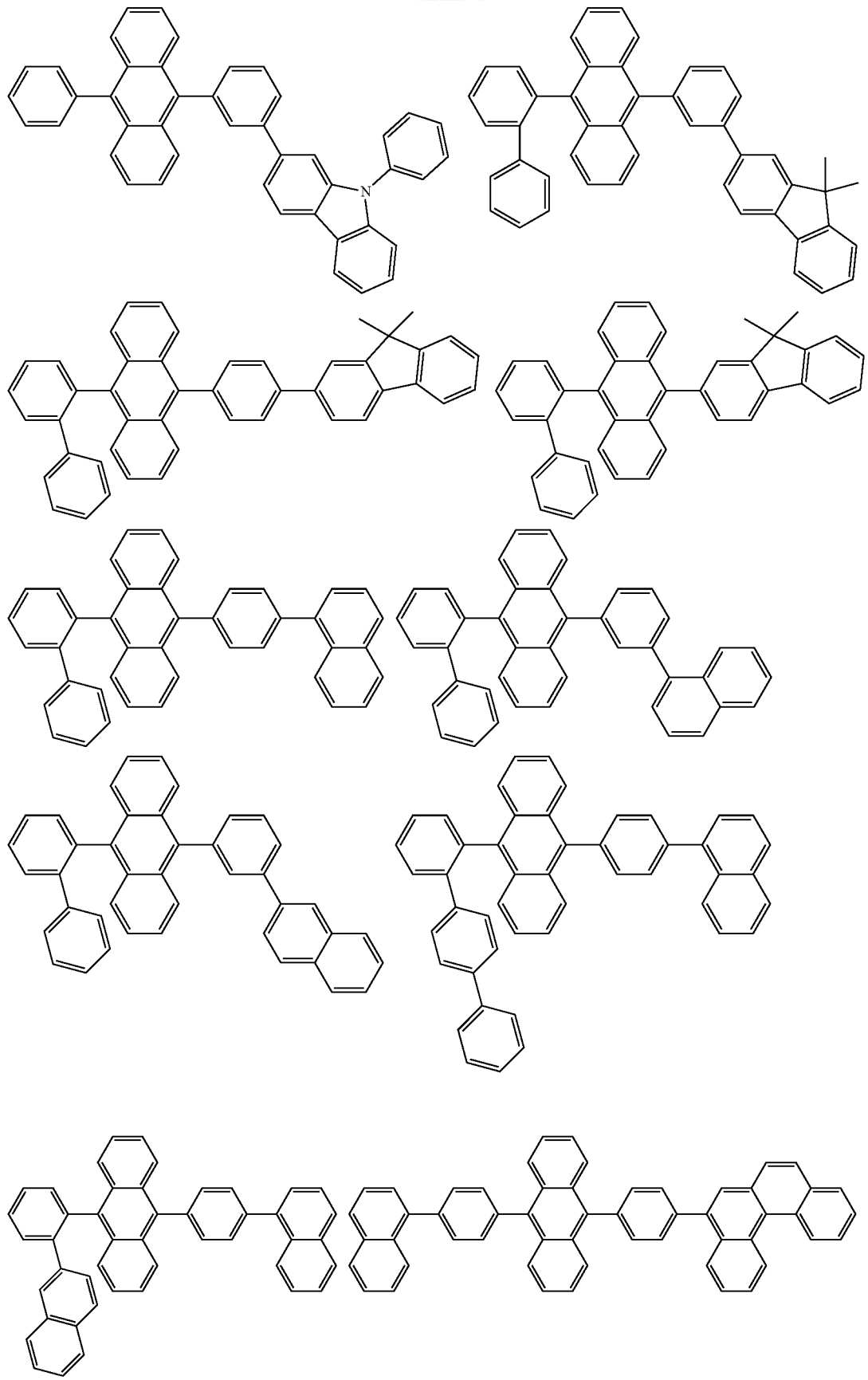
-continued

-continued
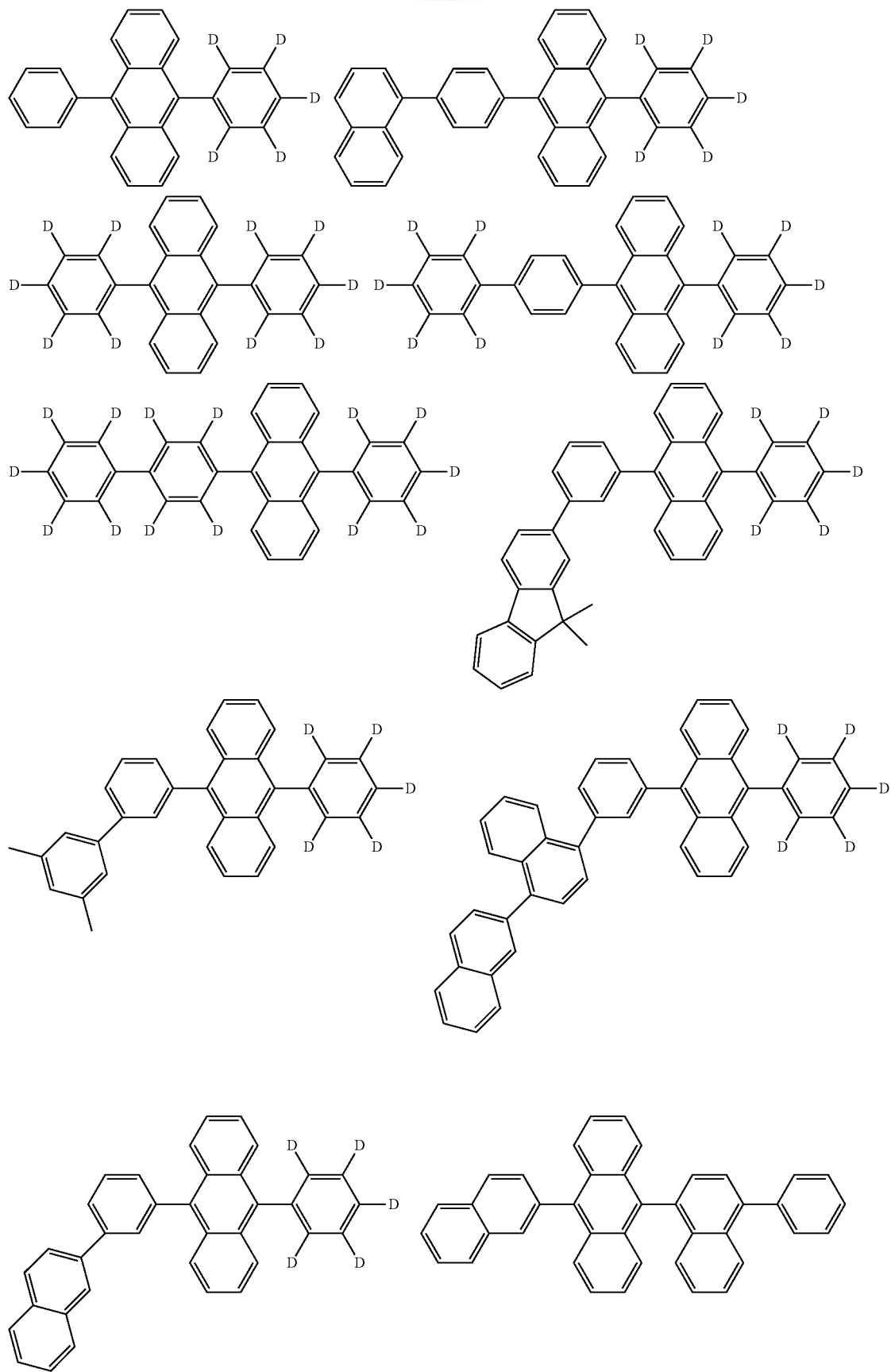

-continued
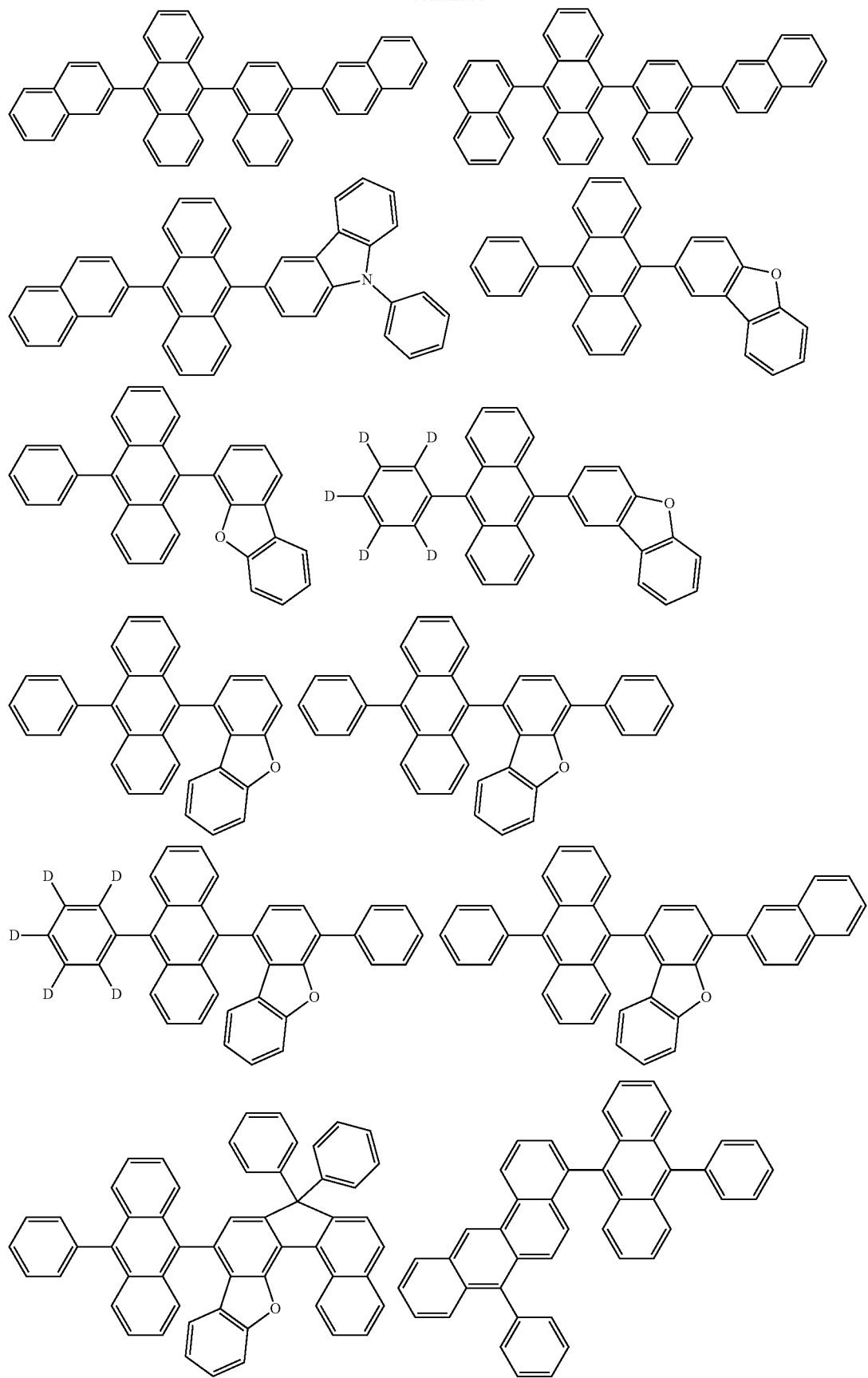

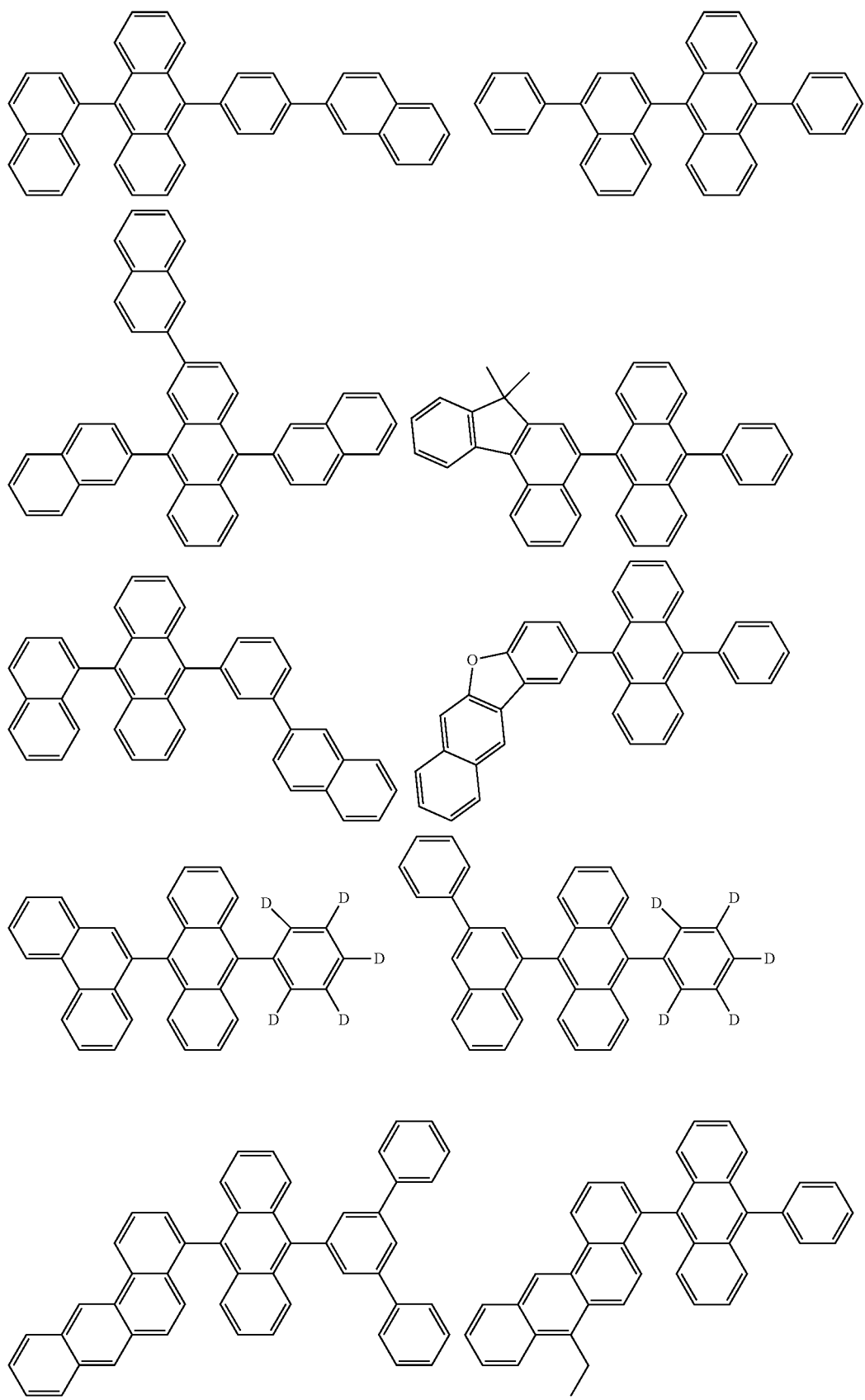

-continued
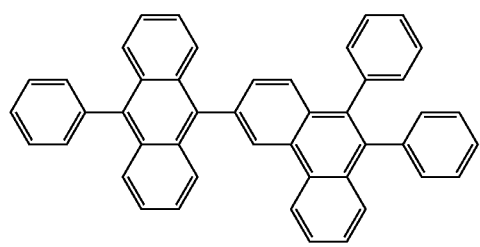
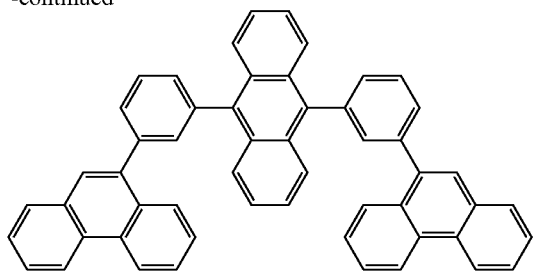
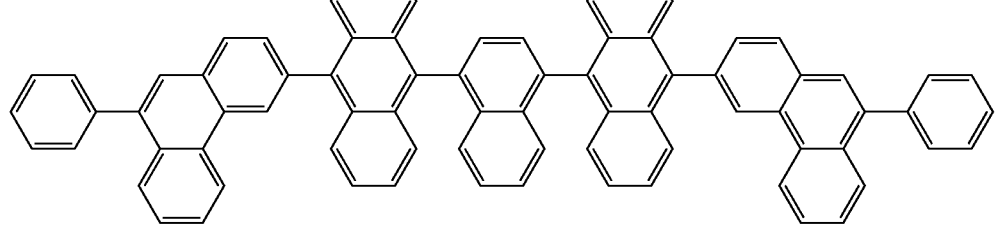
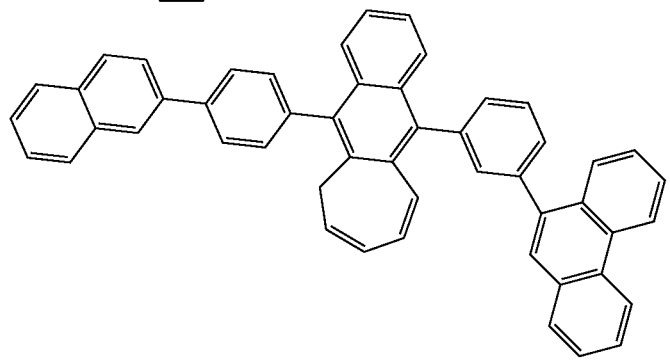
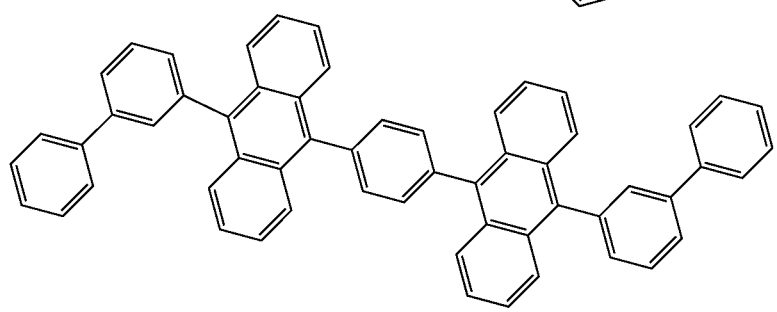
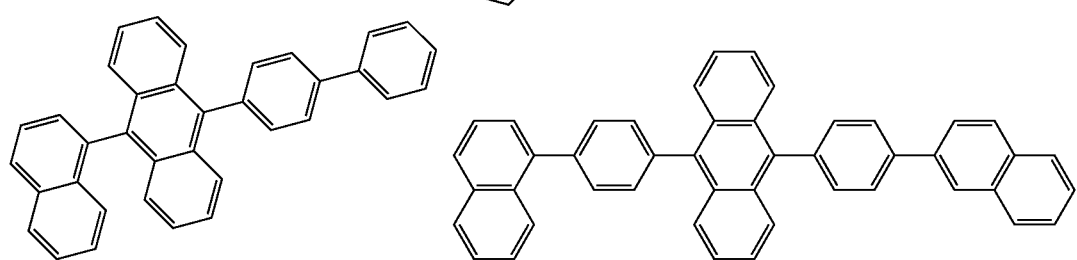
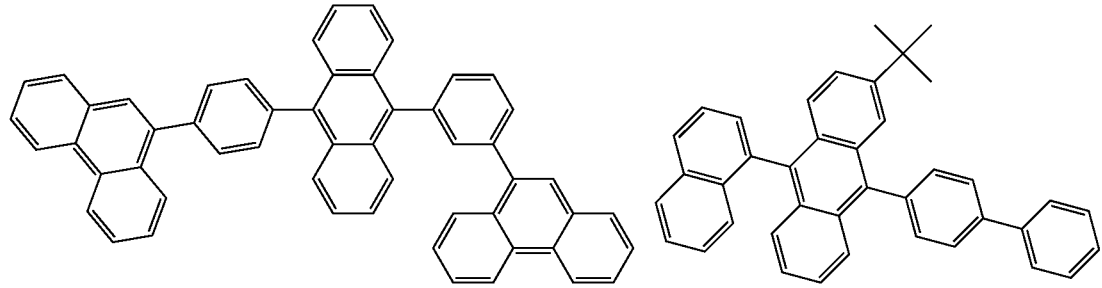

-continued
183
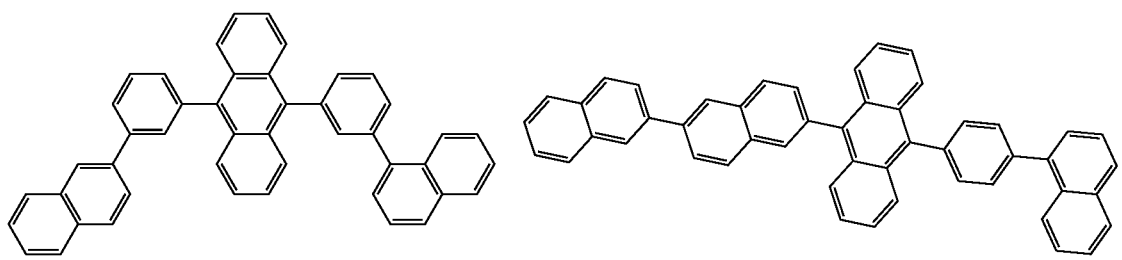
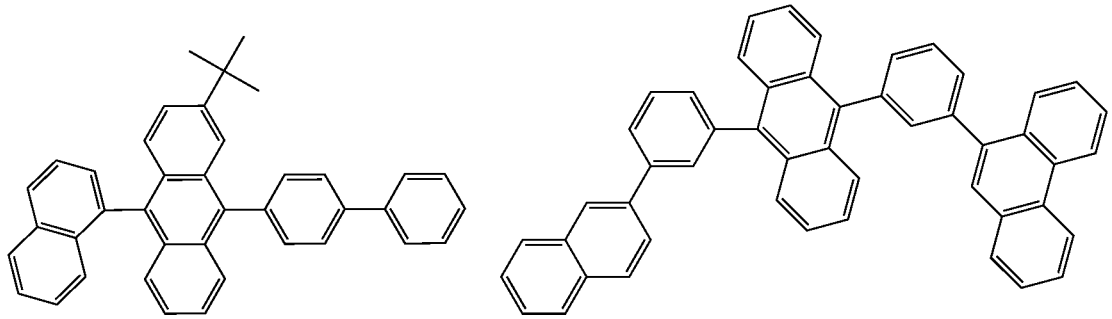
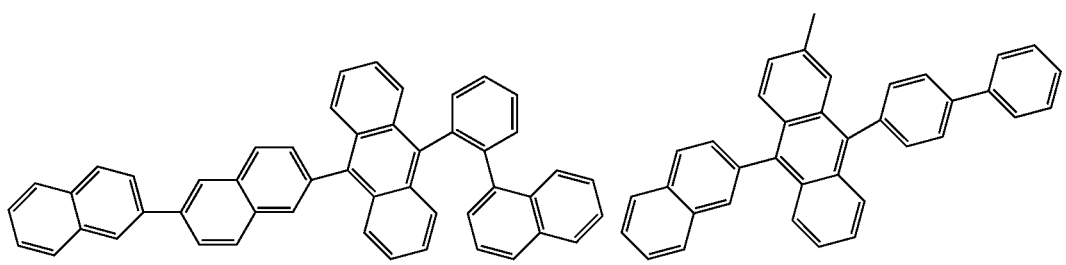
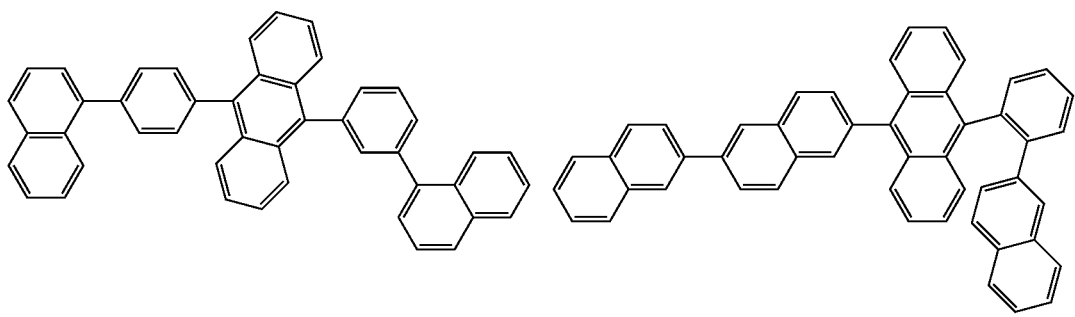
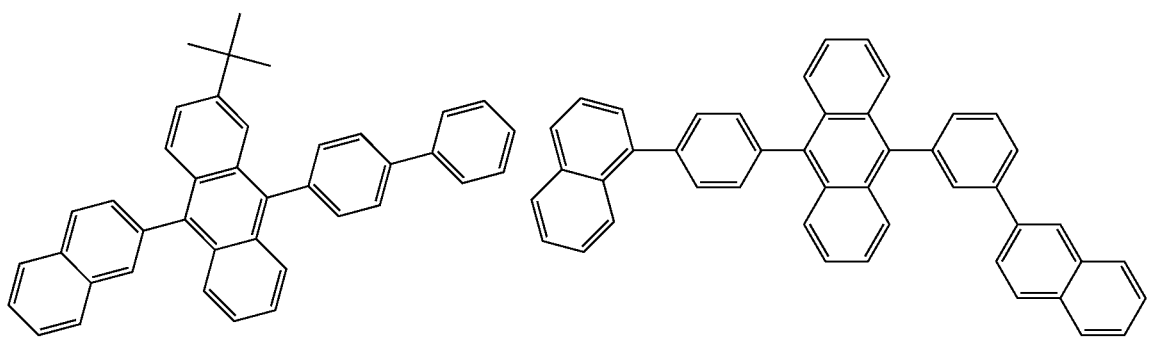
184

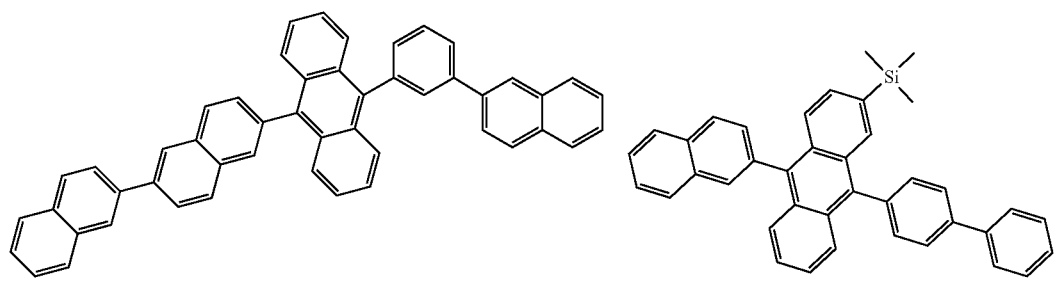
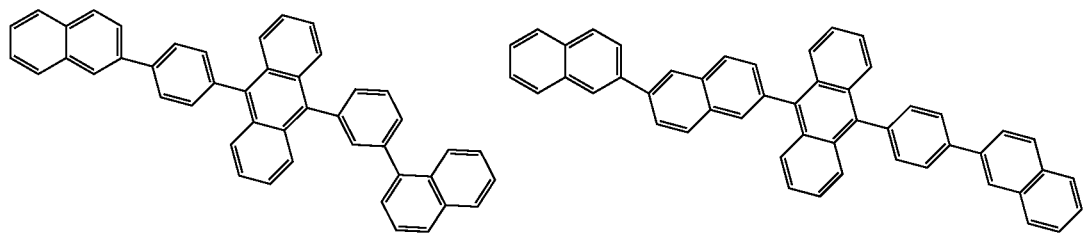
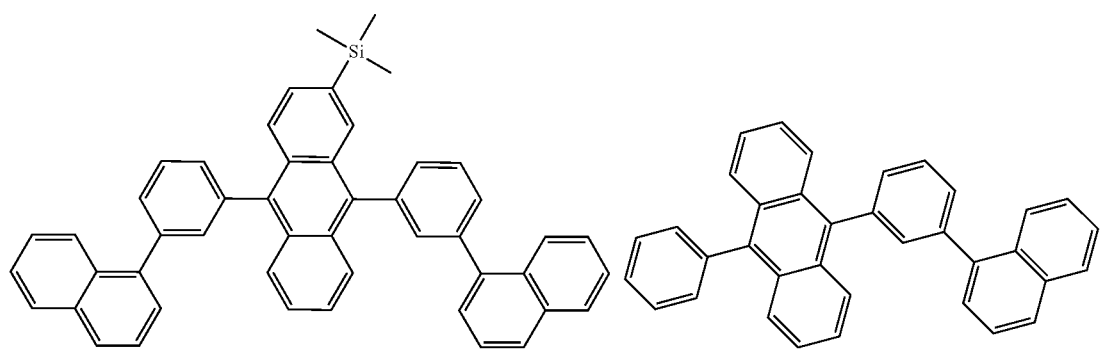
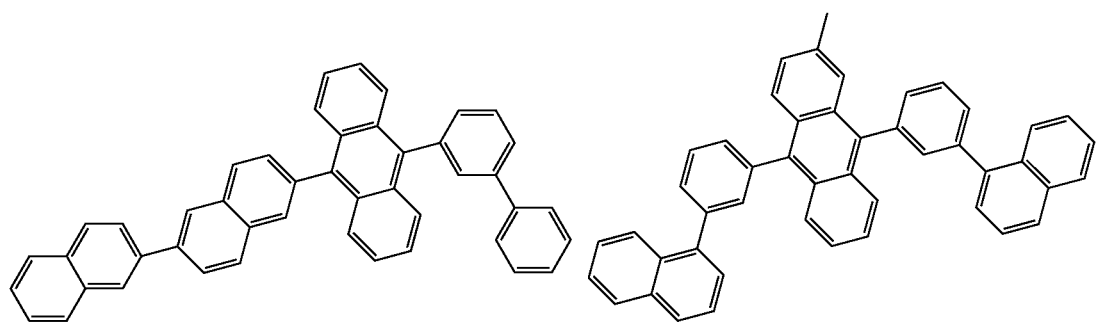
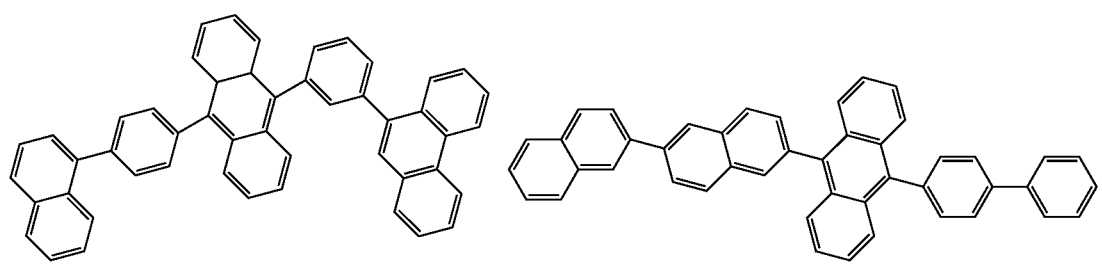

-continued
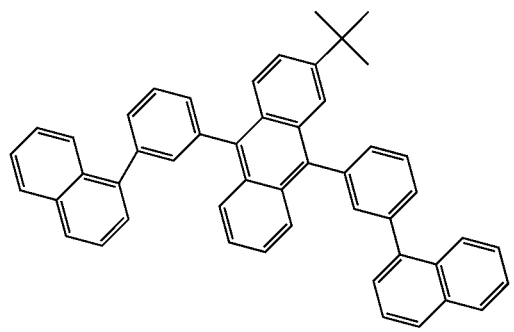
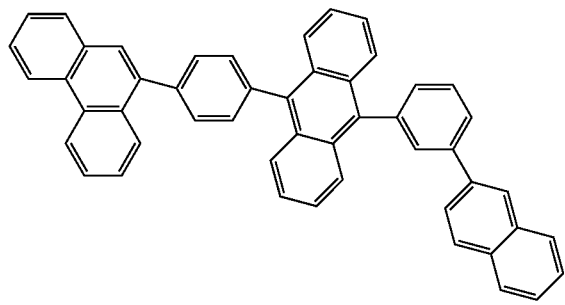
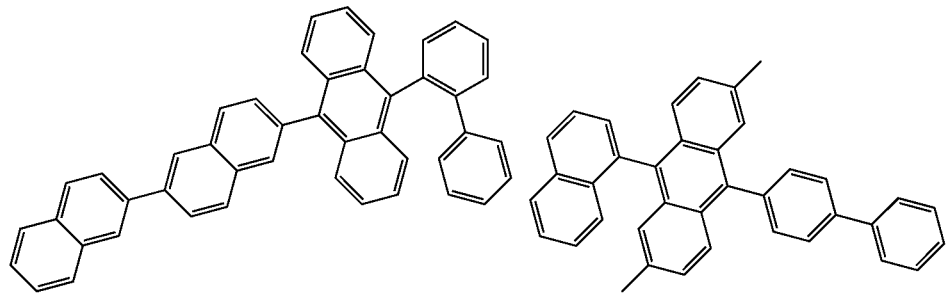
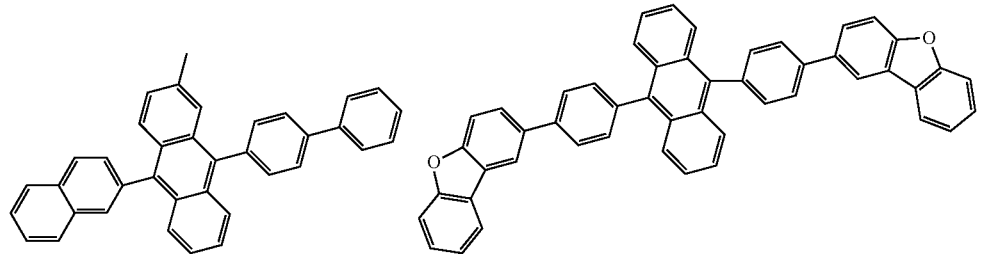
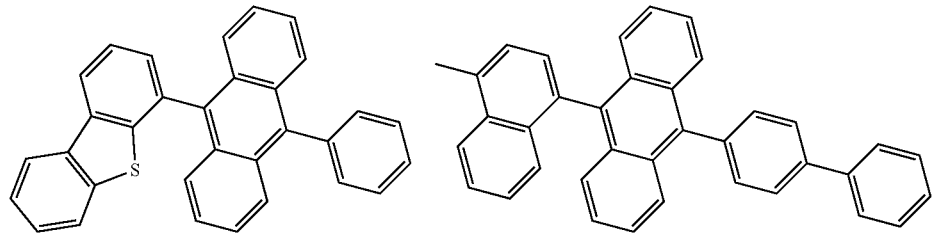
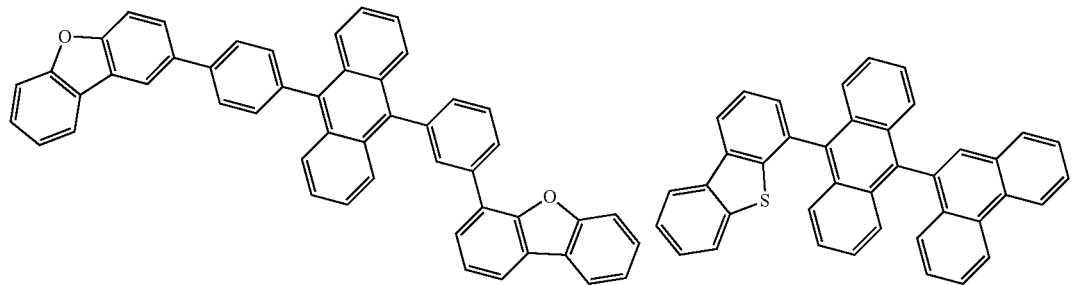
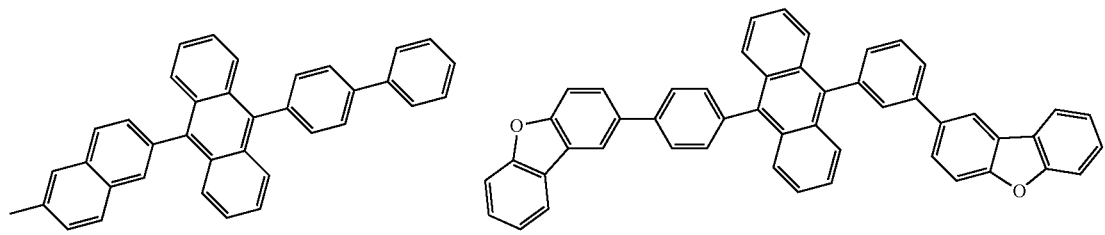

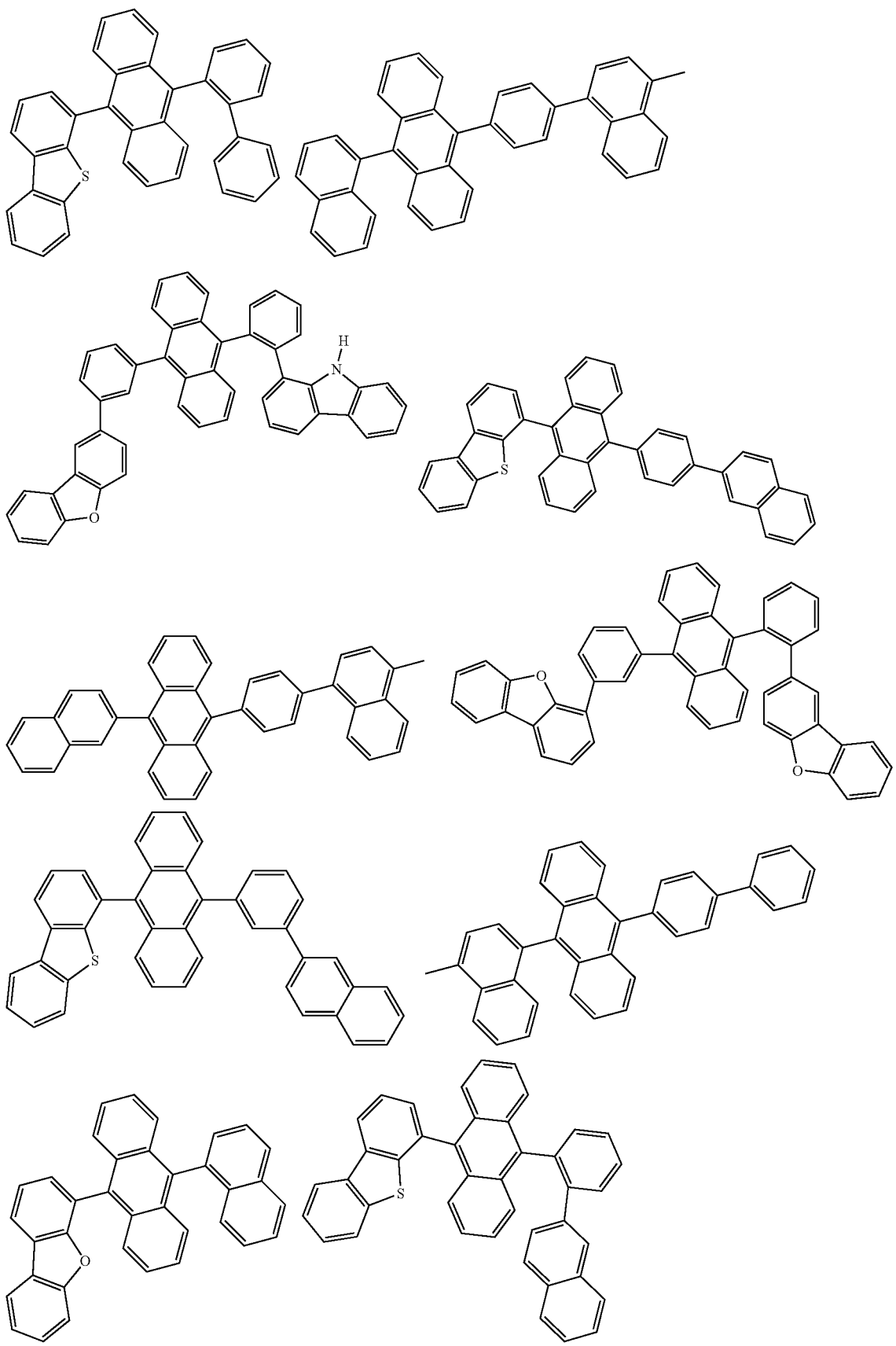

191 192
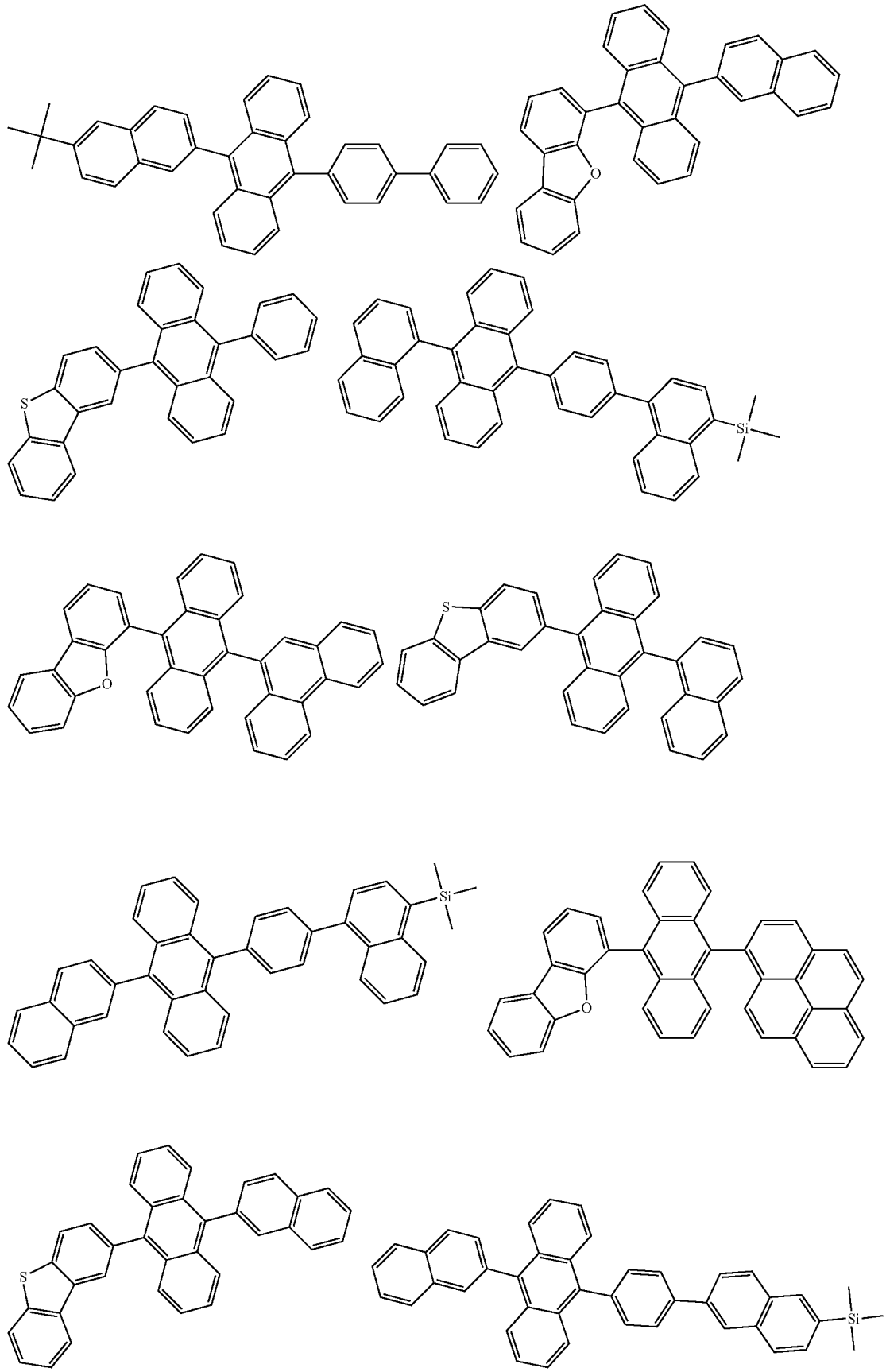
-continued

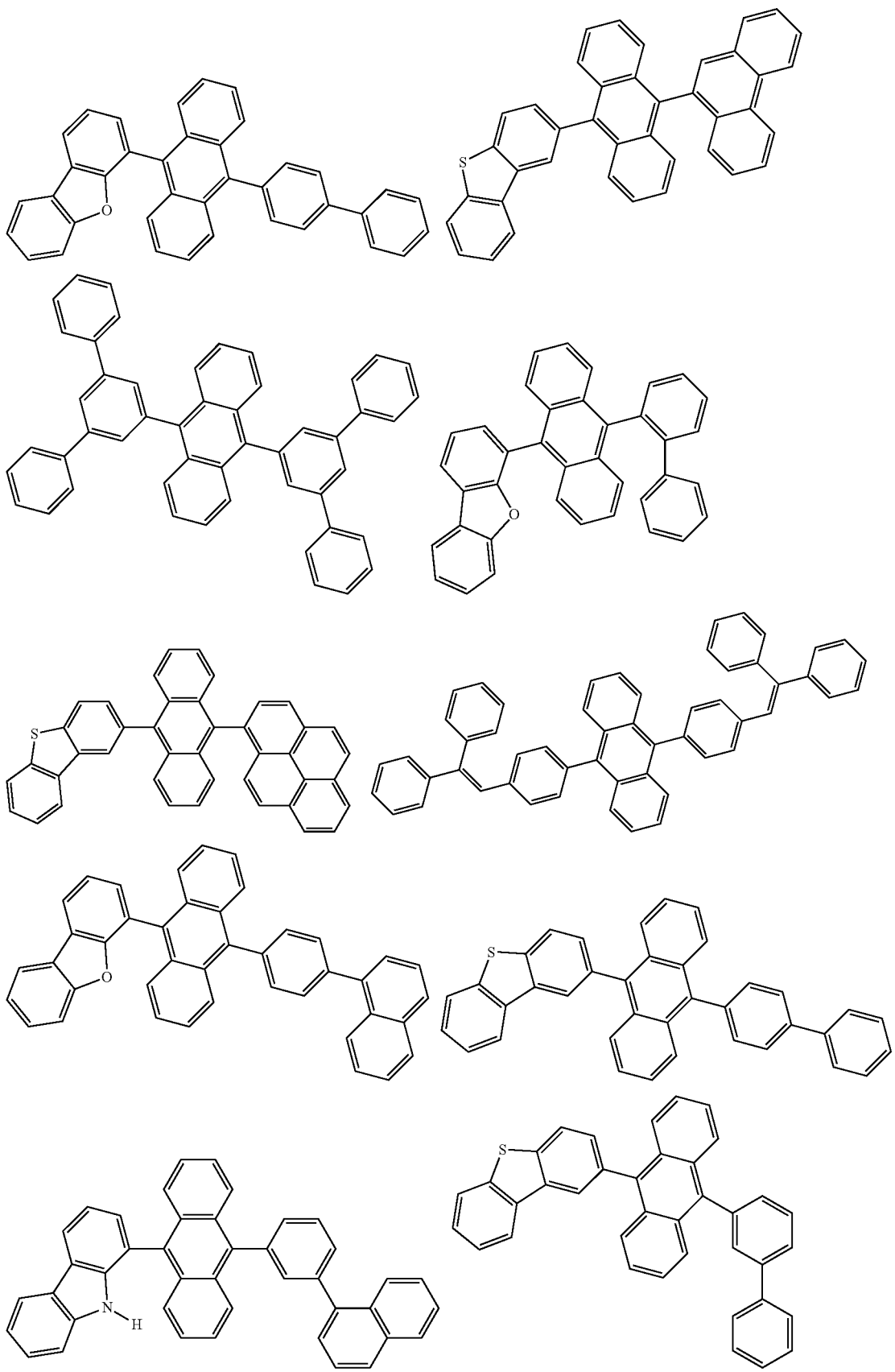

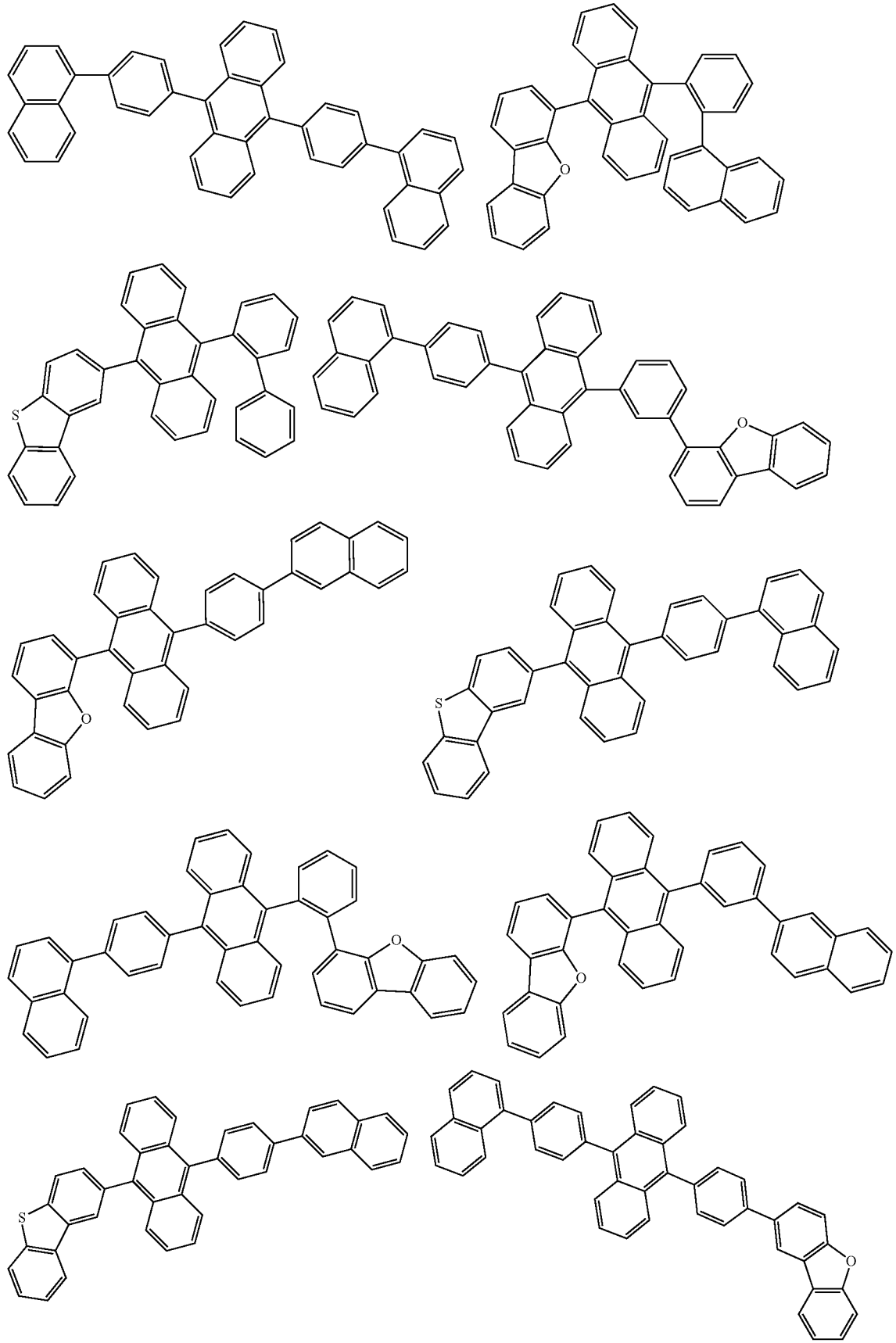

197
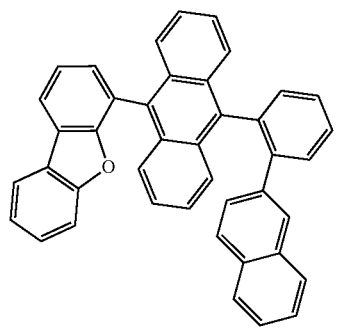
198
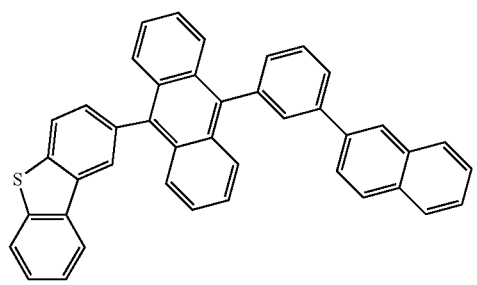
-continued
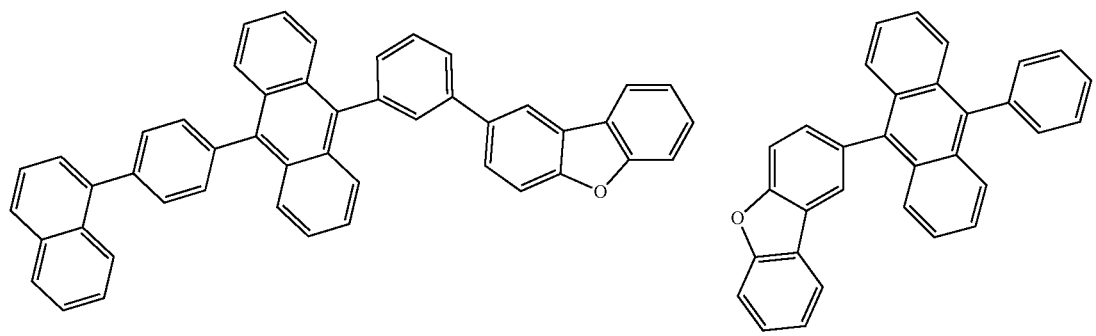
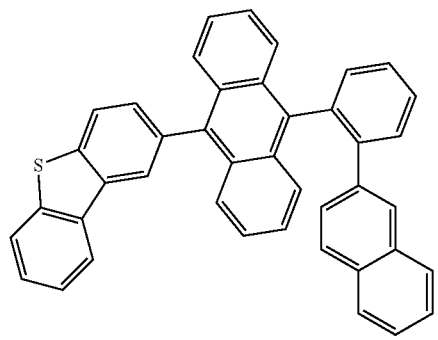
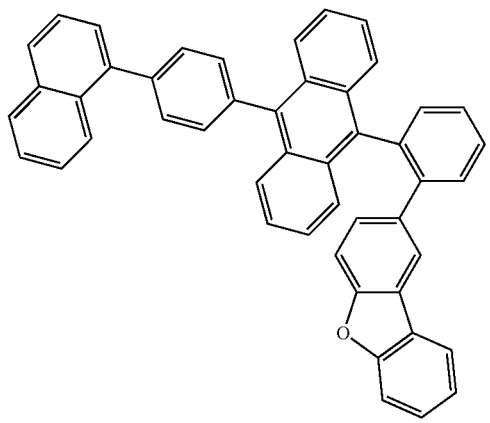
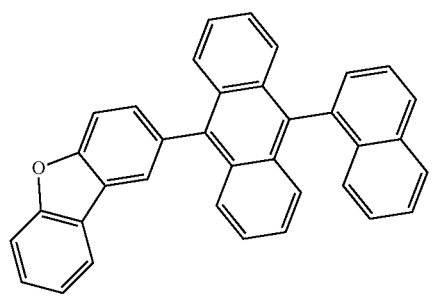
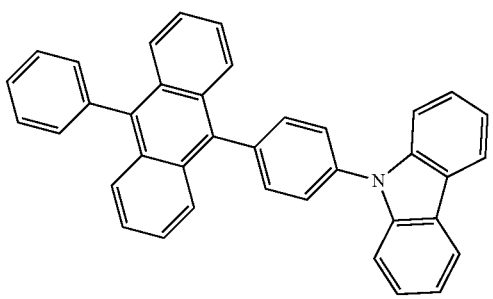

199 200
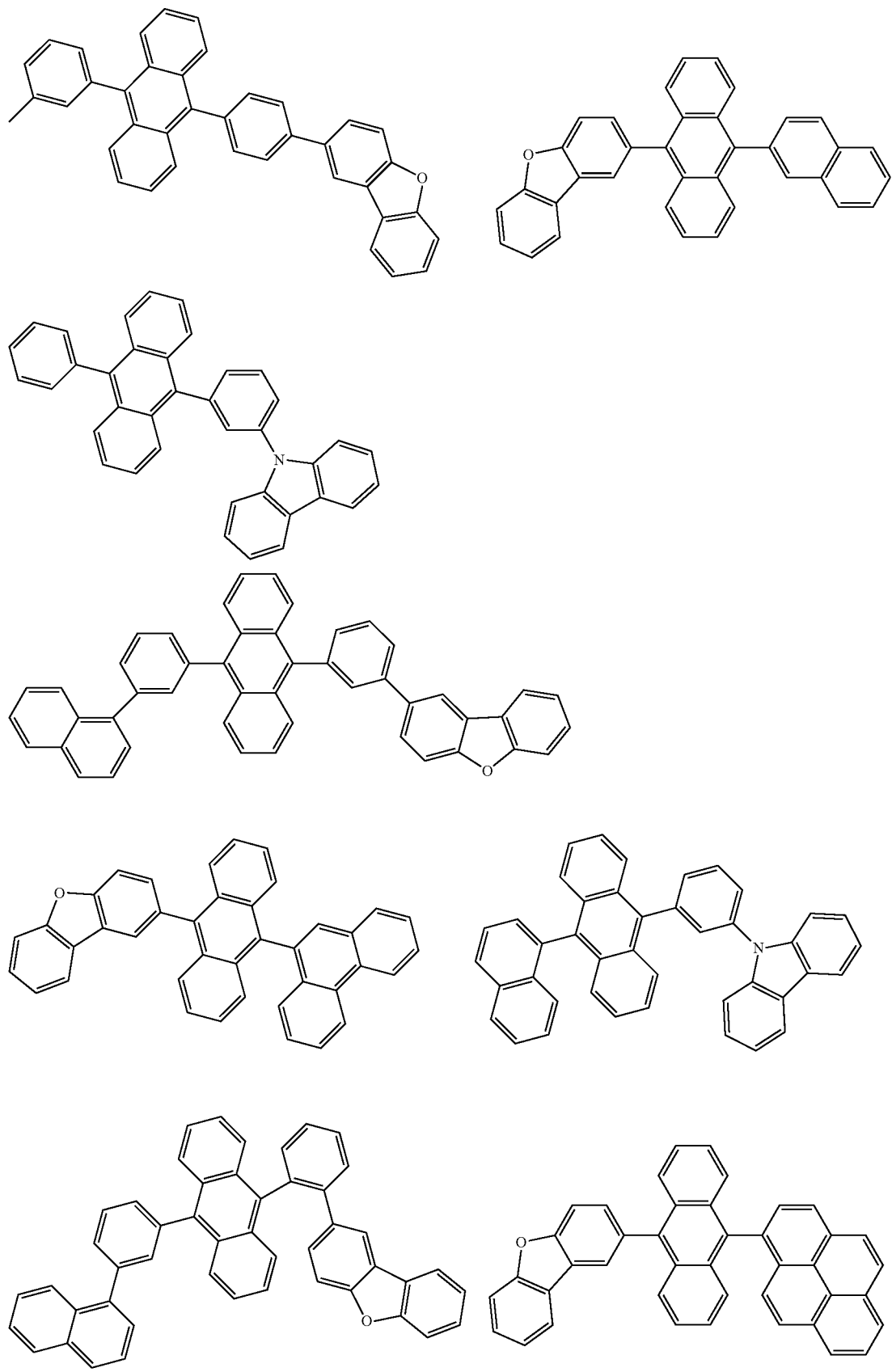

-continued
| 201 | 202 |
|---|---|
| 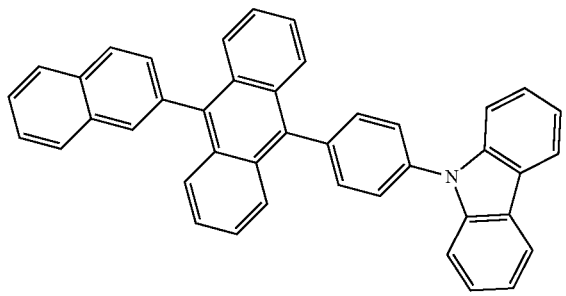 | 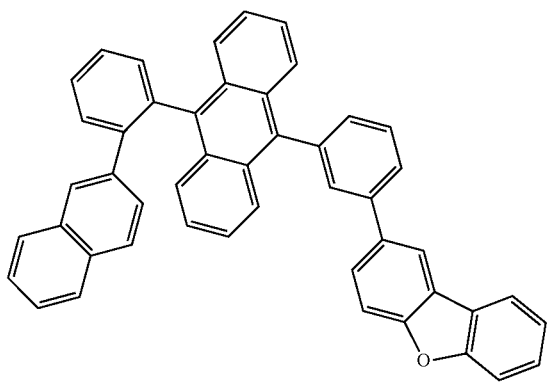 |
| 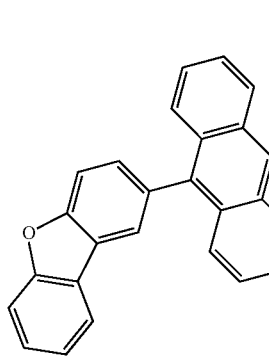 | 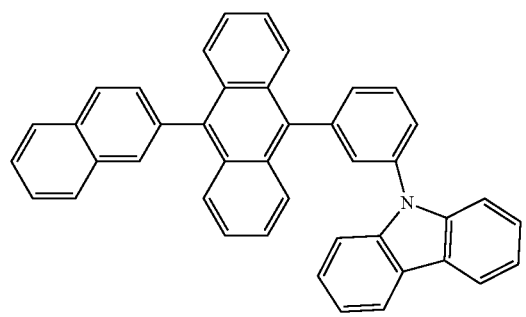 |
| 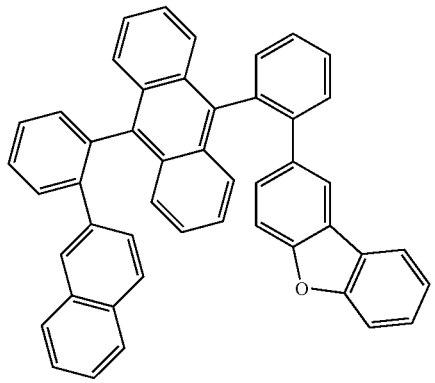 | 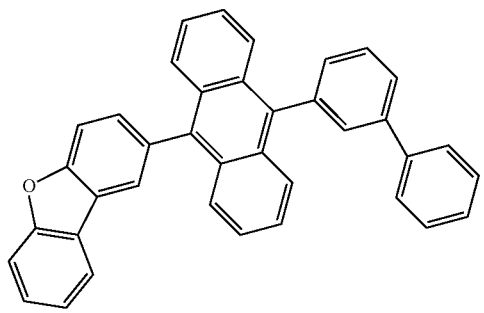 |
| 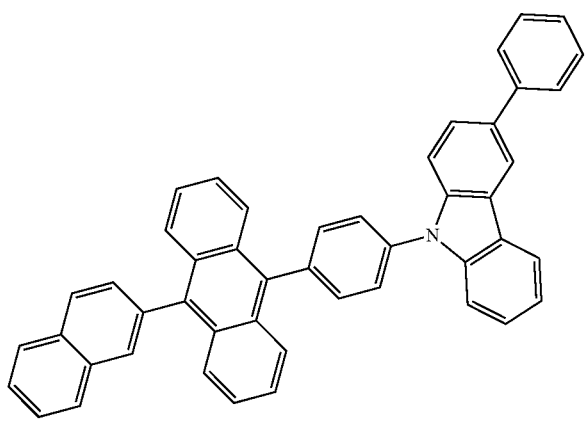 | |

-continued
203
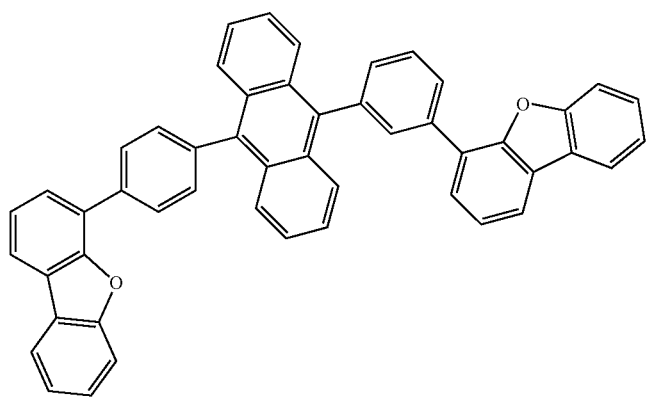
204
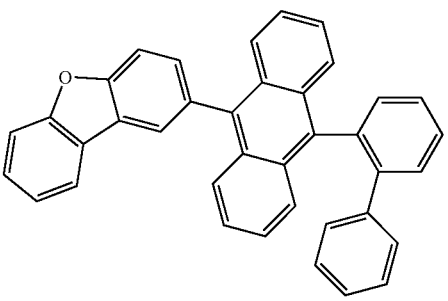
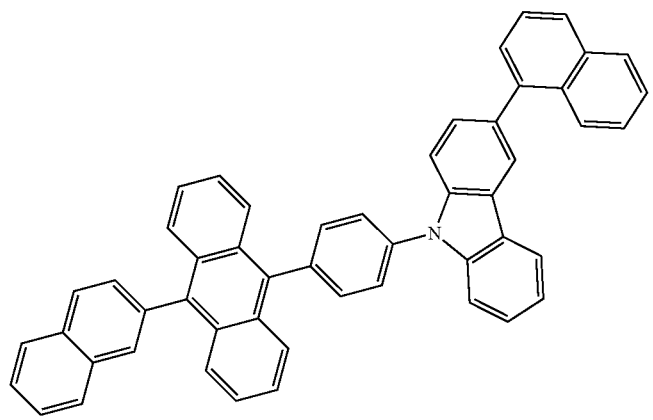
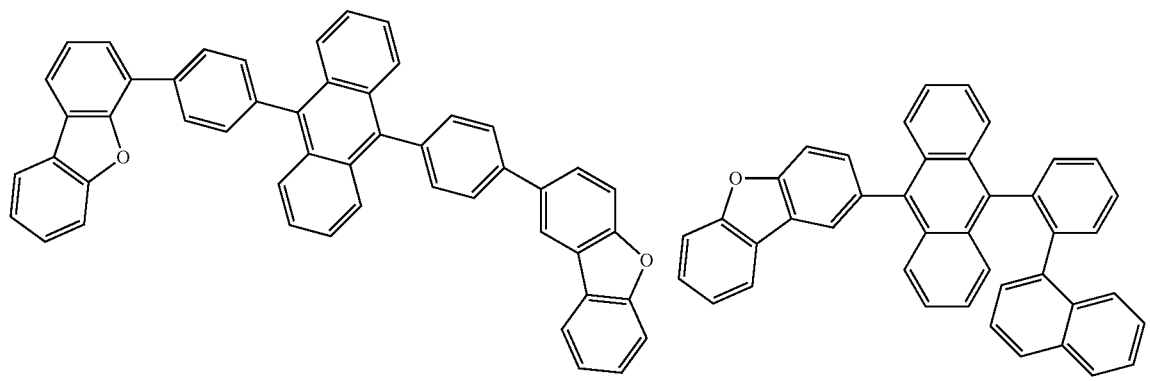
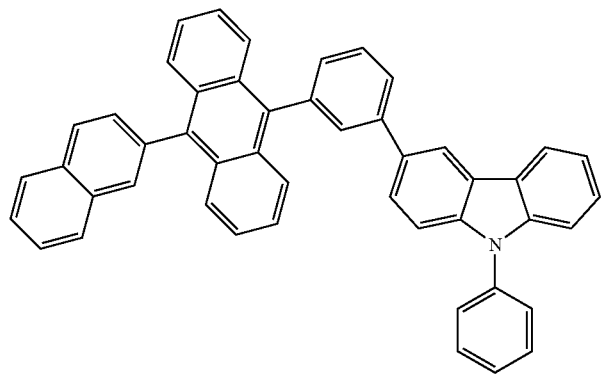

205
-continued
206
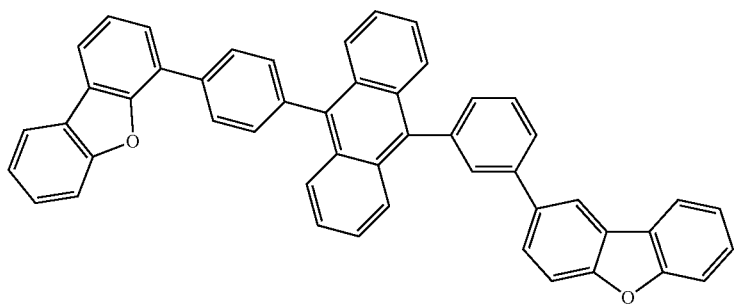
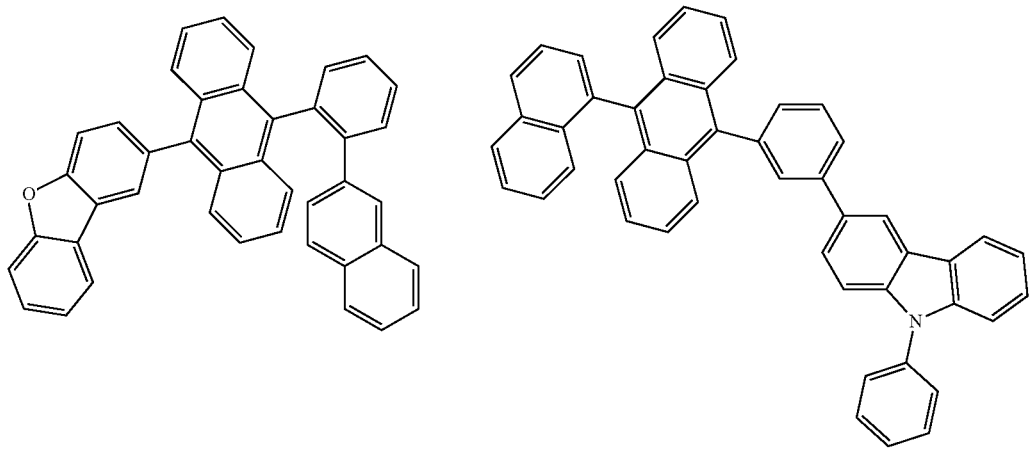
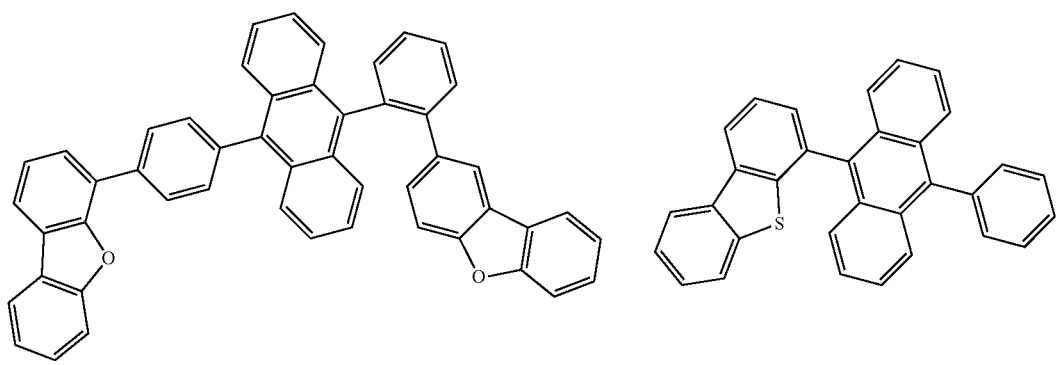
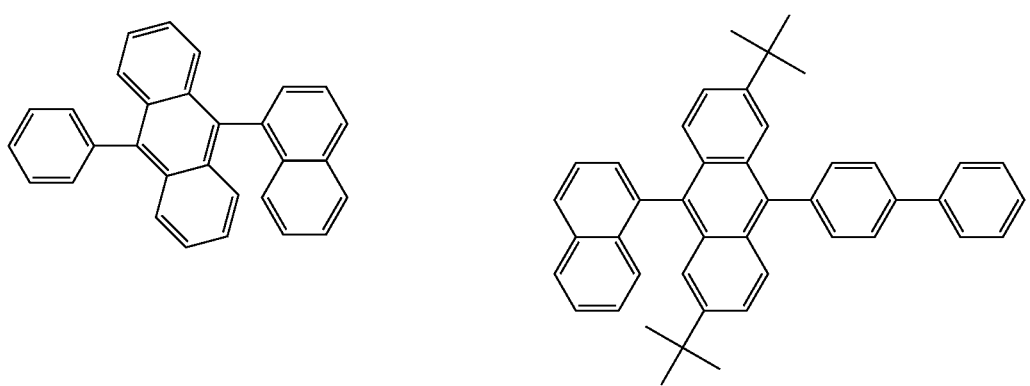

| 207 | 208 |
|---|---|
| 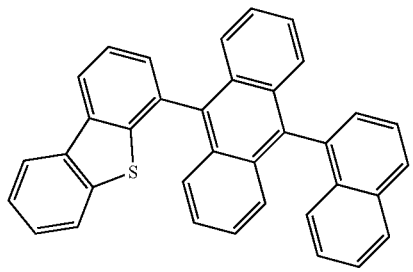 | 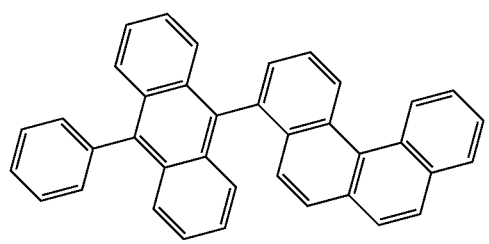 |
| 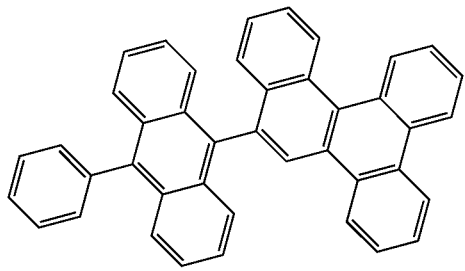 | 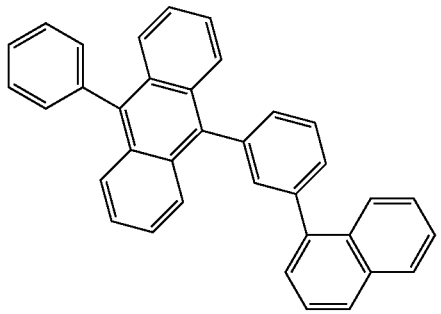 |
| 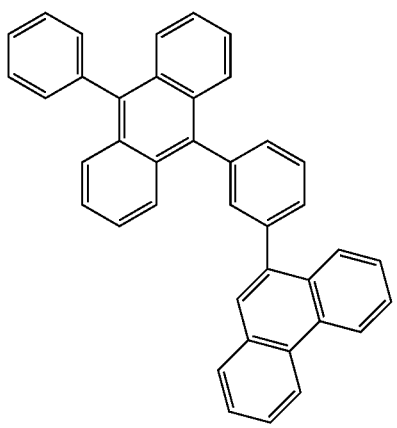 | 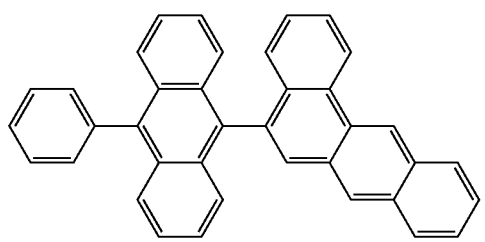 |
| 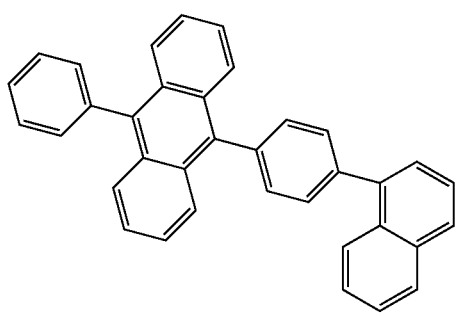 | 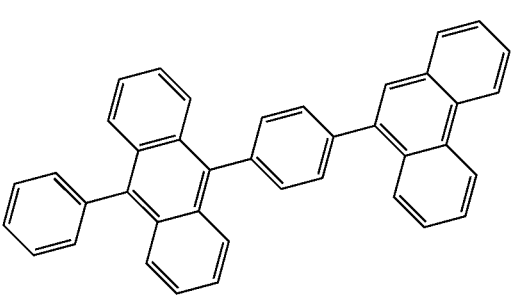 |
| 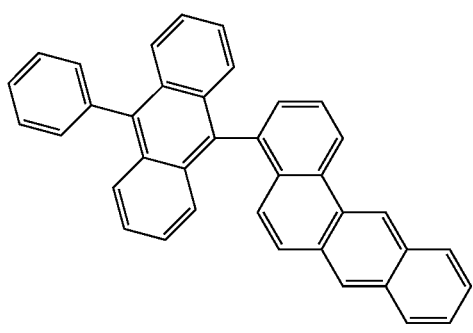 | 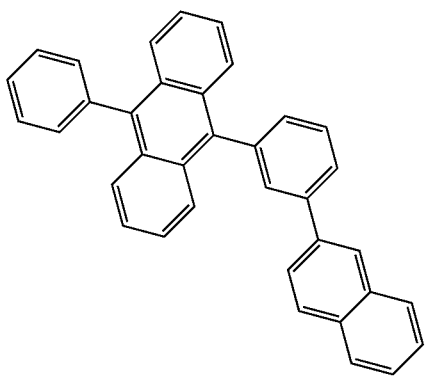 |

209
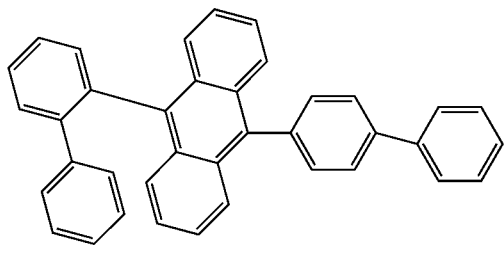
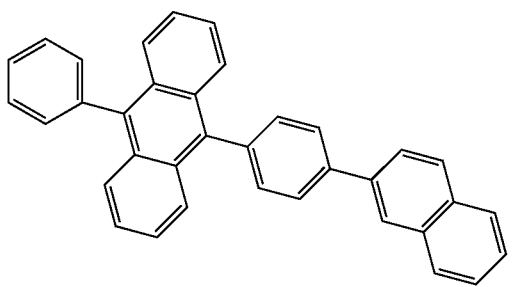
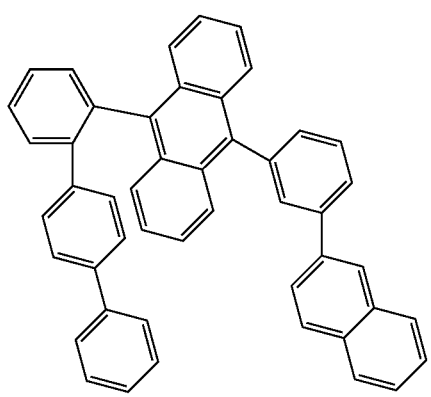
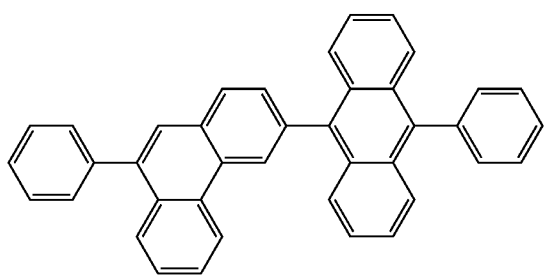
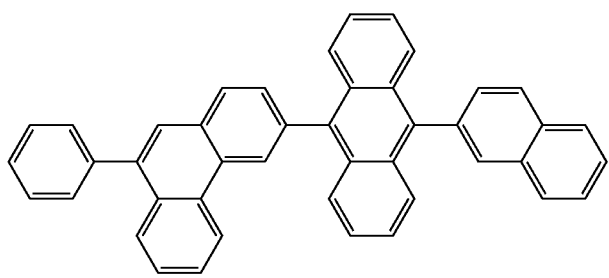
210
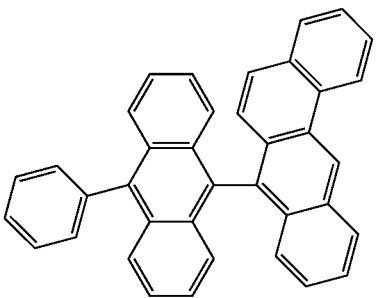
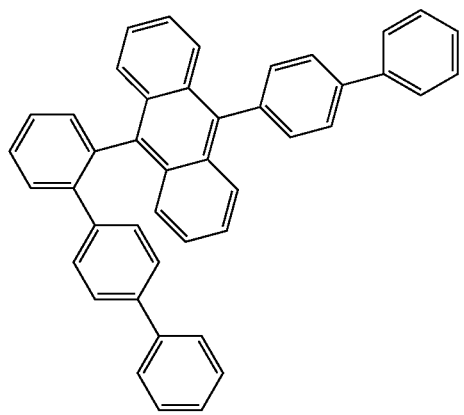
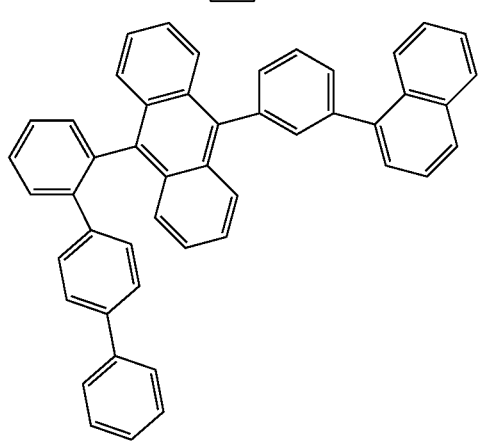
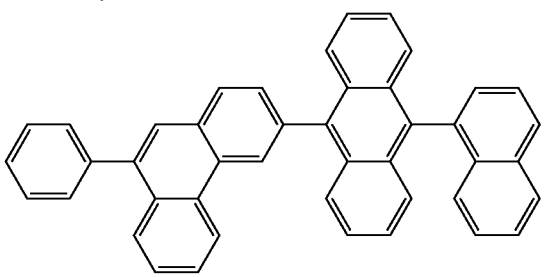

-continued
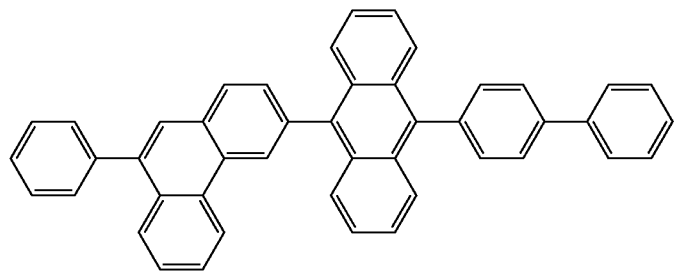
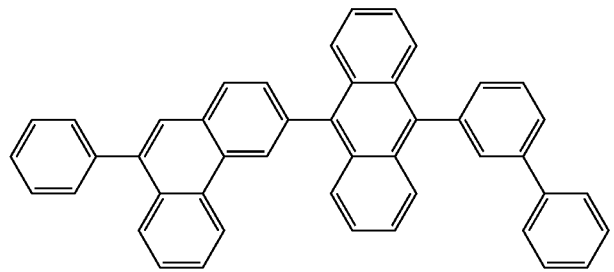
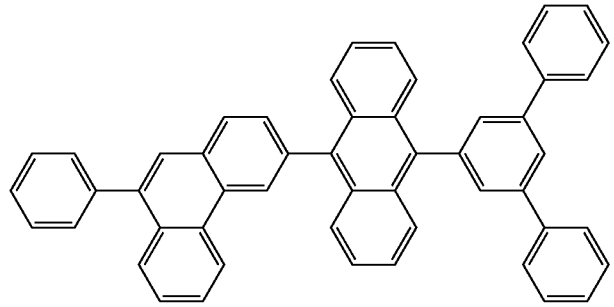
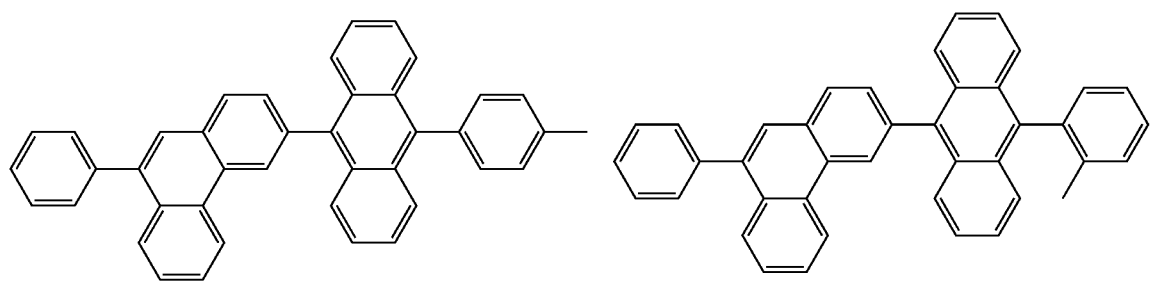
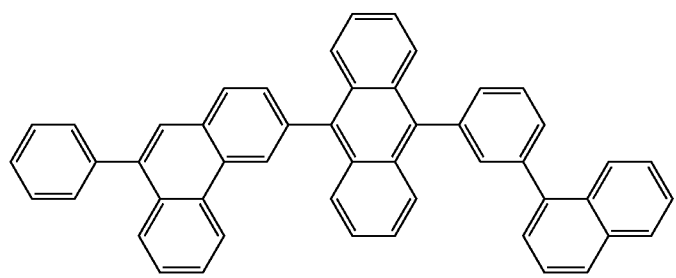
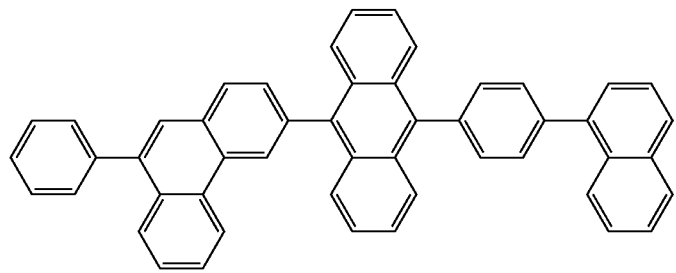

-continued
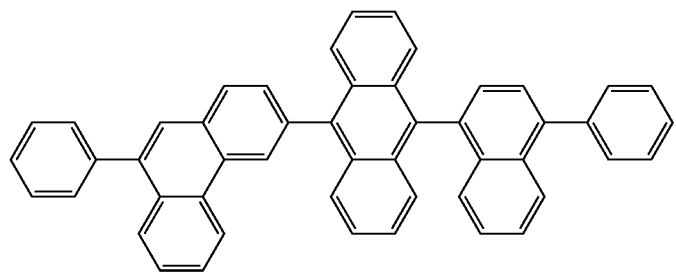
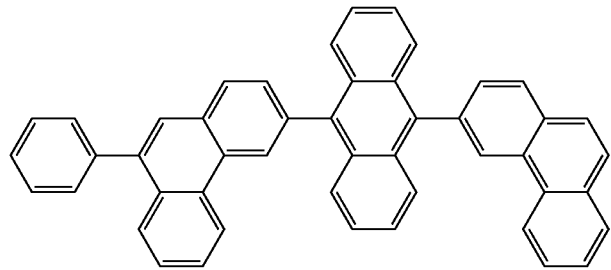
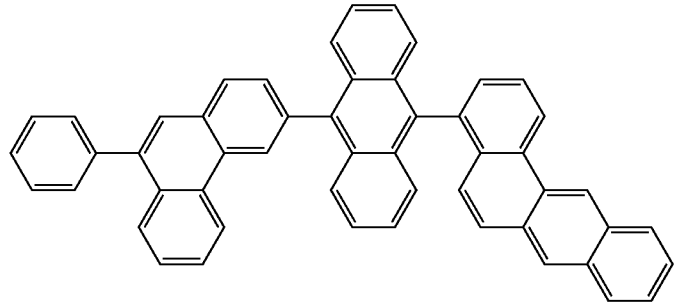
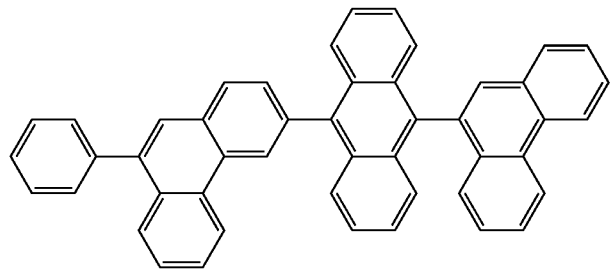
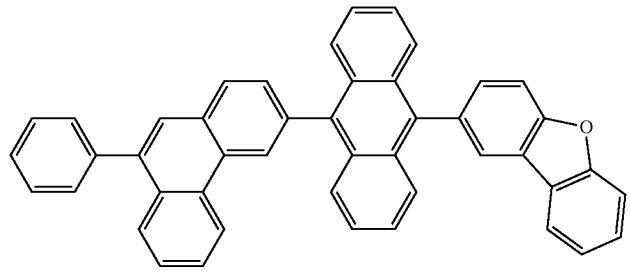
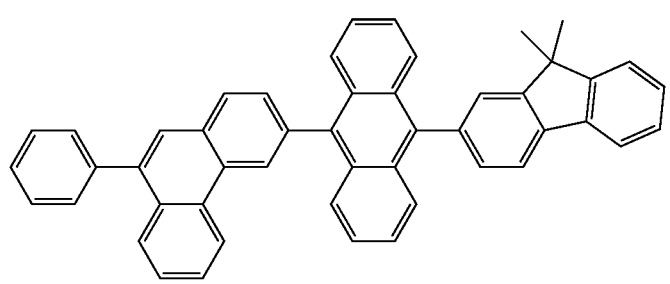

-continued
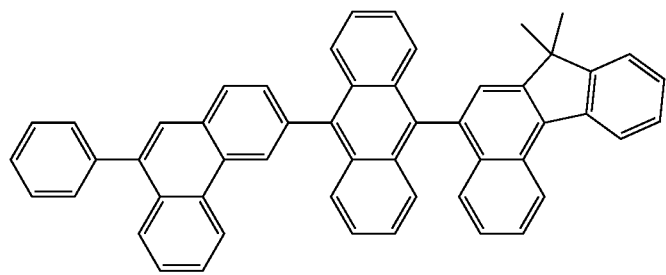
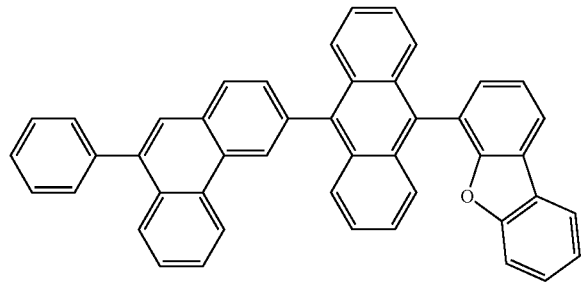
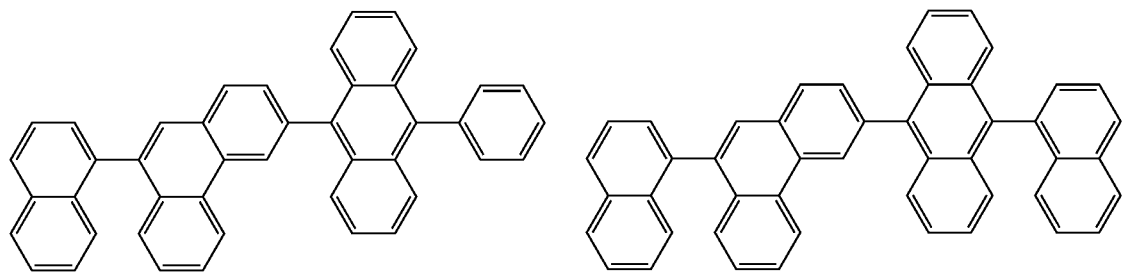
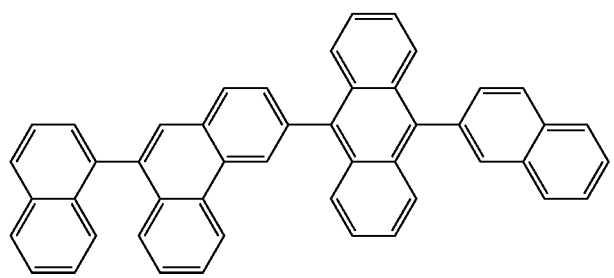
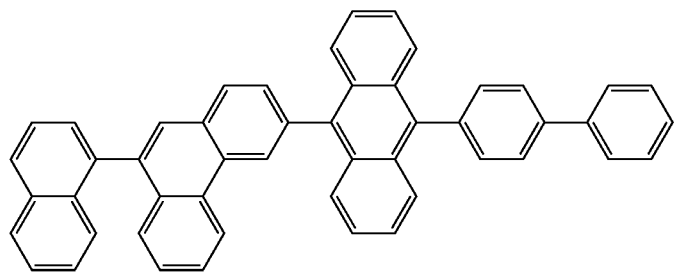
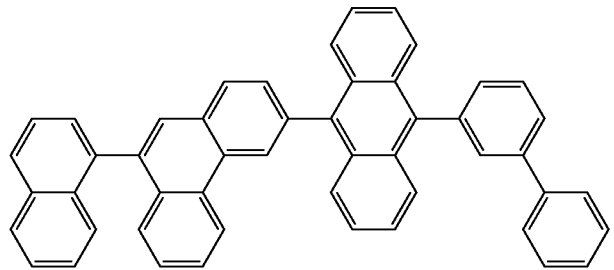

-continued
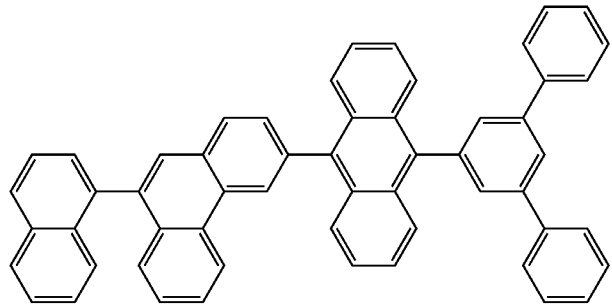
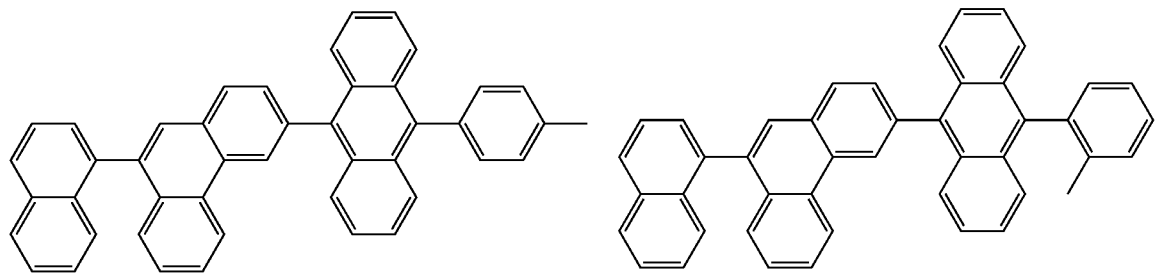
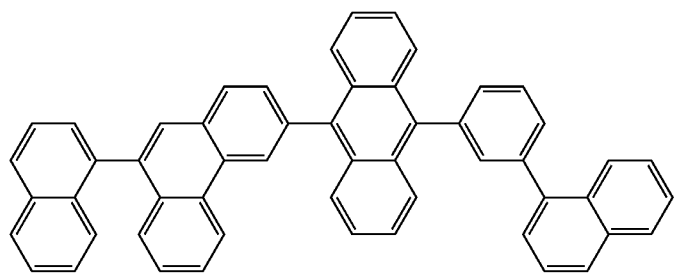
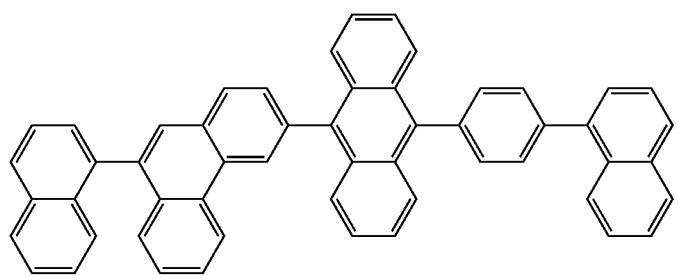
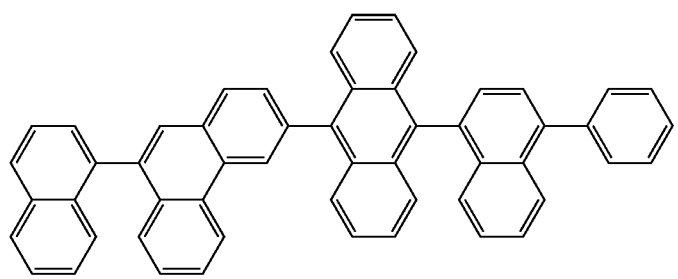
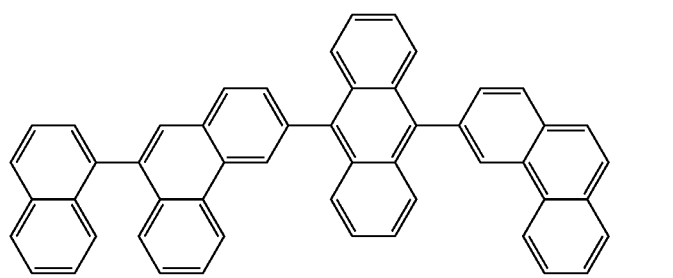

-continued
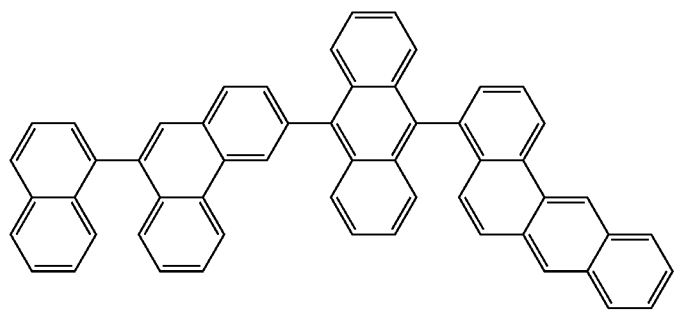
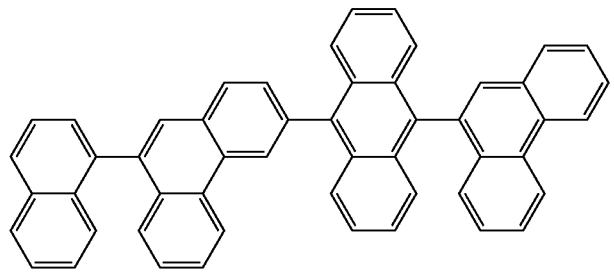
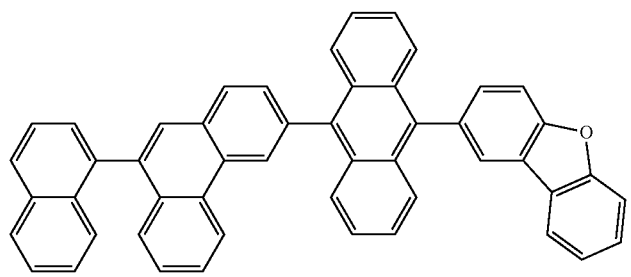
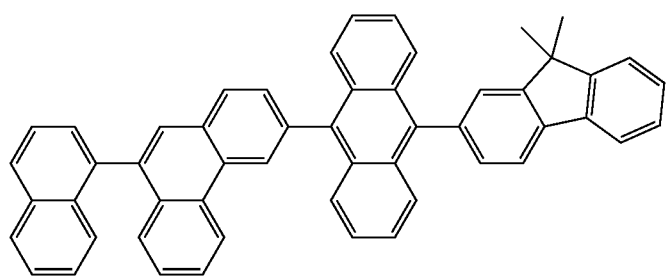
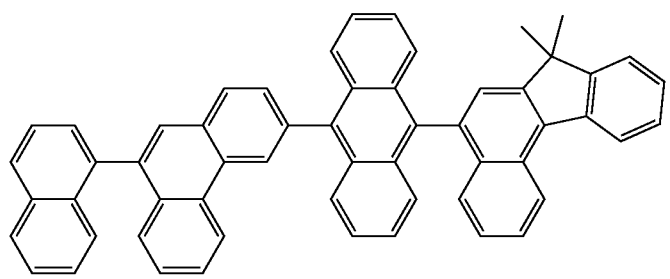
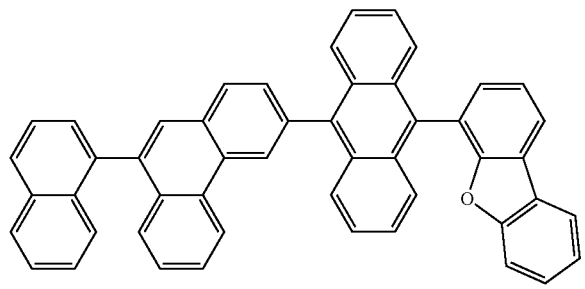

-continued
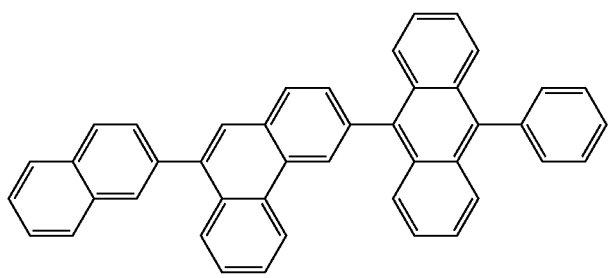
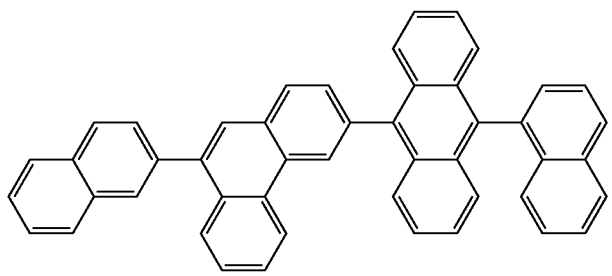
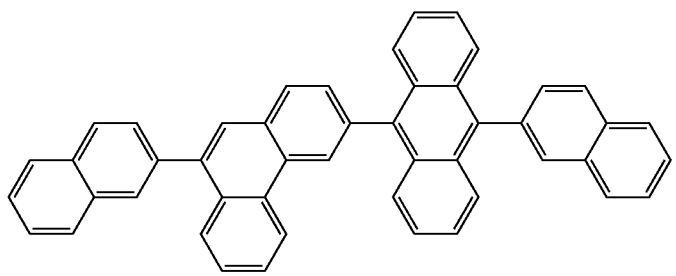
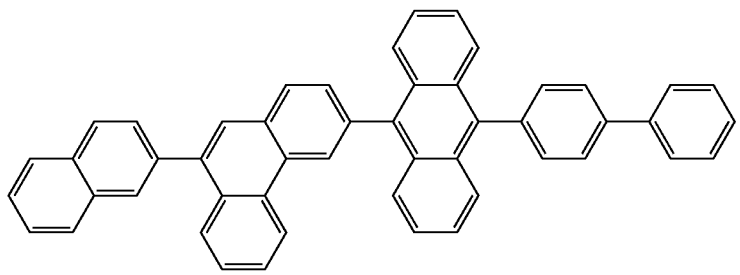
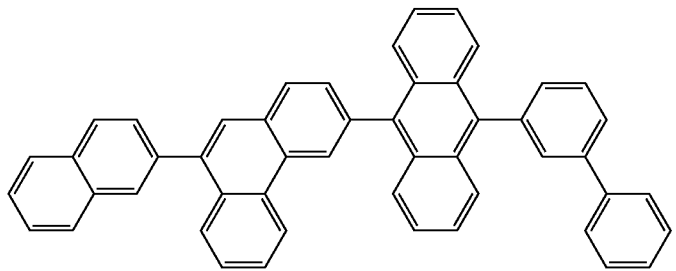
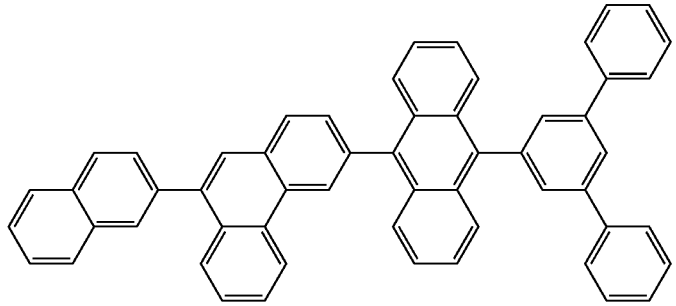

-continued
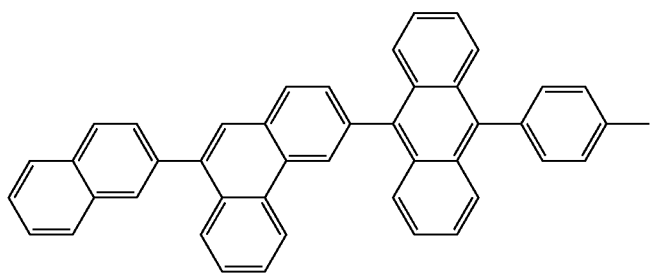
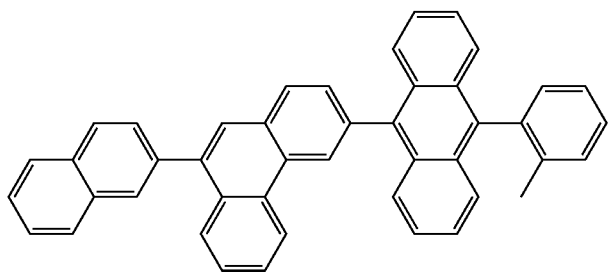
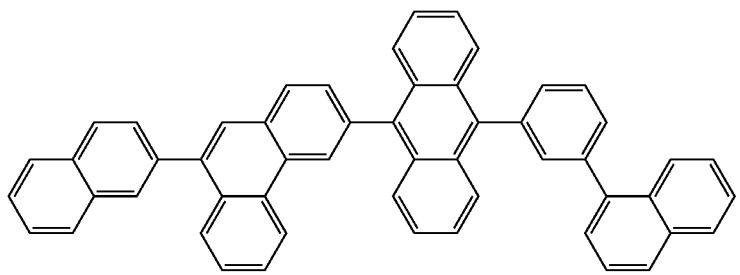
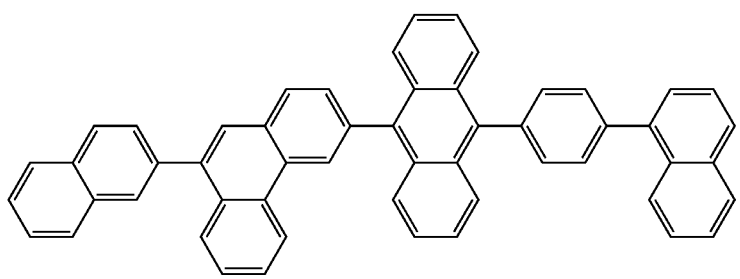
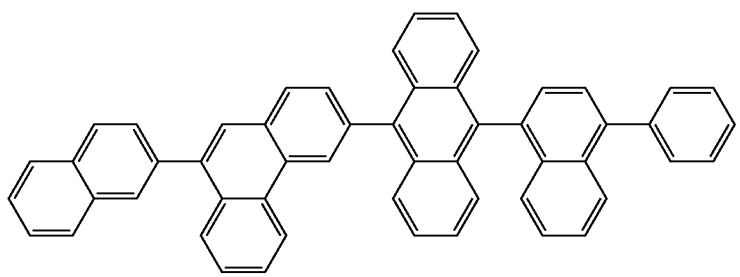
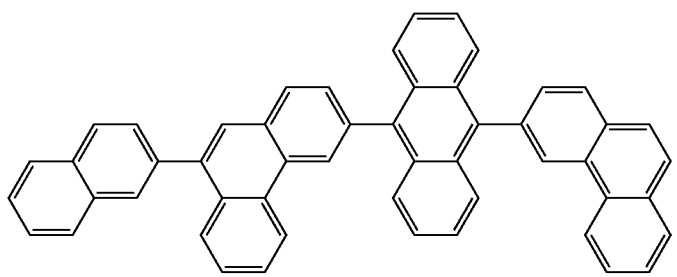

-continued
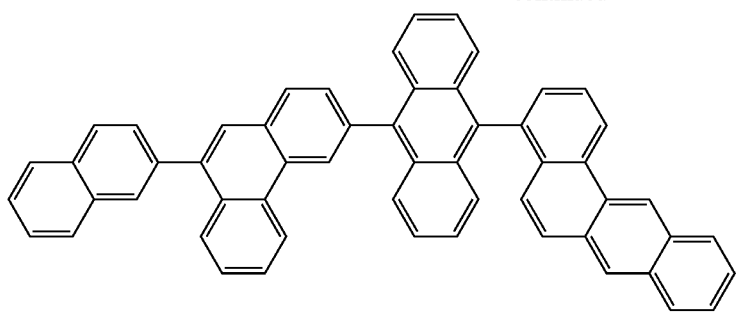
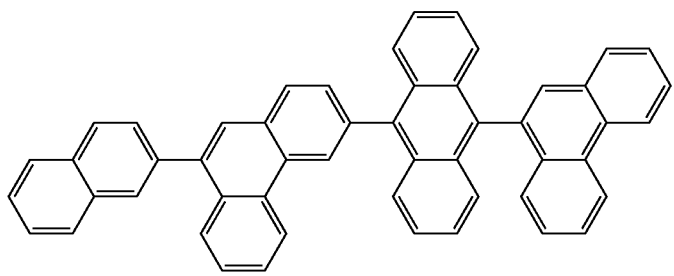
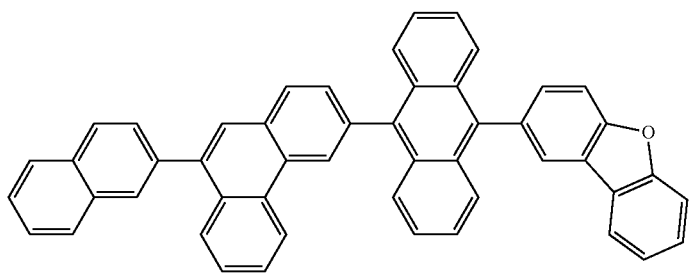
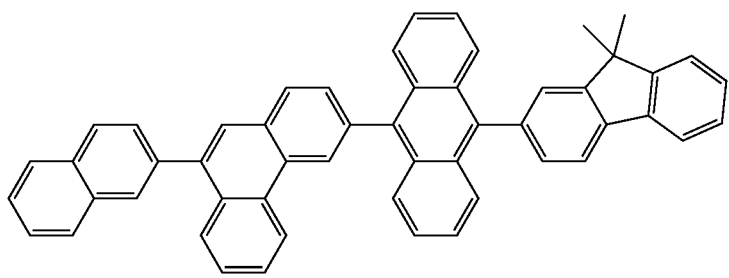
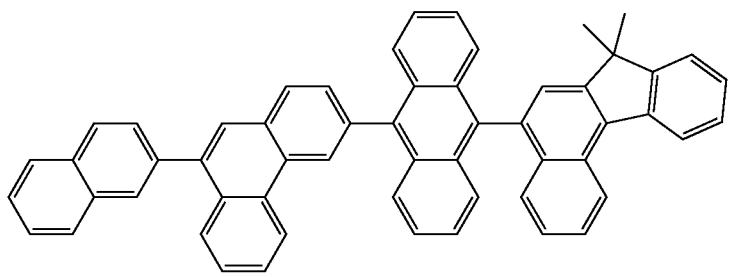
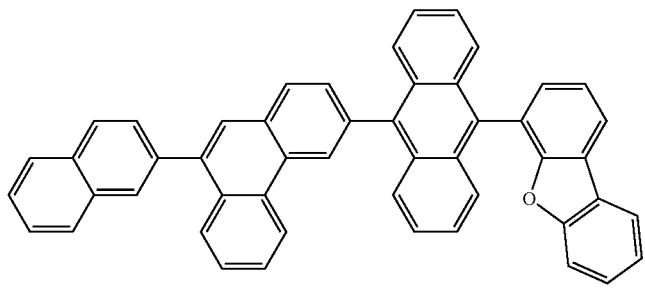

-continued
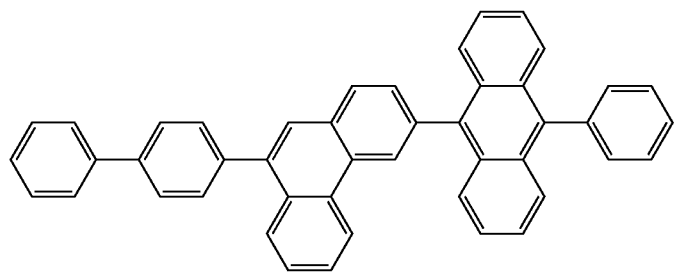
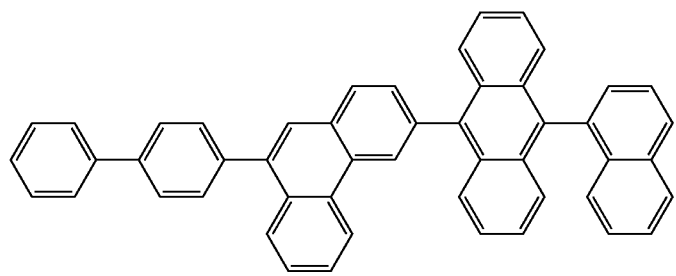
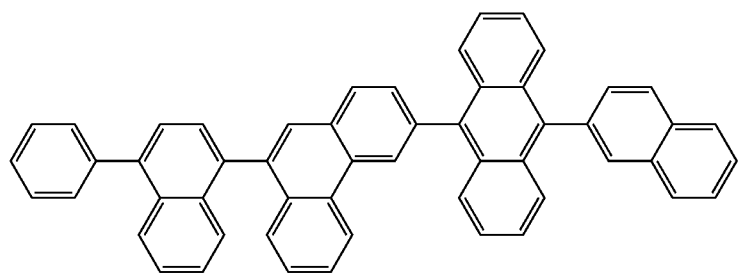
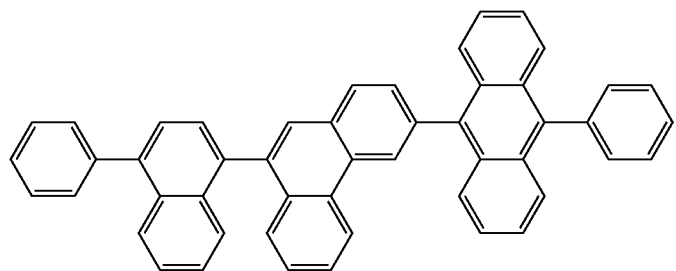
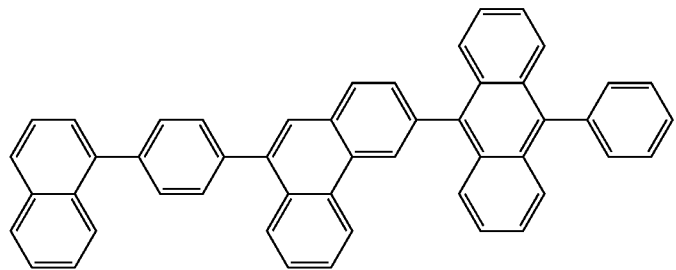
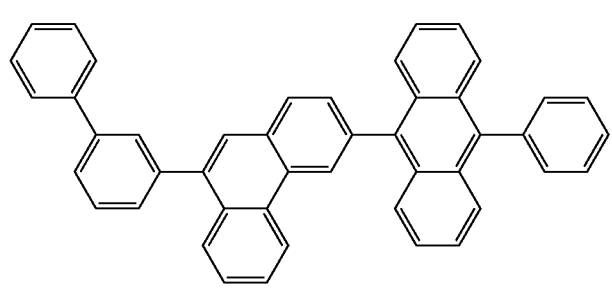

-continued
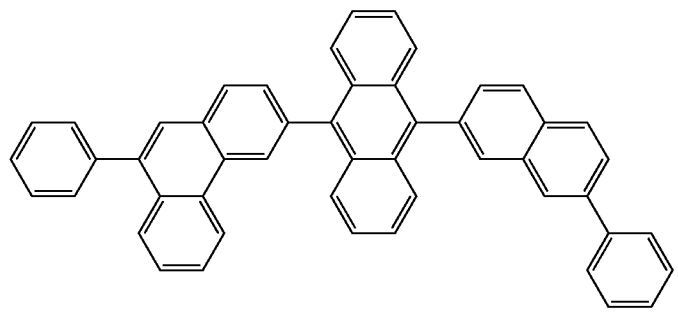
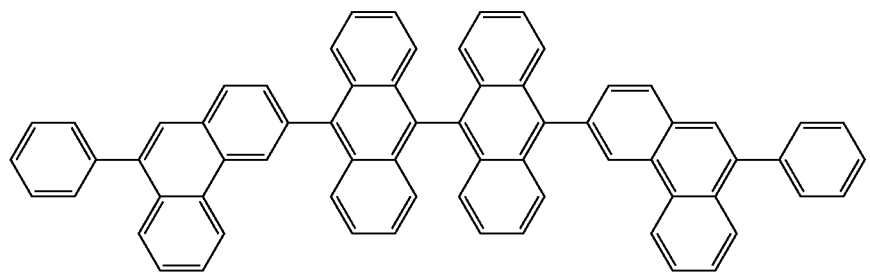
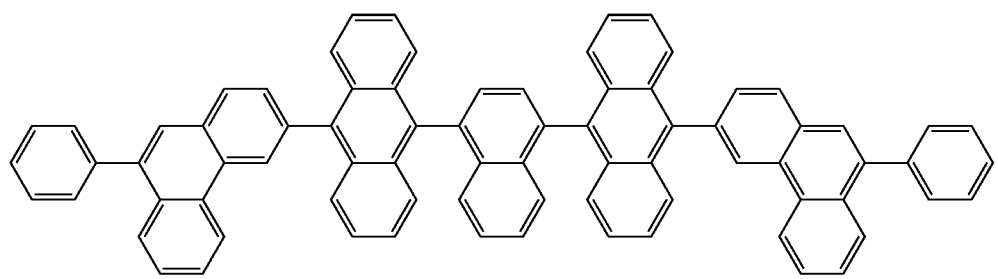
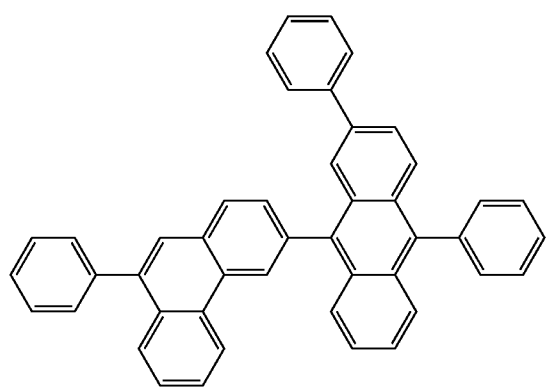
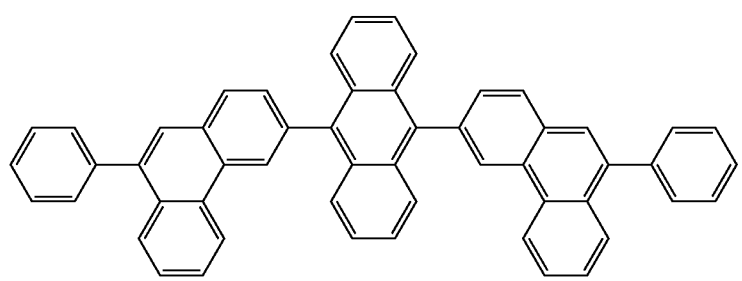

-continued
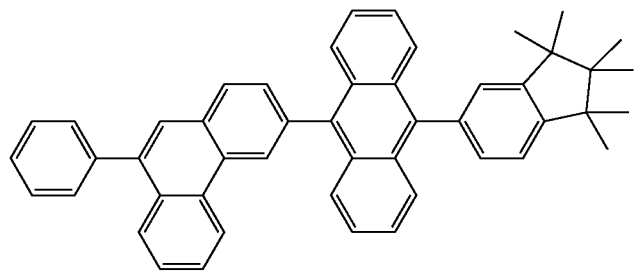
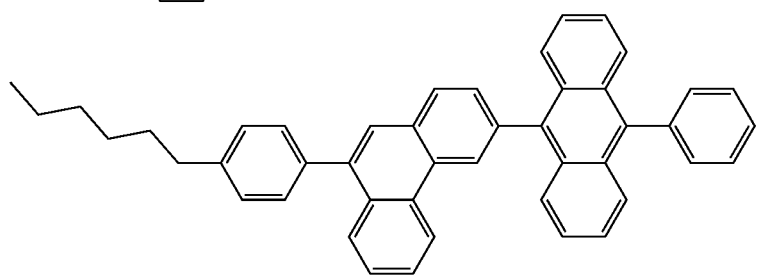
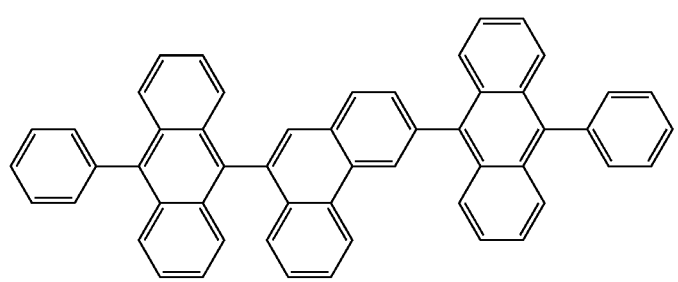
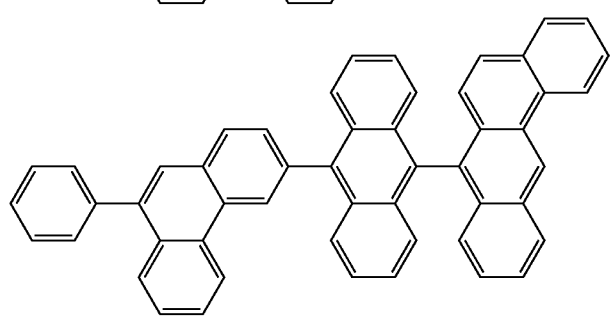
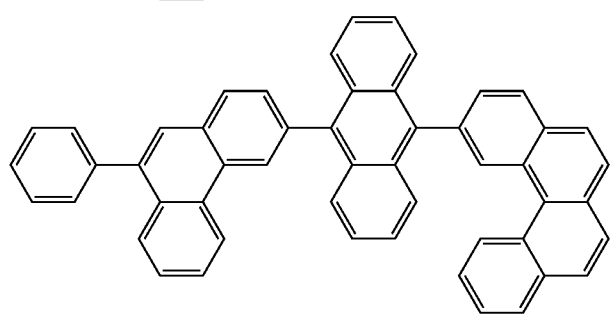
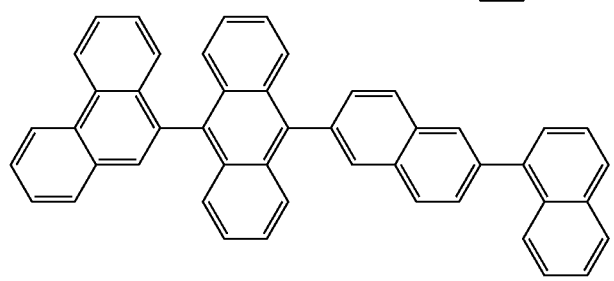

-continued
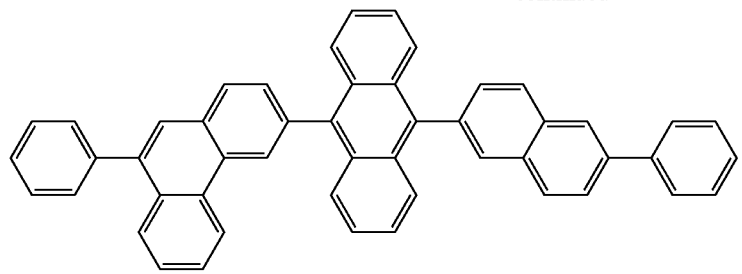
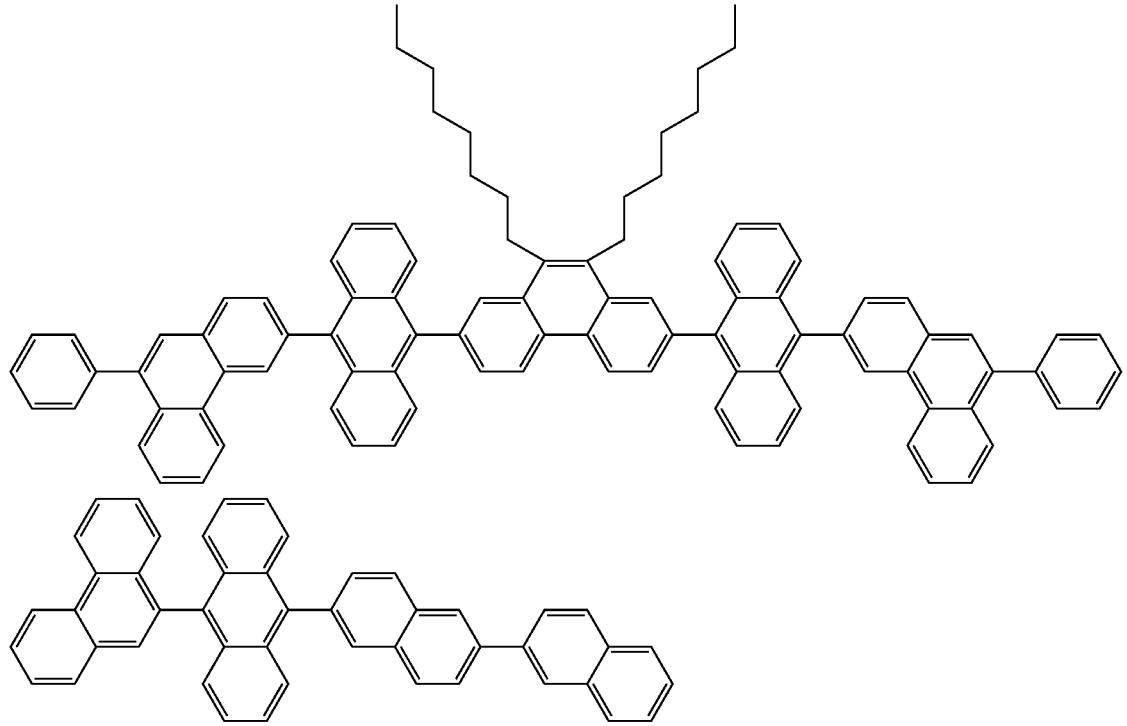
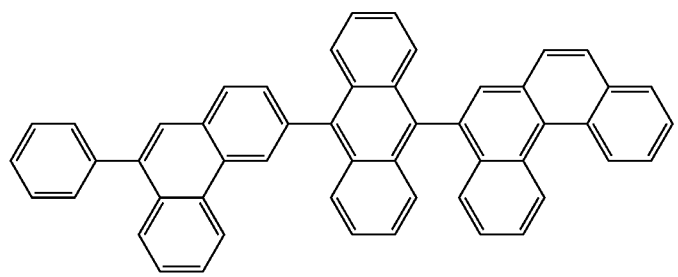
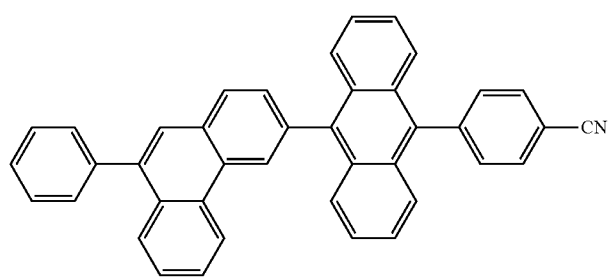

-continued
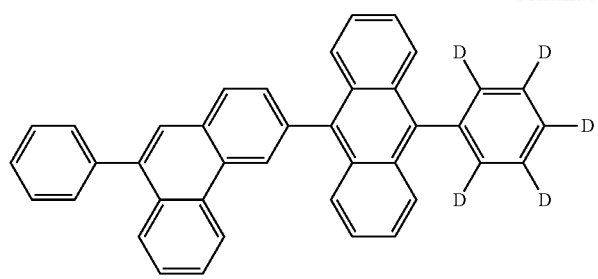
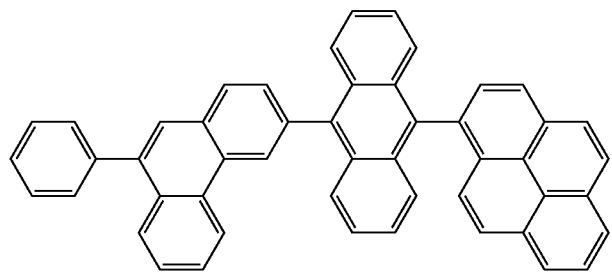
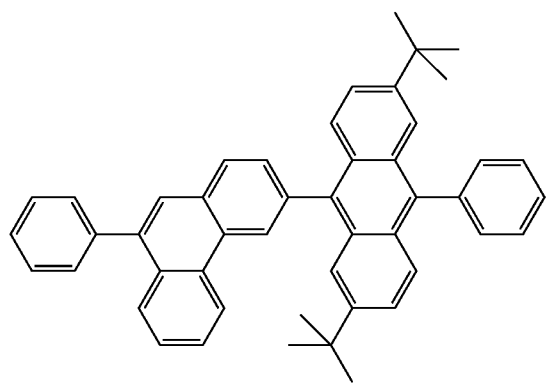
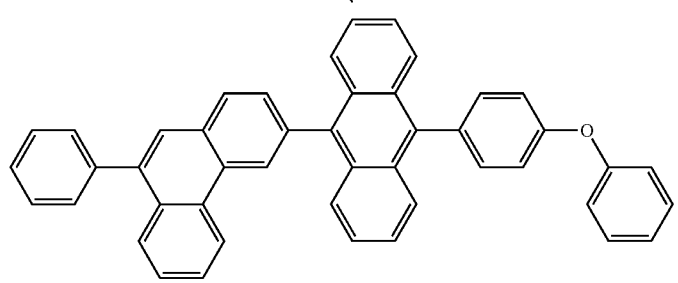
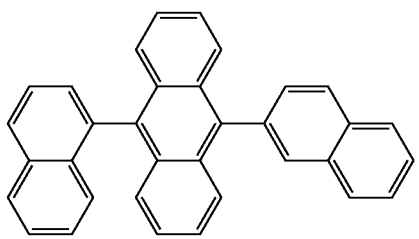
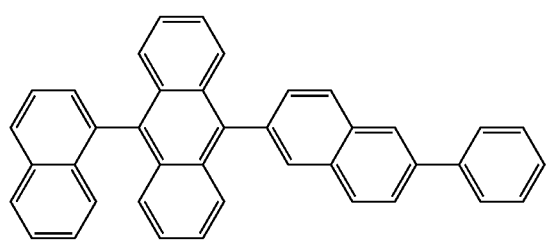
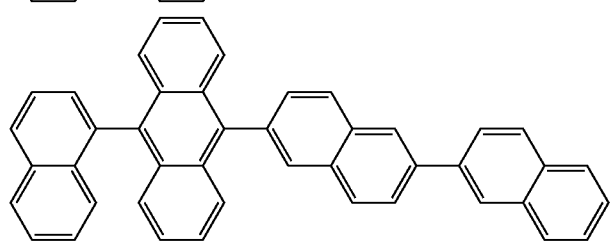

-continued
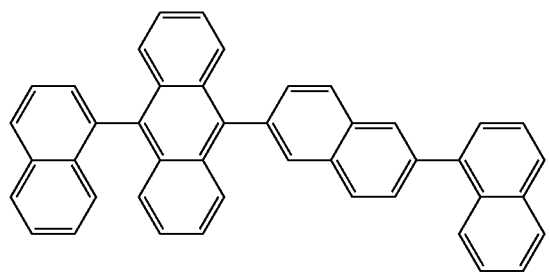
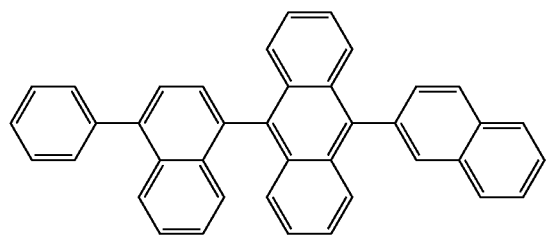
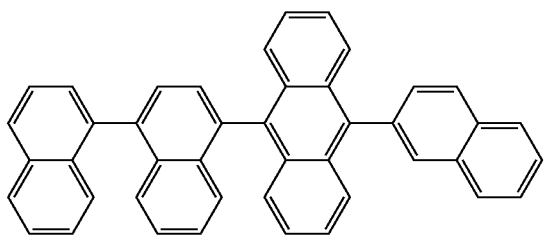
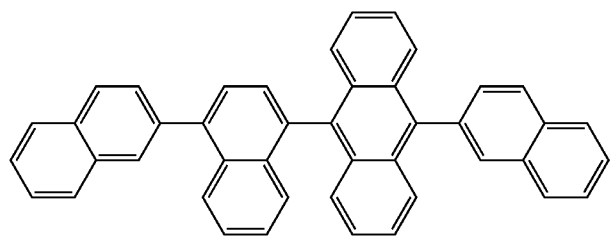
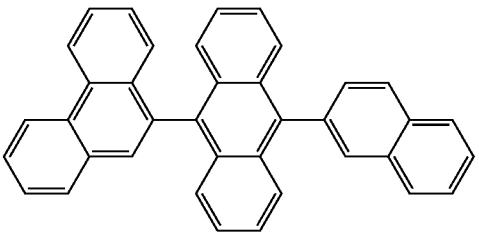
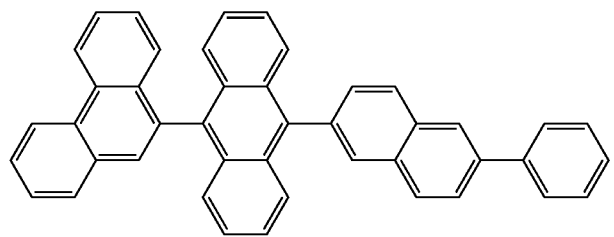
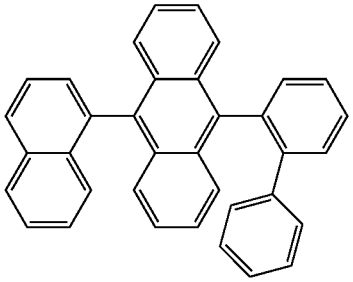
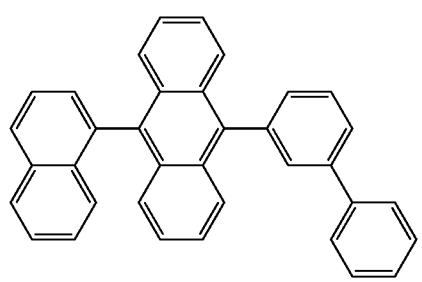
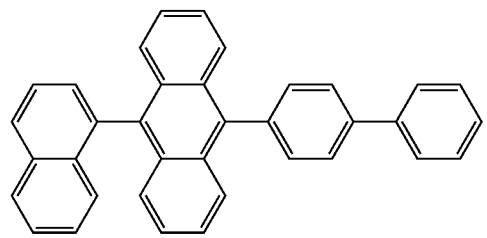
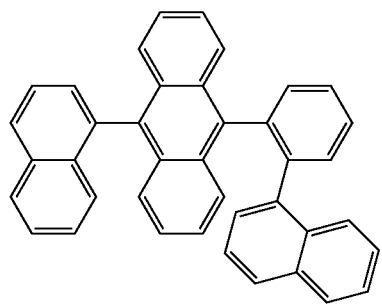
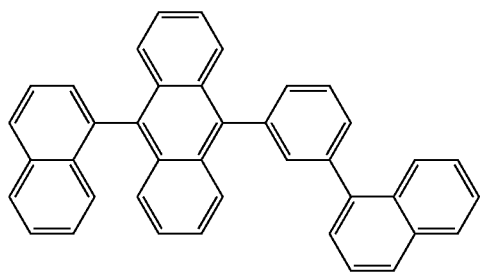

-continued
| 239 | 240 |
|---|---|
| 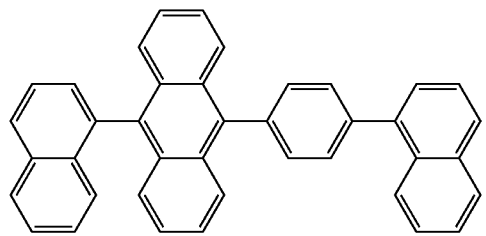 | 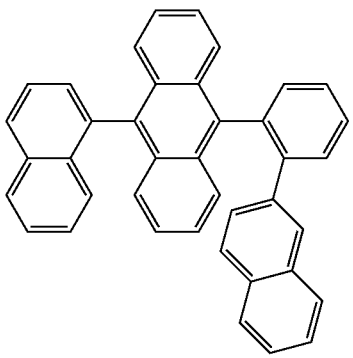 |
| 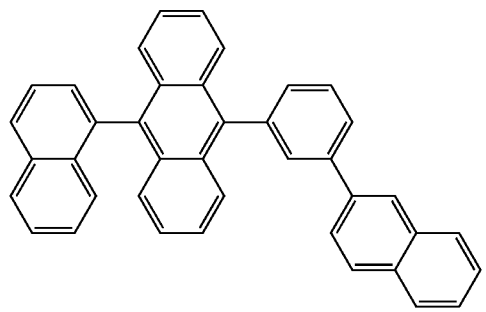 | 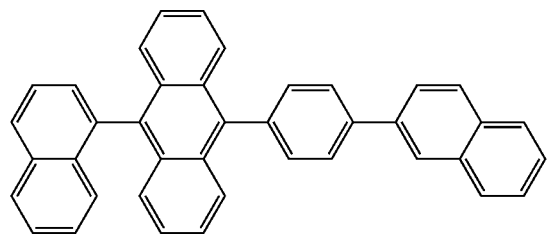 |
| 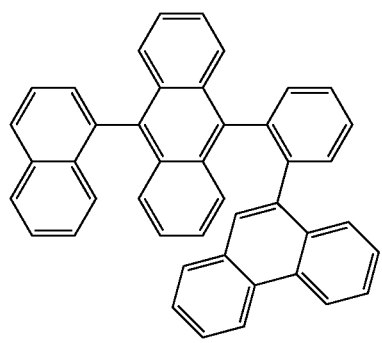 | 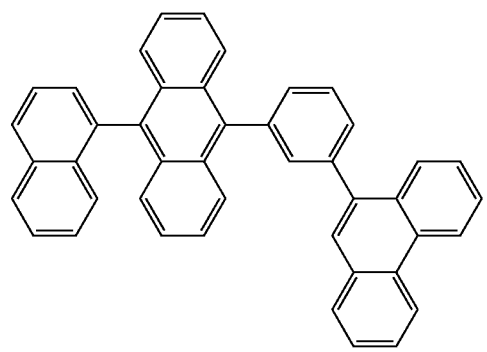 |
| 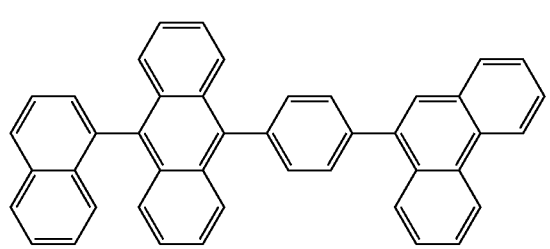 | 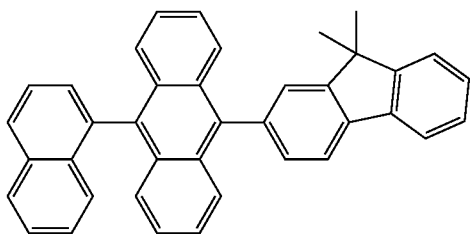 |
| 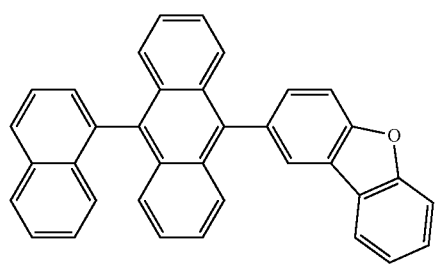 | 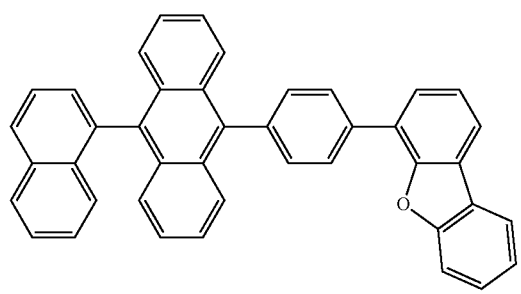 |

-continued
| 241 | 242 |
|---|---|
| 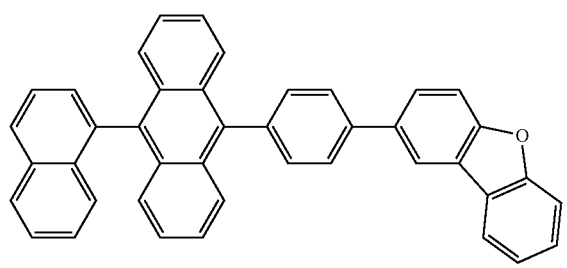 | 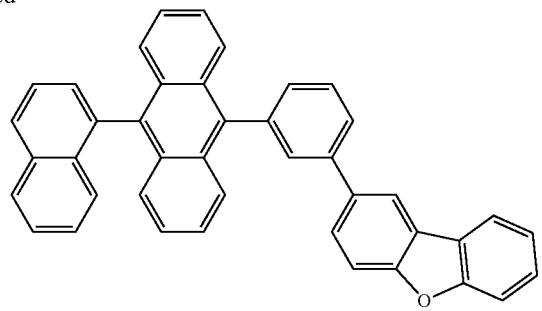 |
| 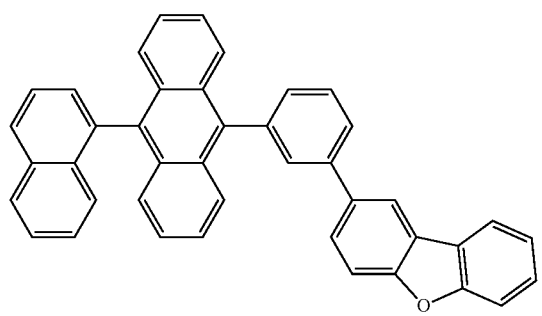 | 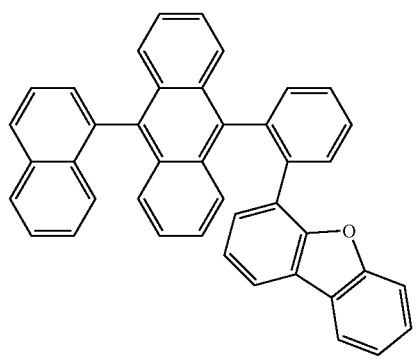 |
| 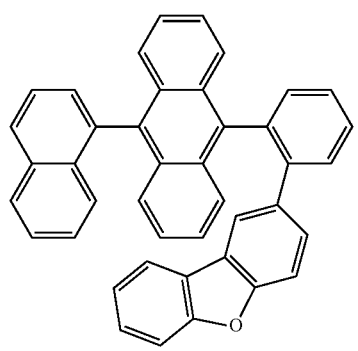 | 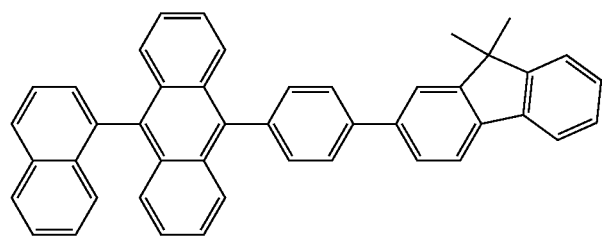 |
| 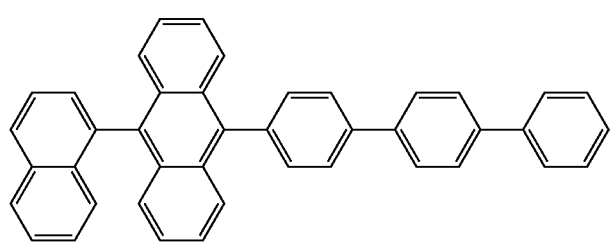 | 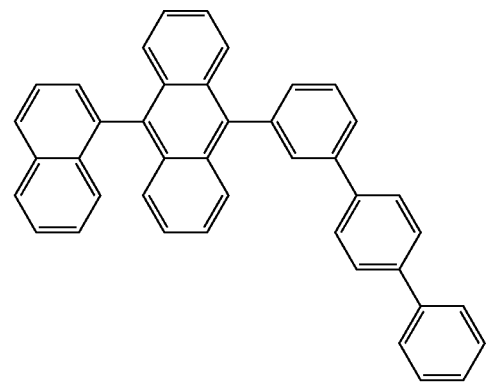 |

-continued
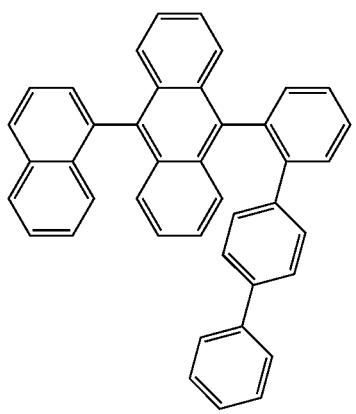
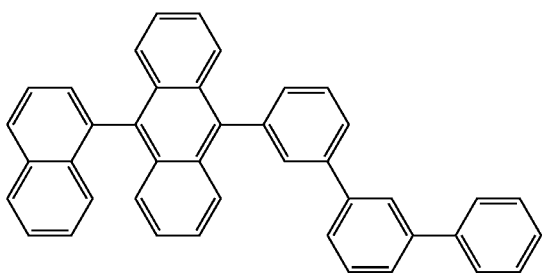
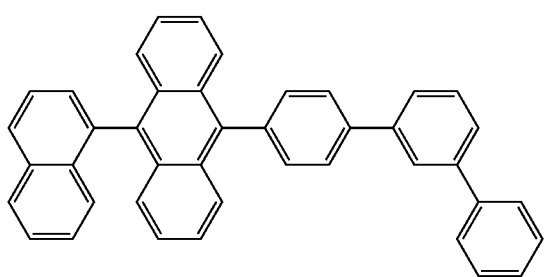
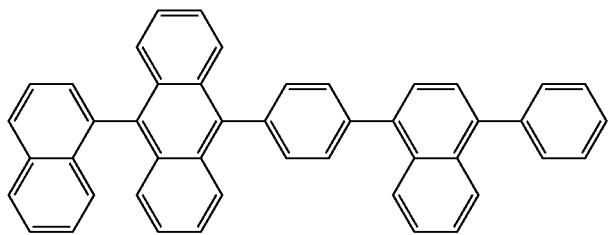
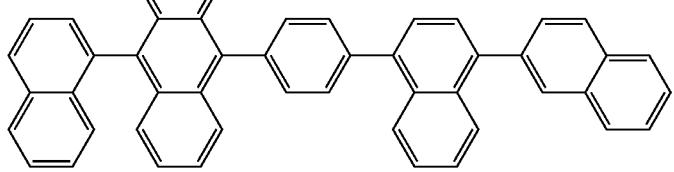
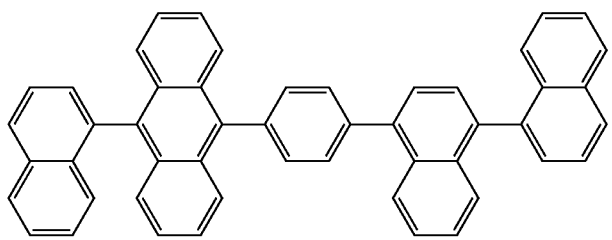
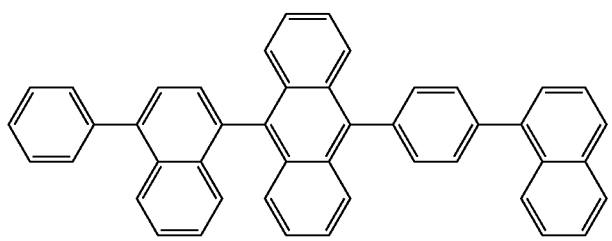

-continued
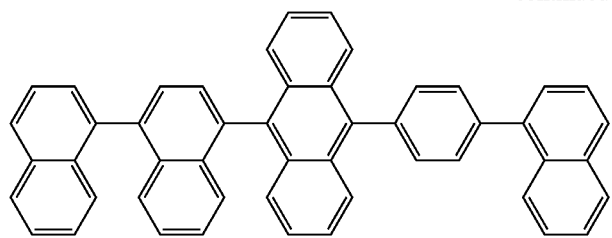
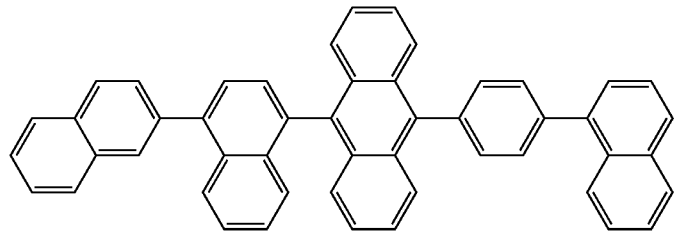
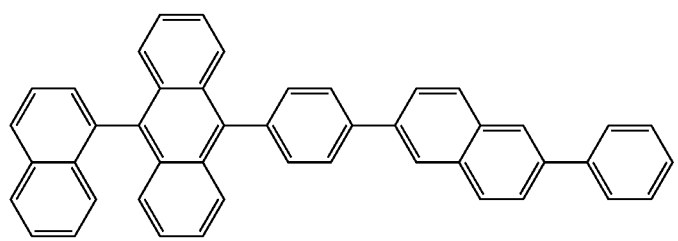
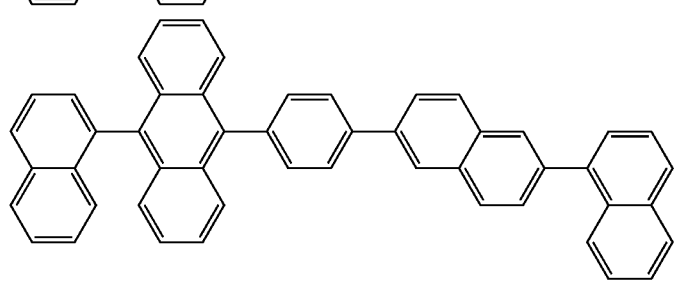
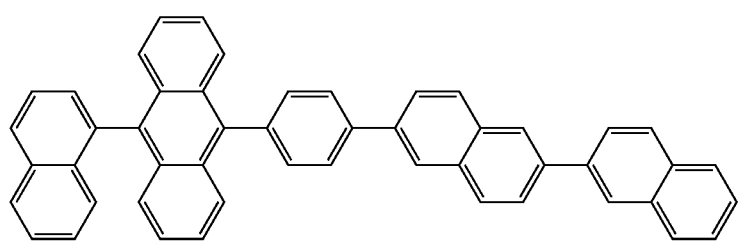
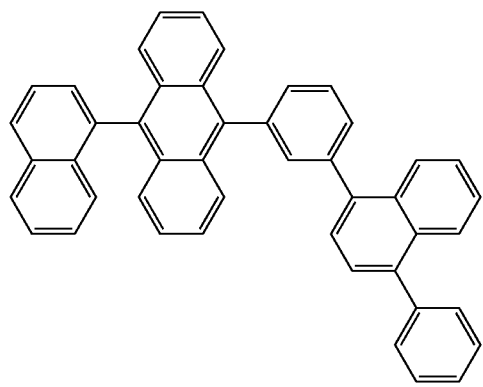

-continued
247
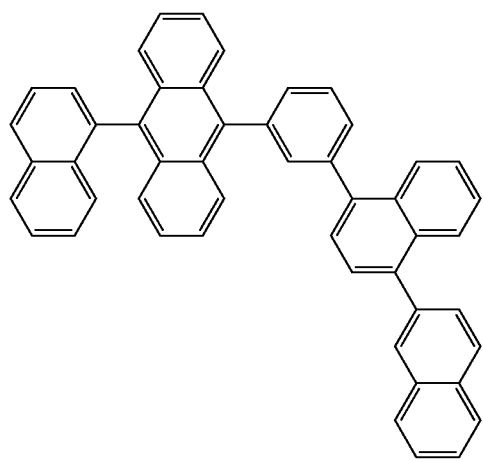
248
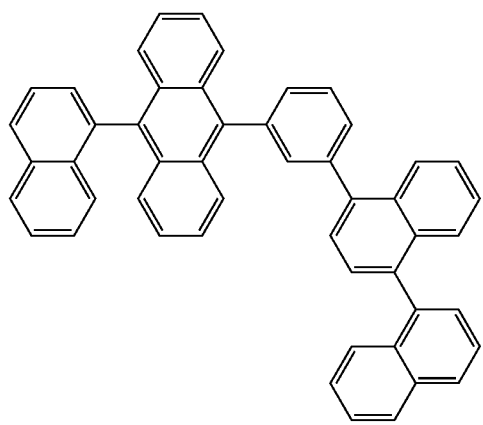
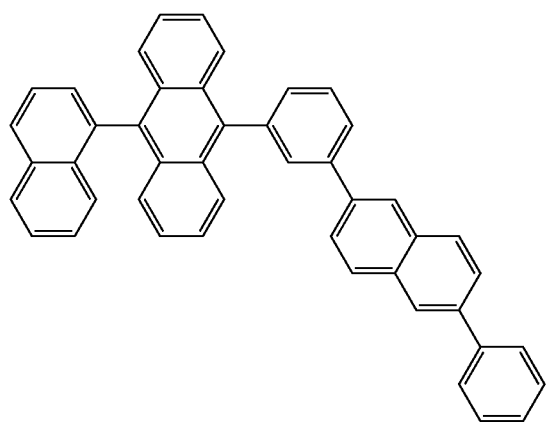
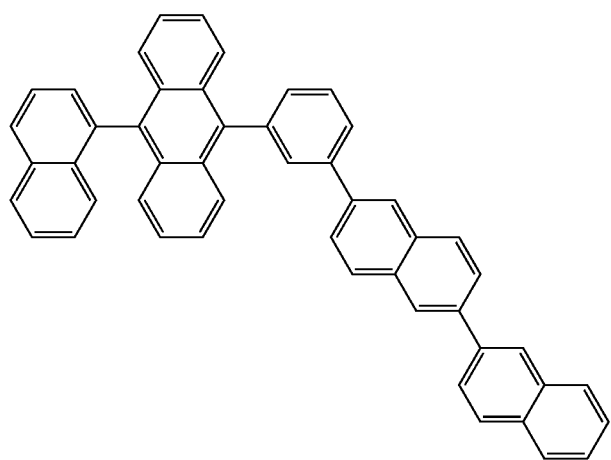

249
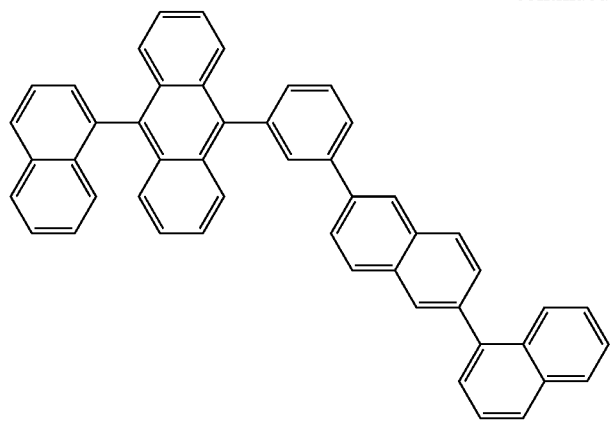
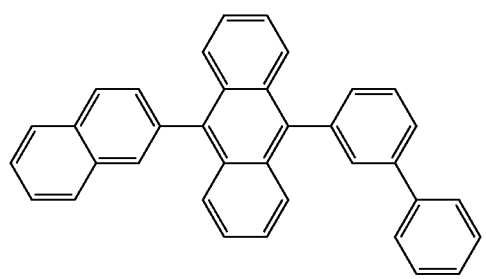
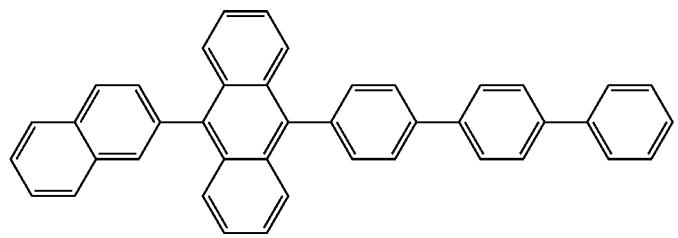
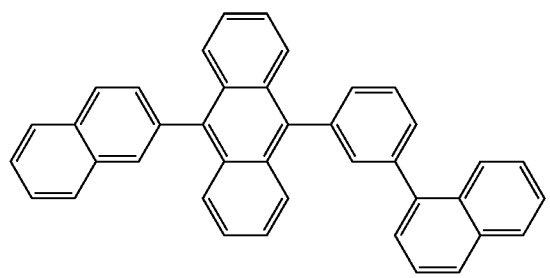
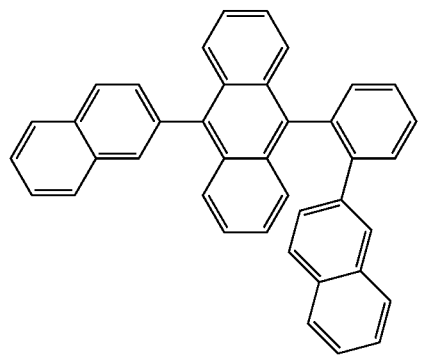
250
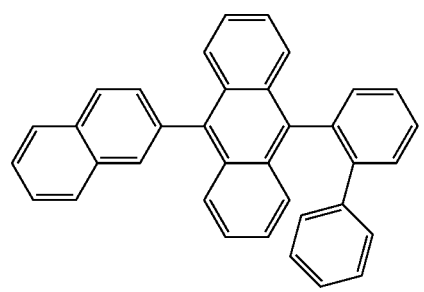
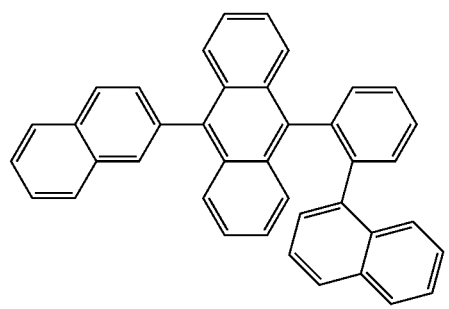
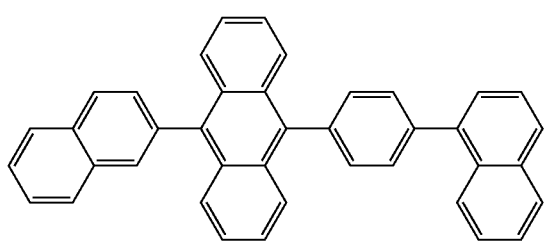
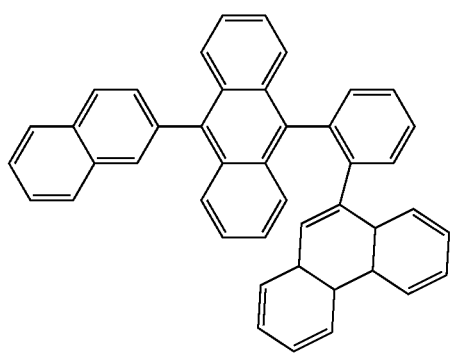

251
-continued
252
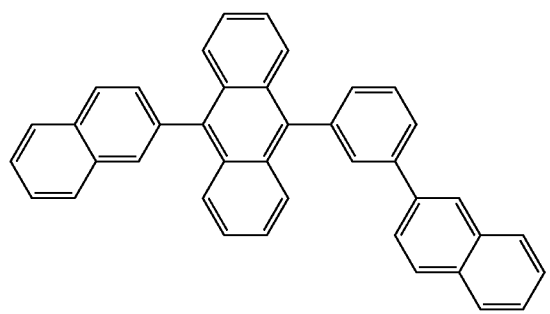
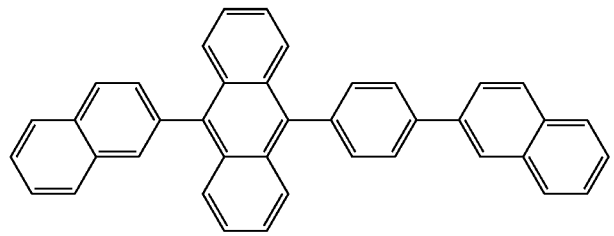
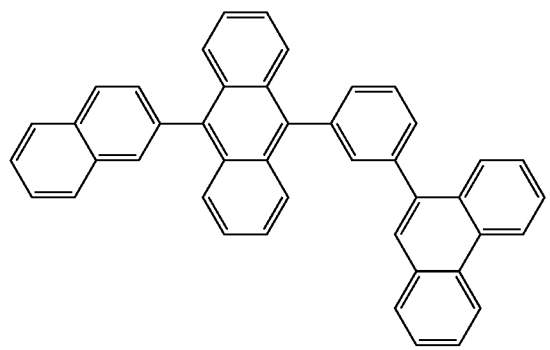
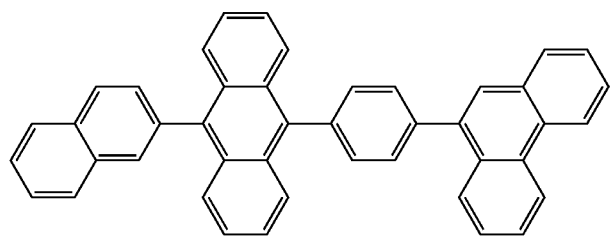
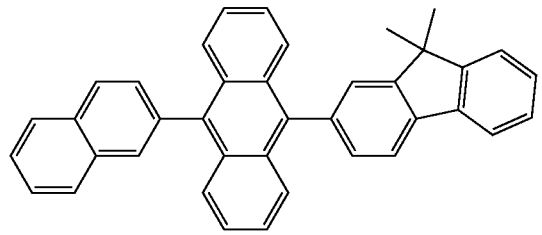
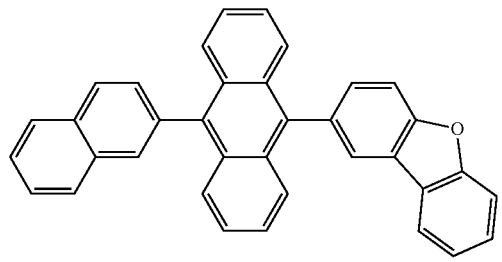
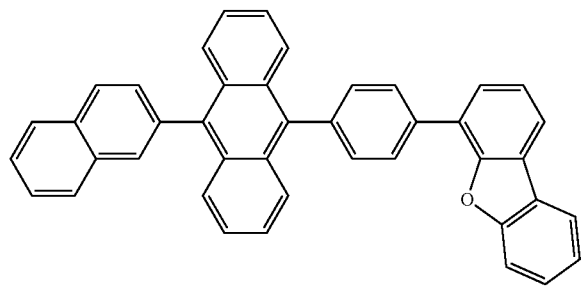

253
-continued
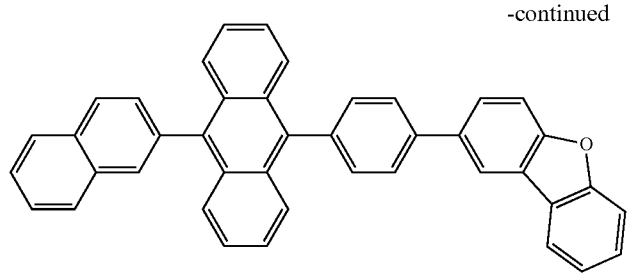
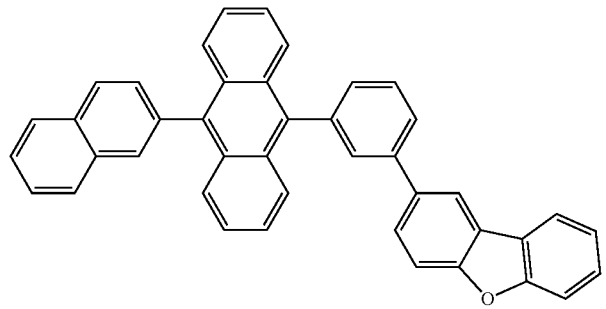
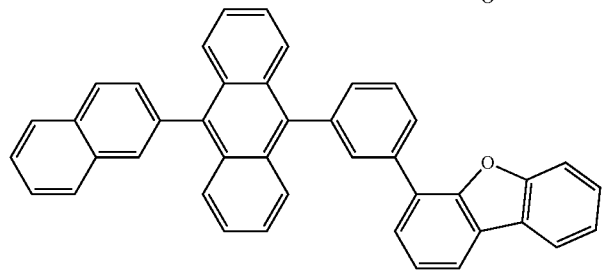
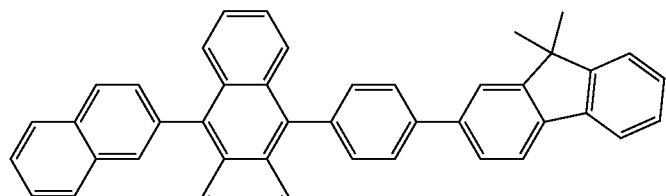
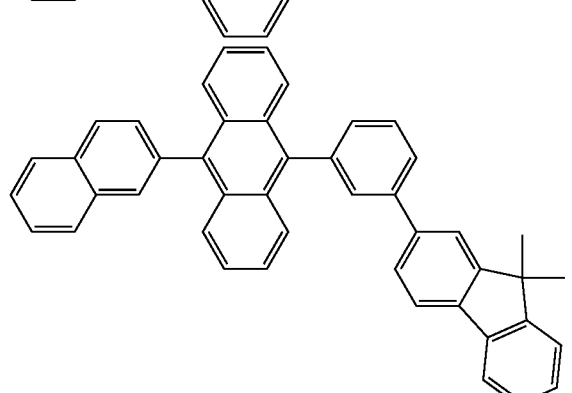
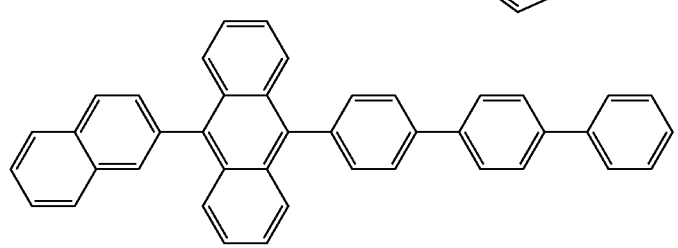
254
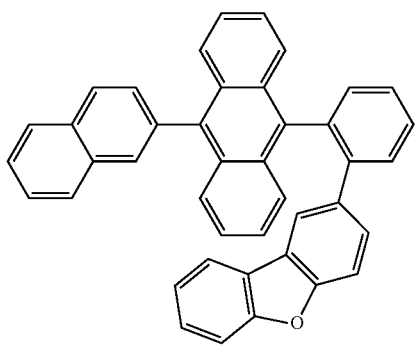

-continued
255
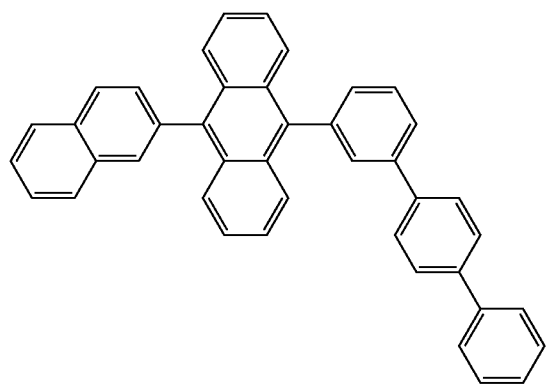
256
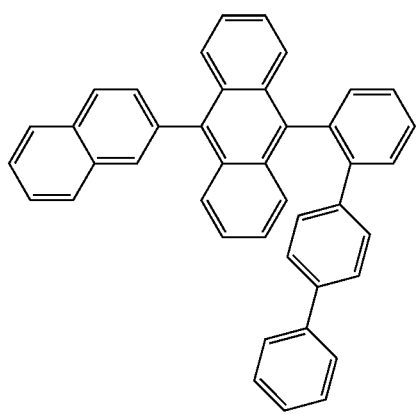
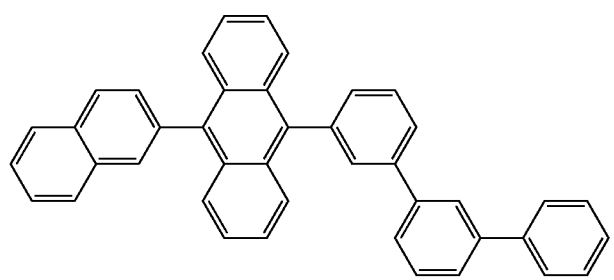
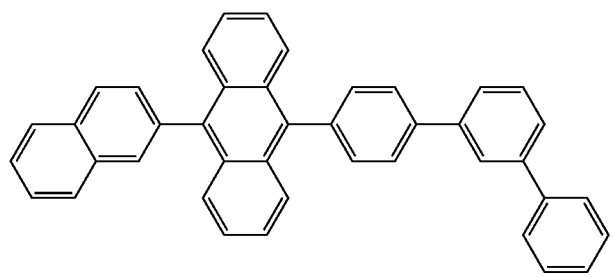
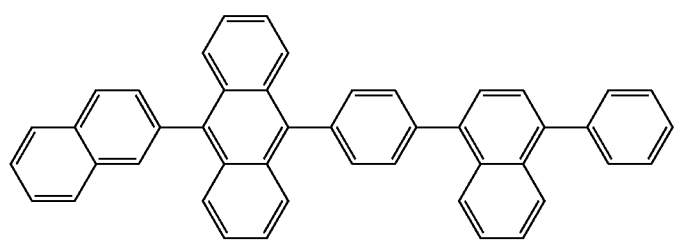
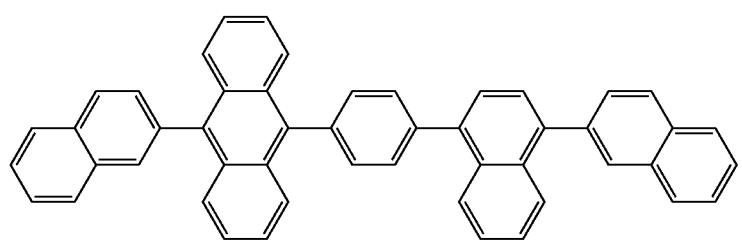

257
258
-continued
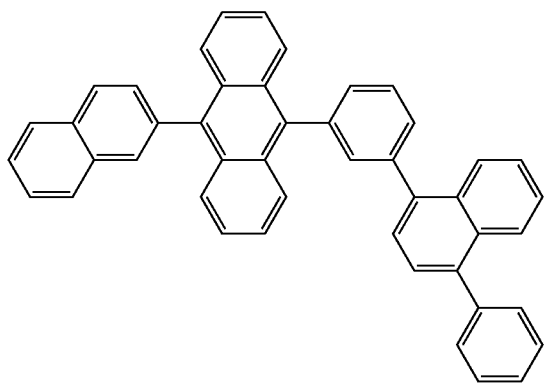
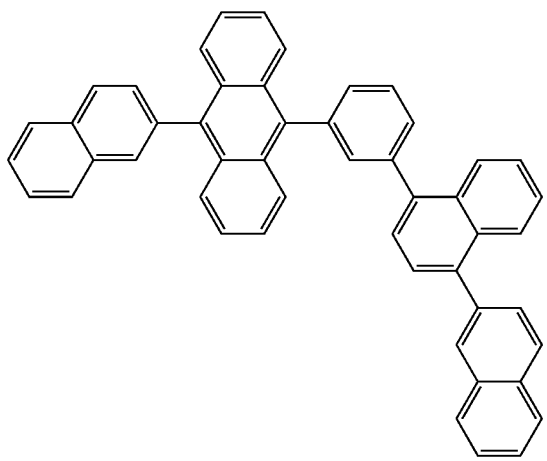
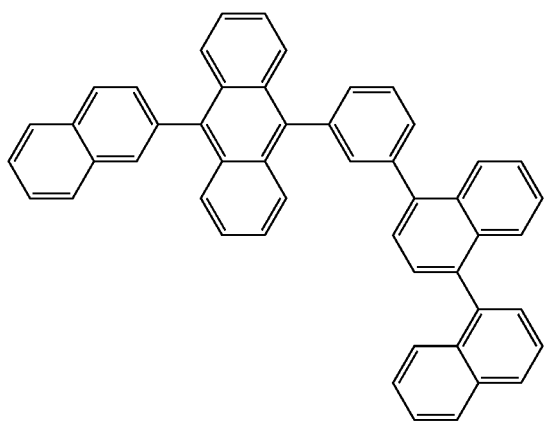
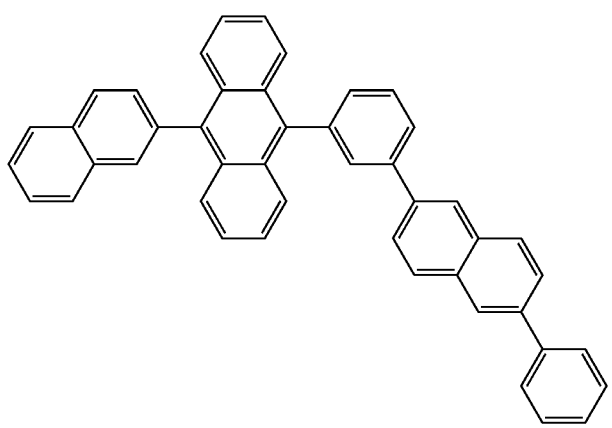

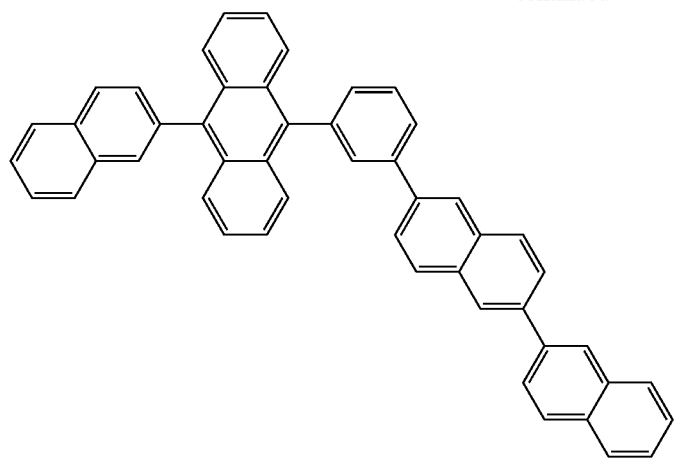
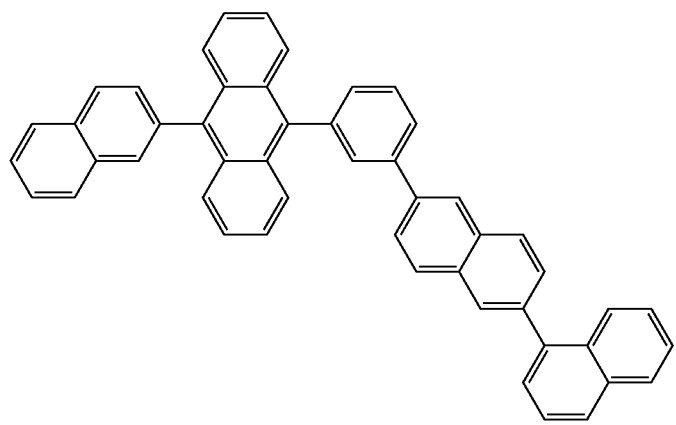
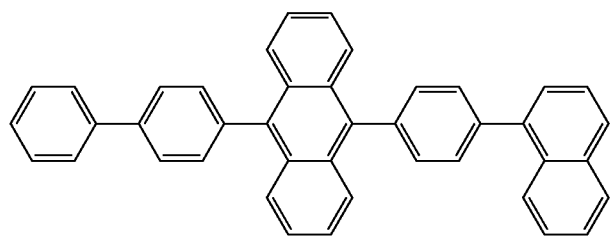
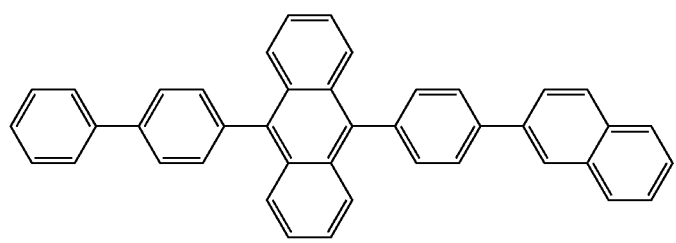
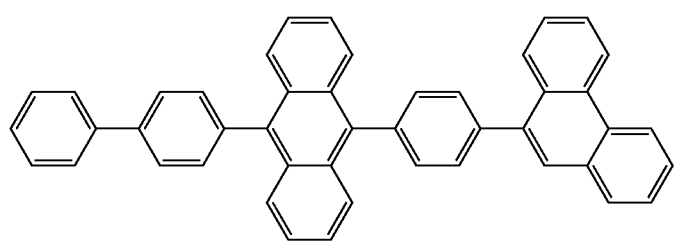

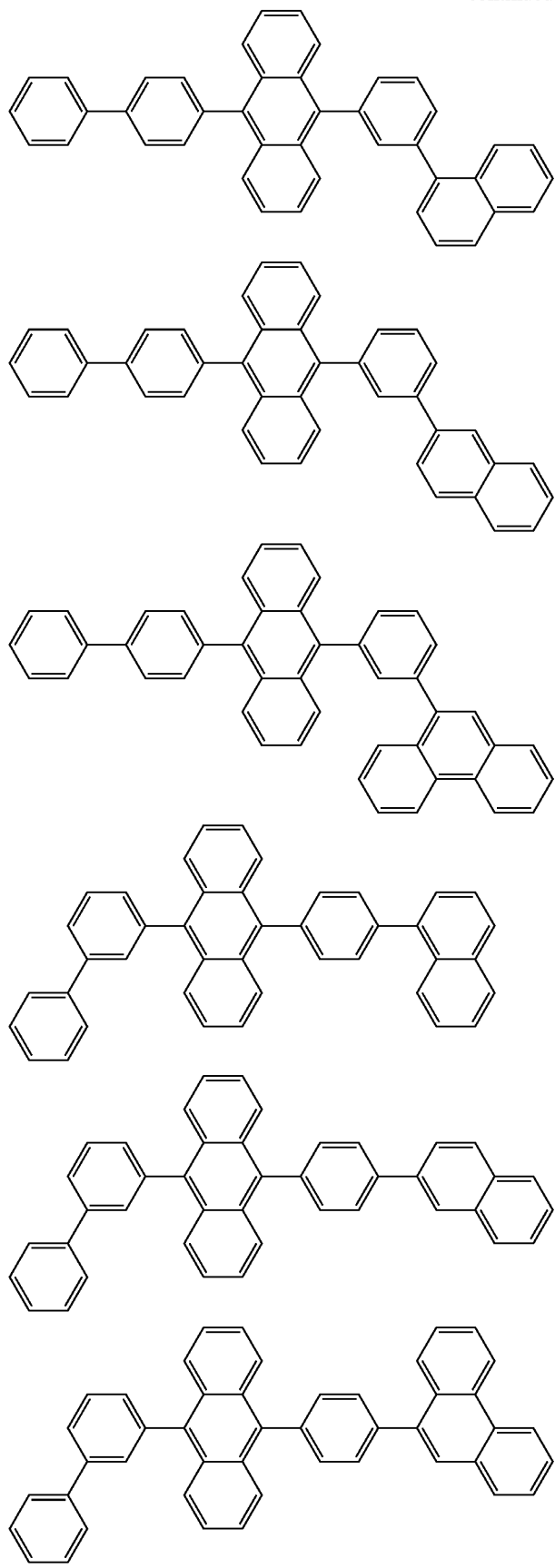

263
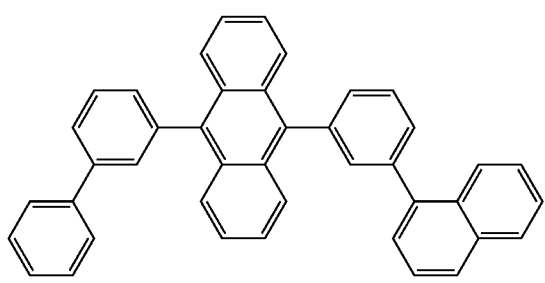
264
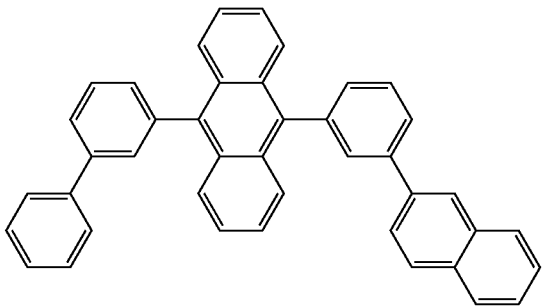
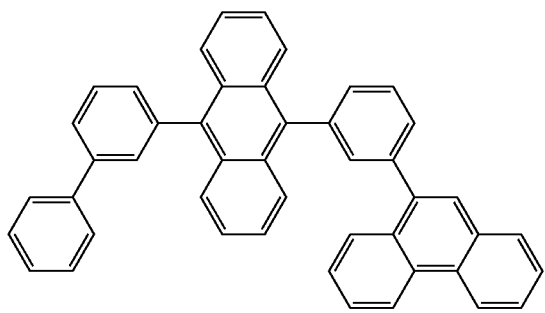
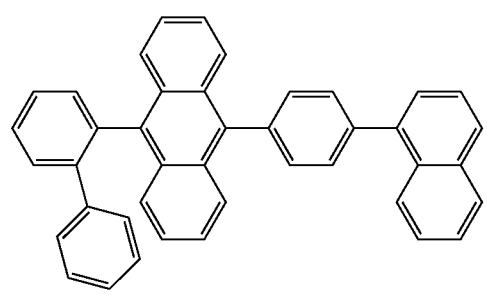
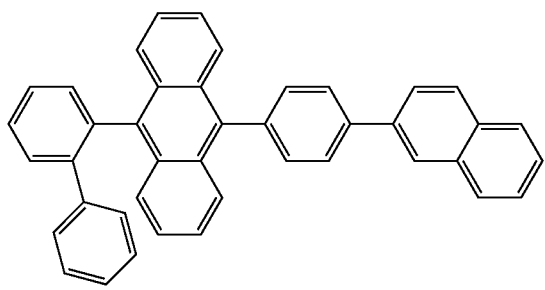
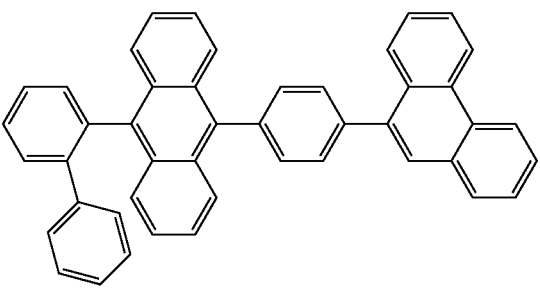
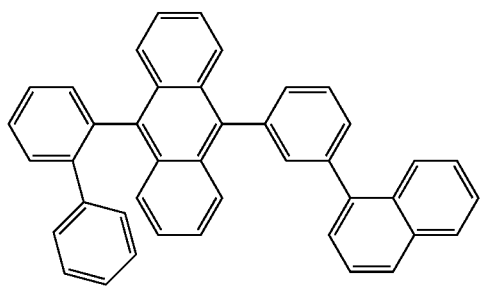
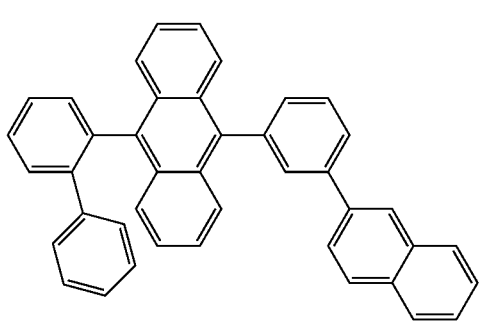
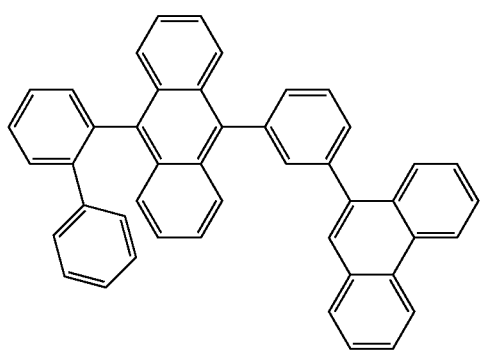

-continued

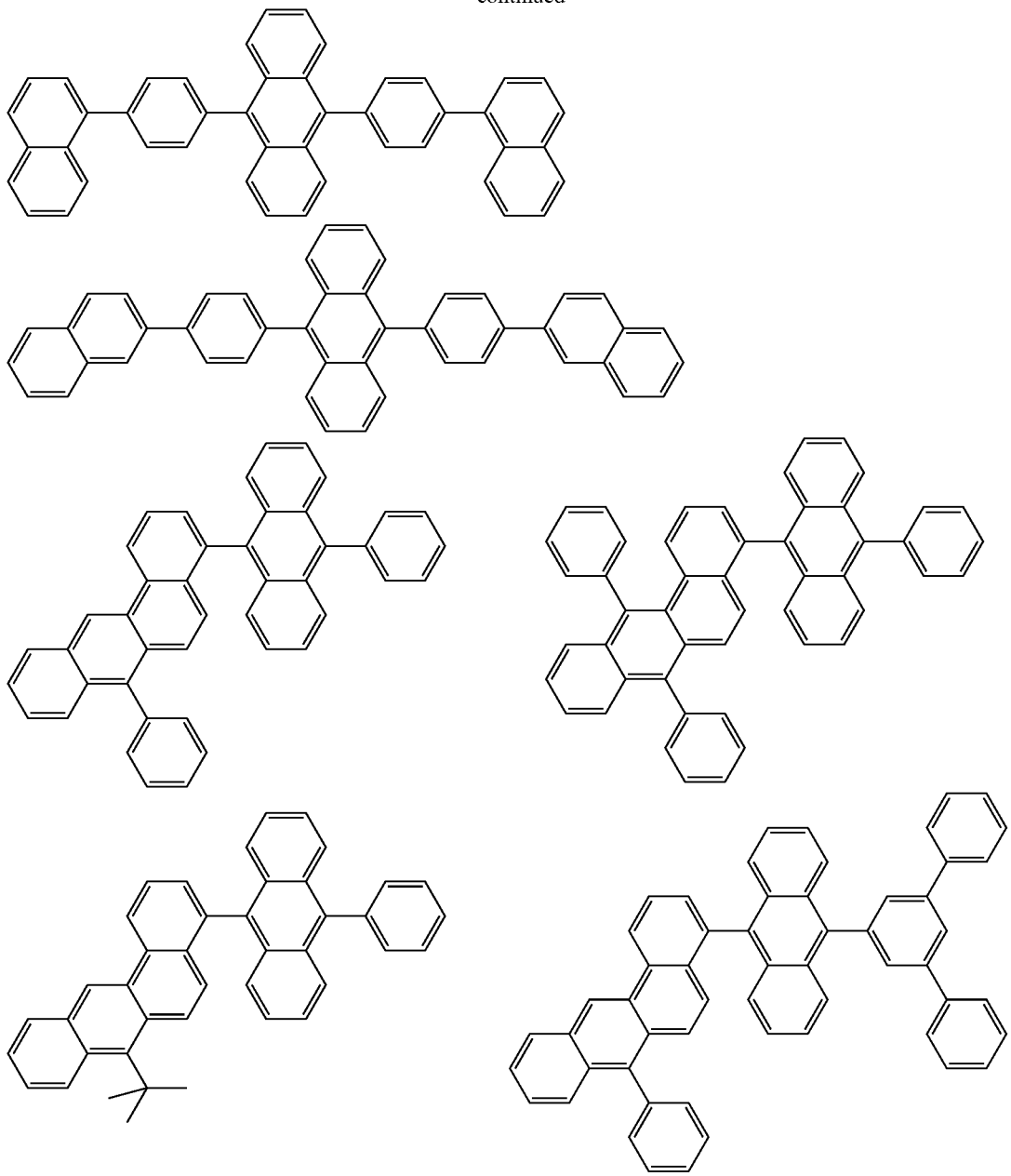

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Examples of preferred hole-transport materials which can be used in a hole-transport, hole-injection or electron-blocking layer in the electroluminescent device according to the invention, besides the compounds of the formula (1), are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with WO 2014/015937, WO 2014/015938 and WO 2014/015935), spirodibenzopyranamines (for example in accordance with WO 2013/083216) and dihydroacridine derivatives (for example in accordance with WO 2012/150001).

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing.

For the production of an organic electroluminescent device according to the invention, it is furthermore preferred to apply one or more layers from solution and one or more layers by a sublimation process.

Owing to the good solubility of the compounds of the formula (1), it is preferred for the layer comprising one or more compounds of the formula (1) to be applied from solution. This is preferably the emitting layer of an organic electroluminescent device.

In accordance with the invention, the electronic devices comprising one or more compounds according to the invention can be employed in displays, as light sources in lighting applications and as light sources in medical and/or cosmetic applications (for example light therapy).

WORKING EXAMPLES

A) Synthesis Examples

A-1)

Synthesis Scheme:

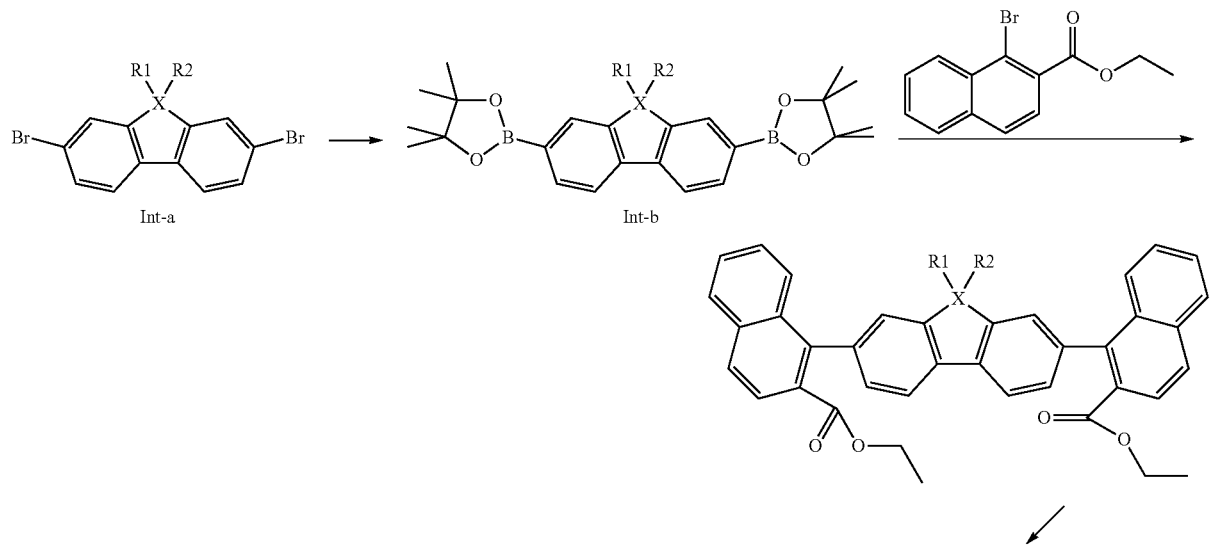

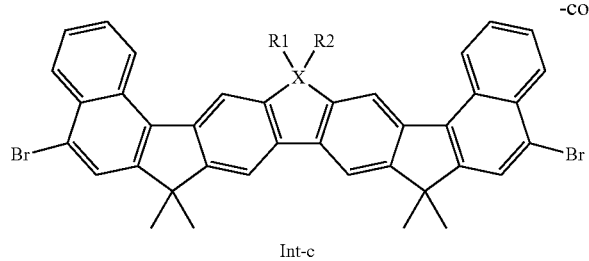

Int-c

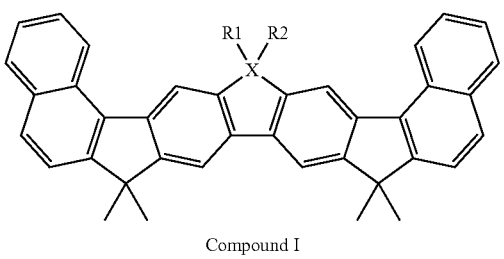

Compound I

| Compound | | Synthesis/ Yield |
|---|---|---|
| Int-a1 | (structure) | commercially available CAS 198964-46-4 |
| Compound Int-b | (structure) | |

2,7-Dibromo-9,9-dioctyl-9H-fluorene (100 g, 0.17 mol), bis(pinacolato)diboron (94.9 g, 0.37 mol) and potassium acetate (50 g, 0.51 mol) were suspended in 1.4 L dioxane. The solution was saturated with argon. PdCl$_2$(dppf)-CH$_2$Cl$_2$ (4.2 g, 0.01 mol) was added. The reaction mixture was refluxed for sixteen hours and then cooled to room temperature. Ethyl acetate and water were added. The organic phase was washed with water (3×500 mL). The organic phase was concentrated under reduced pressure and the residue was purified by recrystallization from ethanol. Yield: 98 g (90%). Purity>95% (NMR in CDCl$_3$).

Compound I

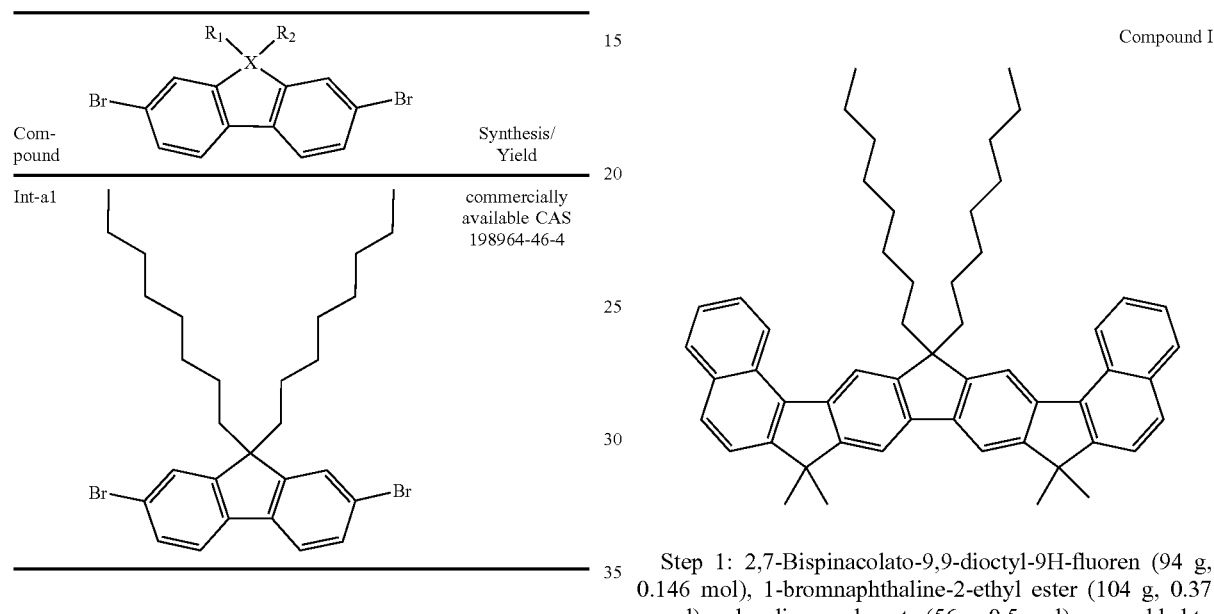

Step 1: 2,7-Bispinacolato-9,9-dioctyl-9H-fluoren (94 g, 0.146 mol), 1-bromnaphthaline-2-ethyl ester (104 g, 0.37 mmol) and sodium carbonate (56 g, 0.5 mol) were added to water/toluene/dioxane (1:1:1, 1.5 L). The solution was saturated with argon. Tetrakis(triphenylphosphin)-palladium(0) (15.2 g, 0.01 mol) was added and the reaction mixture was refluxed for 6 hours. After cooling down to room temperature toluene (500 mL) was added and the organic phase was washed with water (3×500 mL) and then concentrated under reduced pressure. The residue was purified by recrystallization from ethanol. Yield: 115 g (0.145 mol; 99%). Purity>95% (NMR, CDCl$_3$)

Step 2: 115 g (0.145 mol) of the intermediate (Step 1) diluted in 1 L THF were added 145 g (0.60 mol) cerium(III) chloride and 500 ml THF and the mixture was stirred for 30 minutes and cooled to 0° C. 390 ml (1.17 mol) methylmagnesiumchloride (3M in THF) was added dropwise to the reaction mixture at 0° C. The reaction mixture was allowed to warm to room temperature. After 16 hours 800 ml sat. aq. ammonium chloride was added at 0° C. Ethyl acetate (2×500 mL) was added, the combined organic phases were washed with water (2×500 mL) and concentrated under reduced pressure. The residue was purified by recrystallization from ethanol. Yield: 103 g (0.146 mol, 93%).

Step 3: 103 g (0.14 mol) of the intermediate (Step 2) were solved in 1.5 L toluene and 275 g amberlyst 15 were added. The reaction mixture was refluxed for 16 hours using a Dean-Stark apparatus. After cooling down to room temperature amberlyst was removed by filtration and the organic phase was concentrated under reduced pressure. The residue was purified by several recrystallizations from ethanol or heptane/toluene.

Yield: 73 g (0.101 mol; 75%).

Compound Int-c

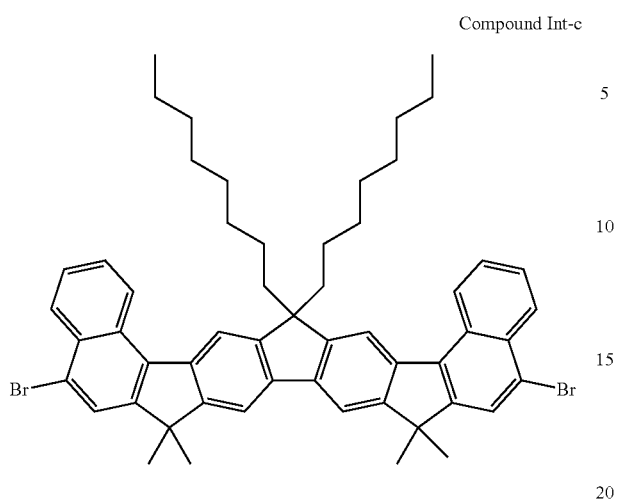

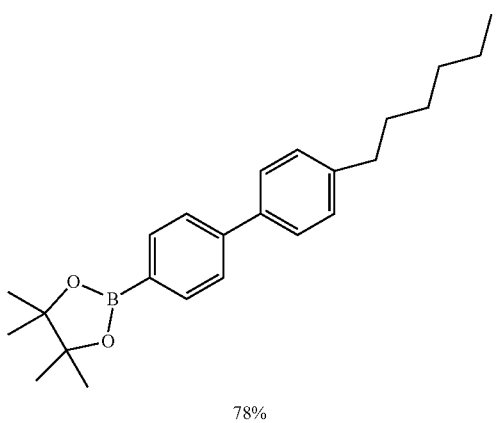

78%

Synthesis of Compound C1

Ia (73 g, 101 mmol) was dissolved in 1 L DCM and cooled to −10° C. Br$_2$ (33.1 g, 207 mmol) in 500 ml DCM was added dropwise. The reaction mixture was stirred one hour at 0° C. and then allowed to warm to room temperature. After 16 hours, 20 ml aqueous, saturated sodium thiosulfate solution was added and the mixture was stirred for 15 minutes. Water (1 L) was added, the organic phase was washed with water (3×500 mL) and the combined organic phases were concentrated under reduced pressure. The residue was purified by several recrystallizations from ethanol or heptane/toluene.

Yield: 66.4 g (75 mmol; 74%)

Synthesis of Compound B

Compound B can be synthesized in an analogous manner to Int-B:

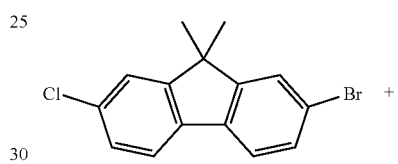

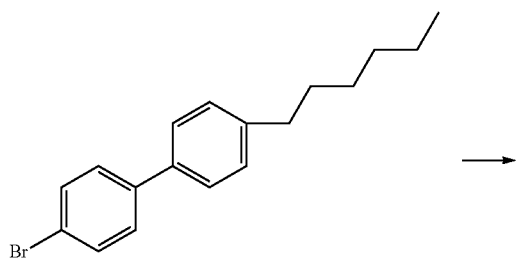

CAS 63619-60-3

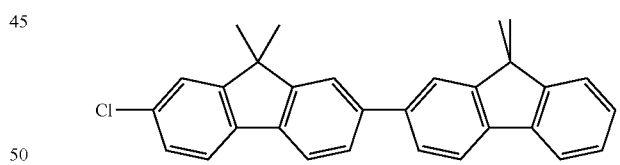

30 g (97.5 mmol) 2-Bromo-7-Chloro-9,9-dimethyl-9H-fluorene (see JP 2003277305 A), 25.5 g (107.3 mmol) (9,9-dimethylfluoren-2-yl)boronic acid 90 g (390 mmol), 0.9 g (4 mmol) palladium(II)acetate and 3.6 g (11.7 mmol) tri(o-tolyl)-phosphine were dissolved in 1 L toluene, dioxane, water (1:1:1) and stirred at reflux overnight. After cooling down to room temperature 200 ml toluene were added and the organic phase was separated and washed with water (2×200 ml) and the combined organic phases were concentrated under reduced pressure. The residue was purified by recrystallization from toluene/heptane.

Yield: 39.1 g (93 mmol; 96%)

Following compounds can be synthesized in an analogous manner:

| Compound | Starting material | Product | Yield |
|---|---|---|---|
| C2 | 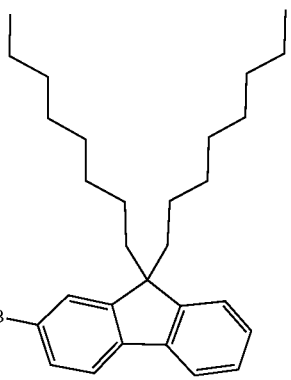 CAS 302554-81-0 | 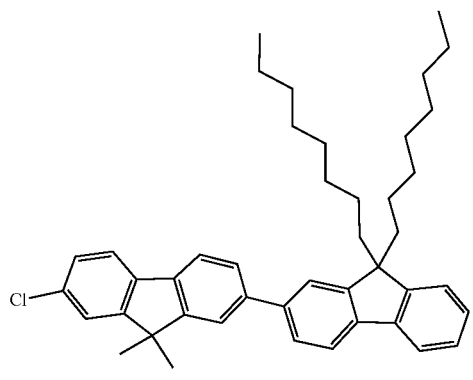 [SMILES: CCCCCCCCC1(CCCCCCCC)c2ccccc2-c2ccc(-c3ccc4c(c3)C(C)(C)c3cc(Cl)ccc3-4)cc21] | 89% |
| C3 | 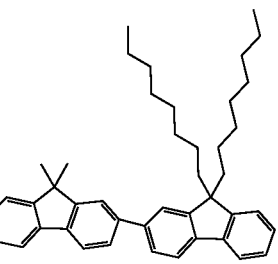 D2 | 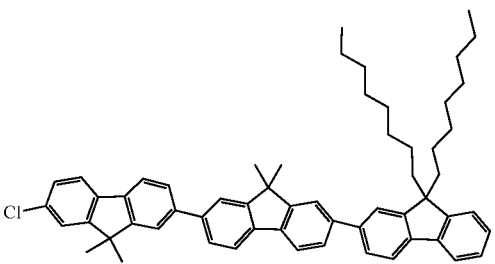 [SMILES: CCCCCCCCC1(CCCCCCCC)c2ccccc2-c2ccc(-c3ccc4c(c3)C(C)(C)c3cc(-c5ccc6c(c5)C(C)(C)c5cc(Cl)ccc5-6)ccc3-4)cc21] | 78% |

Synthesis of D1

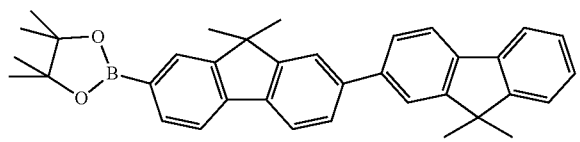 [SMILES: CC1(C)c2ccccc2-c2ccc(-c3ccc4c(c3)C(C)(C)c3cc(B5OC(C)(C)C(C)(C)O5)ccc3-4)cc21]

40 g (95 mmol) C1, 38.6 g (152 mmol) bis-(pinacolato)-diboron, 4.2 g (5.7 mmol) trans-dichloro(tricyclohexylphosphine)palladium(II) and 28 g (285 mmol) potassium acetate were dissolved in 400 ml dioxane and stirred for 16 h at reflux. The reaction mixture was allowed to cool to room temperature and 400 ml toluene were added. The organic phase was separated, washed with water (2×200 mL) and filtered through Celite. The solution was concentrated to dryness under reduced pressure. The residue was purified by recrystallization from toluene/heptane.

Yield: 36 g (70 mmol; 74%)

Following compounds can be synthesized in an analogous manner:

| compound | Starting material | Product | Yield |
|---|---|---|---|
| D2 | C2 | 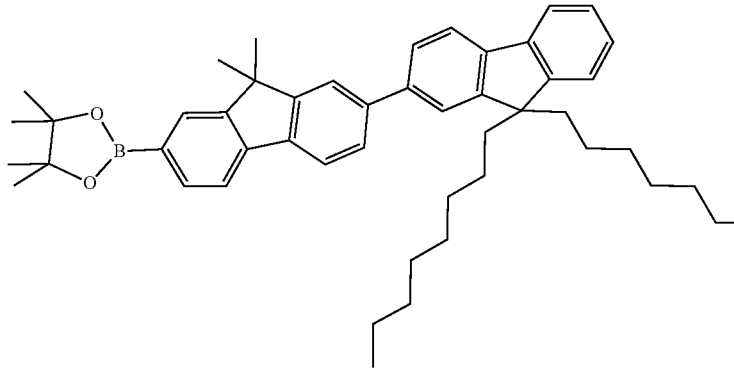 | 89% |

| com-pound | Starting material | Product | Yield |
|---|---|---|---|
| D3 | C3 | 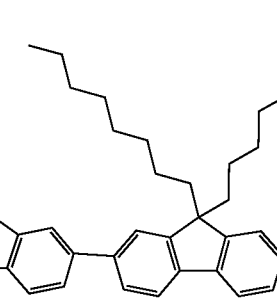 | 87% |

Synthesis of E1

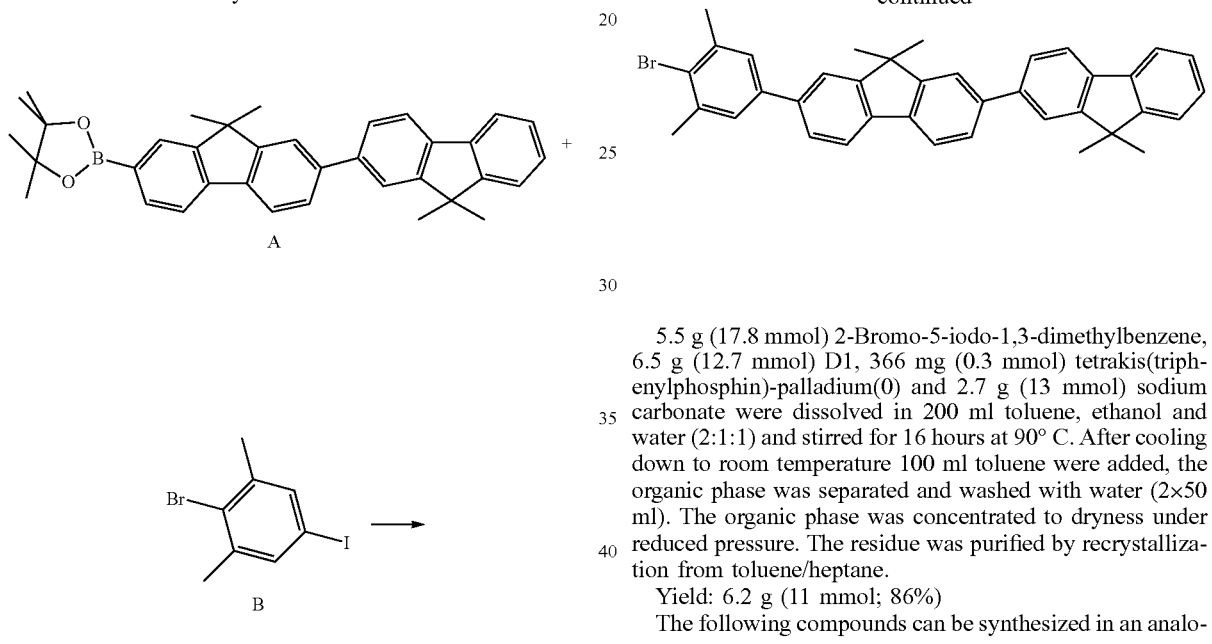

5.5 g (17.8 mmol) 2-Bromo-5-iodo-1,3-dimethylbenzene, 6.5 g (12.7 mmol) D1, 366 mg (0.3 mmol) tetrakis(triphenylphosphin)-palladium(0) and 2.7 g (13 mmol) sodium carbonate were dissolved in 200 ml toluene, ethanol and water (2:1:1) and stirred for 16 hours at 90° C. After cooling down to room temperature 100 ml toluene were added, the organic phase was separated and washed with water (2×50 ml). The organic phase was concentrated to dryness under reduced pressure. The residue was purified by recrystallization from toluene/heptane.

Yield: 6.2 g (11 mmol; 86%)

The following compounds can be synthesized in an analogous manner:

| Compound | Starting material A | Starting material B | Product | Yield |
|---|---|---|---|---|
| E2 | D2 | CAS 689260-53-5 | 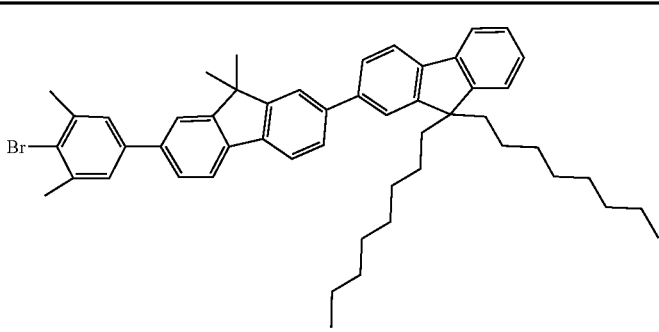 | 89% |

-continued

| Compound | Starting material A | Starting material B | Product | Yield |
|---|---|---|---|---|
| E3 | D2 | CAS 699119-05-6 | | 87% |
| E4 | D1 | CAS 699119-05-6 | | 83% |
| E5 | D2 | CAS 844856-42-4 | | 85% |
| E6 | D1 | CAS 844856-42-4 | | 81% |
| E7 | D2 | (structure shown) see JP 2003277305 A | | 78% |

-continued
| Compound | Starting material A | Starting material B | Product | Yield |
|---|---|---|---|---|
| E8 | D3 | CAS 689260-53-5 | 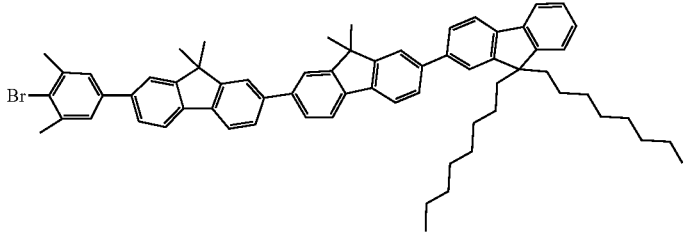 [SMILES: CCCCCCCCC1(CCCCCCCC)c2ccccc2-c2ccc(-c3ccc4c(c3)C(C)(C)c3cc(-c5ccc6c(c5)C(C)(C)c5cc(-c7cc(C)c(Br)c(C)c7)ccc5-6)ccc3-4)cc21] | 82% |
| E9 | D2 | CAS 637-87-6 | 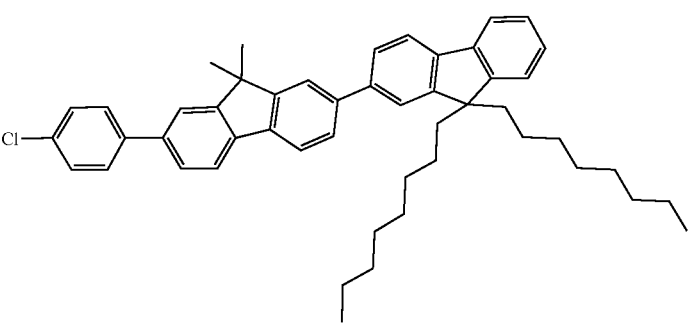 [SMILES: CCCCCCCCC1(CCCCCCCC)c2ccccc2-c2ccc(-c3ccc4c(c3)C(C)(C)c3cc(-c5ccc(Cl)cc5)ccc3-4)cc21] | 87% |
| E10 | D2 | CAS 23055-77-8 | 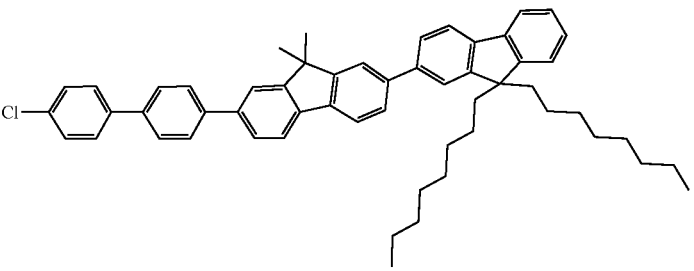 [SMILES: CCCCCCCCC1(CCCCCCCC)c2ccccc2-c2ccc(-c3ccc4c(c3)C(C)(C)c3cc(-c5ccc(-c6ccc(Cl)cc6)cc5)ccc3-4)cc21] | 78% |
Synthesis of Compounds F
Compounds F can be synthesized in an analogous manner to E1:
| Compound | Starting material A | Starting material B | Product | Yield |
|---|---|---|---|---|
| F1 | CAS 1679-18-1 | E1 | 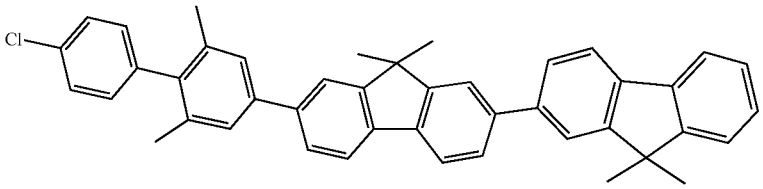 [SMILES: Cc1cc(-c2ccc3c(c2)C(C)(C)c2cc(-c4ccc5c(c4)C(C)(C)c4ccccc4-5)ccc2-3)cc(C)c1-c1ccc(Cl)cc1] | 68% |

-continued
| Compound | Starting material A | Starting material B | Product | Yield |
|---|---|---|---|---|
| F2 | CAS 1679-18-1 | E2 | 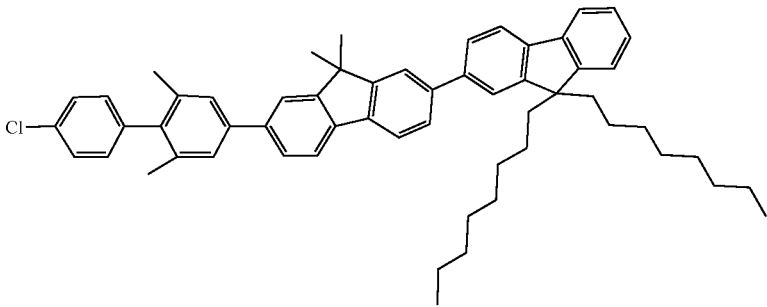 [SMILES: CCCCCCCCC1(CCCCCCCC)c2ccccc2-c2ccc(-c3ccc4c(c3)C(C)(C)c3cc(-c5cc(C)c(-c6ccc(Cl)cc6)c(C)c5)ccc3-4)cc21] | 67% |
| F3 | CAS 1679-18-1 | E3 | 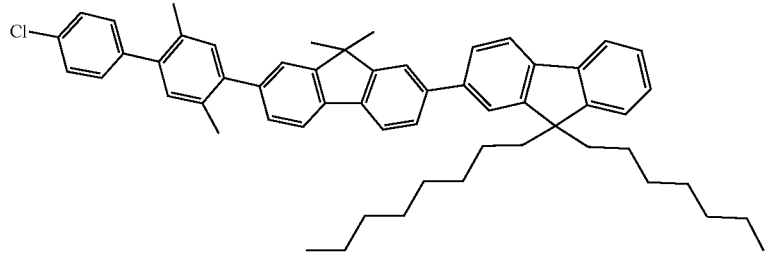 [SMILES: CCCCCCCCC1(CCCCCCC)c2ccccc2-c2ccc(-c3ccc4c(c3)C(C)(C)c3cc(-c5cc(C)c(-c6ccc(Cl)cc6)cc5C)ccc3-4)cc21] | 72% |
| F4 | CAS 1679-18-1 | E4 | 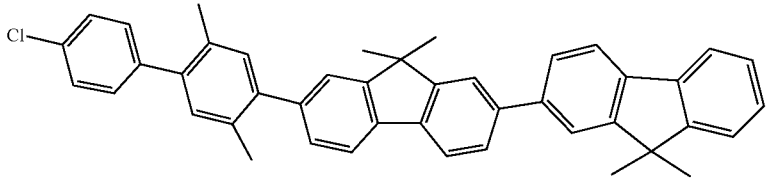 [SMILES: Cc1cc(-c2ccc3c(c2)C(C)(C)c2cc(-c4ccc5c(c4)C(C)(C)c4ccccc4-5)ccc2-3)c(C)cc1-c1ccc(Cl)cc1] | 69% |
| F5 | CAS 1679-18-1 | E8 | 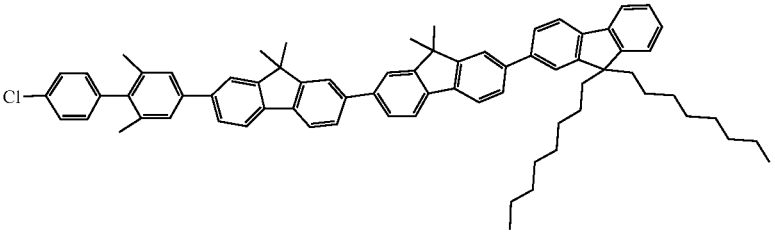 [SMILES: CCCCCCCCC1(CCCCCCCC)c2ccccc2-c2ccc(-c3ccc4c(c3)C(C)(C)c3cc(-c5ccc6c(c5)C(C)(C)c5cc(-c7cc(C)c(-c8ccc(Cl)cc8)c(C)c7)ccc5-6)ccc3-4)cc21] | 72% |

Synthesis of Compounds G

Compounds G can be synthesized in an analogous manner to D1:

| Compound | Starting material | Product | Yield |
|---|---|---|---|
| G1 | E5 | | 82% |
| G2 | E6 | | 79% |
| G3 | F1 | | 78% |
| G4 | F2 | | 81% |
| G5 | F3 | | 83% |

-continued
| Compound | Starting material | Product | Yield |
|---|---|---|---|
| G6 | F4 | 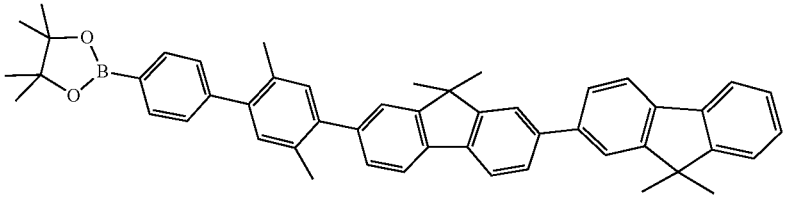 [SMILES: Cc1cc(-c2ccc3c(c2)C(C)(C)c2cc(-c4ccc5c(c4)C(C)(C)c4ccccc4-5)ccc2-3)c(C)cc1-c1ccc(B2OC(C)(C)C(C)(C)O2)cc1] | 70% |
| G7 | E7 | 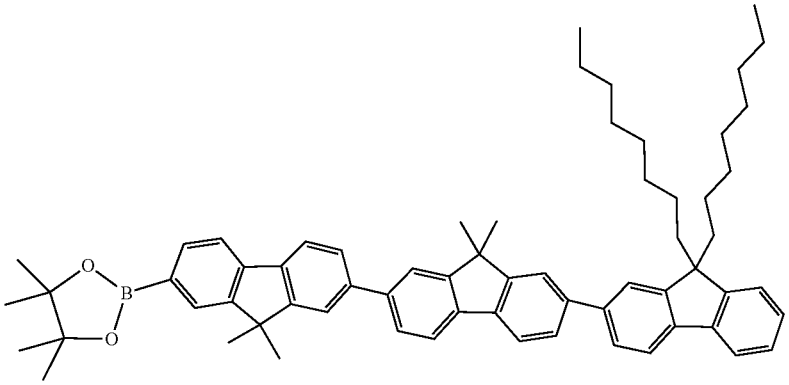 [SMILES: CCCCCCCCC1(CCCCCCCC)c2ccccc2-c2ccc(-c3ccc4c(c3)C(C)(C)c3cc(-c5ccc6c(c5)C(C)(C)c5cc(B7OC(C)(C)C(C)(C)O7)ccc5-6)ccc3-4)cc21] | 72% |
| G9 | F5 | 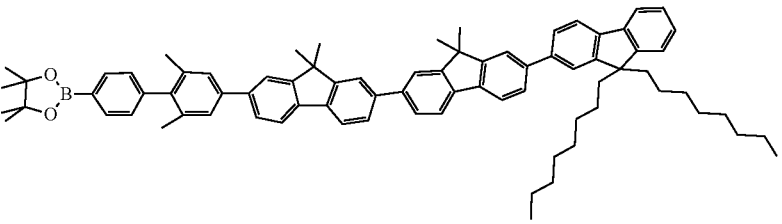 [SMILES: CCCCCCCCC1(CCCCCCCC)c2ccccc2-c2ccc(-c3ccc4c(c3)C(C)(C)c3cc(-c5ccc6c(c5)C(C)(C)c5cc(-c7cc(C)c(-c8ccc(B9OC(C)(C)C(C)(C)O9)cc8)c(C)c7)ccc5-6)ccc3-4)cc21] | 69% |
| G10 | E9 | 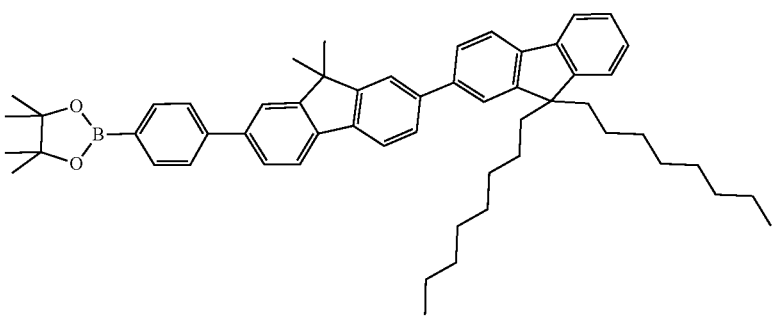 [SMILES: CCCCCCCCC1(CCCCCCCC)c2ccccc2-c2ccc(-c3ccc4c(c3)C(C)(C)c3cc(-c5ccc(B6OC(C)(C)C(C)(C)O6)cc5)ccc3-4)cc21] | 73% |
| G11 | E10 | 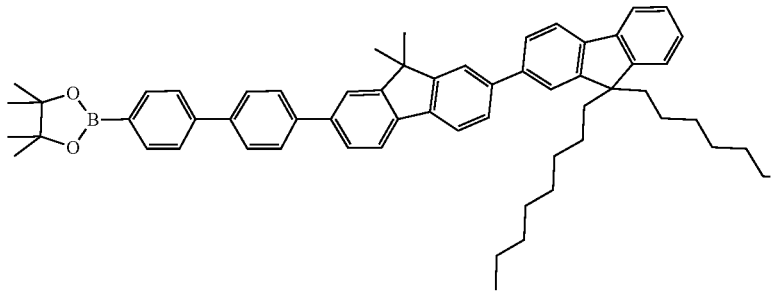 [SMILES: CCCCCCCCC1(CCCCCCC)c2ccccc2-c2ccc(-c3ccc4c(c3)C(C)(C)c3cc(-c5ccc(-c6ccc(B7OC(C)(C)C(C)(C)O7)cc6)cc5)ccc3-4)cc21] | 81% |

Compound IIa

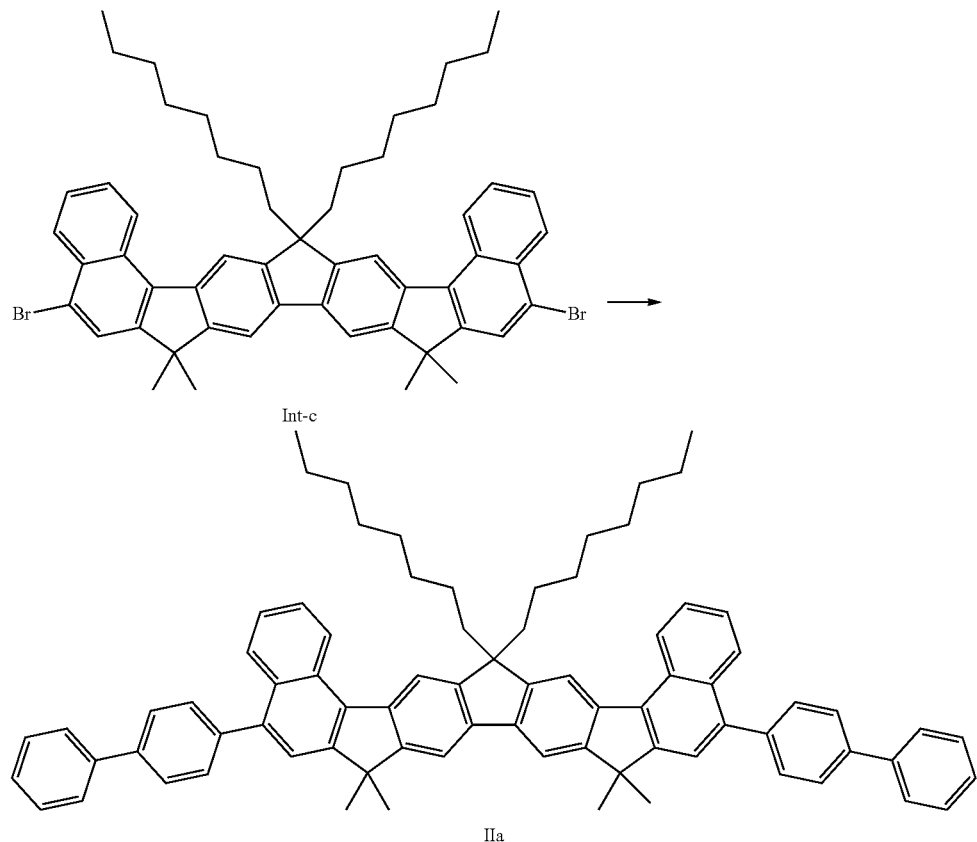

Int-c (18.7 g, 21.2 mmol), 4-biphenylboronic acid (9.25 g, 46.7 mmol) and sodium carbonate (4.5 g, 42.4 mmol) were dissolved in a mixture of toluene, ethanol and water (2:1:1) and the solution was saturated with argon. Tetrakis(triphenylphosphine)-palladium(0) (613 mg, 0.53 mmol) was added and stirred for 6 hours at 110° C. The reaction mixture was allowed to cool to room temperature, toluene (400 mL) and water (200 mL) were added and the organic phase was separated and washed twice with water (400 mL). The organic phase was concentrated under reduced pressure. The residue was further purified by filtration through silica (eluting with toluene), recrystallization from heptane/toluene.

Yield: 13.3 g (12.9 mmol; 61%)

Following compounds IIb to IIm can be synthesized in an analogous manner:

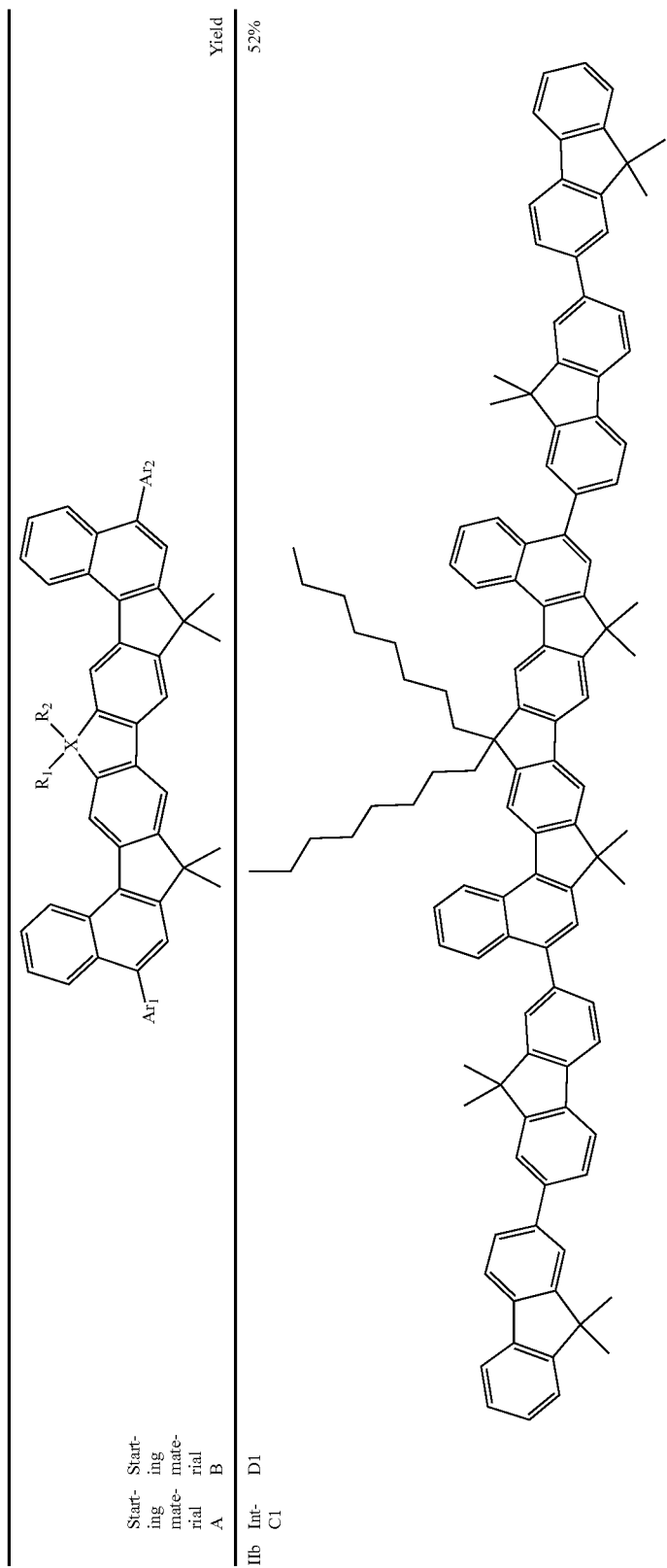
| Starting material A | Starting material B | | Yield |
|---|---|---|---|
| IIb | Int-C1 | D1 | 52% |

-continued
| Starting material A | Starting material B | | Yield |
|---|---|---|---|
| | | 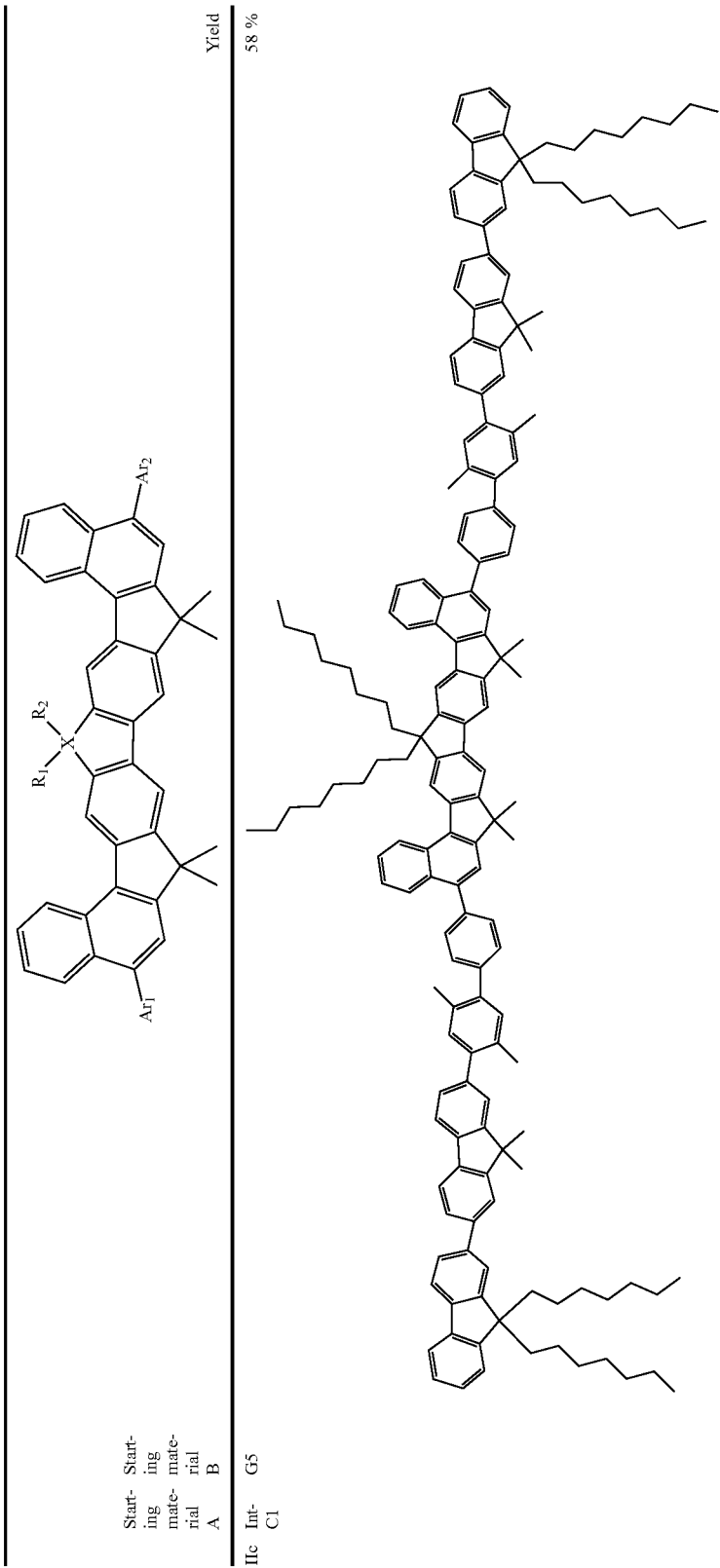 | 58% |
| IIc | G5 Int-C1 | | |

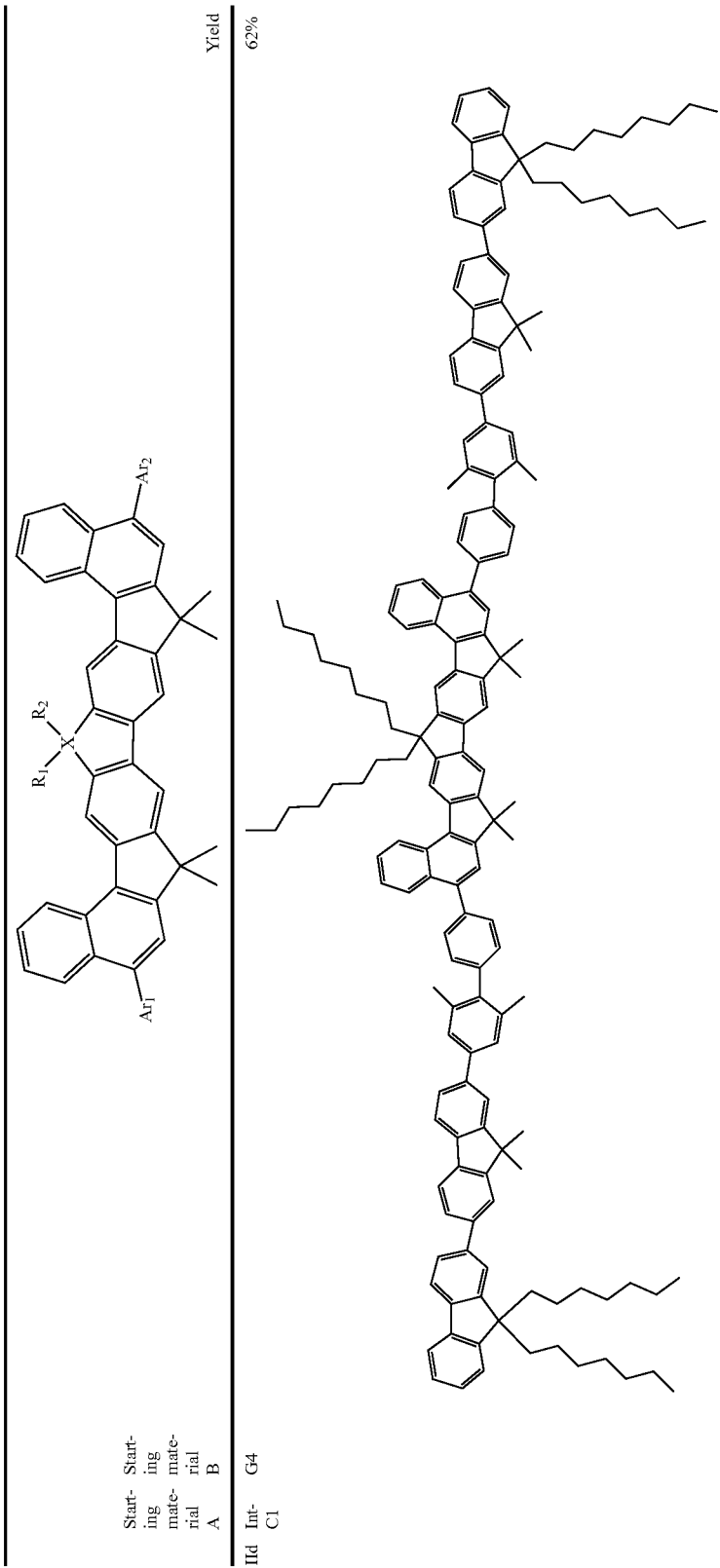

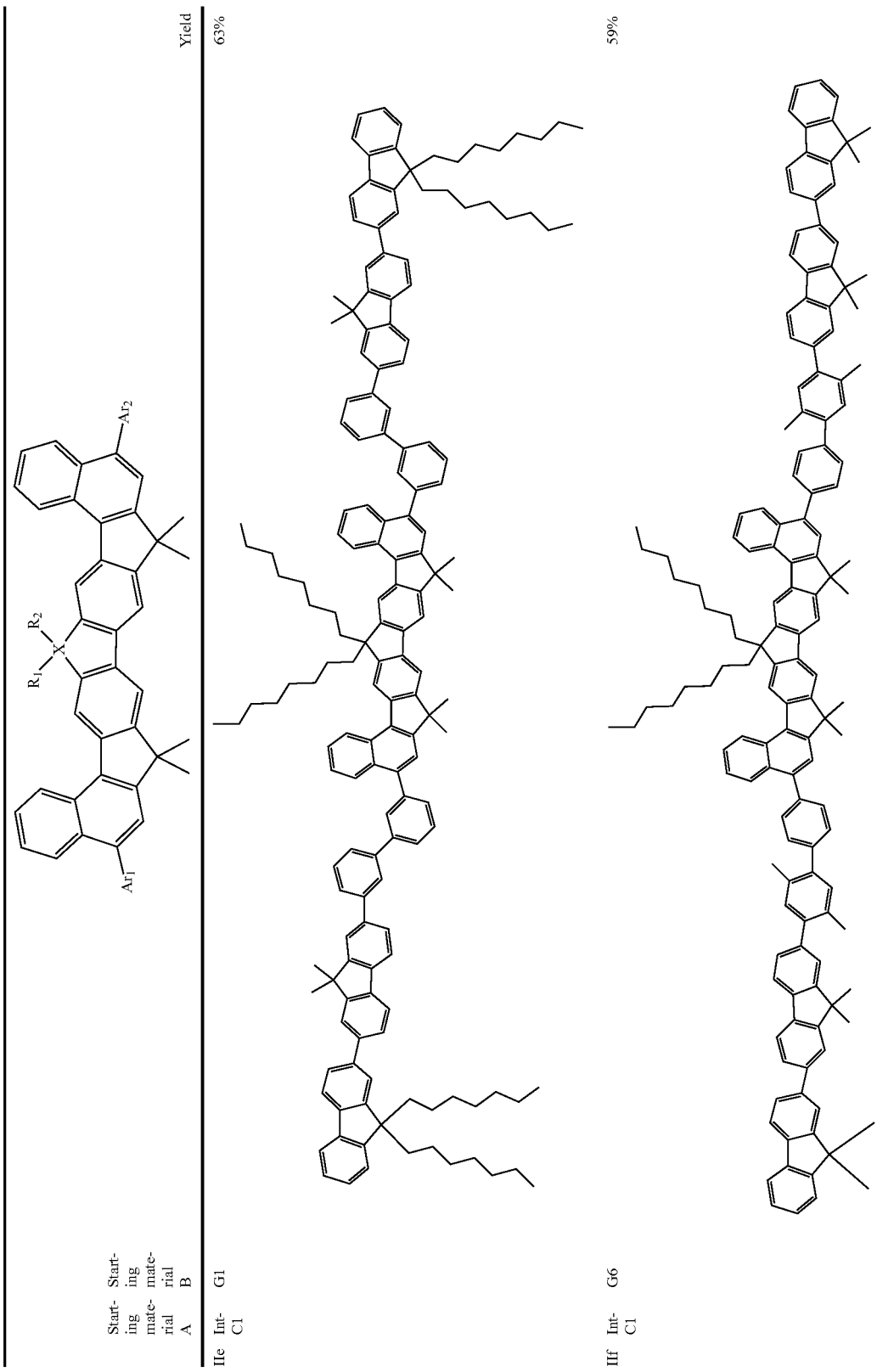

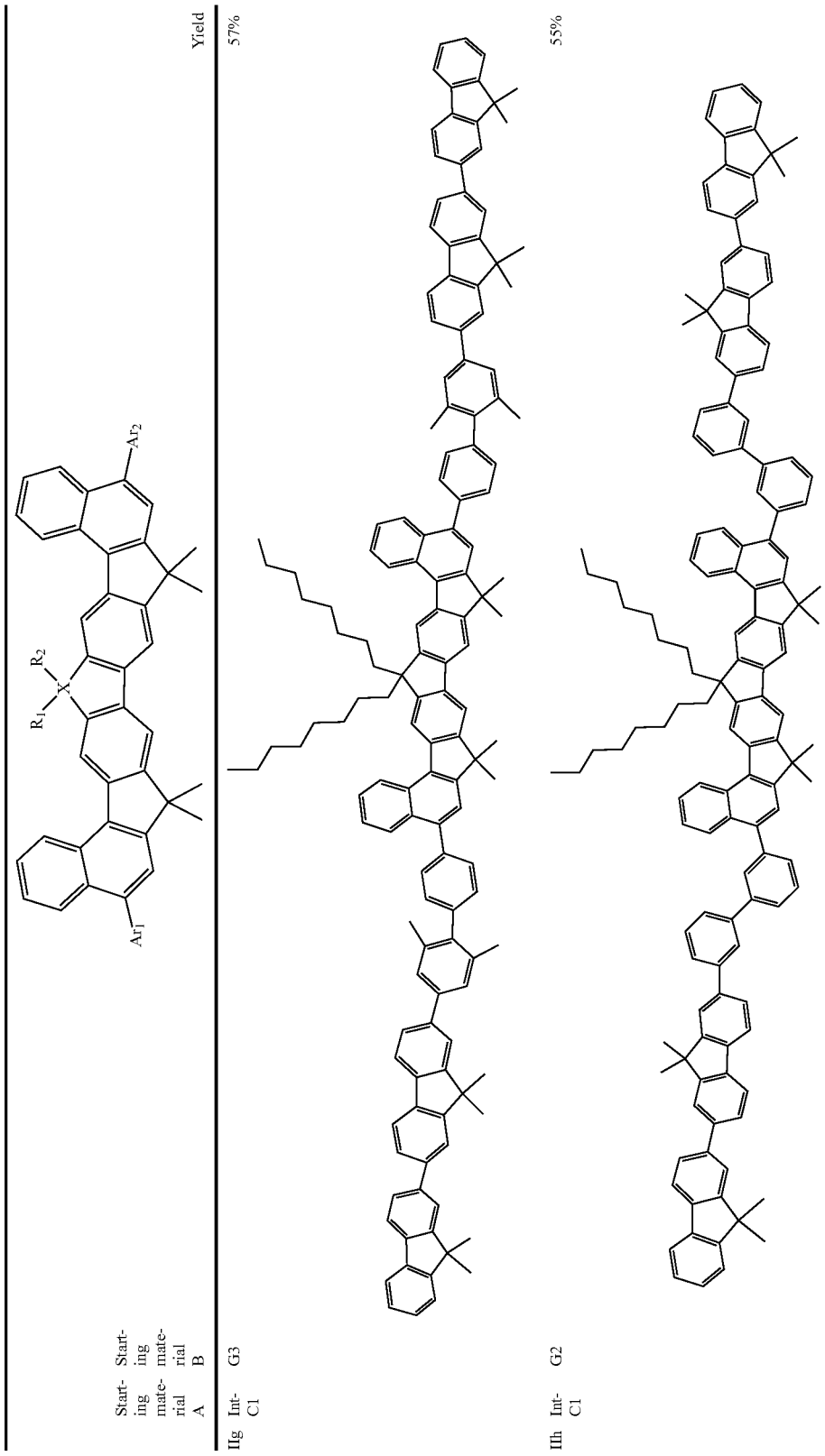

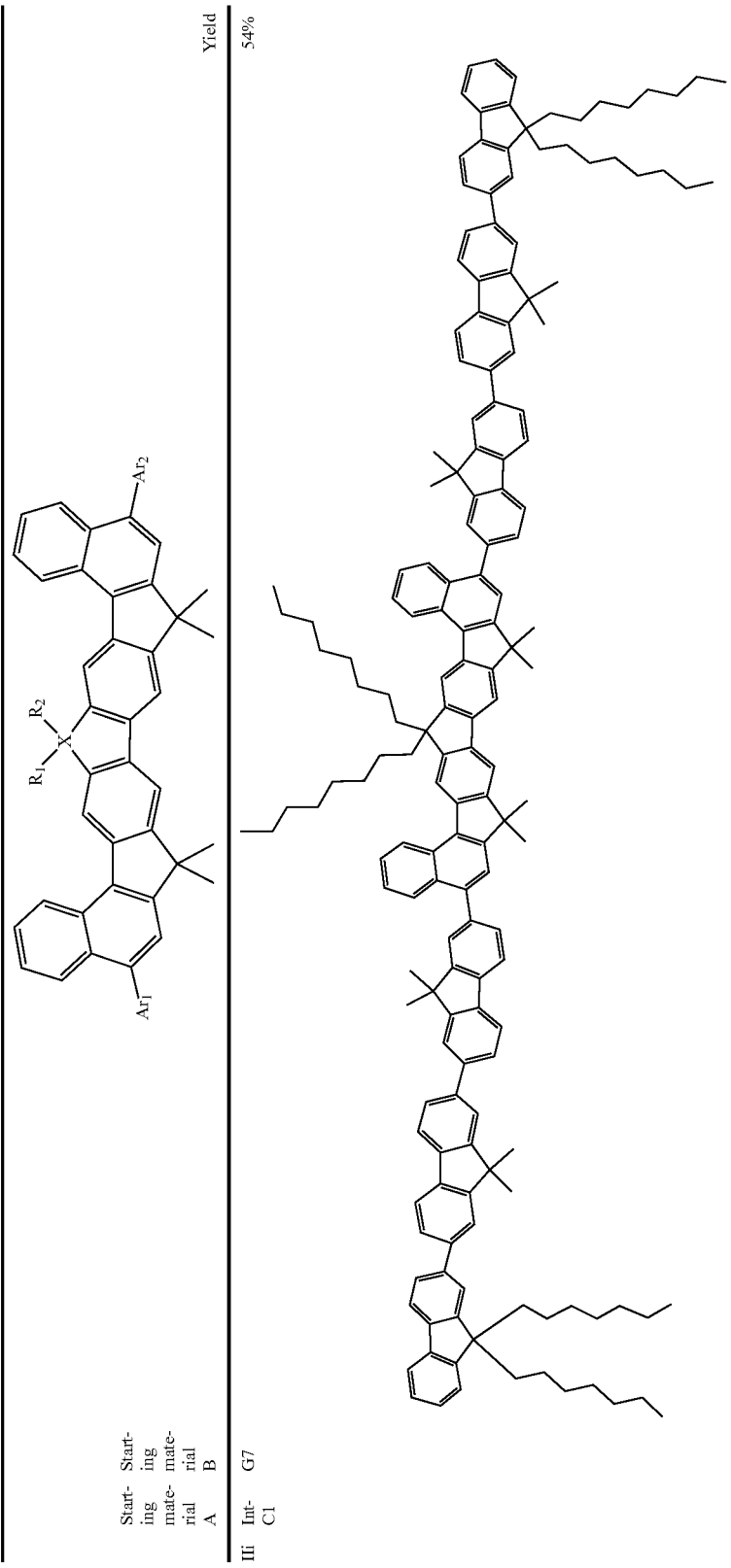

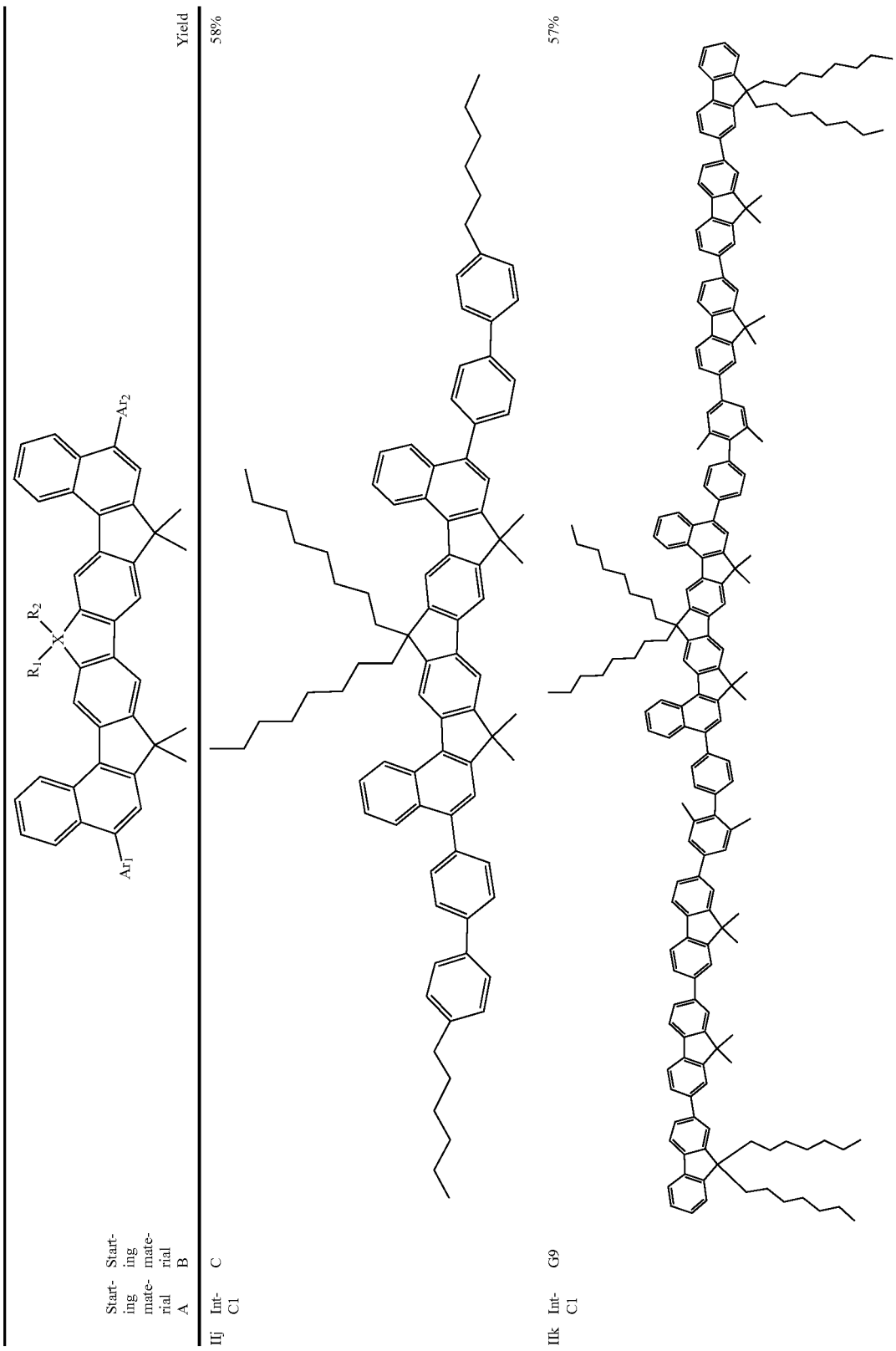

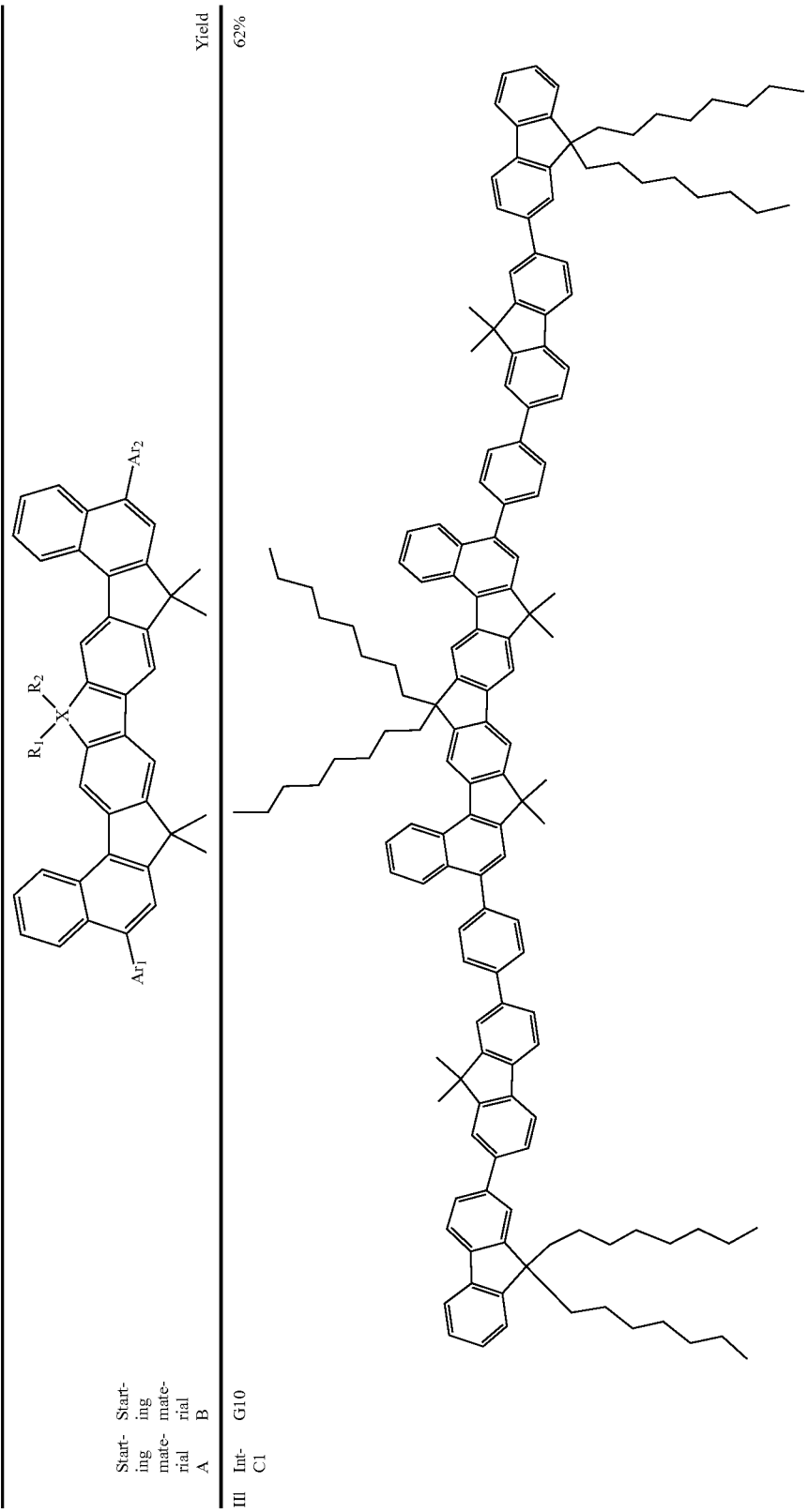

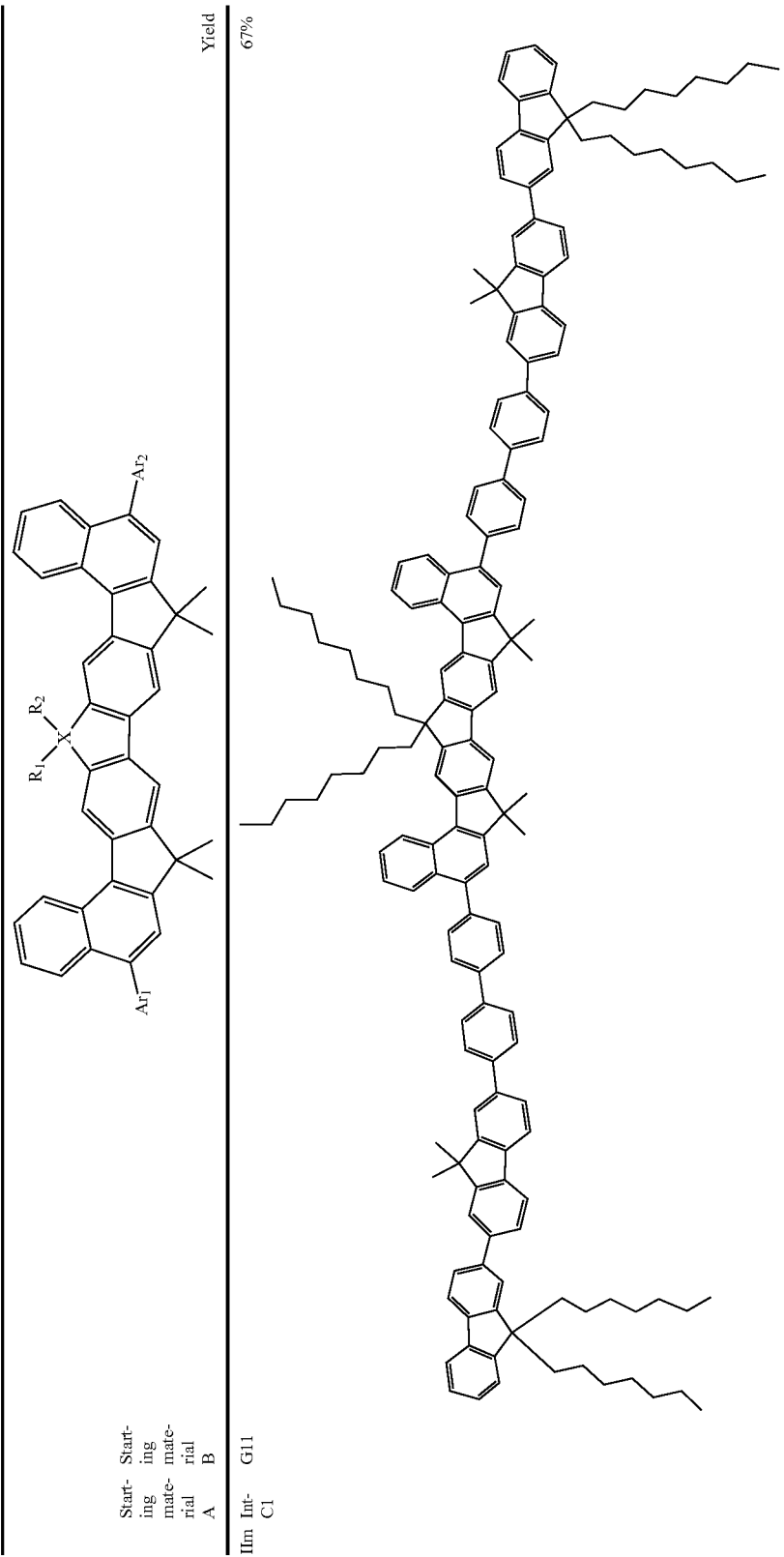

B) Device Examples

B-1) Device Examples Processed from Solution: Production of OLEDs

The production of solution-based OLEDs is described in principle in the literature, for example in WO2004/037887 and WO 2010/097155. In the following examples, the two production methods (application from gas phase and solution processing) were combined, so that processing up to and including the emission layer was carried out from solution and the subsequent layers (hole-blocking layer/electron-transport layer) were applied by vacuum vapour deposition. The general processes described above are for this purpose adapted to the circumstances described here (layer-thickness variation, materials) and combined as follows.

The device structure used is thus as follows:
substrate,
ITO (50 nm),
PEDOT (20 nm),
hole-transport layer (HTL) (20 nm),
emission layer (92% of host, 8% of dopant) (60 nm),
electron-transport layer (ETL) (20 nm),
electron-injection layer (EIL) (3 nm)
cathode (Al) (100 nm).

The substrates used are glass plates coated with structured ITO (indium tin oxide) in a thickness of 50 nm. For better processing, these are coated with the buffer (PEDOT) Clevios P VP AI 4083 (Heraeus Clevios GmbH, Leverkusen). The spin coating of the buffer is carried out from water in air. The layer is subsequently dried by heating at 180° C. for 10 minutes. The hole-transport and emission layers are applied to the glass plates coated in this way.

The hole-transport layer is the polymer of the structure shown in Table 2, which was synthesised in accordance with WO 2010/097155. The polymer is dissolved in toluene, so that the solution typically has a solid content of approx. 5 g/l if, as here, the layer thickness of 20 nm which is typical for a device is to be achieved by means of spin coating. The layers are applied by spin coating in an inert-gas atmosphere, in the present case argon, and dried by heating at 180° C. for 60 min.

The emission layer (EML) is always composed of at least one matrix material (host=H) and an emitting dopant (emitter=D). An expression such as H1 (92%):D1 (8%) here means that material H1 is present in the emission layer in a proportion by weight of 92% and dopant D1 is present in the emission layer in a proportion by weight of 8%. The mixture for the emission layer is dissolved in toluene. The typical solid content of such solutions is approx. 18 g/l if, as here, the layer thickness of 60 nm which is typical for a device is to be achieved by means of spin coating. The layers are applied by spin coating in an inert-gas atmosphere, in the present case argon, and dried by heating at 140° C. for 10 minutes. The materials used are shown in Table 2.

The materials for the electron-transport layer, the electron-injection layer and for the cathode are applied by thermal vapour deposition in a vacuum chamber. The electron-transport layer, for example, may consist of more than one material, which are admixed with one another in a certain proportion by volume by co-evaporation. An expression such as ETM:EIL (50%:50%) would mean that materials ETM and EIL are present in the layer in a proportion by volume of 50% each. The materials used in the present case are shown in Table 2.

The OLEDs are characterised by standard methods. For this purpose, the electroluminescence spectra are recorded, the current efficiency (measured in cd/A) and the external quantum efficiency (EQE, measured in percent) as a function of the luminous density assuming Lambert emission characteristics are calculated from current/voltage/luminous density characteristic lines (IUL characteristic lines), and finally the lifetime of the components is determined. The electroluminescence spectra are recorded at a luminous density of 1000 cd/m$^2$, and the CIE 1931 x and y colour coordinates are calculated from this data. The term EQE @ 1000 cd/m$^2$ denotes the external quantum efficiency at an operating luminous density of 1000 cd/m$^2$. The lifetime LD80 @ 10 mA/cm$^2$ is the time which passes until the initial luminance at a driving current density of 10 mA/cm$^2$ has dropped by 20%. The data obtained for the various OLEDs are summarised in Table 1.

Use of Compounds According to the Invention as Fluorescent Emitter Materials in Organic Light Emitting Diodes The compounds according to the invention are particularly suitable as emitter materials in blue-fluorescent OLEDs. Emitters D1, D2, D3 and D4 are shown as compounds according to the invention. The state-of-the-art compound for comparison is represented by V-D1 and V-D2. All emitters are used in combination with either host H1 or H2.

Examples E1 to E8 show in a comparative examination with Comparative Examples V1 and V2 that compounds D1, D2, D3 and D4 according to the invention achieve an improved external quantum efficiency (EQE) and an increased lifetime (LD80) with deep-blue emission as compared to comparative material V-D1 and V-D2. Especially the comparison of material V-D1 (Device V1 and V2) with D3 (Example E5) and D4 (Example E6) shows the technical effect of the present invention, in which an expansion of the Bis-Indenofluorene-Core leads to an improved device performance compared to the state-of-the-art while maintaining the same deep blue color.

TABLE 1

Data of the OLEDs

| Example | Host 92% | Emitter 8% | EQE@ 1000 cd/m$^2$ % | LD80@ 10 mA/ cm$^2$ [h] | CIE x | y |
|---|---|---|---|---|---|---|
| V1 | H1 | V-D1 | 2.9 | 140 | 0.144 | 0.132 |
| V2 | H2 | V-D1 | 3.2 | 150 | 0.142 | 0.138 |
| V3 | H1 | V-D2 | 3.1 | 150 | 0.144 | 0.129 |
| V4 | H2 | V-D2 | 3.3 | 160 | 0.147 | 0.134 |
| E1 | H1 | D1 | 4.1 | 200 | 0.146 | 0.158 |
| E2 | H2 | D1 | 4.3 | 220 | 0.138 | 0.164 |
| E3 | H1 | D2 | 4.5 | 220 | 0.139 | 0.162 |
| E4 | H2 | D2 | 4.6 | 230 | 0.137 | 0.165 |
| E5 | H2 | D3 | 4.5 | 190 | 0.142 | 0.130 |
| E6 | H1 | D4 | 4.3 | 210 | 0.144 | 0.128 |

TABLE 2
Structures of the materials used
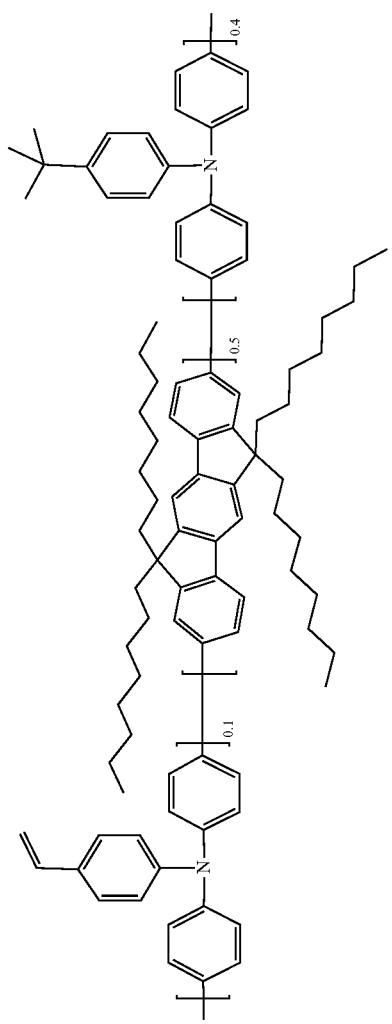
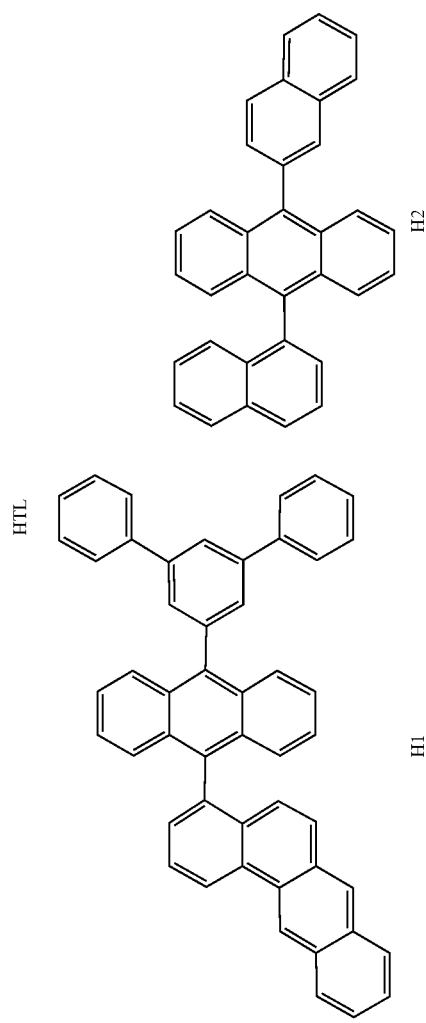

TABLE 2-continued
Structures of the materials used
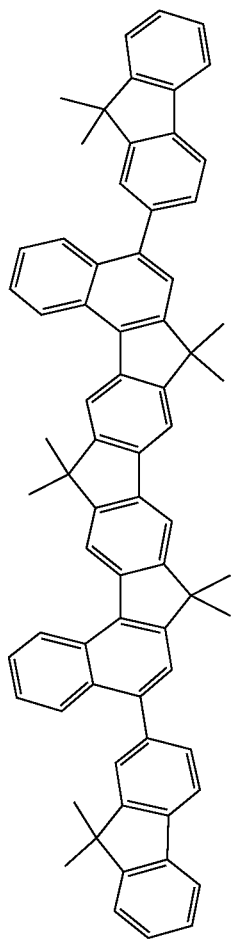
V-D1
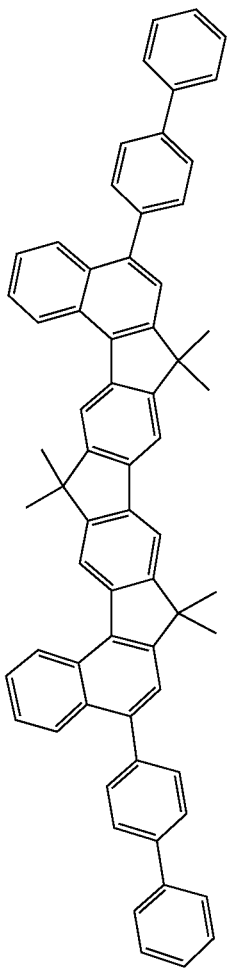
V-D2
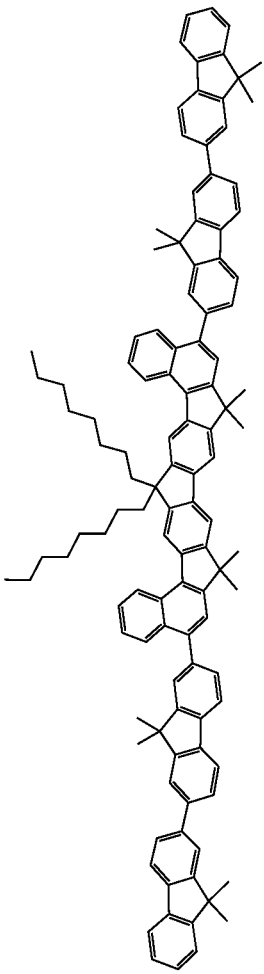
D1

TABLE 2-continued
Structures of the materials used
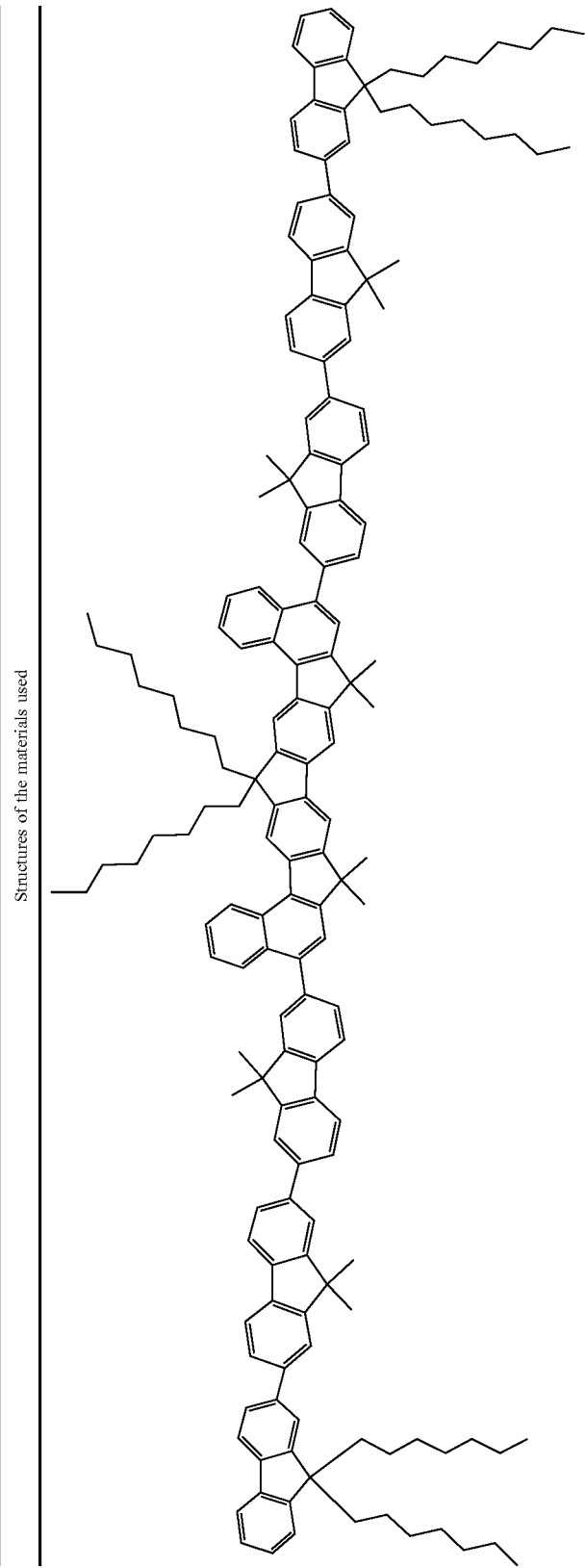
D2

TABLE 2-continued
Structures of the materials used
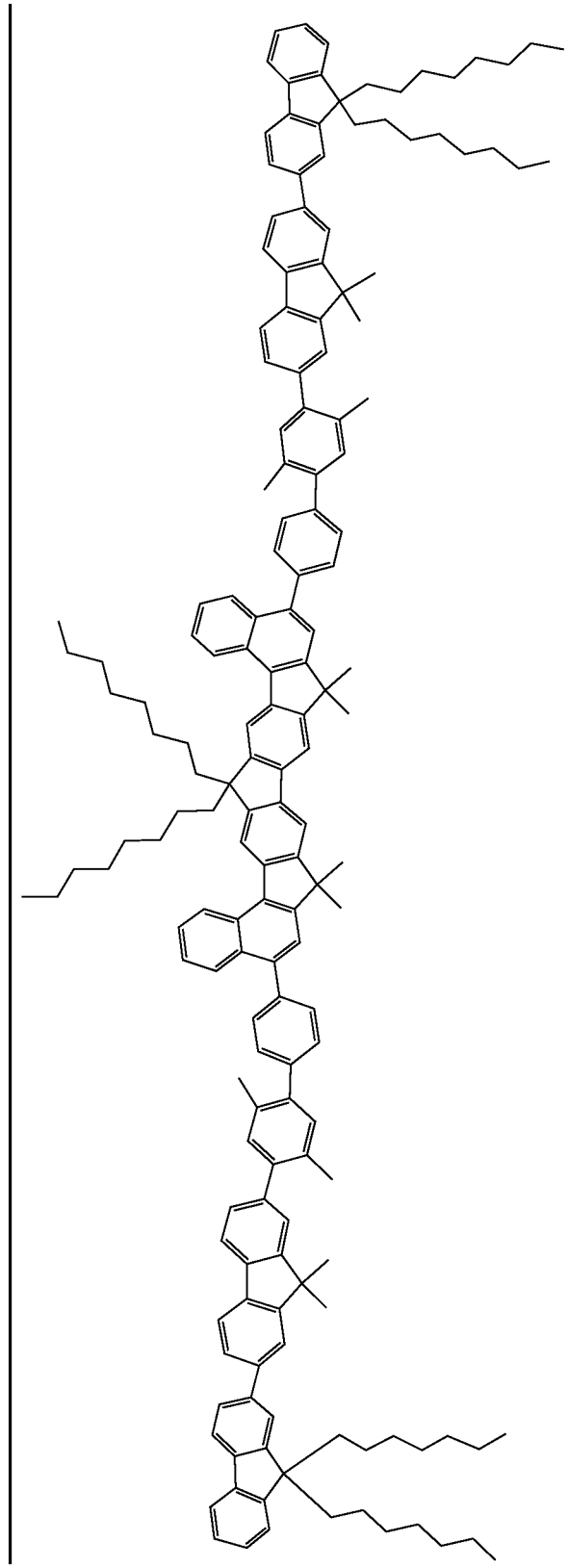
D3

TABLE 2-continued
Structures of the materials used
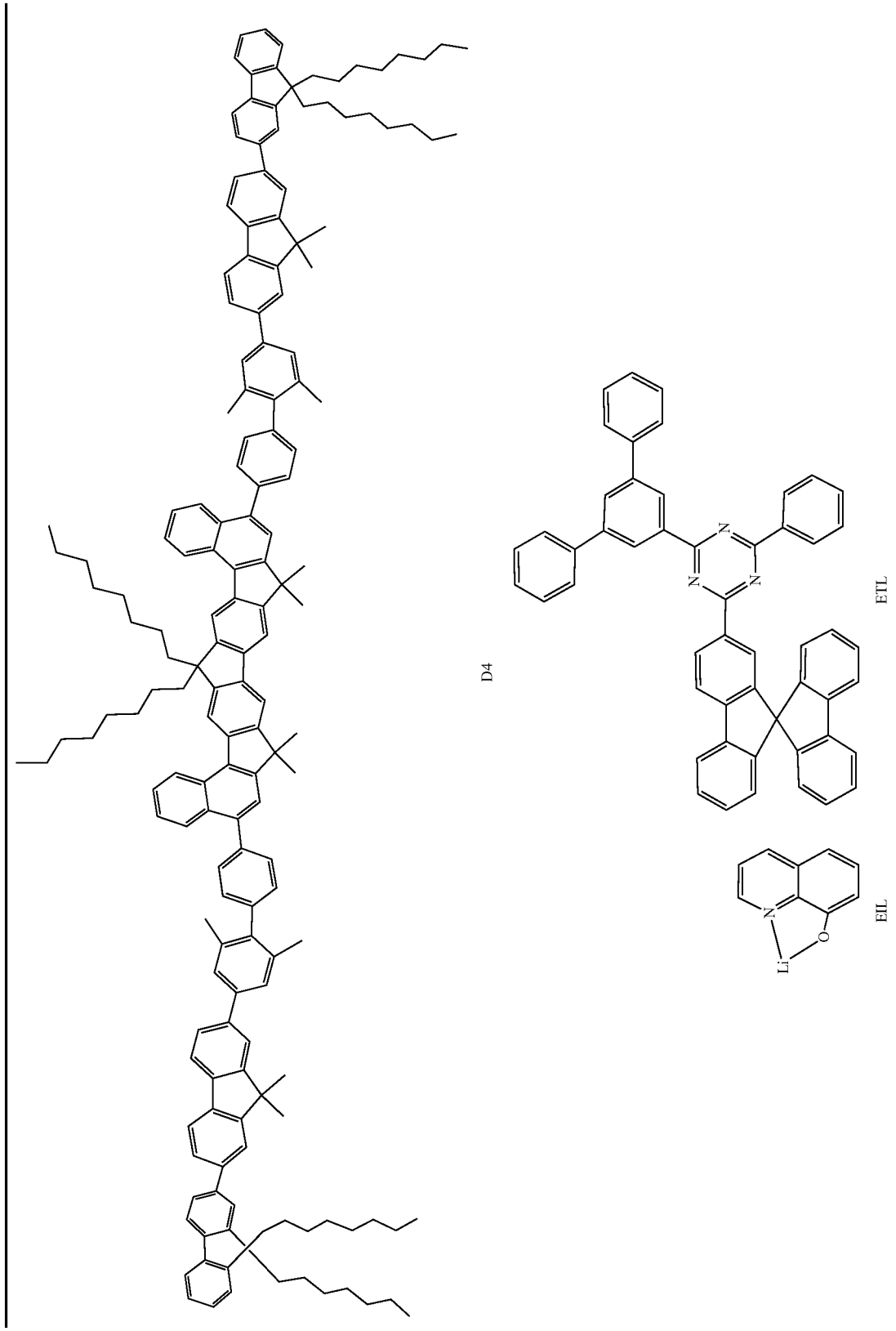

Compounds according to the invention possess decent solubility and thus are well suitable for solution processing. By this technique, electronic devices based on blue fluorescent emitters with excellent performance data can be generated.

Alternatively, or in addition, the compounds according to the invention may serve as host materials inside the emission layer (EML), as hole injection material (HIL), as hole transporting material (HTL), as electron transporting material (ETL) or as electron-injection material (EIL) in an organic light emitting diode.

The invention claimed is:
1. A compound of formula (1):

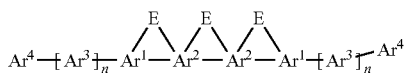

wherein
$Ar^1$ is on each occurrence, identically or differently, an aryl or heteroaryl group having 6 to 18 aromatic ring atoms, which in each case is optionally substituted by one or more radicals $R^1$, wherein at least one $Ar^1$ has 10 or more aromatic ring atoms;
$Ar^2$ is on each occurrence, identically or differently, an aryl or heteroaryl group having 6 aromatic ring atoms, which in each case is optionally substituted by one or more radicals $R^1$;
$Ar^3$ and $Ar^4$
are on each occurrence, identically or differently, an aromatic or heteroaromatic ring systems having 5 to 25 aromatic ring atoms, which in each case is optionally substituted by one or more radicals $R^1$;
wherein at least one $Ar^3$ is a group of formula (Ar3-2) and/or at least one $Ar^4$ is a group of formula (Ar4-2):

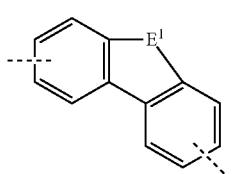
(Ar3-2)

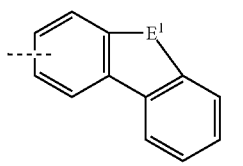
(Ar4-2)

wherein
the dashed bonds in the group of formula (Ar3-2) indicate the bonding to $Ar^1$ and to a group $Ar^3$ or $Ar^4$;
the dashed bond in the group of formula (Ar4-2) indicates the bonding to $Ar^3$;
$E^1$ stands for —C($R^0$)$_2$; and
the groups of formulae (Ar3-2) and (Ar4-2) are optionally substituted at each free position by a group $R^1$;
E is identically or differently on each occurrence, selected from the group consisting of —BR$^0$—, —C(R$^0$)$_2$—, —C(R$^0$)$_2$—C(R$^0$)$_2$—, —C(R$^0$)$_2$—O—, C(R$^0$)$_2$—S—, —R$^0$C═CR$^0$—, —R$^0$C═N—, —Si(R$^0$)$_2$—, —Si(R$^0$)$_2$—Si(R$^0$)$_2$—, —C(═O)—, —C(═NR$^0$)—, —C(═C(R$^0$)$_2$)—, —O—, —S—, —S(═O)—, —SO$_2$—, —N(R$^0$)—, —P(R$^0$)—, and —P((═O)R$^0$)—, wherein two groups E are optionally in a cis or trans position relative to each other;
$R^0$ and $R^1$
are on each occurrence, identically or differently, H, D, F, Cl, Br, I, CHO, CN, N(Ar$^5$)$_2$, C(═O)Ar$^5$, P(═O) (Ar$^5$)$_2$, S(═O)Ar$^5$, S(═O)$_2$Ar$^5$, NO$_2$, Si(R$^2$)$_3$, B(OR$^2$)$_2$, OSO$_2$R$^2$, a straight-chain alkyl, alkoxy, or thioalkyl group having 1 to 40 C atoms or a branched or cyclic alkyl, alkoxy, or thioalkyl group having 3 to 40 C atoms, each of which is optionally substituted by one or more radicals R$^2$, wherein in each case one or more non-adjacent CH$_2$ groups are optionally replaced by R$^2$C═CR$^2$, C≡C, Si(R$^2$)$_2$, Ge(R$^2$)$_2$, Sn(R$^2$)$_2$, C═O, C═S, C═Se, P(═O)(R$^2$), SO, SO$_2$, O, S, or CONR$^2$ and wherein one or more H atoms is optionally replaced by D, F, Cl, Br, I, CN, or NO$_2$, an aromatic or heteroaromatic ring system having 5 to 60 aromatic ring atoms, which in each case is optionally substituted by one or more radicals R$^2$, or an aryloxy group having 5 to 40 aromatic ring atoms, which is optionally substituted by one or more radicals R$^2$, and wherein two adjacent substituents R$^0$ and/or two adjacent substituents R$^1$ optionally define a mono- or polycyclic, aliphatic ring system or aromatic ring system, which is optionally substituted by one or more radicals R$^2$;
$R^2$ is on each occurrence, identically or differently, H, D, F, Cl, Br, I, CHO, CN, N(Ar$^5$)$_2$, C(═O)Ar$^5$, P(═O) (Ar$^5$)$_2$, S(═O)Ar$^5$, S(═O)$_2$Ar$^5$, NO$_2$, Si(R$^3$)$_3$, B(OR$^3$)$_2$, OSO$_2$R$^3$, a straight-chain alkyl, alkoxy or thioalkyl group having 1 to 40 C atoms or a branched or cyclic alkyl, alkoxy, or thioalkyl group having 3 to 40 C atoms, each of which is optionally substituted by one or more radicals R$^3$, wherein in each case one or more non adjacent CH$_2$ groups is optionally replaced by R$^3$C═CR$^3$, C≡C, Si(R$^3$)$_2$, Ge(R$^3$)$_2$, Sn(R$^3$)$_2$, C═O, C═S, C═Se, P(═O)(R$^3$), SO, SO$_2$, O, S, or CONR$^3$ and wherein one or more H atoms is optionally replaced by D, F, Cl, Br, I, CN, or NO$_2$, an aromatic or heteroaromatic ring system having 5 to 60 aromatic ring atoms, which in each case is optionally substituted by one or more radicals R$^3$, or an aryloxy group having 5 to 60 aromatic ring atoms, which is optionally substituted by one or more radicals R$^3$, and where two adjacent substituents R$^2$ optionally define a mono- or polycyclic, aliphatic ring system or aromatic ring system, which is optionally substituted by one or more radicals R$^3$;
$R^3$ is on each occurrence, identically or differently, H, D, F, Cl, Br, I, CN, a straight-chain alkyl, alkoxy, or thioalkyl group having 1 to 20 C atoms or a branched or cyclic alkyl, alkoxy, or thioalkyl group having 3 to 20 C atoms, wherein in each case one or more non adjacent CH$_2$ groups is optionally replaced by SO, SO$_2$, O, or S and wherein one or more H atoms is optionally replaced by D, F, Cl, Br, or I, or an aromatic or heteroaromatic ring system having 5 to 24 C atoms;
$Ar^5$ is an aromatic or heteroaromatic ring system having 5 to 24 aromatic ring atoms, which in each case is optionally substituted by one or more radicals R$^3$;
n is an integer from 2 to 20.
2. The compound of claim 1, wherein n is an integer from 2 to 8.
3. The compound of claim 1, wherein the compound of formula (1) contains at least one group $R^0$ or $R^1$ that is a straight-chain alkyl group having 2 to 40 C atoms or a branched or cyclic alkyl group having 3 to 40 C atoms, each of which is optionally substituted by one or more radicals $R^2$.

4. The compound of claim 1, wherein the compound of formula (1) is selected from the group consisting of compounds of formula (1-1) and formula (1-2):

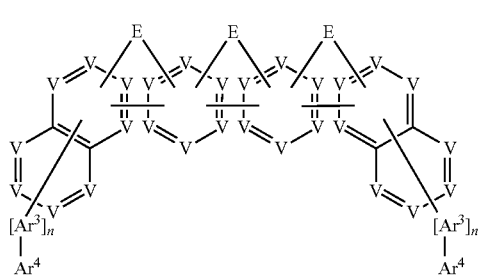

formula (1-1)

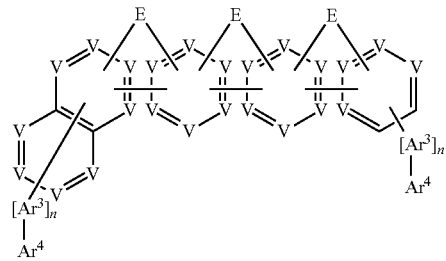

formula (1-2)

wherein
V is on each occurrence, identically or differently, $CR^1$ or N, wherein V is C when V is bonded to a group $Ar^3$ or to a group E.

5. The compound of claim 4, wherein the compound of formula (1) is selected from the group consisting of compounds of formulae (1-1-1) to (1-1-11) and (1-2-1) to (1-2-7):

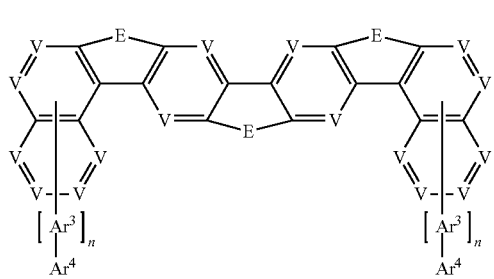

(1-1-1)

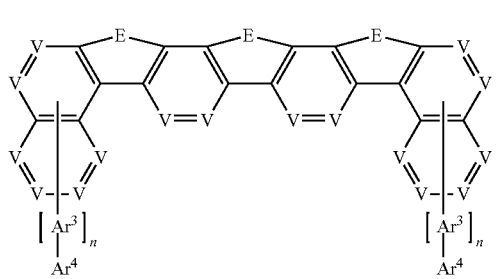

(1-1-2)

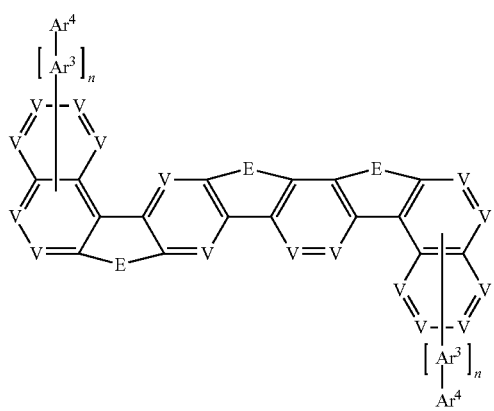

(1-1-3)

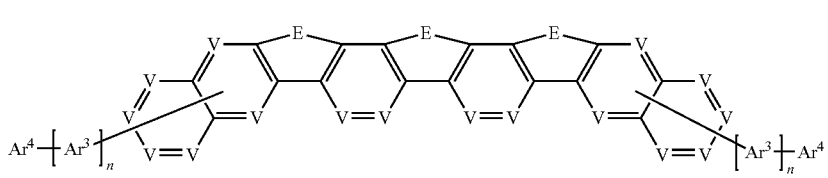

(1-1-4)

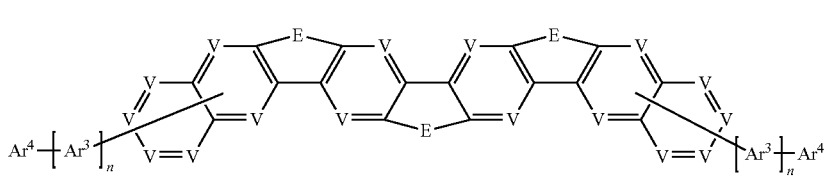

(1-1-5)

(1-1-6)
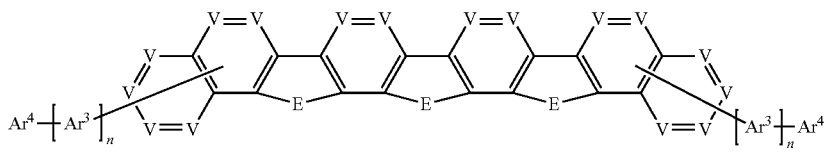
(1-1-7)
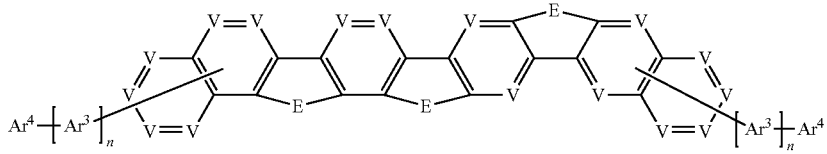
(1-1-8)
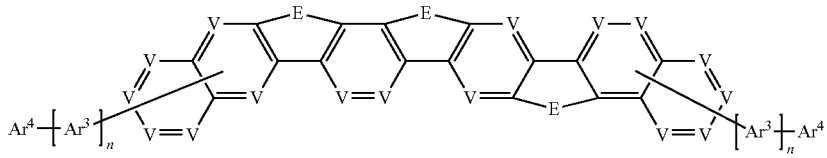
(1-1-9)
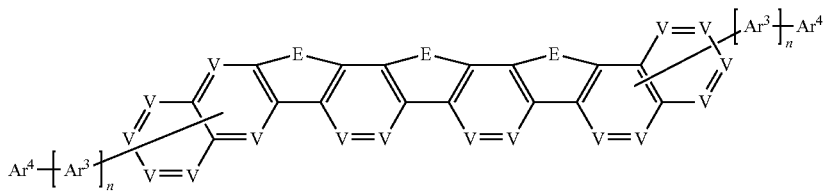
(1-1-10)
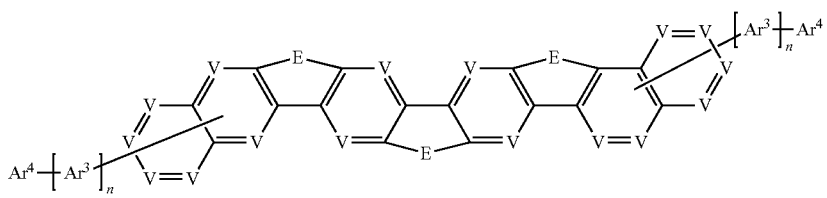
(1-1-11)
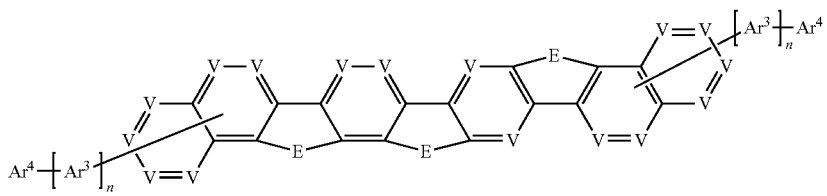
(1-2-1)
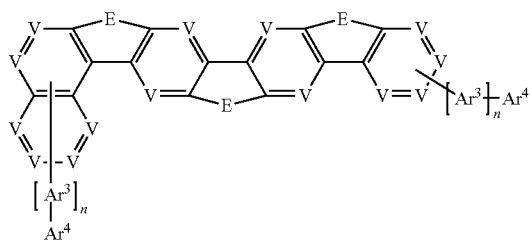
(1-2-2)
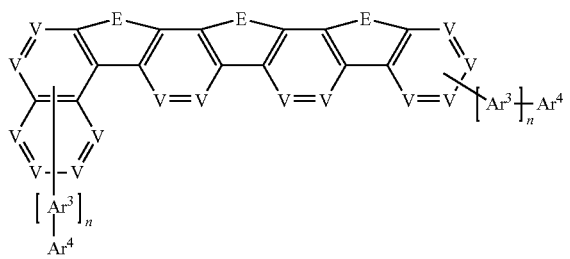
(1-2-3)
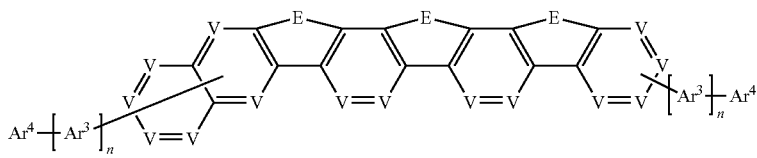

-continued
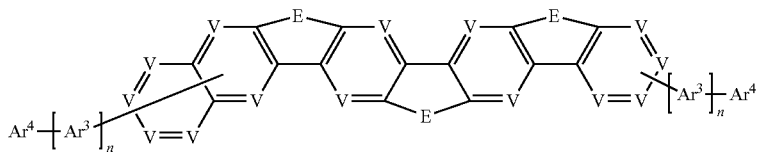
(1-2-4)
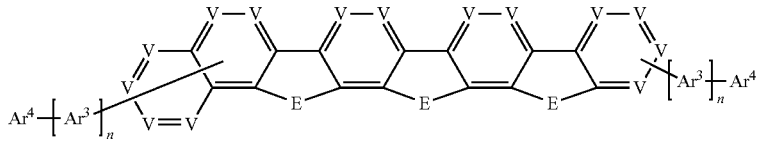
(1-2-5)
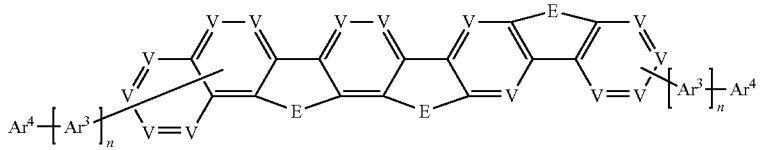
(1-2-6)
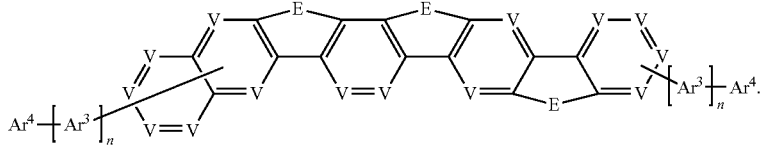
(1-2-7)
6. The compound of claim 4, wherein the compound of formula (1) is selected from the group consisting of compounds of formulae (1-1-1-a) to (1-1-11-a) and (1-2-1-a) to (1-2-7-a):
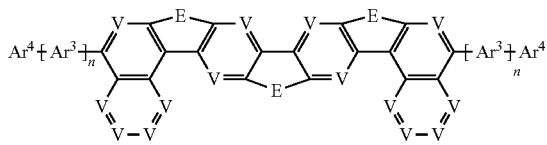
(1-1-1-a)
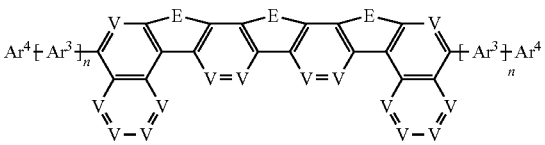
(1-1-2-a)
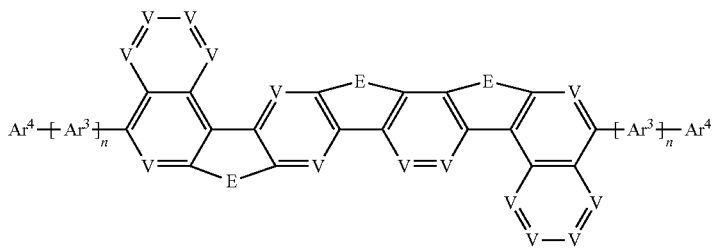
(1-1-3-a)
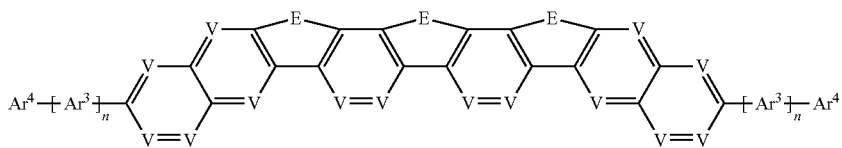
(1-1-4-a)
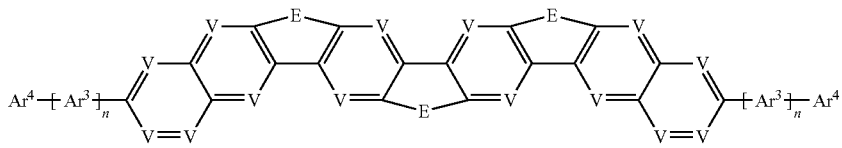
(1-1-5-a)

-continued
(1-1-6-a)
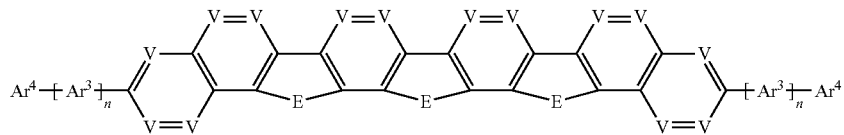
(1-1-7-a)
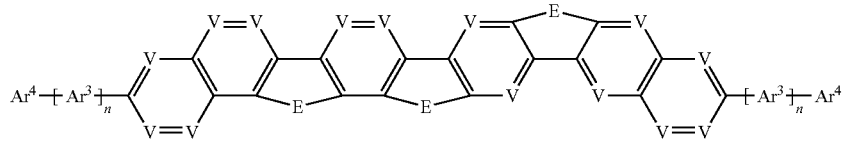
(1-1-8-a)
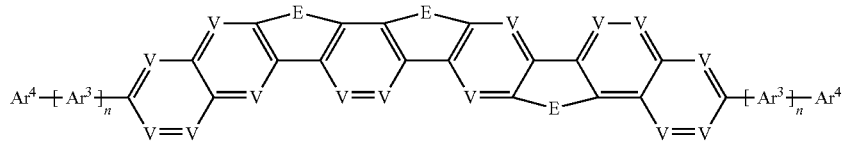
(1-1-9-a)
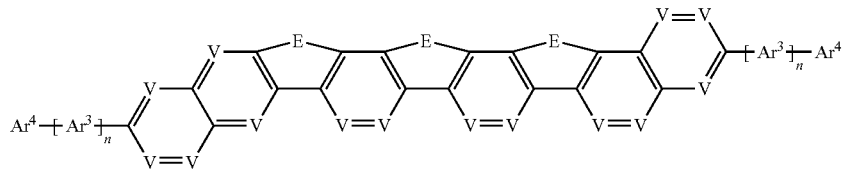
(1-1-10-a)
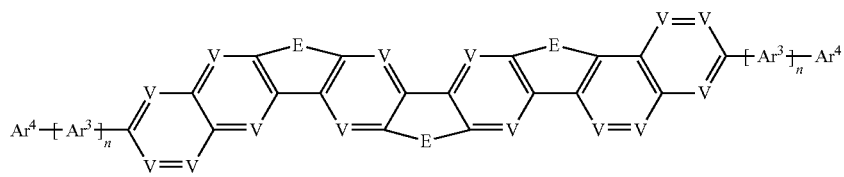
(1-1-11-a)
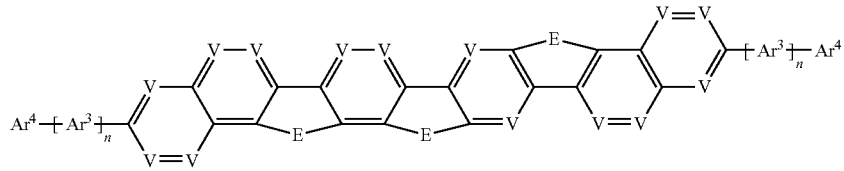
(1-2-1-a)
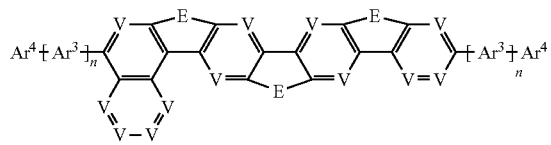
(1-2-2-a)
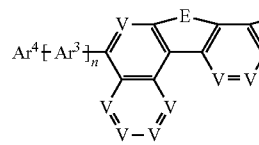
(1-2-3-a)
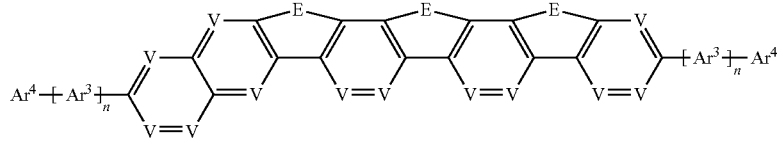
(1-2-4-a)
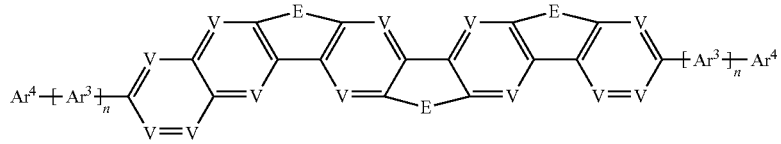
(1-2-5-a)
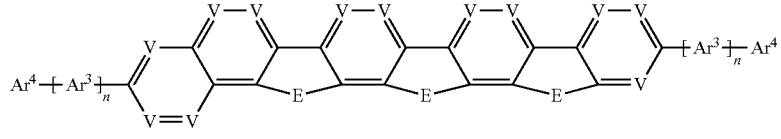

-continued
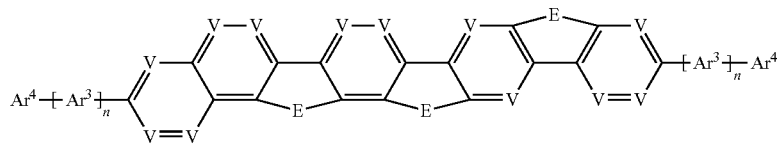
(1-2-6-a)
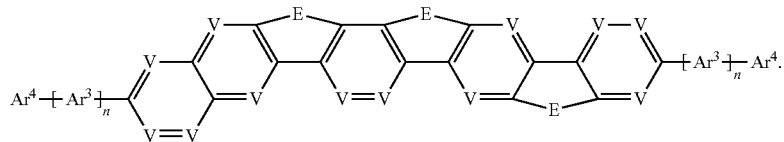
(1-2-7-a)
7. The compound of claim 1, wherein Ar³ is selected from the group consisting of formulae (Ar3-1) to (Ar3-25):
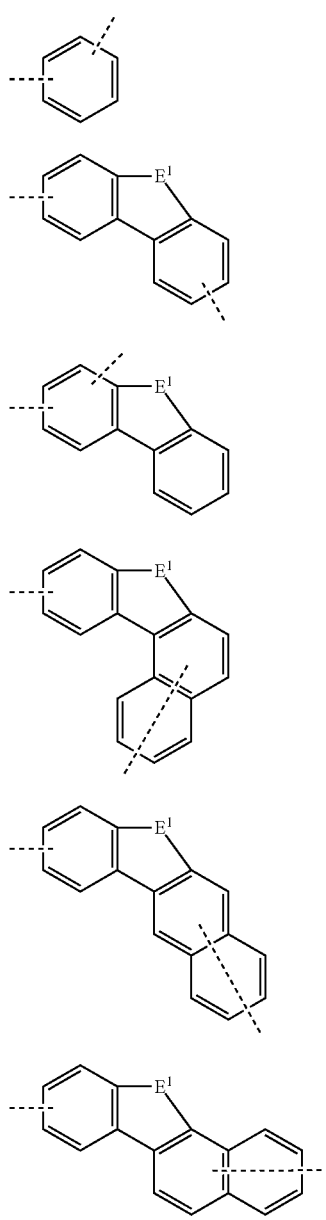
-continued
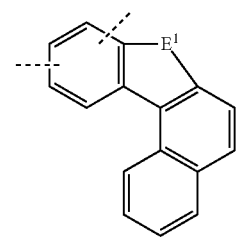
(Ar3-7)
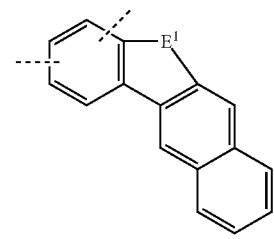
(Ar3-8)
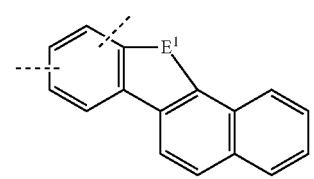
(Ar3-9)
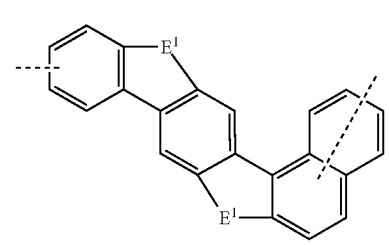
(Ar3-10)
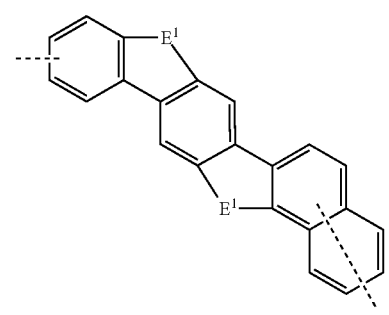
(Ar3-11)

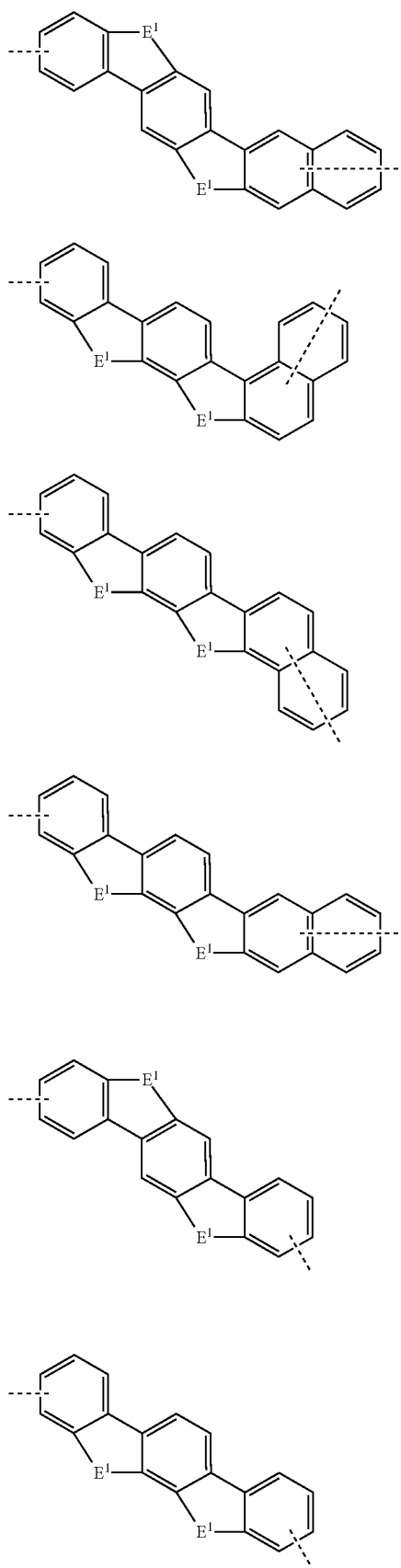
(Ar3-12)
(Ar3-13)
(Ar3-14)
(Ar3-15)
(Ar3-16)
(Ar3-17)
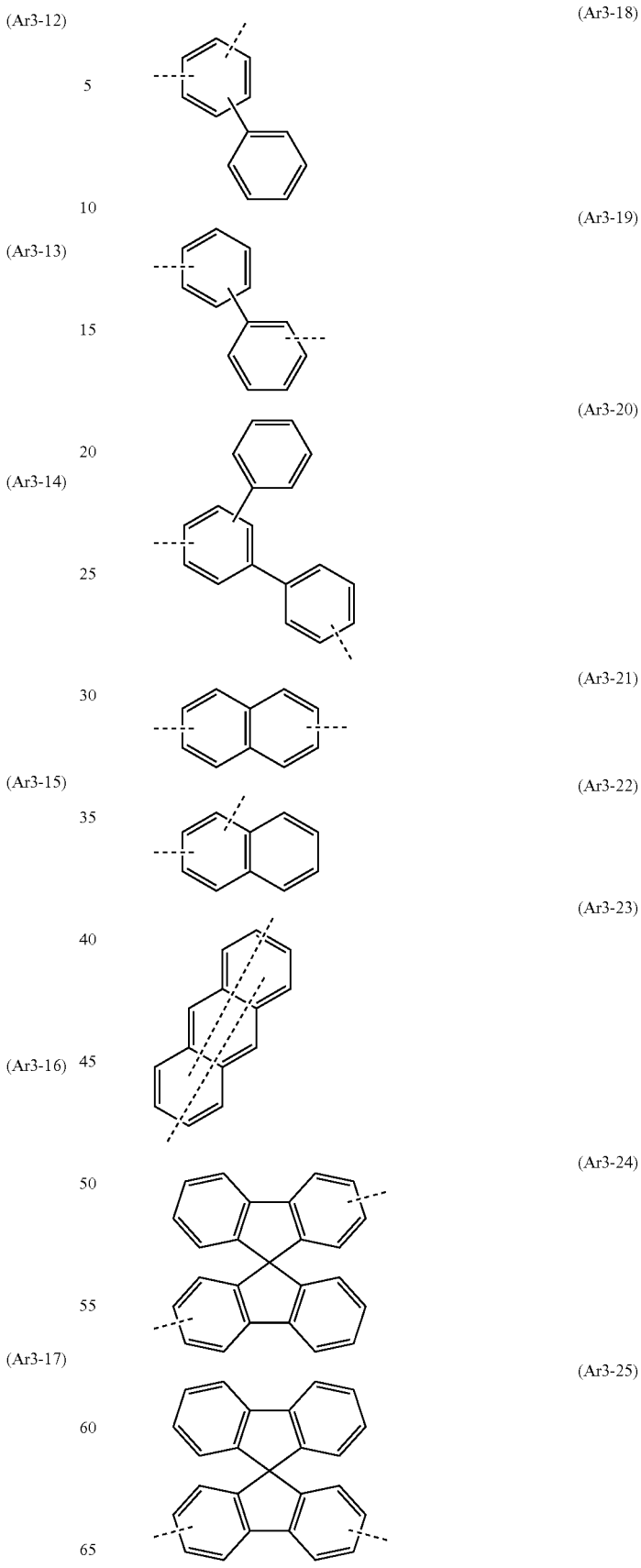
(Ar3-18)
(Ar3-19)
(Ar3-20)
(Ar3-21)
(Ar3-22)
(Ar3-23)
(Ar3-24)
(Ar3-25)

wherein
the dashed bonds indicate the bonding to Ar¹ and to a group Ar³ or Ar⁴;

the groups of formulae (Ar3-1) to (Ar3-25) are optionally substituted at each free position by a group R¹; and E¹ is selected from the group consisting of —B(R⁰—), —C(R⁰)₂—, —C(R⁰)₂—C(R⁰)₂—, —Si(R⁰)₂—, —C(=O)—, —C(=NR⁰)—, —C=(C(R⁰)₂—, —O—, —S—, —S(=O)—, —N(R⁰)—, —P(R⁰)—, and P((=O)R⁰—.

8. The compound of claim 1, wherein Ar⁴ is selected from the group consisting of formulae (Ar4-1) to (Ar4-27):

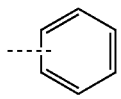
(Ar4-1)

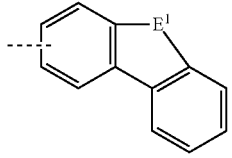
(Ar4-2)

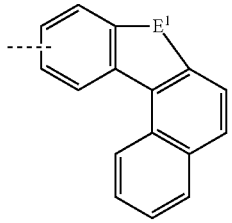
(Ar4-3)

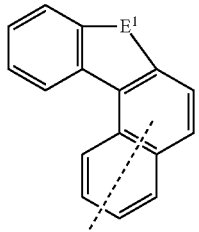
(Ar-4)

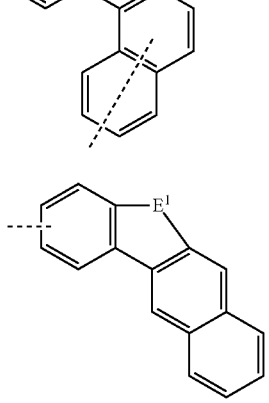
(Ar4-5)

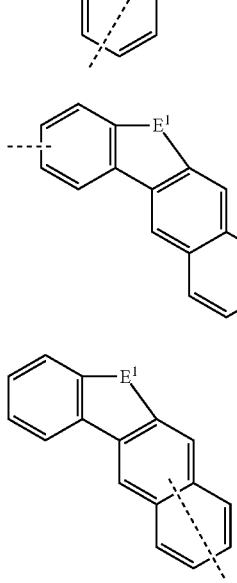
(Ar4-6)

-continued

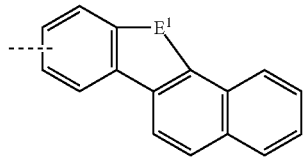
(Ar4-7)

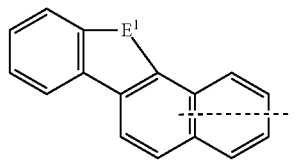
(Ar4-8)

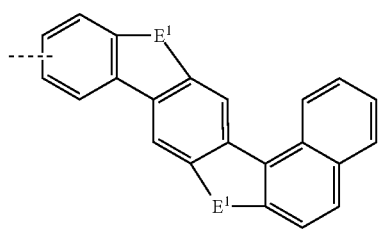
(Ar4-9)

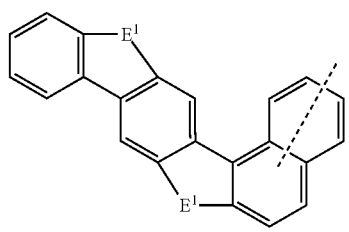
(Ar4-10)

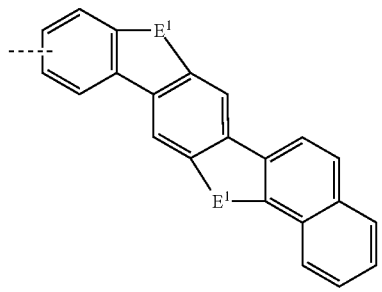
(Ar4-11)

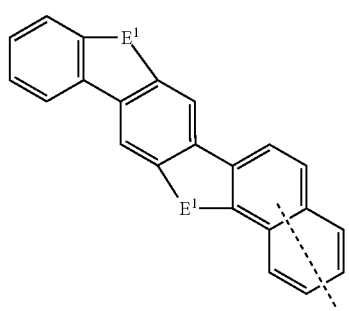
(Ar4-12)

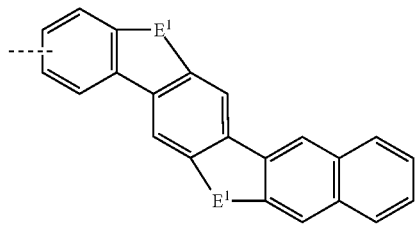
(Ar4-13)

(Ar4-14)
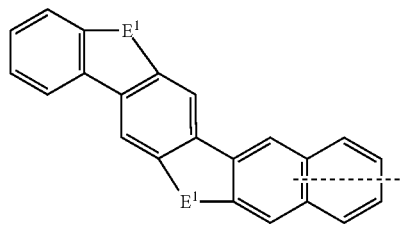
(Ar4-15)
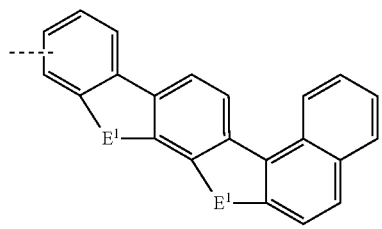
(Ar4-16)
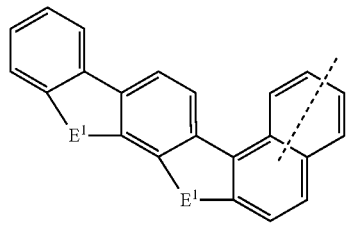
(Ar4-17)
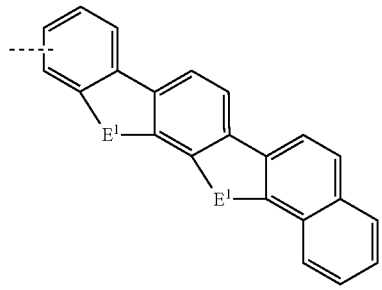
(Ar4-18)
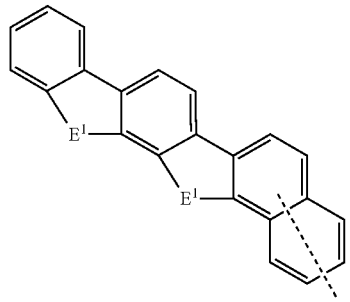
(Ar4-19)
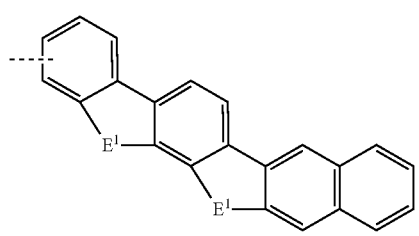
(Ar4-20)
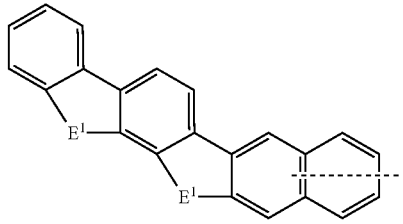
(Ar4-21)
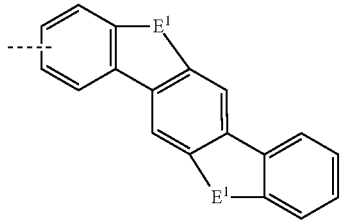
(Ar4-22)
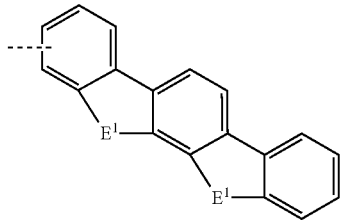
(Ar4-23)
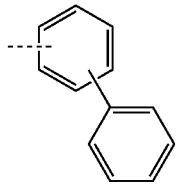
(Ar4-24)
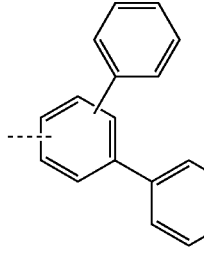
(Ar4-25)
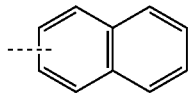
(Ar4-26)
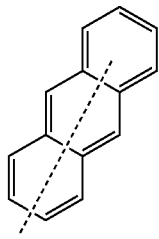

-continued

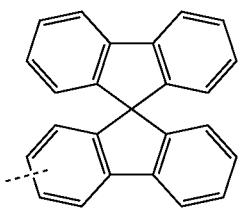

(Ar4-27)

wherein
the dashed bond indicates the bonding to Ar³;
E¹ is selected from the group consisting of —B(R⁰⁻), —C(R⁰)₂—, —C(R⁰)₂—C(R⁰)₂—, —Si(R⁰)₂—, —C(=O)—, —C(=NR⁰)—, —C=(C(R⁰)²—, —O—, —S—, —S(=O)—, —N(R⁰)—, —P(R⁰)—, and —P((=O)R⁰)—.

9. The compound of claim 1, wherein at least one group AP is a group of formula (Ar3-2-1) and/or at least one group Ar⁴ is a group of formula (Ar4-2-1):

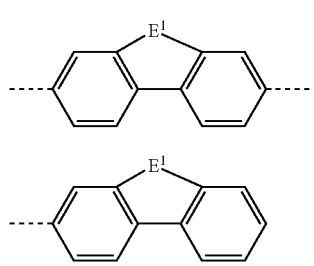

(Ar3-2-1)

(Ar4-2-1)

wherein
the dashed bonds in the group of formula (Ar3-2-1) indicate the bonding to Ar¹ and to a group Ar³ or Ar⁴;
the dashed bond in the group of formula (Ar4-2-1) indicates the bonding to Ar³;
E¹ is —C(R⁰)₂—; and
the groups of formulae (Ar3-2-1) and (Ar4-2-1) are optionally substituted at each free position by a group R¹.

10. The compound of claim 1, wherein at least one group Ar³ is a group of formula (Ar3-2-1b) and/or at least one group Ar⁴ is a group of formula (Ar4-2-1b):

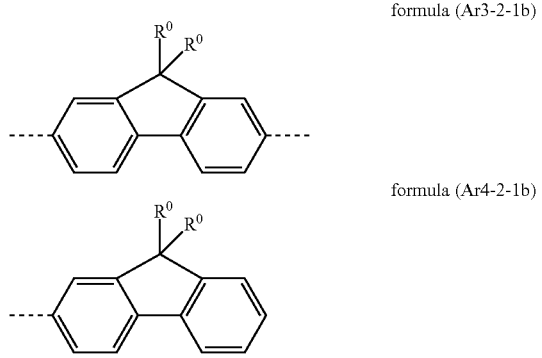

formula (Ar3-2-1b)

formula (Ar4-2-1b)

wherein
the dashed bonds in the group of formula (Ar3-2-1b) indicate the bonding to A¹ and to a group Ar³ or Ar⁴;
the dashed bonds in the group of formula (Ar4-2-1b) indicates the bonding to Ar³; and
the groups of formulae (Ar3-2-1b) and (Ar4-2-1b) are optionally substituted at each free position by a group R¹.

11. The compound of claim 1, wherein E is, identically or differently, on each occurrence, selected from the group consisting of —C(R⁰)₂—, —C(R⁰)₂—C(R⁰)₂—, —O—, —S—, and —N(R⁰)—.

12. The compound of claim 1, wherein E is —C(R⁰)₂—.

13. The compound of claim 1, wherein
R⁰ is on each occurrence, identically or differently, H, D, F, CN, Si(R²)₃, a straight-chain alkyl group having 1 to 10 C atoms or a branched or cyclic alkyl group having 3 to 10 C atoms, each of which is optionally substituted by one or more radicals R², wherein in each case one or more H atoms is optionally replaced by F, or an aryl or heteroaryl group having 5 to 40 aromatic ring atoms, which in each case is optionally substituted by one or more radicals R², and wherein two adjacent substituents optionally define a mono- or polycyclic, aliphatic ring system or aromatic ring system, which is optionally substituted by one or more radicals R².

14. An oligomer, polymer, or dendrimer comprising one or more compounds of claim 1, where the one or more compounds is bonded to the polymer, oligomer, or dendrimer at any position in formula (1) substituted by R¹.

15. A formulation comprising at least one compound of claim 1 and at least one solvent.

16. A formulation comprising at least one oligomer, polymer, or dendrimer of claim 14 and at least one solvent.

17. An electronic device comprising at least one compound of claim 1, wherein the electronic device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes, and organic plasmon emitting devices.

18. An electronic device comprising at least one oligomer, polymer, or dendrimer of claim 14, wherein the electronic device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes, and organic plasmon emitting devices.

19. The electronic device of claim 17, wherein the electronic device is an organic electroluminescent device and the at least one compound is employed as a fluorescent emitter or as a matrix material for fluorescent emitters.

20. The electronic device of claim 18, wherein the electronic device is an organic electroluminescent device and the at least one oligomer, polymer, or dendrimer is employed as a fluorescent emitter or as a matrix material for fluorescent emitters.

* * * * *